United States Patent
Bhide et al.

(10) Patent No.: US 9,546,153 B2
(45) Date of Patent: *Jan. 17, 2017

(54) BICYCLIC HETEROCYCLE SUBSTITUTED PYRIDYL COMPOUNDS USEFUL AS KINASE MODULATORS

(71) Applicant: BRISTOL-MYERS SQUIBB COMPANY, Princeton, NJ (US)

(72) Inventors: Rajeev S. Bhide, Princeton Junction, NJ (US); John V. Duncia, Newtown, PA (US); John Hynes, Washington Crossing, PA (US); Satheesh K. Nair, Bangalore (IN); William J. Pitts, Newtown, PA (US); Sreekantha R. Kumar, Bangalore (IN); Daniel S. Gardner, Furlong, PA (US); Natesan Murugesan, Princeton Junction, NJ (US); Venkatram Reddy Paidi, Bangalore (IN); Joseph B. Santella, Springfield, PA (US); Ramesh Sistla, Bangalore (IN); Hong Wu, New Hope, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/441,698

(22) PCT Filed: Nov. 7, 2013

(86) PCT No.: PCT/US2013/068829
§ 371 (c)(1),
(2) Date: May 8, 2015

(87) PCT Pub. No.: WO2014/074657
PCT Pub. Date: May 15, 2014

(65) Prior Publication Data
US 2015/0274696 A1 Oct. 1, 2015

Related U.S. Application Data

(60) Provisional application No. 61/723,851, filed on Nov. 8, 2012.

(51) Int. Cl.
| | | |
|---|---|---|
| C07D 401/12 | (2006.01) |
| C07D 413/12 | (2006.01) |
| C07D 417/12 | (2006.01) |
| C07D 487/04 | (2006.01) |
| C07D 513/04 | (2006.01) |
| C07D 417/14 | (2006.01) |
| C07D 471/04 | (2006.01) |

(52) U.S. Cl.
CPC .......... C07D 401/12 (2013.01); C07D 413/12 (2013.01); C07D 417/12 (2013.01); C07D 417/14 (2013.01); C07D 471/04 (2013.01); C07D 487/04 (2013.01); C07D 513/04 (2013.01)

(58) Field of Classification Search
None
See application file for complete search history.

(56) References Cited

U.S. PATENT DOCUMENTS

| | | |
|---|---|---|
| 8,058,045 B2 | 11/2011 | Collins et al. |
| 8,148,411 B2 | 4/2012 | Bothe et al. |
| 8,586,751 B2 | 11/2013 | De Lucca et al. |
| 8,987,311 B2 | 3/2015 | Dodd et al. |
| 9,102,625 B2 * | 8/2015 | Bauer ................. C07D 213/82 |
| 2005/0272753 A1 | 12/2005 | Nagashima et al. |
| 2006/0148800 A1 | 7/2006 | Stadtmueller et al. |
| 2009/0082329 A1 | 3/2009 | Halley et al. |
| 2009/0203715 A1 | 8/2009 | Bothe et al. |
| 2011/0224225 A1 | 9/2011 | Zeitlmann et al. |
| 2011/0237590 A1 | 9/2011 | Kitamura et al. |

(Continued)

FOREIGN PATENT DOCUMENTS

| | | |
|---|---|---|
| EP | 2532656 | 12/2012 |
| GB | 2388596 | 11/2003 |

(Continued)

OTHER PUBLICATIONS

Buckley, G. M. et al., "IRAK-4 inhibitors: Part I: A series of amides," Bioorganic & Medicinal Chemistry Letters, 18(11), pp. 3211-3214 (2008).
Buckley, G. M. et al., "IRAK-4 inhibitors: Part II: A structure-based assessment of imidazo[1,2-a]pyridine binding," Bioorganic & Medicinal Chemistry Letters, 18(11), pp. 3291-3295 (2008).
Buckley, G. M. et al., "IRAK-4 inhibitors. Part III: A series of imidazo[1,2-a]pyridines," Bioorganic & Medicinal Chemistry Letters, 18(12), pp. 3656-3660 (2008).
International Search Report for PCT/US2013/068829 issued Jan. 7, 2014.
International Preliminary Report on Patentability for PCT/US2013/068829 issued May 12, 2015.
Hussein, W.M., et al., Toll-like receptor agonists: a patent review (2011-2013), Expert Opinion on Therapeutic Patents, 24(4) pp. 453-470 (2014).

(Continued)

*Primary Examiner* — David K O'Dell
(74) *Attorney, Agent, or Firm* — Gary D. Greenblatt

(57) ABSTRACT

Compounds having the following formula (I) or a stereoisomer or a pharmaceutically-acceptable salt thereof, wherein $R^2$ is a bicyclic heterocycle, and $R^1$, $R^3$, $R^4$, $R^5$ and $R^6$ are as defined herein, that are useful as kinase modulators, including IRAK-4 modulation.

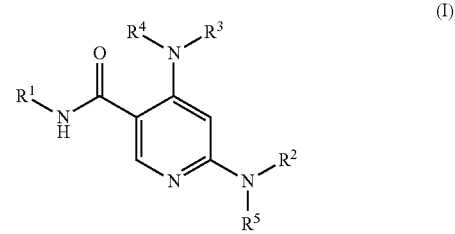

9 Claims, No Drawings

(56) References Cited

U.S. PATENT DOCUMENTS

| 2012/0108566 | A1* | 5/2012 | Bauer | C07D 213/82 |
| | | | | 514/210.18 |
| 2015/0011532 | A1 | 1/2015 | Paidi et al. | |
| 2015/0018344 | A1 | 1/2015 | Paidi et al. | |

FOREIGN PATENT DOCUMENTS

| WO | WO 02/102800 A1 | 12/2002 |
| WO | WO 03/013523 A1 | 2/2003 |
| WO | WO 2004/065378 A1 | 8/2004 |
| WO | WO 2005/007646 A1 | 1/2005 |
| WO | WO 2005/075468 A2 | 8/2005 |
| WO | WO 2008/148889 A1 | 12/2008 |
| WO | WO 2009/046416 A1 | 4/2009 |
| WO | WO 2011/053701 A1 | 5/2011 |
| WO | WO 2012/149567 A1 | 11/2012 |
| WO | WO 2014/074675 A1 | 5/2014 |
| WO | WO 2015/103453 A1 | 7/2015 |

OTHER PUBLICATIONS

Quesniaux, V.F.J., et al., "Toll-like receptors: emerging targets of immunomodulation," Expert Opinion on Therapeutic Patents, 14(1), pp. 85-100 (2004).

Flannery, S., et al., "The interleukin-1 receptor-associated kinases: Critical regulators of innate immune signaling," Biochemical Pharmacology 80, pp. 1981-1991 (2010).

Hynes Jr, J. et al., "Chapter Nine—Advances in the Discovery of Small-Molecule IRAK4 inhibitors," Annual Reports in Medicinal Chemistry, vol. 49, pp. 117-133 (2014).

* cited by examiner

BICYCLIC HETEROCYCLE SUBSTITUTED PYRIDYL COMPOUNDS USEFUL AS KINASE MODULATORS

FIELD OF THE INVENTION

This invention relates to compounds useful as kinase inhibitors, including the modulation of IRAK-4. Provided herein are bicyclic heterocycle-substituted pyridyl compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including IRAK-4 in a mammal.

BACKGROUND OF THE INVENTION

Toll/IL-1 receptor family members are important regulators of inflammation and host resistance. The Toll like receptor (TLR) family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Members of the IRAK family of serine/threonine kinases are recruited to the receptor via interactions with MyD88. The family consists of four members. Several lines of evidence indicate that IRAK4 plays a critical and non-redundant role in initiating signaling via MyD88 dependent TLRs and IL-1R family members. Structural data confirms that IRAK4 directly interacts with MyD88 and subsequently recruits either IRAK1 or IRAK2 to the receptor complex to facilitate downstream signaling (Lin, S. et al., *Nature*, 465: 885-890 (2010)). IRAK4 directly phosphorylates IRAK1 to facilitate downstream signaling to the E3 ubiquitin ligase TRAF6, resulting in activation of the serine/threonine kinase TAK1 with subsequent activation of the NFκB pathway and MAPK cascade (Flannery, S. et al., *Biochem. Pharmacol.*, 80:1981-1991 (2010)). A subset of human patients was identified who lack IRAK4 expression (Picard, C. et al., *Science*, 299:2076-2079 (2003)). Cells from these patients fail to respond to all TLR agonists with the exception of TLR3 as well as to members of the IL-1 family including IL-1β and IL-18 (Ku, C. et al., J. Exp. Med., 204:2407-2422 (2007)). Deletion of IRAK4 in mice results in a severe block in IL-1, IL-18 and all TLR dependent responses with the exception of TLR3 (Suzuki, N. et al., *Nature*, 416:750-754 (2002)). In contrast, deletion of either IRAK1 (Thomas, J. A. et al., *J. Immunol.*, 163:978-984 (1999); Swantek, J. L. et al., *J. Immunol.*, 164:4301-4306 (2000) or IRAK2 (Wan, Y. et al., *J. Biol. Chem.*, 284:10367-10375 (2009)) results in partial loss of signaling. Furthermore, IRAK4 is the only member of the IRAK family whose kinase activity has been shown to be required for initiation of signaling. Replacement of wild type IRAK4 in the mouse genome with a kinase inactive mutant (KDKI) impairs signaling via all MyD88 dependent receptors including IL-1, IL-18 and all TLRs with the exception of TLR3 (Koziczak-Holbro, M. et al., *J. Biol. Chem.*, 282:13552-13560 (2007); Kawagoe, T. et al., *J. Exp. Med.*, 204:1013-1024 (2007); and Fraczek, J. et al., *J. Biol. Chem.*, 283:31697-31705 (2008)).

As compared to wild type animals, IRAK4 KDKI mice show greatly reduced disease severity in mouse models of multiple sclerosis (Staschke, K. A. et al., *J. Immunol.*, 183:568-577 (2009)), rheumatoid arthritis (Koziczak-Holbro, M. et al., *Arthritis Rheum.*, 60:1661-1671 (2009)), atherosclerosis (Kim, T. W. et al., *J. Immunol.*, 186:2871-2880 (2011) and Rekhter, M. et al., *Biochem. Biophys. Res. Comm.*, 367:642-648 (2008)), and myocardial infarction (Maekawa, Y. et al., *Circulation*, 120:1401-1414 (2009)). As described, IRAK4 inhibitors will block all MyD88 dependent signaling. MyD88 dependent TLRs have been shown to contribute to the pathogenesis of multiple sclerosis, rheumatoid arthritis, cardiovascular disease, metabolic syndrome, sepsis, systemic lupus erythematosus, inflammatory bowel diseases including Crohn's disease and ulcerative colitis, autoimmune uveitis, asthma, allergy, type I diabetes, and allograft rejection (Keogh, B. et al., *Trends Pharmacol. Sci.*, 32:435-442 (2011); Mann, D. L., *Circ. Res.*, 108:1133-1145 (2011); Horton, C. G. et al., *Mediators Inflamm.*, Article ID 498980 (2010), doi:10.1155/2010/498980; Goldstein, D. R. et al., *J. Heart Lung Transplant.*, 24:1721-1729 (2005); and Cario, E., *Inflamm. Bowel Dis.*, 16:1583-1597 (2010)). Oncogenically active MyD88 mutations in diffuse large B cell lymphomas have been identified that are sensitive to IRAK4 inhibition (Ngo, V. N. et al., *Nature*, 470:115-121 (2011)). Whole genome sequencing also identified mutations in MyD88 associated with chronic lymphatic leukemia suggesting that IRAK4 inhibitors may also have utility in treating leukemias (Puente, X. S. et al., *Nature*, 475:101-105 (2011)).

In addition to blocking TLR signaling, IRAK4 inhibitors will also block signaling by members of the IL-1 family. Neutralization of IL-1 has been shown to be efficacious in multiple diseases including gout; gouty arthritis; type 2 diabetes; auto-inflammatory diseases including Cryopyrin-Associated Periodic Syndromes (CAPS), TNF Receptor Associated Periodic Syndrome (TRAPS), Familial Mediterranean Fever (FMF), adult onset stills; systemic onset juvenile idiopathic arthritis; stroke; Graft-versus-Host Disease (GVHD); smoldering multiple myeloma; recurrent pericarditis; osteoarthritis; emphysema (Dinarello, C. A., *Eur. J. Immunol.*, 41:1203-1217 (2011) and Couillin, I. et al., *J. Immunol.*, 183:8195-8202 (2009)). In a mouse model of Alzheimer's disease, blockade of IL-1 receptor improved cognitive defects, attenuated tau pathology and reduced oligomeric forms of amyloid-β (Kitazawa, M. et al., *J. Immunol.*, 187:6539-6549 (2011)). IL-1 has also been shown to be a critical link to adaptive immunity, driving differentiation of the TH17 effector T cell subset (Chung, Y. et al., *Immunity*, 30:576-587 (2009)). Therefore, IRAK4 inhibitors are predicted to have efficacy in TH17 associated diseases including multiple sclerosis, psoriasis, inflammatory bowel diseases, autoimmune uveitis, and rheumatoid arthritis (Wilke, C. M. et al., *Trends Immunol.*, 32:603-661 (2011)).

In view of the conditions that may benefit by treatment involving modulation of protein kinases, it is immediately apparent that new compounds capable of modulating protein kinases such as IRAK-4 and methods of using these compounds could provide substantial therapeutic benefits to a wide variety of patients.

The present invention relates to a new class of heterocyclic-substituted pyridyl compounds found to be effective inhibitors of protein kinases including IRAK-4.

SUMMARY OF THE INVENTION

Modulators of kinase activity which may generally be described as heterocyclic-substituted pyridyl compounds found are provided herein.

The invention is directed to compounds of Formula (I) that which are useful as inhibitors of IRAK-4, and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides processes and intermediates for making the compounds of the present invention or stereoisomers, tautomers, pharmaceutically acceptable salts, solvates, or prodrugs thereof The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of IRAK-4 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

A preferred embodiment is a method for treating inflammatory and autoimmune diseases wherein the treatment of inflammatory diseases is even more preferred. Particular, inflammatory and autoimmune diseases include, but are not limited to, Crohn's disease, ulcerative colitis, asthma, graft versus host disease, allograft rejection, chronic obstructive pulmonary disease; Graves' disease, rheumatoid arthritis, systemic lupus erythematosis, psoriasis; CAPS, TRAPS, FMF, adult onset stills, systemic onset juvenile idiopathic arthritis, multiple sclerosis, neuropathic pain, gout, and gouty arthritis.

An alternate preferred embodiment is a method for treating metabolic diseases, including type 2 diabetes and atherosclerosis.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancers.

These and other features of the invention will be set forth in the expanded form as the disclosure continues.

DETAILED DESCRIPTION OF THE EMBODIMENTS OF THE INVENTION

Provided herein is at least one chemical entity chosen from compounds of Formula (I):

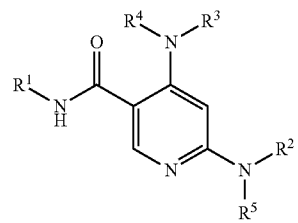

or a stereoisomer or pharmaceutically-acceptable salt thereof, wherein $R^1$ is $C_{1-6}$ alkyl substituted with 0-7 $R^{1a}$, $C_{1-6}$ haloalkyl, $C_{2-6}$ alkenyl substituted with 0-7 $R^{1a}$, $C_{2-6}$ alkynyl substituted with 0-7 $R^{1a}$, —$(CH_2)_r$—$C_{3-10}$ cycloalkyl substituted with 0-7 $R^{1a}$, —$(CH_2)_r$—$C_{6-10}$ aryl substituted with 0-7 $R^{1a}$, or —$(CH_2)_r$-5-10 membered heterocycle containing 1-4 heteroatoms selected from N, O, and S, substituted with 0-7 $R^{1a}$;

$R^{1a}$ at each occurrence is independently hydrogen, =O, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^2$ is an 8-11 membered heterocycle containing 1-4 heteroatoms selected from N, 0, and S substituted with 0-4 $R^{2a}$;

$R^{2a}$ at each occurrence is independently selected from hydrogen, =O, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-1 $R^a$, and —$(CH_2)_r$-5-7 membered heterocycle comprising carbon atoms and 1-4 heteroatoms selected from N, O, and $S(O)_p$ substituted with 0-2 $R^a$;

$R^3$ is $C_{1-6}$ alkyl substituted with 0-3 $R^{3a}$, $C_{1-6}$ haloalkyl, $C_{2-6}$ alkenyl substituted with 0-3 $R^{3a}$, $C_{2-6}$ alkynyl substituted with 0-3 $R^{3a}$, $C_{3-10}$ cycloalkyl substituted with 0-3 $R^{3a}$, or $C_{6-10}$ aryl substituted with 0-3 $R^{3a}$;

$R^{3a}$ at each occurrence is independently hydrogen, =O, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-3 $R^a$, $C_{1-6}$ haloalkyl, —$(CH_2)_r$-3-14 membered carbocycle substituted with 0-3 $R^a$, or —$(CH_2)_r$-5-10 membered heterocycle comprising carbon atoms and 1-4 heteroatoms selected from N, O, and $S(O)_p$ substituted with 0-3 $R^a$;

$R^4$ and $R^5$ are independently selected from hydrogen and $C_{1-4}$ alkyl substituted with 0-1 $R^f$;

$R^{11}$ at each occurrence is independently hydrogen, $C_{1-6}$ alkyl substituted with 0-1 $R^f$, $CF_3$, $C_{3-10}$ cycloalkyl substituted with 0-1 $R^f$, —$(CH)_r$-phenyl substituted with 0-3 $R^d$, or —(CH$_2$)$_r$-5-7 membered heterocycle comprising carbon atoms and 1-4 heteroatoms selected from N, O, and S(O)$_p$ substituted with 0-3 R$^d$; or one R$^{11}$ together with a second R$^{11}$ and the nitrogen atom to which they are both attached may be combined to form an azetidinyl, pyrrolidinyl, piperidinyl, morpholinyl, or 4-(C$_{1-6}$ alkyl)piperazinyl ring;

R$^a$ at each occurrence is independently hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$ substituted with 0-3 R$^f$, alternatively two R$^a$ on adjacent or the same carbon atom form a cyclic acetal of the formula —O—(CH$_2$)$_n$—O—, or —O—CF$_2$—O—, wherein n is selected from 1 or 2;

R$^b$ is hydrogen, C$_{1-6}$ alkyl substituted with 0-2 R$^d$, C$_{1-6}$ haloalkyl, C$_{3-6}$ cycloalkyl substituted with 0-2 R$^d$, or —(CH$_2$)$_r$-phenyl substituted with 0-3 R$^d$;

R$^c$ is C$_{1-6}$ alkyl substituted with 0-3 R$^f$, —(CH$_2$)$_r$—C$_{3-6}$ cycloalkyl substituted with 0-3 R$^f$, or —(CH$_2$)$_r$-phenyl substituted with 0-3 R$^f$; or R$^d$ at each occurrence is independently hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl, or —(CH$_2$)$_r$-phenyl substituted with 0-3 R$^f$;

R$^e$ is selected from hydrogen, C$_{1-6}$ alkyl, C$_{3-6}$ cycloalkyl, and —(CH$_2$)$_r$-phenyl substituted with 0-3 R$^f$;

R$^f$ at each occurrence is independently hydrogen, halo, NH$_2$, OH, C$_{3-6}$ cycloalkyl, CF$_3$, or —O(C$_{1-6}$ alkyl);

p is 0, 1, or 2; and r is 0, 1, 2, 3, or 4.

In another embodiment are provided compounds of Formula (I), or a stereoisomer or pharmaceutically-acceptable salt thereof, wherein R$^2$ is benzothiazphenyl, pyrazolopyrimidinyl, benzothiazolyl, pyrazolopyridinyl, benzoisothiazolyl, triazolopyridinyl, imidazopyridinyl, benzooxazolyl, triazolopyridinyl, imidazopyridinyl, pyridopyrazinyl, quinazolinyl, pyridopyrazinyl, benzooxadiazolyl, benzothiadiazolyl, benzoimidazolyl, triazolopyridinyl, imidazopyridazinyl, pyridopyrazinyl, naphthyridinyl, quinoxalinyl, phthalazinyl, quinolinyl, indolyl, thiazolopyridinyl, benzodioxolyl, benzothienyl, isoquinolinyl, benzopyranyl, indolizinyl, benzofuranyl, chromonyl, coumarinyl, benzopyranyl, cinnolinyl, pyrrolopyridyl, furopyridyl, or isoindolyl.

In another embodiment, there is provided a compound of Formula (I), or a stereoisomer or pharmaceutically-acceptable salt thereof, wherein both R$^4$ and R$^5$ are hydrogen.

In another embodiment, there is provided a compound of Formula (II), wherein

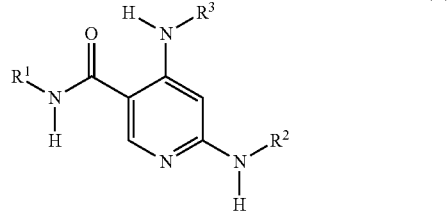

(II)

or a stereoisomer or pharmaceutically-acceptable salt thereof, wherein:

R$^1$ is C$_{1-6}$ alkyl, —(CH$_2$)$_r$C$_{3-10}$ cycloalkyl, —(CH$_2$)$_r$-5-7 membered heterocycle containing 1-4 heteroatoms selected from N, O and S, or —(CH$_2$)$_r$phenyl, each group substituted with 0-4 R$^{1a}$;

R$^{1a}$ at each occurrence is independently hydrogen, =O, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-4 R$^a$, C$_{1-6}$ haloalkyl, —(CH$_2$)$_r$-3-14 membered carbocycle substituted with 0-4 R$^a$ (hydrogen or —C(O)NHCH$_3$), or —(CH$_2$)$_r$-5-7 membered heterocycle comprising carbon atoms and 1-4 heteroatoms selected from N, O, and S(O)$_p$ substituted with 0-4 R$^a$;

R$^2$ is benzothiazphenyl, pyrazolopyrimidinyl, benzothiazolyl, pyrazolopyridinyl, benzoisothiazolyl, triazolopyridinyl, imidazopyridinyl, benzooxazolyl, triazolopyridinyl, imidazopyridinyl, pyridopyrazinyl, quinazolinyl, pyridopyrazinyl, benzooxadiazolyl, benzothiadiazolyl, benzoimidazolyl, triazolopyridinyl, imidazopyridazinyl, pyridopyrazinyl, naphthyridinyl, quinoxalinyl, phthalazinyl, quinolinyl, indolyl, thiazolopyridinyl, benzodioxolyl, benzothienyl, isoquinolinyl, benzopyranyl, indolizinyl, benzofuranyl, chromonyl, coumarinyl, benzopyranyl, cinnolinyl, pyrrolopyridyl, furopyridyl, or isoindolyl, each group substituted by 0-4 groups selected from R$^{2a}$;

R$^{2a}$ at each occurrence is independently hydrogen, =O, F, Cl, Br, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-2 R$^a$, C$_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-1 R$^a$;

R$^3$ is C$_{1-6}$ alkyl, C$_{3-10}$ cycloalkyl, phenyl, or a 5-10 membered heterocycle containing 1-4 heteroatoms selected from N, O, and S substituted with 0-3 R$^{3a}$;

R$^{3a}$ at each occurrence is independently hydrogen, =O, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^a$, C$_{1-6}$ haloalkyl, —(CH$_2$)$_r$-3-14 membered carbocycle substituted with 0-3 R$^a$, or —(CH$_2$)$_r$-5-10 membered heterocycle comprising carbon atoms and 1-4 heteroatoms selected from N, O, and S(O)$_p$ substituted with 0-3 R$^a$;

R$^{11}$ at each occurrence is independently hydrogen, C$_{1-6}$ alkyl substituted with 0-1 R$^f$, CF$_3$, a C$_{3-10}$ cycloalkyl substituted with 0-1 R$^f$, —CH$_2$-phenyl substituted with 0-3 R$^d$, or —(CH$_2$)-5-7 membered heterocycle comprising carbon atoms and 1-4 heteroatoms selected from N, O, and S(O)$_p$ substituted with 0-3 R$^d$;

R$^a$ at each occurrence is independently hydrogen, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl, $C_{1-6}$ haloalkyl, —$(CH_2)_r$-3-14 membered carbocycle, or —$(CH_2)_r$-5-7 membered heterocycle comprising carbon atoms and 1-4 heteroatoms selected from N, O, and $S(O)_p$;

two $R^a$'s, together with the carbon atoms to which they are attached, combine to form a cyclic acetal of the formula —O—$(CH_2)_n$—O—, or —O—$CF_2$—O—, wherein n is 1 or 2;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or —$(CH_2)_r$-phenyl substituted with 0-3 $R^d$;

$R^c$ is $C_{1-6}$ alkyl, $C_{3-6}$ cycloalkyl, or —$(CH_2)_r$-phenyl substituted with 0-3 $R^f$;

$R^d$ is hydrogen, F, Cl, Br, $OCF_3$, $CF_3$, CN, $NO_2$, —$OR^e$, —$(CH_2)_rC(O)R^e$, —$NR^eR^e$, —$NR^eC(O)OR^e$, $C_{1-6}$ alkyl, or —$(CH_2)_r$-phenyl substituted with 0-3 $R^f$;

$R^e$ is hydrogen, $C_{1-6}$ alkyl, $C_{3-6}$ cycloalkyl, or —$(CH_2)_r$-phenyl substituted with 0-3 $R^f$;

$R^f$ is hydrogen, halo, $NH_2$, OH, or —$O(C_{1-6}alkyl)$;

r is 0, 1, 2, 3, or 4; and p is 0, 1, or 2.

In another embodiment, there is provided a compound, or a stereoisomer or pharmaceutically-acceptable salt thereof, wherein $R^2$ is selected from benzothiazphenyl, pyrazolopyrimidinyl, benzothiazolyl, pyrazolopyridinyl, benzooxazolyl, triazolopyridinyl, pyridopyrazinyl, pyridopyrimidinyl, pyrazolopyrimidinyl, quinazolinyl, pyridopyrazinyl, benzooxadiazolyl, benzothiadiazolyl, triazolopyridinyl, imidazopyridazinyl, pyridopyrazinyl, naphthyridinyl, quinoxalinyl, quinolinyl, indolyl, thiazolopyridinyl, isoquinolinyl, and cinnolinyl, each group substituted by 0-4 $R^{2a}$.

In yet another embodiment, there is provided a compound, or a stereoisomer or pharmaceutically-acceptable salt thereof, wherein $R^2$ is selected from benzothiazphenyl and pyrazolopyrimidinyl, each group substituted by 0-4 $R^{2a}$.

In a preferred embodiment $R^{2a}$ is independently selected from =O, F, Cl, CN, —$(CH_2)_rOR^b$, —$(CH_2)_rC(O)R^b$, —$(CH_2)_rC(O)OR^b$, —$(CH_2)_rNR^{11}R^{11}$, $C_{1-6}$ alkyl substituted with 0-2 $R^a$, and pyridyl (especially wherein $R^b$ is ethyl or methyl, $R^{11}$ is hydrogen and r is 0).

In a more preferred embodiment compounds of formula (I), or a stereoisomer or pharmaceutically-acceptable salt thereof, are provided wherein $R^2$ is selected from:

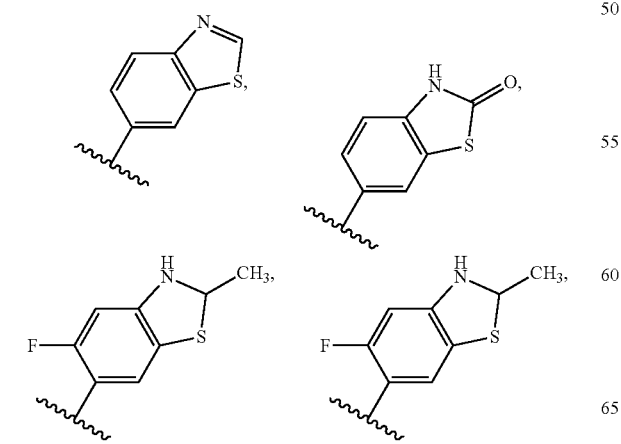

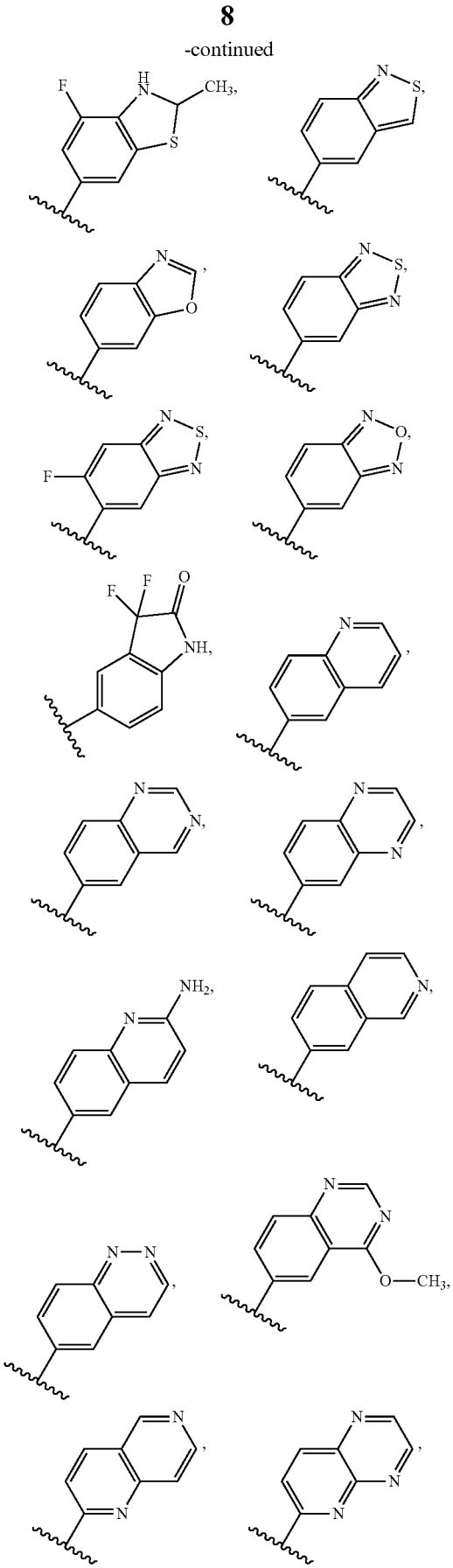

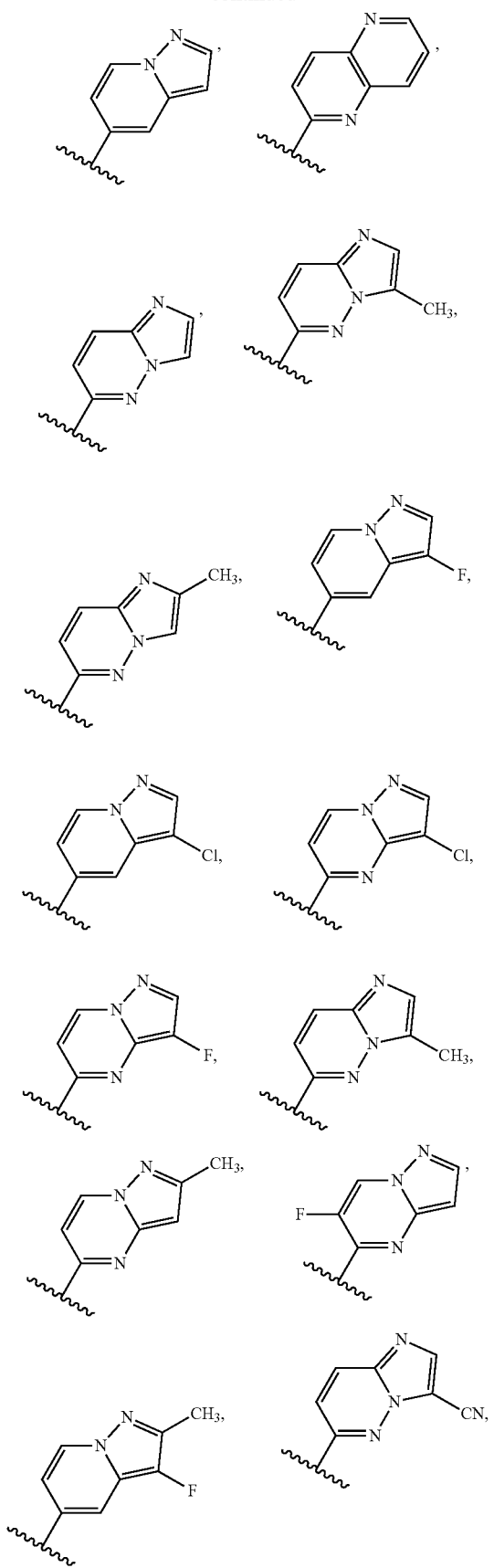
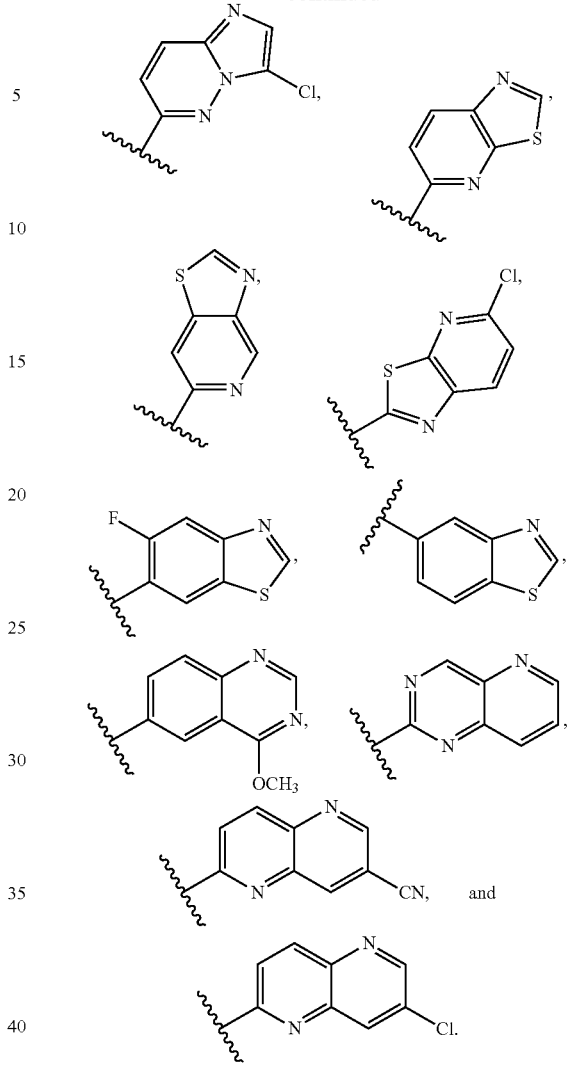

In yet another more preferred embodiment there are provided compounds of formula (I), or a stereoisomer or pharmaceutically-acceptable salt thereof, wherein:

$R^1$ is $C_{1-6}$ alkyl, —$(CH_2)_rC_{3-10}$ cycloalkyl, —$(CH_2)_r$-6-membered heterocycle containing 1-4 heteroatoms selected from N, S and O, or —$(CH_2)_r$phenyl, each group substituted by 0-5 $R^{1a}$; and $R^{1a}$ at each occurrence is independently F, $CF_3$, CN, —$(CH_2)_rOR^b$, —$(CH_2)_rC(O)NR^{11}R^{11}$, —$(CH_2)_rNR^bC(O)R^c$, or —$NR^bC(O)NR^{11}R^{11}$; or $C_{1-6}$ alkyl, $C_{3-10}$ cycloalkyl (especially cyclopropyl or cyclobutyl), phenyl, or a 5-7 membered heterocycle comprising carbon atoms and 1-3 heteroatoms selected from N and O (especially pyrrolidinyl, or morpholinyl), each group substituted with 0-4 $R^a$;

$R^a$ is independently, hydrogen, —$(CH_2)_rC(O)NR^{11}R^{11}$, $C_{1-4}$ alkyl, or a 5-7 membered heterocycle comprising carbon atoms and 1-3 heteroatoms selected from N and O (especially triazolyl);

$R^b$ is hydrogen or methyl;

$R^c$ independently, at each occurrence is $C_{1-4}$ alkyl, OH, or halo; or $C_{5-10}$ cycloalkyl (especially cyclopentyl or cyclohexyl), phenyl, or a 5-7 membered heterocycle containing 1-3 heteroatoms selected from N and O (especially triazolyl, pyranyl, or morpholinyl);

R[11] at each occurrence is independently hydrogen or $C_{1-4}$ alkyl; and r is 0-4.

In another embodiment, there is provided a compound of Formula (I), or a stereoisomer or pharmaceutically-acceptable salt thereof, wherein $R^1$ is $C_{1-6}$ alkyl or cyclohexyl, each substituted by 0-4 $R^{1a}$.

In a further embodiment, there is provided a compound of Formula (I), or a stereoisomer or pharmaceutically-acceptable salt thereof, wherein $R^1$ is selected from: methyl, ethyl, —CH$_2$CHFCH$_2$OH, —CH$_2$CHFCH(CH$_3$)OH, —CH$_2$CHFCH(cyclopropyl)OH, —CH$_2$CHFCH(isopropyl)OH, —CH$_2$CN, —CH$_2$CH$_2$NHC(O)CH$_3$, —CH$_2$CH$_2$C(CH$_3$)$_2$OH, —CH$_2$CHFC(OH)(CF$_3$)CH$_3$, —CH$_2$CHFC(cyclopropyl)(OH)(CF$_3$), —CH$_2$CF$_2$C(CH$_3$)$_2$(OH), —CH$_2$CHFC(CH$_3$)$_2$(OH), —CH$_2$CH$_2$CH(CH$_3$)NHC(O)OC(CH$_3$)$_3$, —CH$_2$CH$_2$CH(CH$_3$)NHC(O)CH$_3$, —CH$_2$CH$_2$CH(CH$_3$)NHC(O)CH$_2$CH$_2$CH$_2$C(CH$_3$)$_2$OH, —CH$_2$CH$_2$CH(CH$_3$)NHC(O)NHCH(CH$_3$)$_2$, —CH$_2$CH$_2$CH(CH$_3$)NHC(O)OC(CH$_3$)$_2$OH, —CH$_2$CH$_2$CH(CH$_3$)NHC(O)CH$_2$CH$_2$C(CH$_3$)$_2$OH, —CH$_2$CH$_2$CH$_2$NHC(O)CH$_3$, —(CH$_2$)$_3$NHC(O)(CH$_2$)$_4$C(CH$_3$)$_2$OH, —CH$_2$CH$_2$CH(CH$_3$)NHC(O)CH$_2$N(CH$_3$)$_2$,

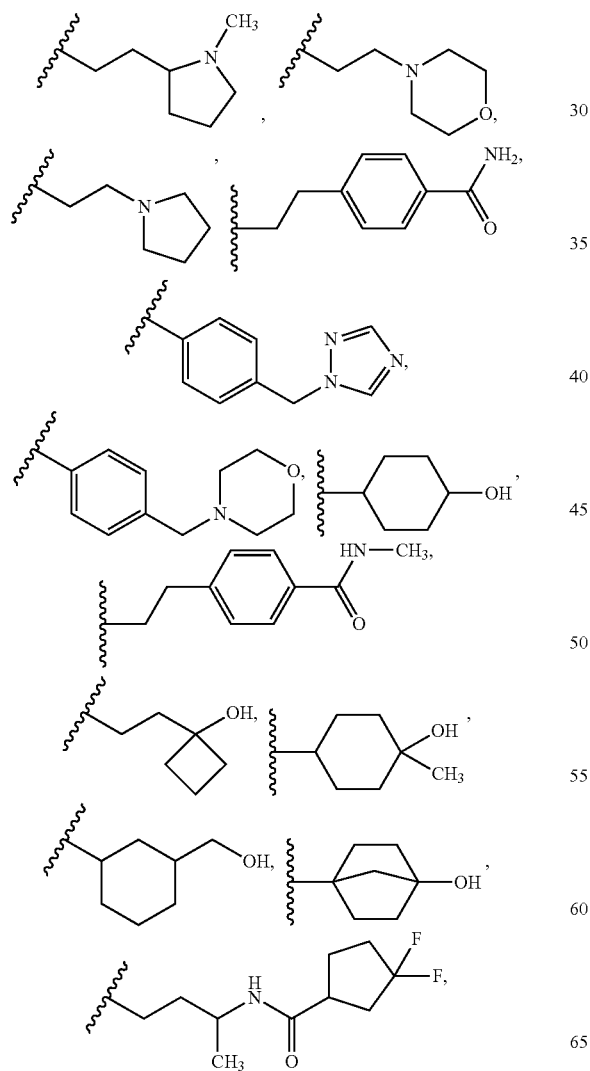

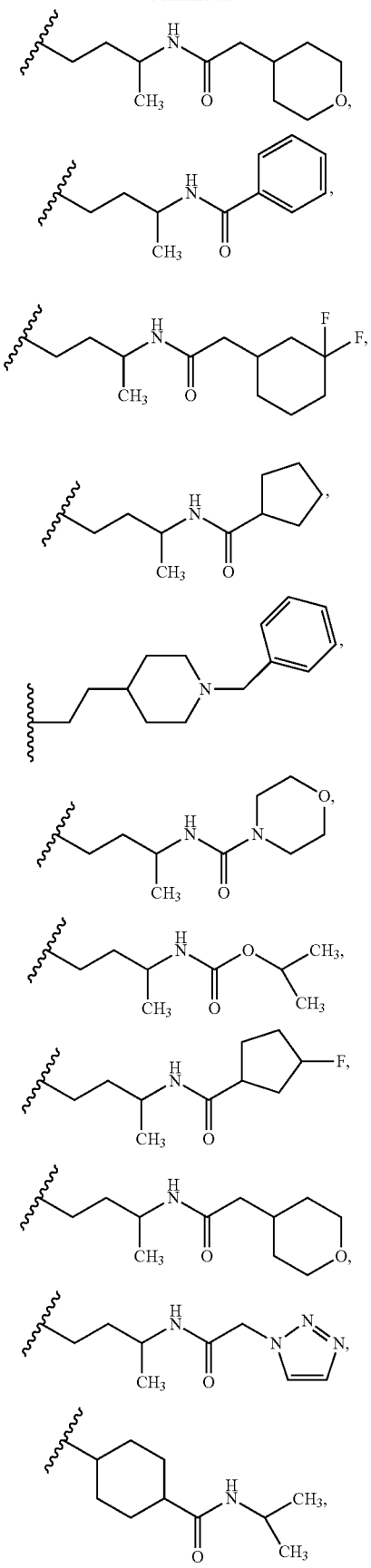

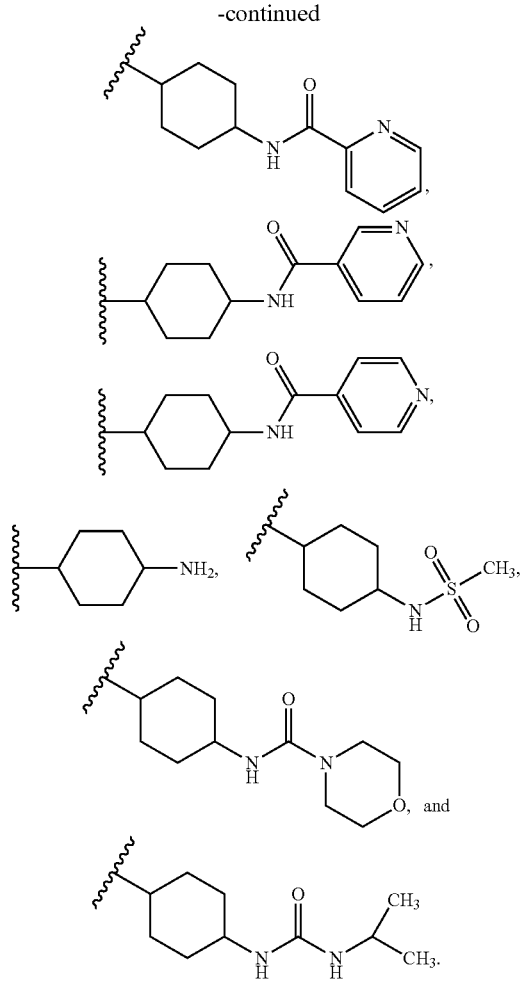

In a more preferred embodiment there are provided compounds of Formula (I), or a stereoisomer or pharmaceutically-acceptable salt thereof, in which $R^3$ is $C_{1-6}$ alkyl, $C_{3-10}$cycloalkyl, phenyl, or a 5-7 membered heterocycle containing 1-3 atoms selected from N, O and S, (tetrahydropyranyl, tetrahydrofuranyl, or oxetanyl), each group optionally substituted with 0-3 $R^{3a}$;

$R^{3a}$ is, independently, hydrogen, F, Cl, $CF_3$, $CHF_2$, —$(CH_2)_rOR^b$, —$(CH_2)_rC(O)OR^b$, —$(CH_2)_rNR^{11}R^{11}$ or —$(CH_2)_rC(O)NR^{11}R^{11}$; or $R^{3a}$ is $C_{1-6}$ alkyl, —$(CH_2)_r$-phenyl, $C_{3-10}$ cycloalkyl, or —$(CH_2)_r$-5-7 membered heterocycle comprising carbon atoms and 1-4 heteroatoms selected from N, O, and $S(O)_p$, each group substituted with 0-3 $R^a$;

$R^a$ is hydrogen, OH, Cl, F, or —$(CH_2)_rOR^b$ $R^b$ is hydrogen, $CHF_2$, or $C_{1-4}$ alkyl;

$R^{11}$ is, independently, hydrogen, $C_{3-10}$ cycloalkyl, $CF_3$, or $C_{1-4}$ alkyl optionally substituted with, OH; and r is 0-4.

In a more preferred embodiment there are provided compounds of Formula
(I), or a stereoisomer or pharmaceutically-acceptable salt thereof, in which wherein $R^3$ is methyl, ethyl, isopropyl, isobutyl, cyclopropyl, cyclopentyl, or pyranyl, each group optionally substituted by 1-2 groups independently selected from F and $CF_3$.

In another embodiment, there is provided a compound of Formula (I), wherein $R^3$ is selected from the following groups: —$CH_2CH_3$, —$CH(CH_3)_2$, —$CH_2CH_2CH_3$, —$C(CH_3)_3$, —$CH_2C(CH_3)_3$, —$CH_2CH(CH_3)_2$, —$CH_2CF_3$, —$CH(CH_3)CF_3$, —$CH_2CH_2CH(CH_3)_2$, —$CH_2CF_2C(CH_3)_2OH$, —$CH_2C(CH_3)_2F$, —$CH_2CH_2OH$, —$CH(CH_3)CH_2OH$, —$CH_2$(cyclopropyl), —$CH_2$(cyclopropyl), —$CH$(cyclopropyl)$_2$, —$CH_2CH_2$(cyclopropyl), cyclopropyl, cyclobutyl,

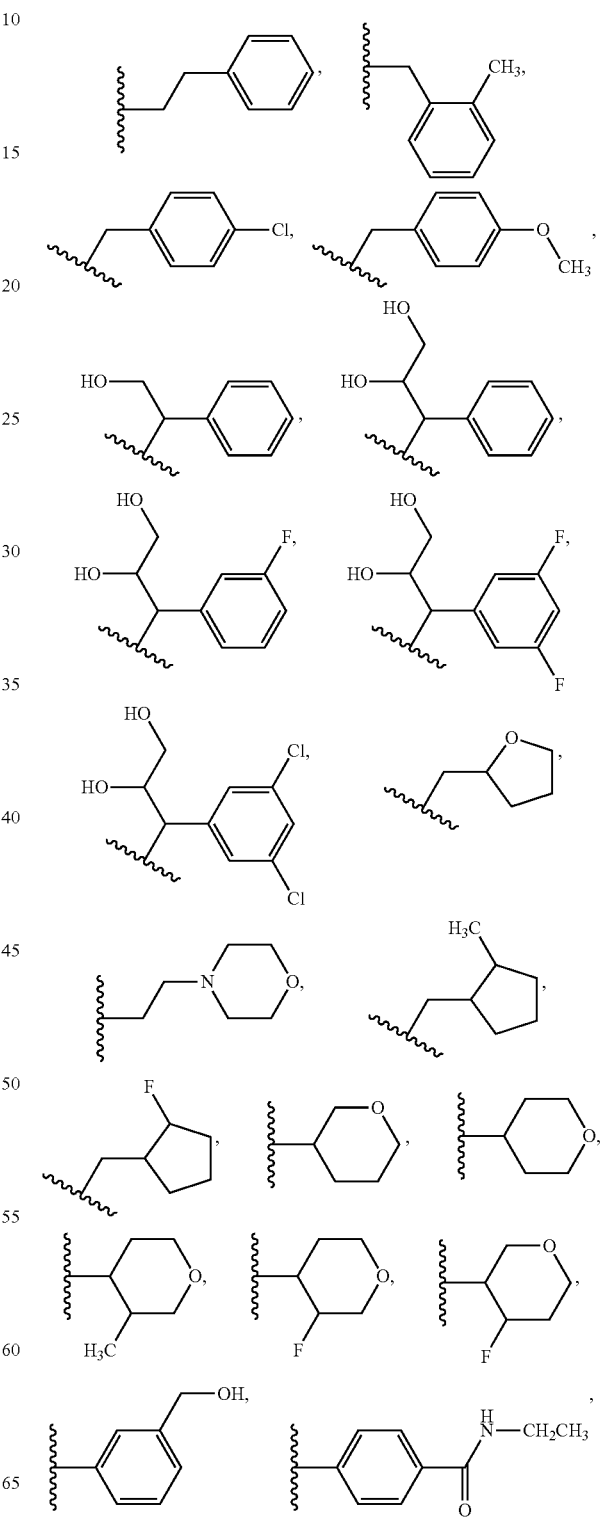

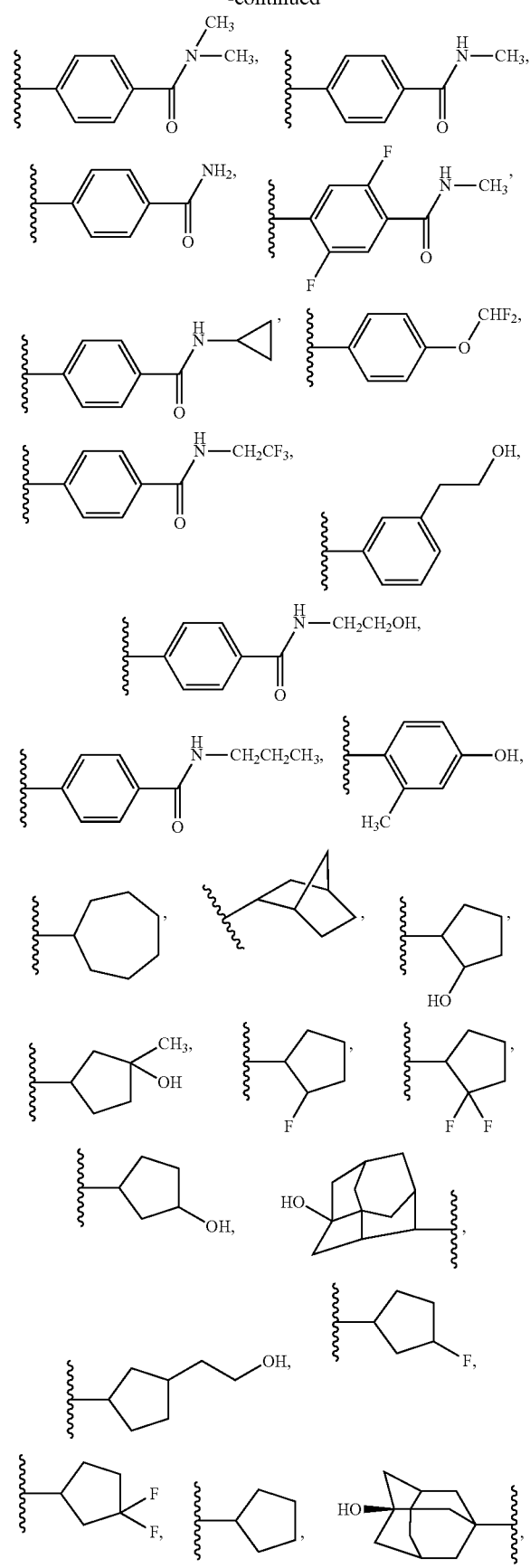

In another embodiment, there is provided a compound of Formula (II) or a stereoisomer or pharmaceutically-acceptable salt thereof, wherein:

$R^1$ is:

(a) $C_{2-3}$ hydroxyalkyl substituted with zero to 4 $R^{1a}$ wherein $R^{1a}$ is independently selected from F, Cl, —OH, —CHF$_2$, —CN, —CF$_3$, —OCH$_3$, and cyclopropyl;

(b) $C_{4-8}$ alkyl substituted with zero to 7 $R^{1a}$ wherein $R^{1a}$ is independently selected from F, Cl, —OH, —CHF$_2$, —CF$_3$, —CN—OCH$_3$, and cyclopropyl;

(c) —(CH$_2$)$_{2-4}$NHC(O)(C$_{1-6}$ alkyl), —(CH$_2$)$_2$CH(CH$_3$)NHC(O)(C$_{1-6}$ alkyl), —(CH$_2$)$_2$CH(CH$_3$)NHC(O)O(C$_{1-6}$ alkyl), —(CH$_2$)$_2$CH(CH$_3$)NHC(O)(CH$_2$)$_{0-1}$NH(C$_{1-6}$ alkyl), —(CH$_2$)$_2$CH(CH$_3$)NHC(O)(CH$_2$)$_{0-1}$N(C$_{1-4}$ alkyl)$_2$, —(CH$_2$)$_2$CH(CH$_3$)NHC(O)(CH$_2$)$_{0-1}$(C$_{3-6}$ cycloalkyl), —(CH$_2$)$_2$CH(CH$_3$)NHC(O)(CH$_2$)$_{0-1}$(C$_{3-6}$ fluorocycloalkyl), —(CH$_2$)$_2$CH(CH$_3$)NHC(O)(C$_{1-6}$ hydroxyalkyl), —(CH$_2$)$_2$CH(CH$_3$)NHC(O)N(C$_{1-3}$ alkyl)(phenyl), or —(CH$_2$)$_2$CH(CH$_3$)NHC(O)(CH$_2$)$_{04}$R wherein R is phenyl, morpholinyl, pyrrolidinyl, triazolyl, or tetrahydropyranyl;

(d) cyclohexyl substituted with zero to 2 substituents selected from —OH, —OCH$_3$, =O, —NH$_2$, C$_{1-6}$ alkyl, C$_{1-6}$ hydroxyalkyl, —NHS(O)$_2$CH$_3$, —NO$_2$, —C(O)NH$_2$, —C(O)NH(C$_{1-3}$ alkyl), —C(O)NH(C$_{1-6}$ hydroxyalkyl), —C(O)NH(C$_{3-6}$ cycloalkyl), —C(O)NH(C$_{3-6}$ cyano cycloalkyl), —NHC(O)(C$_{1-3}$ alkyl), —NHC(O)(pyridinyl), —NHC(O)(morpholinyl), —NHC(O)(hydroxy bicyclo [2.2.1]heptanyl), —NHC(O)NH(C$_{1-4}$ alkyl), and methyl pyrazolyl;

(e) —(CH$_2$)$_2$(phenyl) wherein said phenyl is substituted with —C(O)NH$_2$, —C(O)NH(C$_{1-3}$ alkyl), or —S(O)$_2$NH$_2$; or

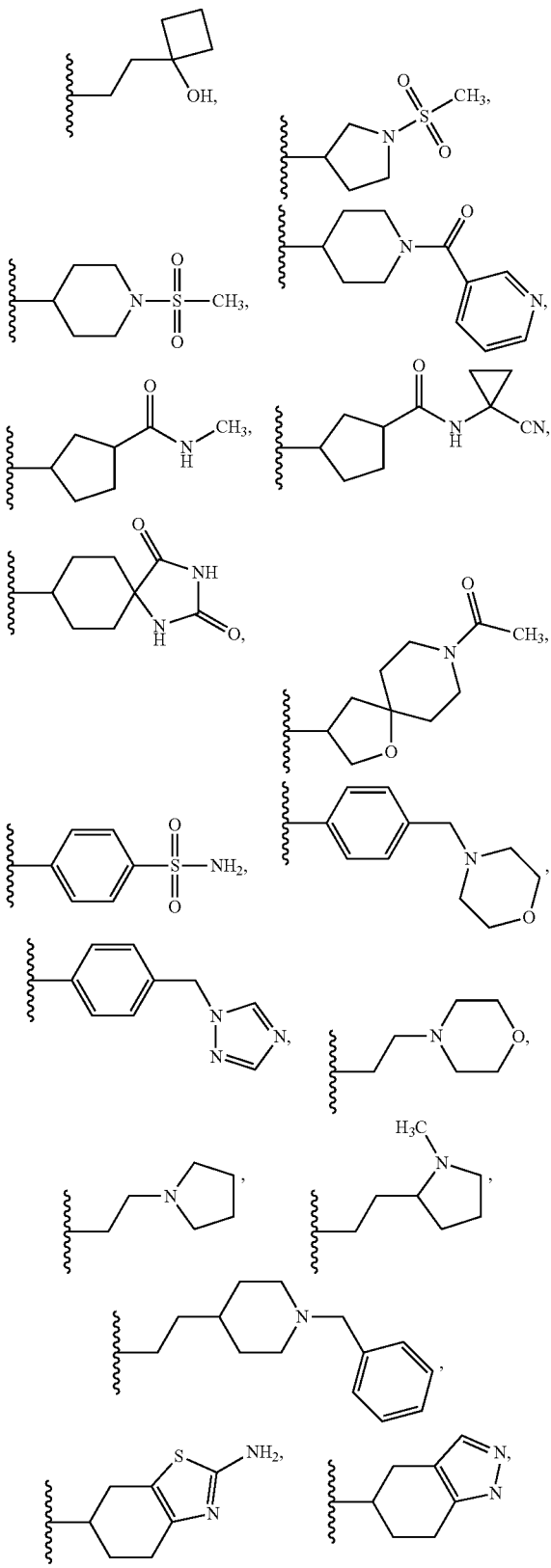

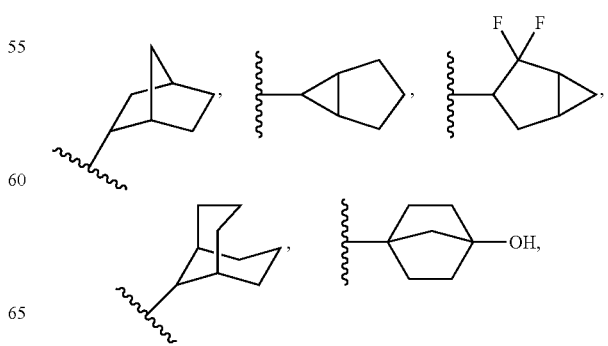

R$^2$ is benzooxazolyl, pyrazolopyridinyl, pyrrolopyridinyl, benzothiazolyl, thiazolopyridinyl, pyrazolopyrimidinyl, benzooxadiazolyl, benzothiadiazolyl, quinolinyl, cinnolinyl, quinazolinyl, quinoxalinyl, 1,5-naphthyrindinyl, pyridopyrazinyl, or pyridopyrimidinyl, each substituted with zero to 2 substituents independently selected from F, Cl, —CH$_3$, —CN, —NH$_2$, —OCH$_3$, =O, and —C(O)NH$_2$;

R$^3$ is:

(a) C$_{2-6}$ alkyl or C$_{2-6}$ fluoroalkyl;

(b) C$_{1-3}$ alkyl substituted with 1 to 2 cyclopropyl;

(c) C$_{1-3}$ alkyl substituted with phenyl, tetrahydrofuranyl, or morpholinyl;

(d) C$_{2-6}$ hydroxyalkyl substituted with zero to 3 substituents selected from F, phenyl, fluorophenyl, difluorophenyl, and dichlorophenyl;

(e) —(CH$_2$)$_{0-2}$(C$_{3-7}$ cycloalkyl) substituted with zero to 2 substituents selected from F, —OH, C$_{1-3}$ hydroxyalkyl, —CH$_3$, —CF$_2$H, —NH$_2$, and —C(O)OCH$_2$CH$_3$;

(f) tetrahydropyranyl or tetrahydrothiopyranyl substituted with zero to 1 substituent selected from F and —CH$_3$;

(g) —(CH$_2$)$_{0-2}$phenyl wherein said phenyl is substituted with zero to 2 substituents selected from F, Cl, C$_{1-3}$ alkyl, C$_{1-3}$ hydroxyalkyl, —OH, —O(C$_{1-3}$ alkyl), —OCF$_3$, —C(O)NH$_2$, —C(O)NH(C$_{1-3}$ alkyl), —C(O)NH(C$_{1-3}$ fluoroalkyl), —C(O)NH(C$_{1-3}$ hydroxyalkyl), —C(O)NH(C$_{3-5}$ cycloalkyl), —C(O)N(C$_{1-3}$ alkyl)$_2$, —S(O)$_2$CH$_3$, and pyrazolyl;

(h) thiazolyl substituted with zero to 2 substituents selected from C$_{1-3}$ hydroxyalkyl; or -continued

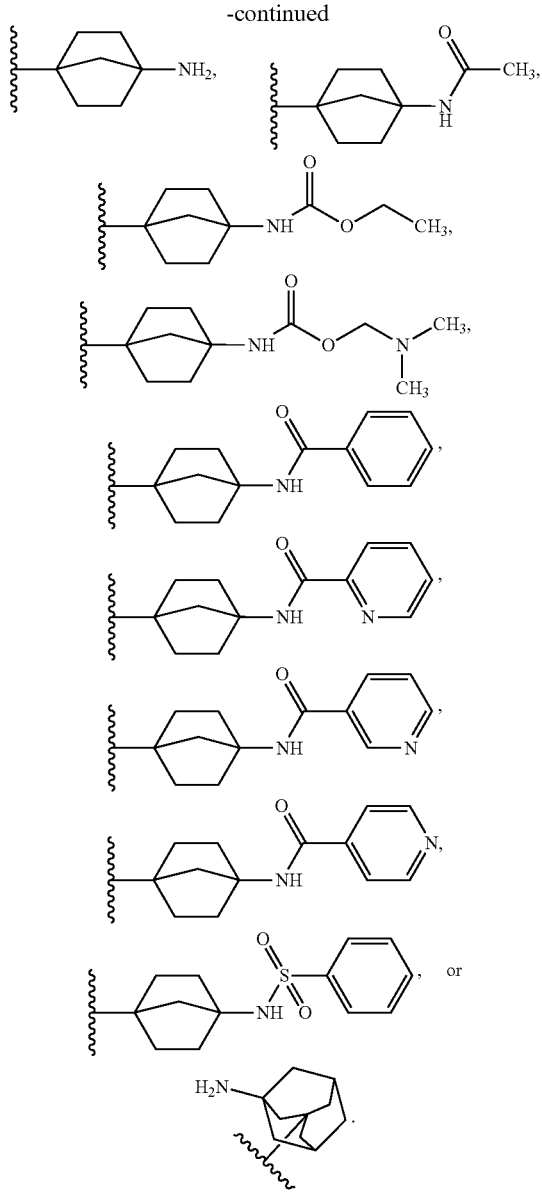

In another embodiment, there is provided a compound of Formula (II) or a stereoisomer or pharmaceutically-acceptable salt thereof, wherein:

$R^1$ is:

(a) hydroxypropyl substituted with zero to 3 $R^{1a}$ wherein $R^{1a}$ is independently selected from F, —CF$_3$, and cyclopropyl;

(b) $C_{4-8}$ alkyl substituted with zero to 5 $R^{1a}$ wherein $R^{1a}$ is independently selected from F, Cl, —OH, —CHF$_2$, —CF$_3$, —CN—OCH$_3$, and cyclopropyl;

(c) —(CH$_2$)$_{2-4}$NHC(O)(C$_{1-3}$ alkyl), —(CH$_2$)$_2$CH(CH$_3$) NHC(O)(C$_{1-3}$ alkyl), —(CH$_2$)$_2$CH(CH$_3$)NHC(O)O(C$_{1-3}$ alkyl), —(CH$_2$)$_2$CH(CH$_3$)NHC(O)(CH$_2$)$_{0-1}$NH(C$_{1-3}$ alkyl), —(CH$_2$)$_2$CH(CH$_3$)NHC(O)(CH$_2$)$_{0-1}$N(C$_{1-3}$ alkyl)$_2$, —(CH$_2$)$_2$CH(CH$_3$)NHC(O)(CH$_2$)$_{0-1}$(C$_{3-6}$ cycloalkyl), —(CH$_2$)$_2$CH(CH$_3$)NHC(O)(CH$_2$)$_{0-1}$(C$_{3-6}$ fluorocycloalkyl), —(CH$_2$)$_2$CH(CH$_3$)NHC(O)(C$_{1-6}$ hydroxyalkyl), —(CH$_2$)$_2$CH(CH$_3$)NHC(O)N(CH$_3$)(phenyl), or —(CH$_2$)$_2$CH(CH$_3$) NHC(O)(CH$_2$)$_{04}$R wherein R is phenyl, morpholinyl, pyrrolidinyl, triazolyl, or tetrahydropyranyl;

(d) cyclohexyl substituted with zero or 2 substituents selected from —OH, —OCH$_3$, =O, —NH$_2$, C$_{1-3}$ alkyl, C$_{1-3}$ hydroxyalkyl, —NHS(O)$_2$CH$_3$, —NO$_2$, —C(O)NH$_2$, —C(O)NH(C$_{1-2}$ alkyl), —C(O)NH(C$_{1-4}$ hydroxyalkyl), —C(O)NH(C$_{3-6}$ cycloalkyl), —C(O)NH(C$_{3-4}$ cyano cycloalkyl), —NHC(O)(C$_{1-3}$ alkyl), —NHC(O)(pyridinyl), —NHC(O)(morpholinyl), —NHC(O)(hydroxy bicyclo [2.2.1]heptanyl), —NHC(O)NH(C$_{1-4}$ alkyl), and methyl pyrazolyl;

(e) —(CH$_2$)$_2$(phenyl) wherein said phenyl is substituted with —C(O)NH$_2$, —C(O)NH(C$_{1-3}$ alkyl), or —S(O)$_2$NH$_2$; or —CH$_2$(phenyl); or

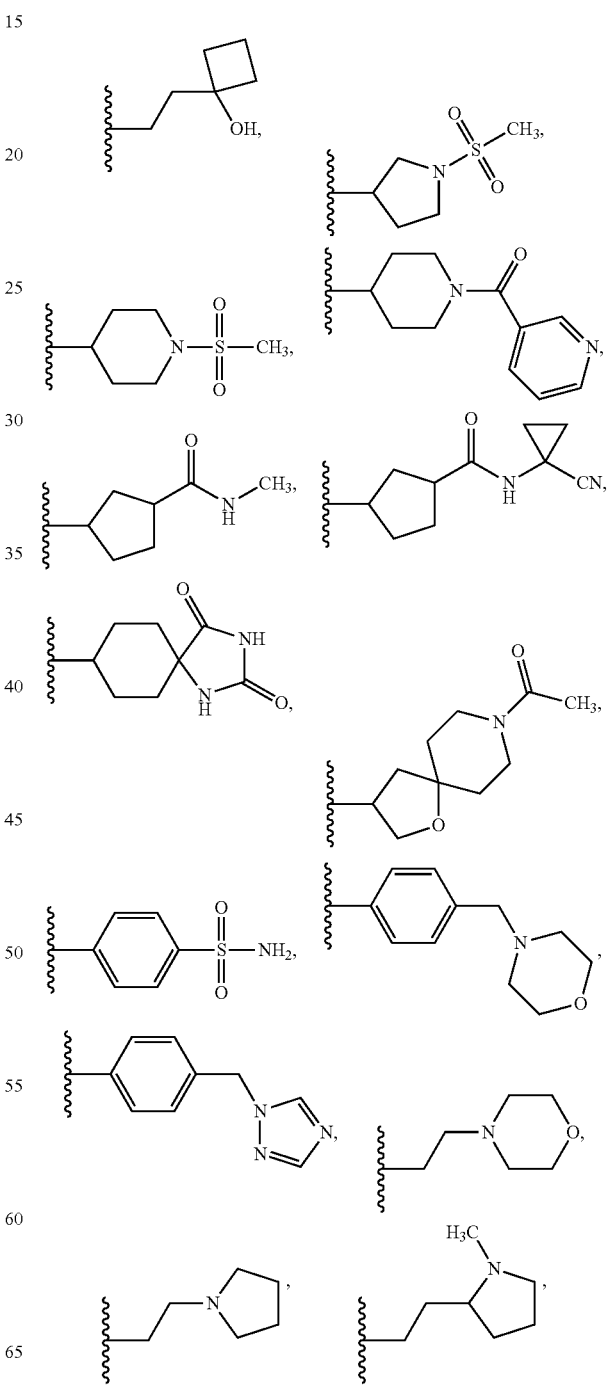

-continued

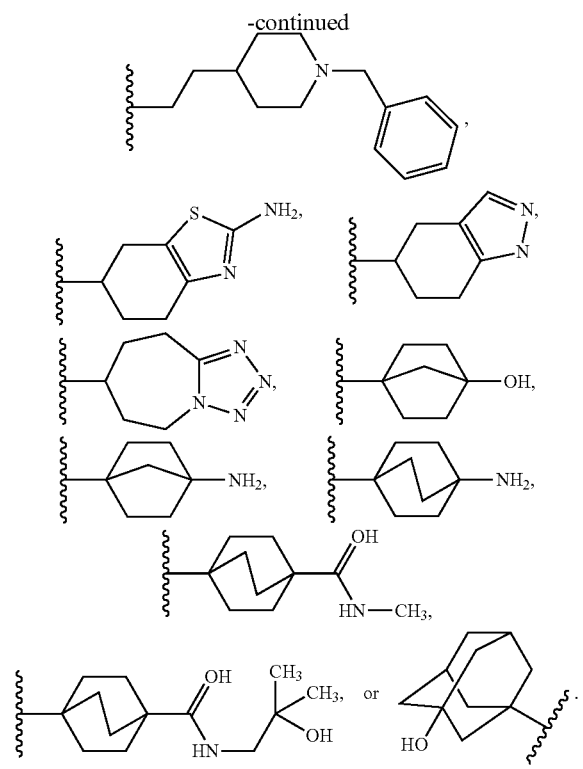

In another embodiment, there is provided a compound of formula (II) or a stereoisomer or pharmaceutically-acceptable salt thereof, wherein:

$R^1$ is: —$CH_2CH_2CH(CH_3)_2$, —$(CH_2)_2C(CH_3)_2OH$, —$CH_2CHFCH_2OH$, —$CH_2CHFCH(CH(CH_3)_2)OH$, —$CH_2CHFCH(cyclopropyl)OH$, —$CH_2CHFCH(CH_3)OH$, —$CH_2CHFCH(cyclopropyl)(CF_3)OH$, —$CH_2CHFC(CH_3)_2OH$, —$CH_2CHFC(CH_3)(CH_2CH_3)OH$, —$CH_2CHFC(CH_2CH_3)_2OH$, —$CH_2CHFC(CH_3)(CF_3)OH$, —$CH_2CF_2C(CH_3)_2OH$, —$(CH_2)_2NHC(O)CH_3$, —$(CH_2)_3NHC(O)CH_3$, —$(CH_2)_4NHC(O)CH_3$, —$(CH_2)_2CH(CH_3)NHC(O)CH_3$, —$(CH_2)_2CH(CH_3)NHC(O)OCH(CH_3)_2$, —$(CH_2)_2CH(CH_3)NHC(O)OC(CH_3)_3$, —$(CH_2)_2CH(CH_3)NHC(O)CH_2N(CH_3)_2$, —$(CH_2)_2CH(CH_3)NHC(O)NHCH(CH_3)_2$, —$(CH_2)_2CH(CH_3)NHC(O)(cyclopropyl)$, —$(CH_2)_2CH(CH_3)NHC(O)(3\text{-fluorocyclopentyl})$, —$(CH_2)_2CH(CH_3)NHC(O)(3,3\text{-difluorocyclopentyl})$, —$(CH_2)_2CH(CH_3)NHC(O)(morpholinyl)$, —$(CH_2)_2CH(CH_3)NHC(O)(phenyl)$, —$(CH_2)_2CH(CH_3)NHC(O)(pyrrolidinyl)$, —$(CH_2)_2CH(CH_3)NHC(O)CH_2(tetrahydropyranyl)$, —$(CH_2)_2CH(CH_3)NHC(O)CH_2(2,2\text{-difluorocyclohexyl})$, —$(CH_2)_2CH(CH_3)NHC(O)CH_2(triazolyl)$, —$(CH_2)_2CH(CH_3)NHC(O)(CH_2)_3C(CH_3)_2OH$, —$(CH_2)_2CH(CH_3)NHC(O)(CH_2)_4C(CH_3)_2OH$, —$(CH_2)_2CH(CH_3)NHC(O)N(CH_3)(phenyl)$,

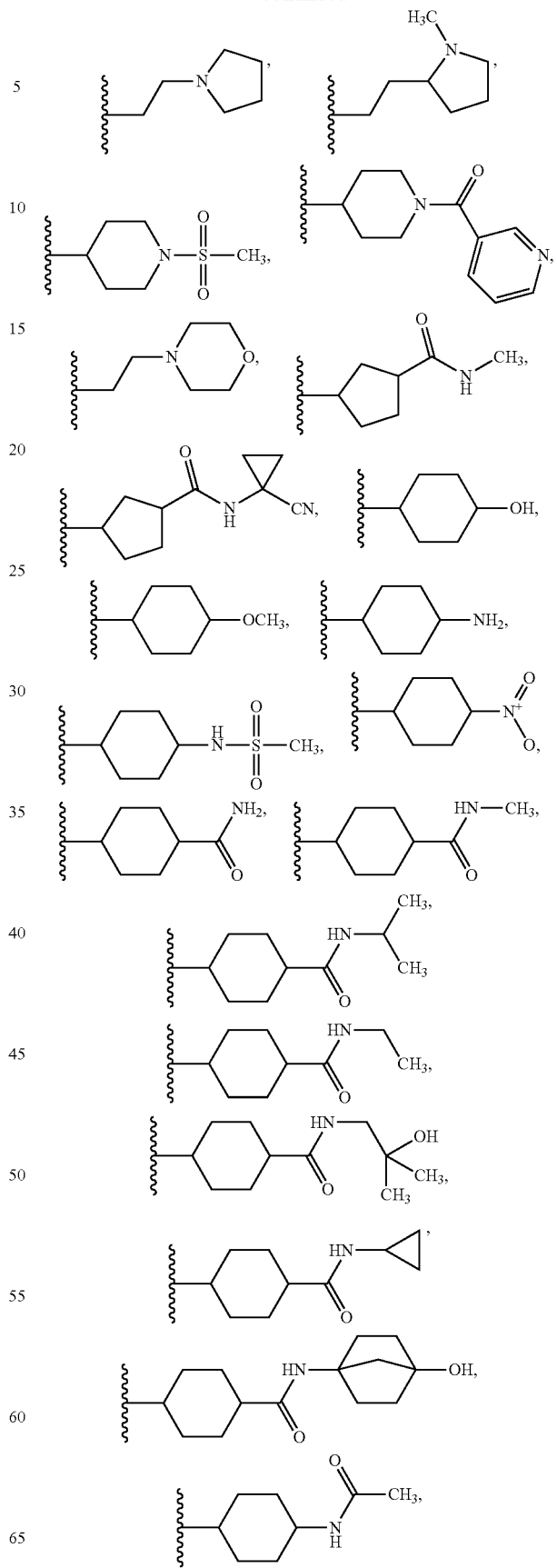

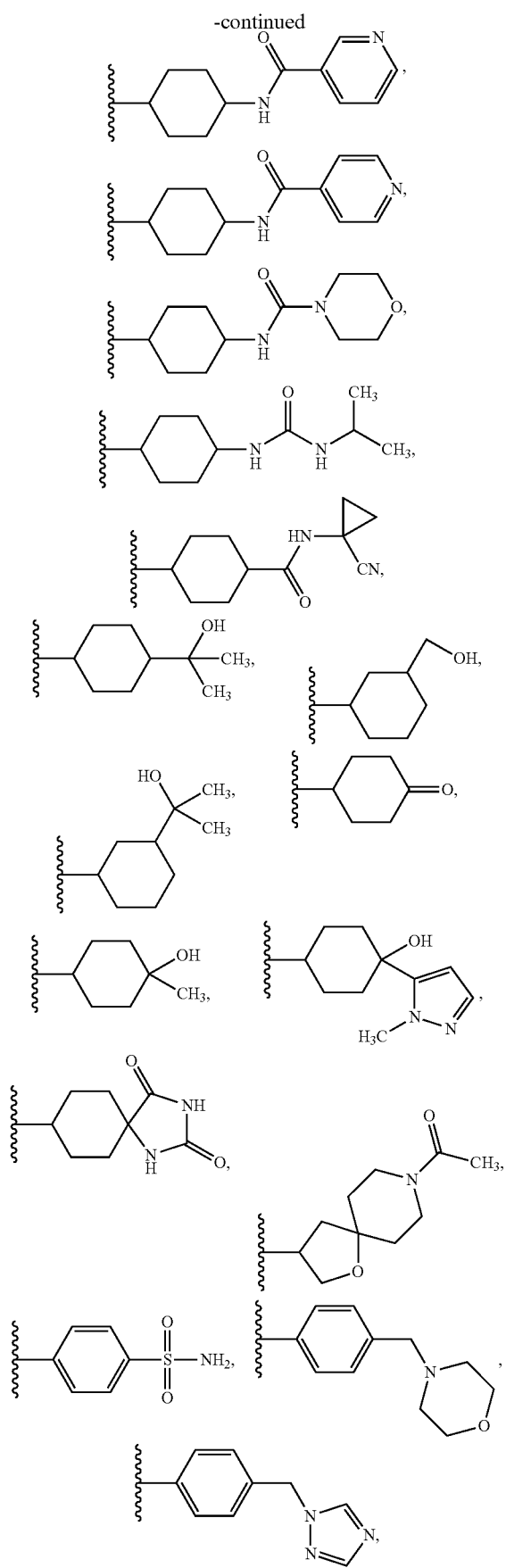
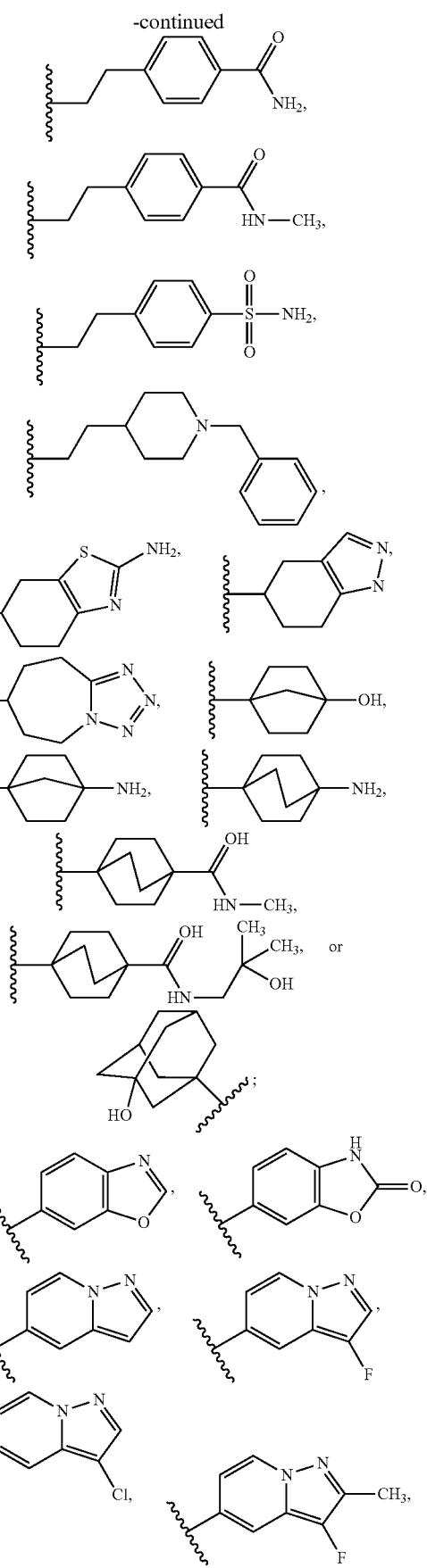
R² is:

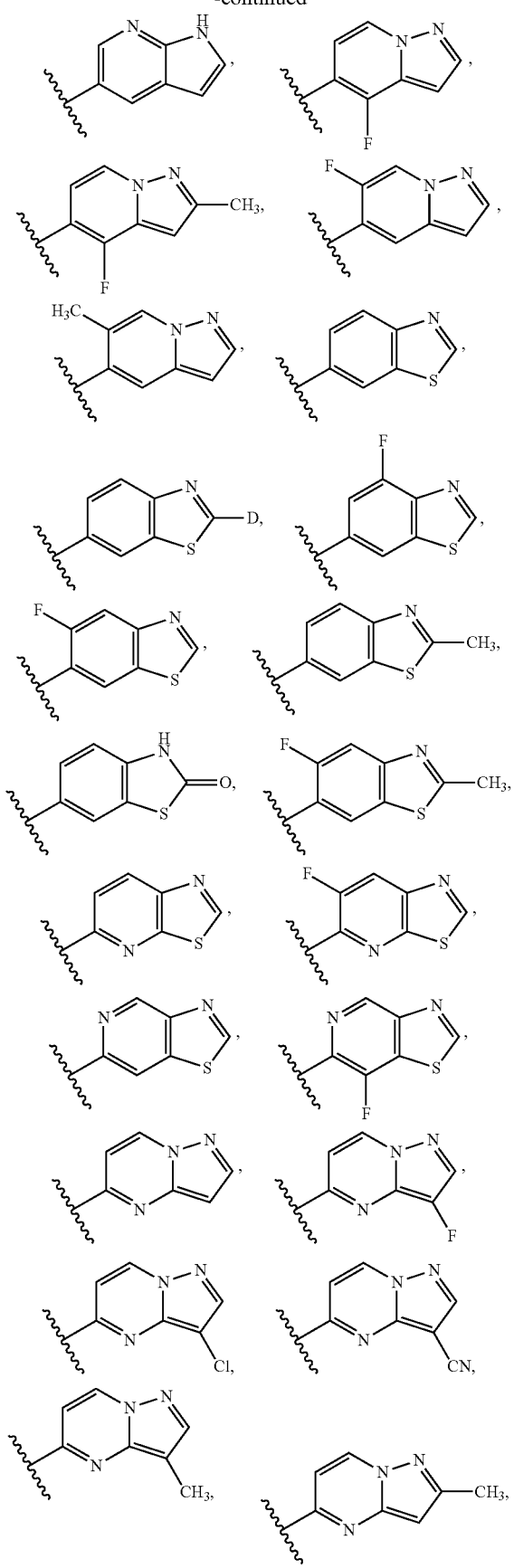
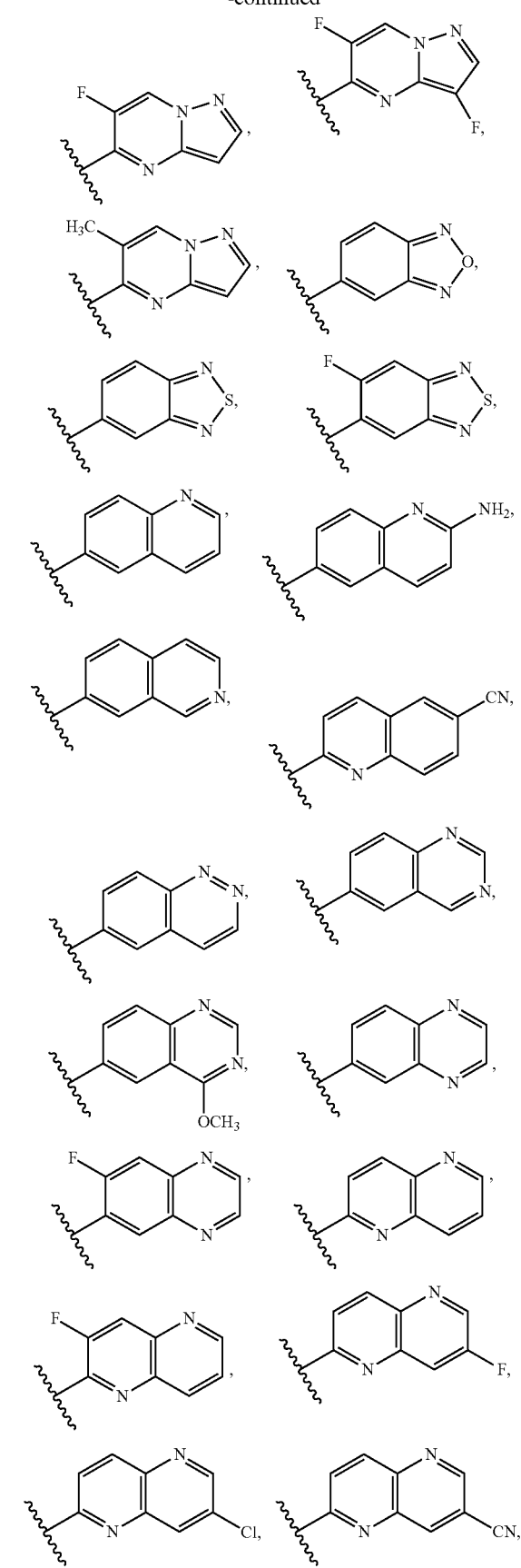

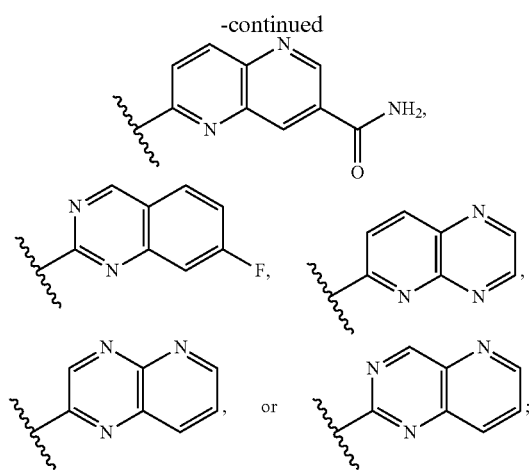

and

R[3] is: $C_{2-5}$ alkyl, —CH$_2$CHF$_2$, —CH$_2$CF$_3$, —CH$_2$CHFCH$_3$, —CH$_2$CF$_2$CH$_3$, —CH(CH$_3$)CF$_3$, CH$_2$CF(CH$_3$)$_2$, —CH(CH$_3$)CH$_2$CH$_2$F, —CH(CH$_3$)(cyclopropyl), —CH(cyclopropyl)$_2$, —CH$_2$(cyclopropyl), —CH$_2$(tetrahydrofuranyl), —CH$_2$CH$_2$OH, —CH(CH$_3$)CH$_2$OH, —(CH$_2$)$_2$(cyclopropyl), $C_{3-7}$ cycloalkyl, tetrahydropyranyl, tetrahydrothiopyranyl, —CH(CH$_3$)CH$_2$OH, —CH(phenyl)CH$_2$OH, —CH$_2$CF$_2$C(CH$_3$)$_2$OH, —CH(phenyl)CH(OH)CH$_2$OH, —CH(3-fluorophenyl)CH(OH)CH$_2$OH, —CH(3,5-difluorophenyl)CH(OH)CH$_2$OH, —CH(2,5-difluorophenyl)CH(OH)CH$_2$OH, —CH(3,5-dichlorophenyl)CH(OH)CH$_2$OH, —(CH$_2$)$_2$(morpholinyl), —(CH$_2$)$_2$(phenyl),

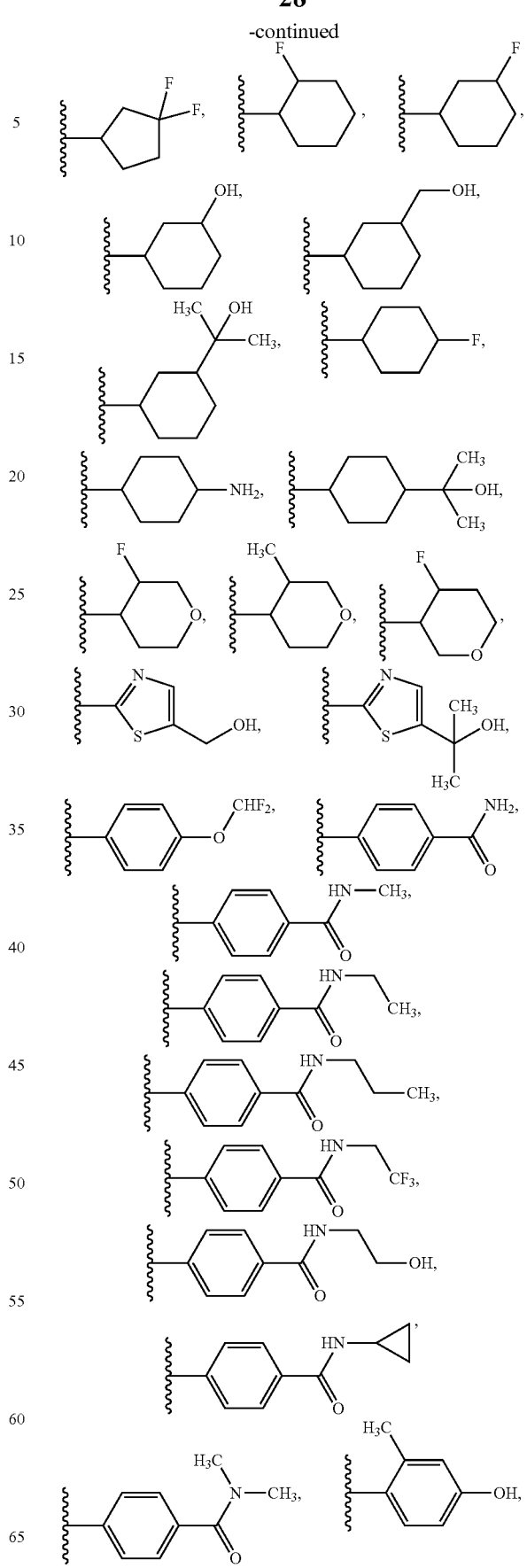

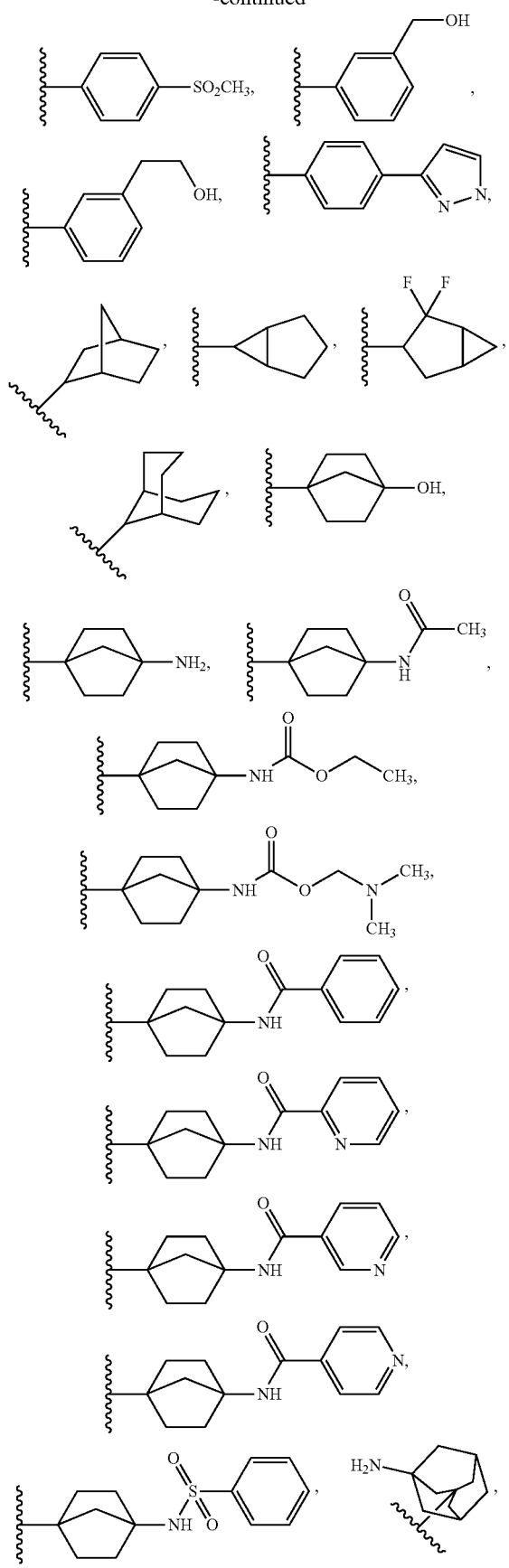

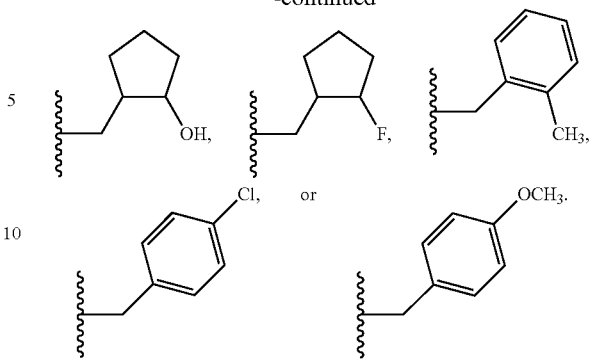

In another embodiment, there is provided a compound of formula (II) or a stereoisomer or pharmaceutically-acceptable salt thereof, wherein $R^1$ is —$CH_2CH_2CH(CH_3)_2$, —$(CH_2)_2C(CH_3)_2OH$, —$CH_2CHFCH_2OH$, —$CH_2CHFCH(CH(CH_3)_2)OH$, —$CH_2CHFCH(cyclopropyl)OH$, —$CH_2CHFCH(CH_3)OH$, —$CH_2CHFC(CH_3)_2OH$, —$CH_2CHFCH(cyclopropyl)(CF_3)OH$, —$CH_2CHFC(CH_3)(CH_2CH_3)OH$, —$CH_2CHFC(CH_2CH_3)_2OH$, —$CH_2CHFC(CH_3)(CF_3)OH$, —$CH_2CF_2C(CH_3)_2OH$, —$(CH_2)_2NHC(O)CH_3$, —$(CH_2)_3NHC(O)CH_3$, —$(CH_2)_4NHC(O)CH_3$, —$(CH_2)_2CH(CH_3)NHC(O)CH_3$, —$(CH_2)_2CH(CH_3)NHC(O)OCH(CH_3)_2$, —$(CH_2)_2CH(CH_3)NHC(O)OC(CH_3)_3$, —$(CH_2)_2CH(CH_3)NHC(O)CH_2N(CH_3)_2$, —$(CH_2)_2CH(CH_3)NHC(O)NHCH(CH_3)_2$, —$(CH_2)_2CH(CH_3)NHC(O)(cyclopropyl)$, —$(CH_2)_2CH(CH_3)NHC(O)(3-fluorocyclopentyl)$, —$(CH_2)_2CH(CH_3)NHC(O)(3,3-difluorocyclopentyl)$, —$(CH_2)_2CH(CH_3)NHC(O)(morpholinyl)$, —$(CH_2)_2CH(CH_3)NHC(O)(phenyl)$, —$(CH_2)_2CH(CH_3)NHC(O)(pyrrolidinyl)$, —$(CH_2)_2CH(CH_3)NHC(O)CH_2(tetrahydropyranyl)$, —$(CH_2)_2CH(CH_3)NHC(O)CH_2(2,2-difluorocyclohexyl)$, —$(CH_2)_2CH(CH_3)NHC(O)CH_2(triazolyl)$, —$(CH_2)_2CH(CH_3)NHC(O)(CH_2)_3C(CH_3)_2OH$, —$(CH_2)_2CH(CH_3)NHC(O)(CH_2)_4C(CH_3)_2OH$, or —$(CH_2)_2CH(CH_3)NHC(O)N(CH_3)(phenyl)$. Included in this embodiment are compounds of formula (II) in which $R^3$ is:

(a) $C_{2-6}$ alkyl or $C_{2-6}$ fluoroalkyl;
(b) $C_{1-3}$ alkyl substituted with 1 to 2 cyclopropyl;
(c) $C_{1-3}$ alkyl substituted with phenyl, tetrahydrofuranyl, or morpholinyl;
(d) $C_{2-6}$ hydroxyalkyl substituted with zero to 3 substituents selected from F, phenyl, fluorophenyl, difluorophenyl, and dichlorophenyl; or
(e) —$(CH_2)_{0-2}(C_{3-6}$ cycloalkyl) substituted with zero to 2 substituents selected from F, —OH, $C_{1-3}$ hydroxyalkyl, —$CH_3$, —$CF_2H$, —$NH_2$, and —$C(O)OCH_2CH_3$.

In another embodiment, there is provided a compound of formula (II) or a stereoisomer or pharmaceutically-acceptable salt thereof, wherein $R^1$ is:

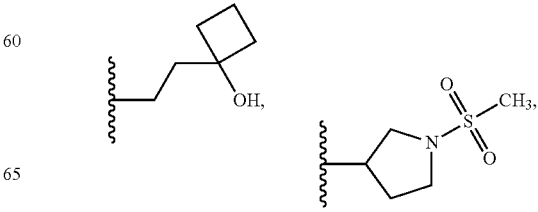

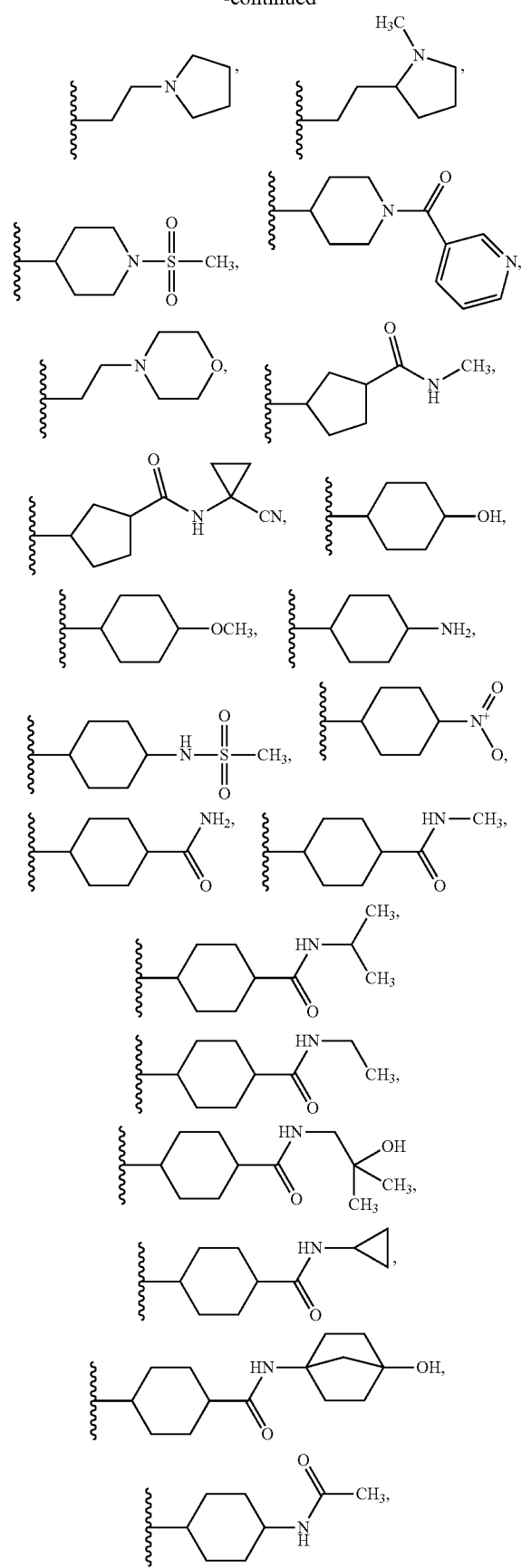
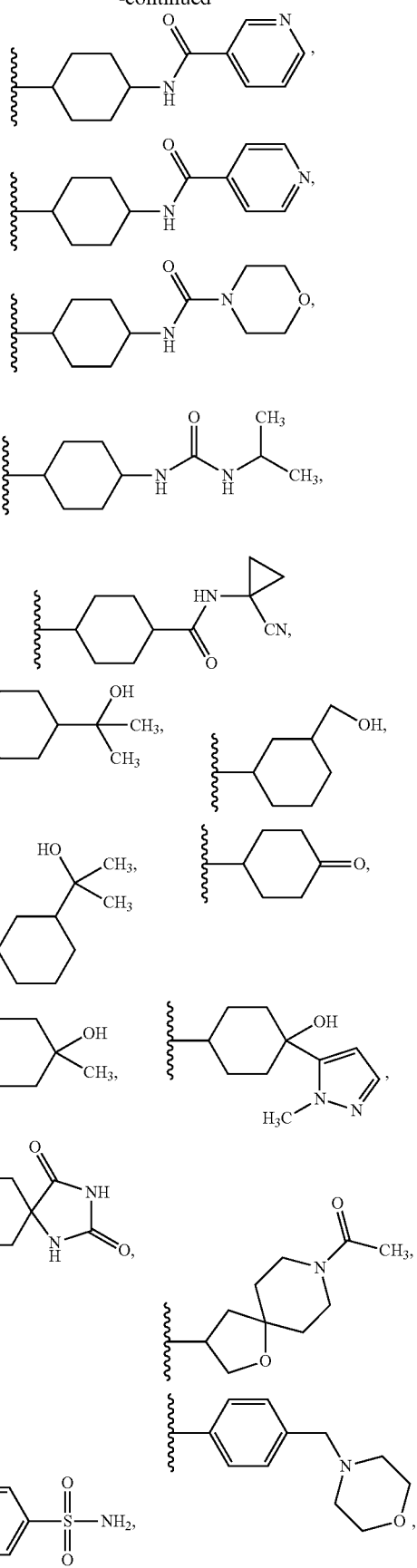

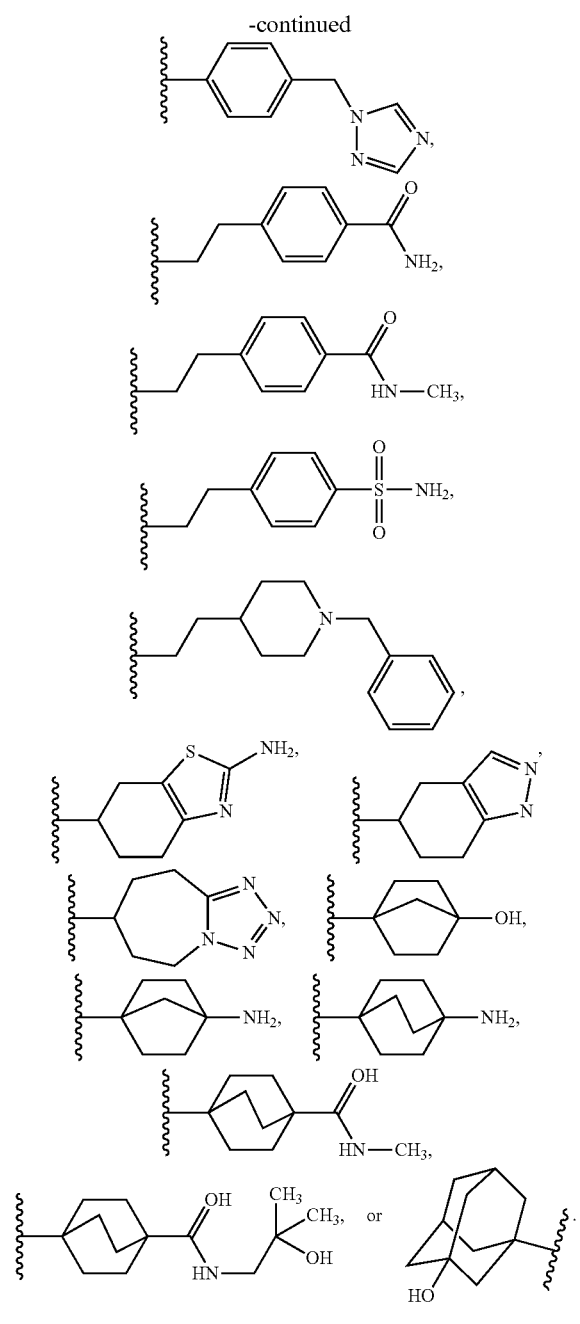
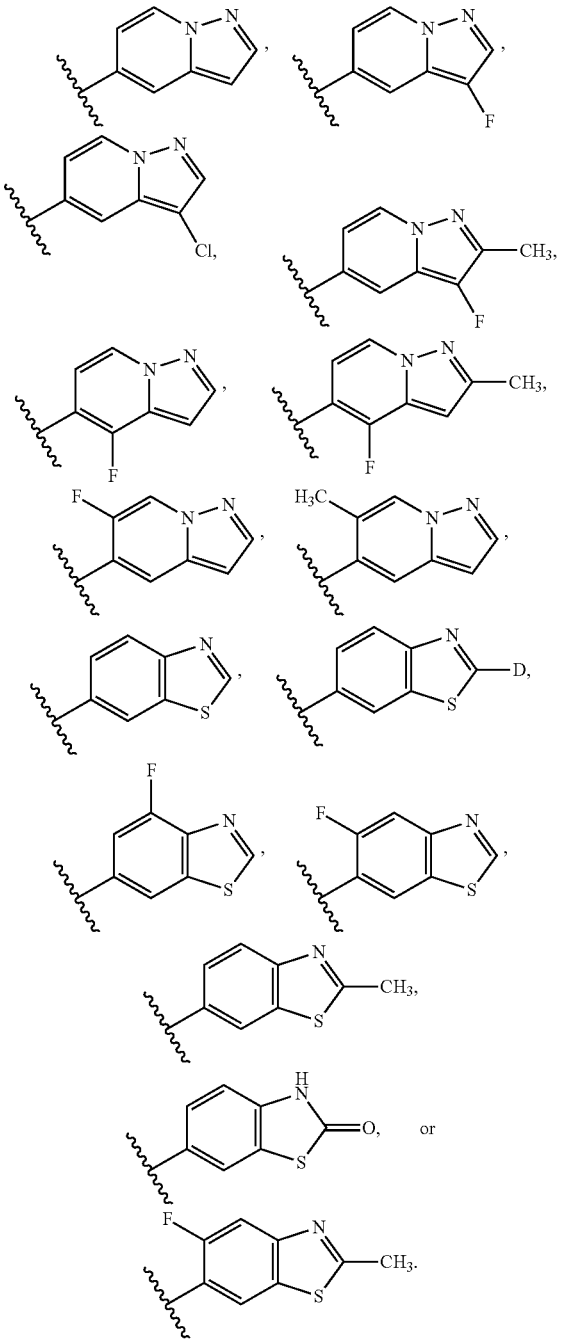

Included in this embodiment are compounds of formula (II) in which $R^3$ is:

(a) $C_{2-6}$ alkyl or $C_{2-6}$ fluoroalkyl;
(b) $C_{1-3}$ alkyl substituted with 1 to 2 cyclopropyl;
(c) $C_{1-3}$ alkyl substituted with phenyl, tetrahydrofuranyl, or morpholinyl;
(d) $C_{2-6}$ hydroxyalkyl substituted with zero to 3 substituents selected from F, phenyl, fluorophenyl, difluorophenyl, and dichlorophenyl; or
(e) —$(CH_2)_{0-2}(C_{3-6}$ cycloalkyl) substituted with zero to 2 substituents selected from F, —OH, $C_{1-3}$ hydroxyalkyl, —$CH_3$, —$CF_2H$, —$NH_2$, and —$C(O)OCH_2CH_3$.

In another embodiment, there is provided a compound of formula (II) or a stereoisomer or pharmaceutically-acceptable salt thereof, wherein $R^2$ is:

Included in this embodiment are compounds of formula (II) in which $R^3$ is:

(a) $C_{2-6}$ alkyl or $C_{2-6}$ fluoroalkyl;
(b) $C_{1-3}$ alkyl substituted with 1 to 2 cyclopropyl;
(c) $C_{1-3}$ alkyl substituted with phenyl, tetrahydrofuranyl, or morpholinyl;
(d) $C_{2-6}$ hydroxyalkyl substituted with zero to 3 substituents selected from F, phenyl, fluorophenyl, difluorophenyl, and dichlorophenyl; or
(e) —$(CH_2)_{0-2}(C_{3-6}$ cycloalkyl) substituted with zero to 2 substituents selected from F, —OH, $C_{1-3}$ hydroxyalkyl, —$CH_3$, —$CF_2H$, —$NH_2$, and —$C(O)OCH_2CH_3$.

In another embodiment, there is provided a compound of formula (II) or a stereoisomer or pharmaceutically-acceptable salt thereof, wherein $R^2$ is:

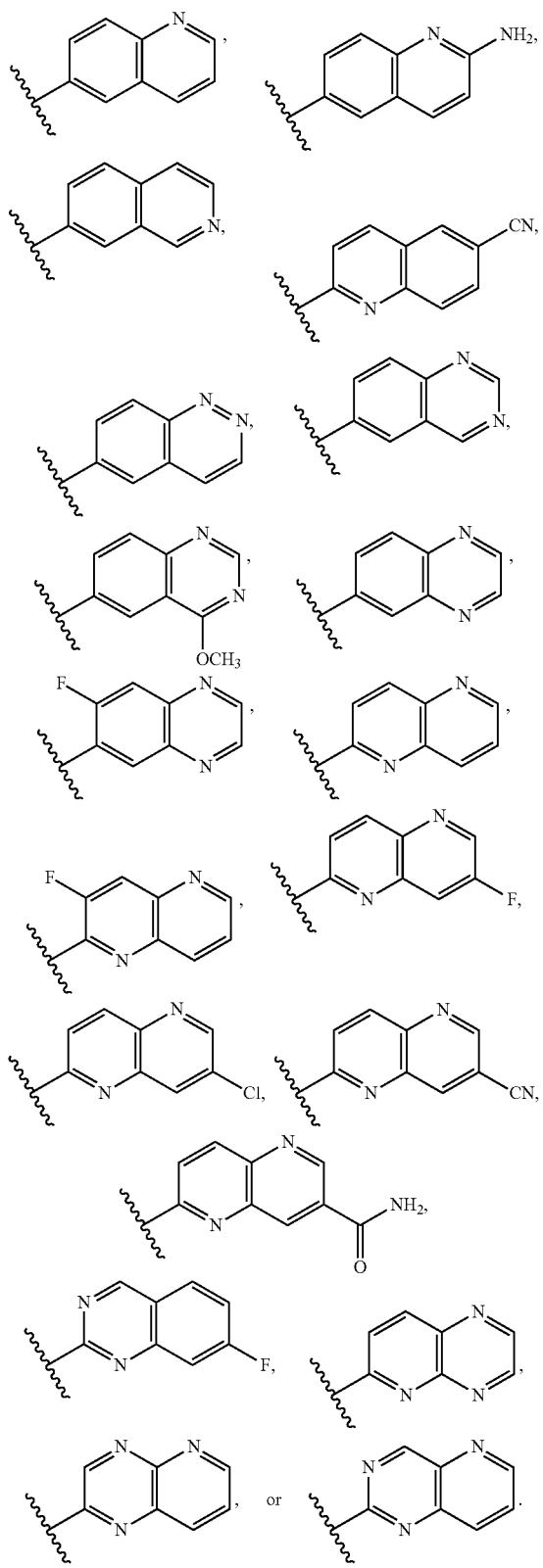

In another embodiment, there is provided a compound of formula (II) or a stereoisomer or pharmaceutically-acceptable salt thereof, wherein $R^3$ is:

(a) $C_{2-6}$ alkyl or $C_{2-6}$ fluoroalkyl;
(b) $C_{1-3}$ alkyl substituted with 1 to 2 cyclopropyl;
(c) $C_{1-3}$ alkyl substituted with phenyl, tetrahydrofuranyl, or morpholinyl;
(d) $C_{2-6}$ hydroxyalkyl substituted with zero to 3 substituents selected from F, phenyl, fluorophenyl, difluorophenyl, and dichlorophenyl; or
(e) $-(CH_2)_{0-2}(C_{3-6}$ cycloalkyl) substituted with zero to 2 substituents selected from F, $-OH$, $C_{1-3}$ hydroxyalkyl, $-CH_3$, $-CF_2H$, $-NH_2$, and $-C(O)OCH_2CH_3$.

In one embodiment, a compound of Formula (II) or a stereoisomer or pharmaceutically-acceptable salt thereof, is provided wherein said compound is selected from Examples 5-20, 22-59, 61-142, 149-259, 261-374, and 379-527.

In another embodiment, there is provided a pharmaceutical composition comprising one or more compounds of formula (I) and a pharmaceutically acceptable carrier or diluent.

The present invention is also directed to pharmaceutical compositions useful in treating diseases associated with kinase modulation, including modulation (especially inhibition) of IRAK-4, comprising compounds of formula (I), or pharmaceutically-acceptable salts thereof, and pharmaceutically-acceptable carriers or diluents.

The invention further relates to methods of treating diseases associated with the kinase modulation, including the modulation of IRAK-4, comprising administering to a patient in need of such treatment a therapeutically-effective amount of a compound according to formula (I).

The present invention also provides processes and intermediates for making the compounds of the present invention or stereoisomers, tautomers, pharmaceutically acceptable salts, solvates, or prodrugs thereof The present invention also provides a method for treating proliferative, metabolic, allergic, autoimmune and inflammatory diseases (or use of the compounds of the present invention or stereoisomers, tautomers, pharmaceutically acceptable salts, solvates, or prodrugs thereof, for the manufacture of a medicament for the treatment of these diseases), comprising administering to a host in need of such treatment a therapeutically effective amount of at least one of the compounds of the present invention or stereoisomers, tautomers, pharmaceutically acceptable salts, solvates, or prodrugs thereof The present invention also provides a method for treating a disease (or use of the compounds of the present invention or stereoisomers, tautomers, pharmaceutically acceptable salts, solvates, or prodrugs thereof, for the manufacture of a medicament for the treatment of these diseases), comprising administering to a patient in need of such treatment a therapeutically-effective amount of a compound of Formula (I), wherein the disease is Crohn's disease, ulcerative colitis, asthma, graft versus host disease, allograft rejection, chronic obstructive pulmonary disease; Graves' disease, rheumatoid arthritis, systemic lupus erythematosis, psoriasis; CAPS, TRAPS, FMF, adult onset stills, systemic onset juvenile idiopathic arthritis, multiple sclerosis, neuropathic pain, gout, and gouty arthritis.

The present invention also provides a method of treating an inflammatory or autoimmune disease (or use of the compounds of the present invention or stereoisomers, tautomers, pharmaceutically acceptable salts, solvates, or prodrugs thereof, for the manufacture of a medicament for the treatment of these diseases) comprising administering to a patient in need of such treatment a therapeutically-effective amount of a compound according to Formula (I).

The present invention also provides a method of treating an inflammatory or autoimmune disease (or use of the compounds of the present invention or stereoisomers, tautomers, pharmaceutically acceptable salts, solvates, or prodrugs thereof, for the manufacture of a medicament for the treatment of these diseases) wherein the disease is selected from Crohn's, ulcerative colitis, asthma, graft versus host disease, allograft rejection, chronic obstructive pulmonary disease; Graves' disease, rheumatoid arthritis, systemic lupus erythematosis, psoriasis; CAPS, TRAPS, FMF, adult onset stills, systemic onset juvenile idiopathic arthritis, multiple sclerosis, neuropathic pain, gout, and gouty arthritis.

In addition, the present invention also provides a method of treating a condition (or use of the compounds of the present invention or stereoisomers, tautomers, pharmaceutically acceptable salts, solvates, or prodrugs thereof, for the manufacture of a medicament for the treatment of these conditions) comprising administering to a patient in need of such treatment a therapeutically-effective amount of a compound of Formula (I), wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans' syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method for treating a rheumatoid arthritis (or use of the compounds of the present invention or stereoisomers, tautomers, pharmaceutically acceptable salts, solvates, or prodrugs thereof, for the manufacture of a medicament for the treatment of rheumatoid arthritis), comprising administering to a patient in need of such treatment a therapeutically-effective amount of a compound of Formula (I).

The present invention also provides a method of treating a TLR/IL-1 mediated disease (or use of the compounds of the present invention or stereoisomers, tautomers, pharmaceutically acceptable salts, solvates, or prodrugs thereof, for the manufacture of a medicament for the treatment of these diseases), comprising administering to a patient in need of such treatment a therapeutically-effective amount of a compound of Formula (I).

The present invention also provides a method of treating a TLR/IL-1 mediated disease (or use of the compounds of the present invention or stereoisomers, tautomers, pharmaceutically acceptable salts, solvates, or prodrugs thereof, for the manufacture of a medicament for the treatment of these diseases), comprising administering to a patient in need of such treatment a therapeutically-effective amount of a compound of Formula (I), wherein the TLR/IL-1 mediated disease is a disease modulated by a kinase selected from IRAK-4.

The present invention also provides a method of treating diseases, comprising administering to a patient in need of such treatment a therapeutically-effective amount of a compound of Formula (I), or pharmaceutically acceptable salt thereof, in combination with other therapeutic agents.

The present invention also provides the compounds of the present invention or stereoisomers, tautomers, pharmaceutically acceptable salts, solvates, or prodrugs thereof, for use in therapy.

In another embodiment, compounds of Formula (I) are selected from exemplified compounds or combinations of exemplified compounds or other embodiments herein.

In another embodiment are compounds having an $IC_{50}$<1000 nM in the IRAK-4 assay described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula (I) (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound".

As used herein, the term "alkyl" or "alkylene" is intended to include both branched and straight-chain saturated aliphatic hydrocarbon groups having the specified number of carbon atoms. For example, "C$_{1-10}$ alkyl" (or alkylene), is intended to include C$_1$, C$_2$, C$_3$, C$_4$, C$_5$, C$_6$, C$_7$, C$_8$, C$_9$, and C$_{10}$ alkyl groups. Additionally, for example, "C$_1$-C$_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "C$_{2-6}$ alkenyl" (or alkenylene), is intended to include C$_2$, C$_3$, C$_4$, C$_5$, and C$_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "C$_{2-6}$ alkynyl" (or alkynylene), is intended to include C$_2$, C$_3$, C$_4$, C$_5$, and C$_6$ alkynyl groups; such as ethynyl, propynyl, butynyl, pentynyl, hexynyl and the like.

One skilled in the field will understand that, when the designation "CO$_2$" is used herein, this is intended to refer to the group

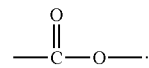

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl(C$_{0-4}$ alkyl) includes a substituted lower alkyl having at least one aryl substituent and also includes an aryl directly bonded to another group, i.e., aryl(C$_0$ alkyl). The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—C$_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. C$_{3-7}$ cycloalkyl is intended to include C$_3$, C$_4$, C$_5$, C$_6$, and C$_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula (I), the term "cycloalkyl" includes cyclopropyl, cyclobutyl, cyclopentyl, cyclohexyl, cycloheptyl, bicyclooctyl, etc., as well as the following ring systems:

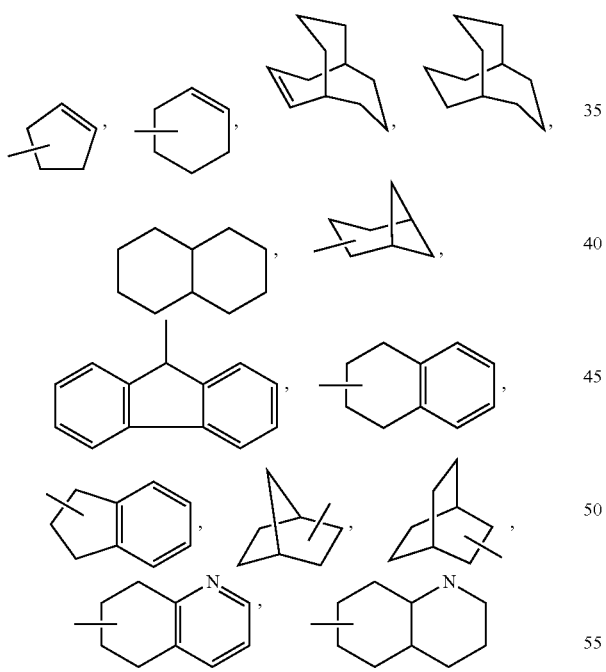

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

Thus, examples of aryl groups include:

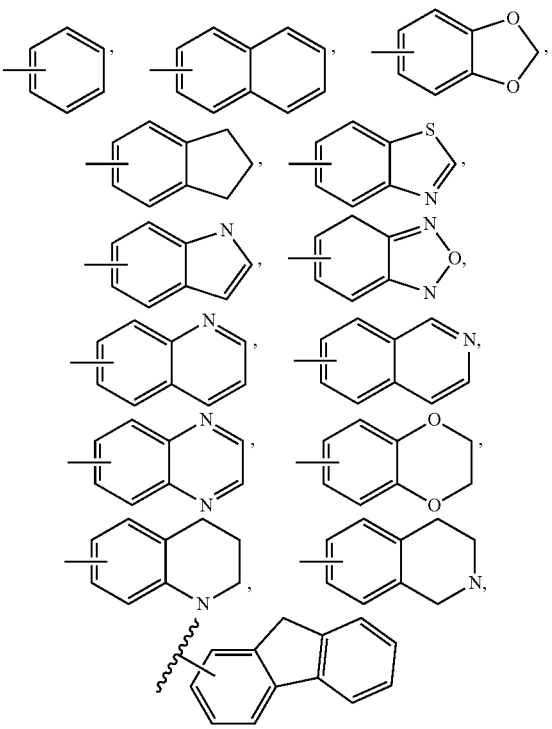

(fluorenyl) and the like, which optionally may be substituted at any available carbon or nitrogen atom. A preferred aryl group is optionally-substituted phenyl.

The terms "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The term "heterocycle" includes "heteroaryl" groups. As valence allows, if said further ring is cycloalkyl or heterocyclo it is additionally optionally substituted with =O (oxo).

Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

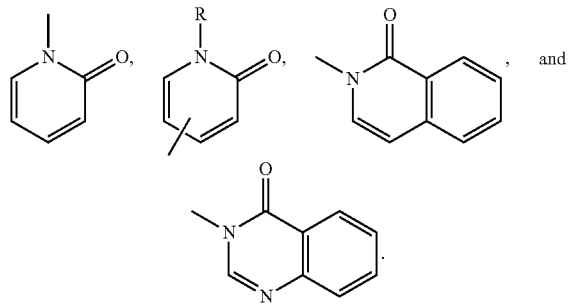

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula (I), preferred heteroaryl groups include

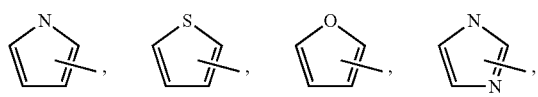

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula (I), contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt.

However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as -CD$_3$.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound for formula (I)) is a prodrug within the scope and spirit of the invention. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and c) Bundgaard, H., *Adv. Drug Deliv. Rev.*, 8:1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula (I) are also with the scope of the present invention. Methods of solvation are generally known in the art.

Utility

The compounds of the invention modulate kinase activity, including the modulation of IRAK-4. Other types of kinase activity that may be modulated by the compounds of the instant invention include, but are not limited to, the Pelle/IRAK family and mutants thereof Accordingly, compounds of formula (I) have utility in treating conditions associated with the modulation of kinase activity, and particularly the selective inhibition of IRAK-4 activity or the inhibition of IRAK and other Pelle family kinases. Such conditions include TLR/IL-1 family receptor associated diseases in which cytokine levels are modulated as a consequence of intracellular signaling. Moreover, the compounds of formula (I) have advantageous selectivity for IRAK-4 activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors IRAK-4, compounds of Formula (I) are useful in treating TLR/IL-1 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the kinase inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional IRAK-4-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

When the terms "IRAK-4-associated condition" or "IRAK-4-associated disease or disorder" are used herein, each is intended to encompass all of the conditions identified above as if repeated at length, as well as any other condition that is affected by IRAK-4 kinase activity.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit IRAK-4 and/or treat diseases.

The methods of treating IRAK-4 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit IRAK-4 and/or treat diseases associated with IRAK-4.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IRAK-4 kinase-associated conditions, including TLR and IL-1 family receptor mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by mediation of IRAK-4 enzyme levels.

Biological Assays

IRAK4 Inhibition Assay

The assays were performed in U-bottom 384-well plates. The final assay volume was 30 µL prepared from 15 µL additions of enzyme and substrates (fluoresceinated peptide and ATP) and test compounds in assay buffer (20 mM HEPES pH 7.2, 10 mM MgCl$_2$, 0.015% Brij35 and 4 mM DTT). The reaction was initiated by the combination of IRAK4 with substrates and test compounds. The reaction was incubated at room temperature for 60 min. and terminated by adding 45 µL of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentrations of reagents in the assays are ATP, 500 µM; FL-IPTSPITT-TYFFFKKK peptide 1.5 µM; IRAK4, 0.6 nM; and DMSO, 1.6%.

PBMC TLR2 Induced IL-6 Assay

Peripheral blood mononuclear cells (PBMCs) were isolated from human blood containing the anti-coagulant EDTA (2.5 mM) by centrifugation over a FICOLL® gradient. PBMCs (250000 cells/well) were cultured in assay media (RPMI with 10% heat inactivated FCS) with compounds for 30 minutes at 37° C. in a 5% CO$_2$ incubator. Following pretreatment with compounds, cells were stimulated for 5 hours with 10 µg/ml lipoteichoic acid (Invivogen, San Diego, Calif.), a TLR2 agonist. At the end of the culture, plates were centrifuged at 1800 rpm for 10 minutes to pellet the cells. Supernatants were harvested and analyzed for IL-6 levels by ELISA (BD Biosciences, San Jose, Calif.). Inhibition was calculated as either an IC$_{50}$ or EC$_{50}$. EC$_{50}$ determinations are indicated with an asterisk.

The table below lists the IRAK4 IC$_{50}$ values and Cell IC$_{50}$ or EC$_{50}$ values for the following Examples of this invention measured in the IRAK4 Inhibition Assay and the PBMC TLR2 Induced IL-6 assay. The compounds of the present invention, as exemplified by the following Examples, showed IRAK IC$_{50}$ inhibition values of less than 0.06 µM.

| Ex No. | IRAK4 Inhibition Data IRAK4 IC$_{50}$ (µM) | Cell IC$_{50}$ (or *EC$_{50}$) (µM) |
| --- | --- | --- |
| 1 | 0.0044 | 0.612 |
| 2 | 0.0132 | 0.925 |
| 3 | 0.0171 | 0.180 |
| 4 | 0.0182 | 0.639 |
| 5 | 0.0096 | 0.484 |
| 6 | 0.0028 | 0.231 |
| 7 | 0.0099 | 0.732 |
| 8 | 0.0041 | 0.290 |
| 9 | 0.0100 | 0.289 |
| 10 | 0.0051 | 0.115 |
| 11 | 0.0078 | 0.726 |
| 12 | 0.0056 | 0.311 |
| 13 | 0.0030 | 0.107 |
| 14 | 0.0043 | 0.461 |
| 15 | 0.0052 | 0.541 |
| 16 | 0.0052 | 0.595 |
| 17 | 0.0047 | 0.221 |
| 18 | 0.0069 | 0.269 |
| 19 | 0.0043 | 0.177 |
| 20 | 0.0049 | 0.562 |
| 21 | 0.0092 | 0.521 |
| 22 | 0.0038 | 0.456 |
| 23 | 0.0028 | 0.165 |
| 24 | 0.0040 | 0.468 |
| 25 | 0.0035 | 0.060 |
| 26 | 0.0073 | 0.121 |
| 27 | 0.0030 | 0.086 |
| 28 | 0.0078 | 0.195 |
| 29 | 0.0092 | 0.128 |

IRAK4 Inhibition Data

| Ex No. | IRAK4 IC$_{50}$ (μM) | Cell IC$_{50}$ (or *EC$_{50}$) (μM) |
|---|---|---|
| 30 | 0.0071 | 0.228 |
| 31 | 0.0052 | 0.249 |
| 32 | 0.0150 | 0.511 |
| 33 | 0.0037 | 0.064 |
| 34 | 0.0033 | 0.152 |
| 35 | 0.0026 | 0.482 |
| 36 | 0.0082 | 0.893 |
| 37 | 0.0039 | 0.297 |
| 38 | 0.0052 | 0.426 |
| 39 | 0.0053 | 0.503 |
| 40 | 0.0108 | 0.503 |
| 41 | 0.0035 | 0.318 |
| 42 | 0.0027 | 0.228 |
| 43 | 0.0060 | 0.353 |
| 44 | 0.0030 | 0.699 |
| 45 | 0.0075 | 0.887 |
| 46 | 0.0033 | 0.183 |
| 47 | 0.0071 | 0.571 |
| 48 | 0.0031 | 0.511 |
| 49 | 0.0034 | 0.444 |
| 50 | 0.0068 | 0.571 |
| 51 | 0.0037 | 0.334 |
| 52 | 0.0027 | 0.116 |
| 53 | 0.0054 | 0.230 |
| 54 | 0.0036 | 0.258 |
| 55 | 0.0059 | 0.349 |
| 56 | 0.0076 | 0.330 |
| 57 | 0.0052 | 0.314 |
| 58 | 0.0070 | 0.545 |
| 59 | 0.0060 | 0.099 |
| 60 | 0.0233 | 0.032 |
| 61 | 0.0070 | 0.257 |
| 62 | 0.0038 | 0.288 |
| 63 | 0.0086 | 0.632 |
| 64 | 0.0052 | 0.440 |
| 65 | 0.0039 | 0.170 |
| 66 | 0.0023 | 0.058 |
| 67 | 0.0068 | 0.248 |
| 68 | 0.0047 | 0.231 |
| 69 | 0.0034 | 0.365 |
| 70 | 0.0087 | 0.530 |
| 71 | 0.0138 | 0.415 |
| 72 | 0.0061 | 0.305 |
| 73 | 0.0027 | 0.327 |
| 74 | 0.0084 | 0.815 |
| 75 | 0.0189 | 0.710 |
| 76 | 0.0057 | 0.156 |
| 77 | 0.0180 | 0.377 |
| 78 | 0.0086 | 0.282 |
| 79 | 0.0056 | 0.048 |
| 80 | 0.0059 | 0.271 |
| 81 | 0.0045 | 0.100 |
| 82 | 0.0080 | 0.366 |
| 83 | 0.0115 | 0.133 |
| 84 | 0.0027 | 0.501 |
| 85 | 0.0051 | 0.195 |
| 86 | 0.0114 | 0.281 |
| 87 | 0.0053 | 0.271 |
| 88 | 0.0090 | 0.457 |
| 89 | 0.0026 | 0.032 |
| 90 | 0.0051 | 0.183 |
| 91 | 0.0037 | 0.064 |
| 92 | 0.0048 | 0.177 |
| 93 | 0.0160 | 0.619 |
| 94 | 0.0130 | 0.339 |
| 95 | 0.0019 | 0.058 |
| 96 | 0.0043 | 0.170 |
| 97 | 0.0164 | 0.302 |
| 98 | 0.0072 | 0.165 |
| 99 | 0.0064 | 0.258 |
| 100 | 0.0217 | 0.830 |
| 101 | 0.0548 | 0.570 |
| 102 | 0.0029 | 0.312 |
| 103 | 0.0134 | 0.411 |
| 104 | 0.0025 | 0.350 |
| 105 | 0.0019 | 0.321 |
| 106 | 0.0580 | 0.570 |
| 107 | 0.0039 | 0.174 |
| 108 | 0.0023 | 0.507 |
| 109 | 0.0058 | 0.454 |
| 110 | 0.0126 | 0.728 |
| 111 | 0.0014 | 0.183 |
| 112 | 0.0024 | 0.203 |
| 113 | 0.0041 | 0.803 |
| 114 | 0.0042 | 0.491 |
| 115 | 0.0037 | 0.510 |
| 116 | 0.0030 | 0.296 |
| 117 | 0.0056 | 0.363 |
| 118 | 0.0010 | 0.109 |
| 119 | 0.0217 | 0.587 |
| 120 | 0.0059 | 0.459 |
| 121 | 0.0020 | 0.345 |
| 122 | 0.0042 | 0.207 |
| 123 | 0.0036 | 0.271 |
| 124 | 0.0039 | 0.420 |
| 125 | 0.0134 | 0.779 |
| 126 | 0.0015 | 0.102 |
| 127 | 0.0041 | 0.472 |
| 128 | 0.0104 | 0.391 |
| 129 | 0.0026 | 0.143 |
| 130 | 0.0026 | 0.231 |
| 131 | 0.0057 | 0.138 |
| 132 | 0.0073 | 0.350 |
| 133 | 0.0020 | 0.230 |
| 134 | 0.0088 | 0.447 |
| 135 | 0.0369 | — |
| 136 | 0.0020 | 0.054 |
| 137 | 0.0036 | 0.528 |
| 138 | 0.0019 | 0.302 |
| 139 | 0.0031 | 0.310 |
| 140 | 0.0023 | 0.219 |
| 141 | 0.0022 | 0.279 |
| 142 | 0.0158 | 0.360 |
| 143 | 0.0047 | 0.295 |
| 144 | 0.0074 | 0.199 |
| 145 | 0.0189 | 0.260 |
| 146 | 0.0539 | 0.550 |
| 147 | 0.0174 | 0.507 |
| 148 | 0.0245 | 0.456 |
| 149 | 0.0038 | 0.386 |
| 150 | 0.0059 | 0.395 |
| 151 | 0.0042 | 0.191 |
| 152 | 0.0075 | 0.596 |
| 153 | 0.0061 | 0.510 |
| 154 | 0.0068 | 0.535 |
| 155 | 0.0078 | 0.770 |
| 156 | 0.0099 | 0.502 |
| 157 | 0.0042 | 0.836 |
| 158 | 0.0063 | 0.492 |
| 159 | 0.0032 | 0.146 |
| 160 | 0.0048 | 0.109 |
| 161 | 0.0179 | 0.577 |
| 162 | 0.0036 | 0.048 |
| 163 | 0.0069 | 0.230 |
| 164 | 0.0349 | 0.388 |
| 165 | 0.0090 | 0.386 |
| 166 | 0.0084 | 0.266 |
| 167 | 0.0098 | 0.526 |
| 168 | 0.0134 | 0.565 |
| 169 | 0.0028 | 0.480 |
| 170 | 0.0059 | 0.477 |
| 171 | 0.0043 | 0.571 |
| 172 | 0.0067 | 0.300 |
| 173 | 0.0093 | 0.696 |
| 174 | 0.0038 | 0.150 |
| 175 | 0.0051 | 0.402 |

IRAK4 Inhibition Data

| Ex No. | IRAK4 IC$_{50}$ (µM) | Cell IC$_{50}$ (or *EC$_{50}$) (µM) |
|---|---|---|
| 176 | 0.0103 | 0.489 |
| 177 | 0.0017 | 0.191 |
| 178 | 0.0138 | 0.405 |
| 179 | 0.0162 | 0.532 |
| 180 | 0.0037 | 0.415 |
| 181 | 0.0076 | 0.453 |
| 182 | 0.0033 | 0.508 |
| 183 | 0.0039 | 0.436 |
| 184 | 0.0019 | 0.215 |
| 185 | 0.0044 | 0.620 |
| 186 | 0.0024 | 0.361 |
| 187 | 0.0027 | 0.324 |
| 188 | 0.0025 | 0.508 |
| 189 | 0.0034 | 0.300 |
| 190 | 0.0033 | 0.250 |
| 191 | 0.0034 | 0.451 |
| 192 | 0.0061 | 0.264 |
| 193 | 0.0031 | 0.345 |
| 194 | 0.0025 | 0.208 |
| 195 | 0.0020 | 0.162 |
| 196 | 0.0035 | 0.325 |
| 197 | 0.0022 | 0.181 |
| 198 | 0.0026 | 0.307 |
| 199 | 0.0084 | 0.551 |
| 200 | 0.0022 | 0.094 |
| 201 | 0.0045 | 0.499 |
| 202 | 0.0024 | 0.156 |
| 203 | 0.0034 | 0.307 |
| 204 | 0.0026 | 0.252 |
| 205 | 0.0018 | 0.169 |
| 206 | 0.0021 | 0.139 |
| 207 | 0.0017 | 0.158 |
| 208 | 0.0037 | 0.647 |
| 209 | 0.0053 | 0.875 |
| 210 | 0.0152 | 0.551 |
| 211 | 0.0149 | 0.279 |
| 212 | 0.0069 | 0.712 |
| 213 | 0.0031 | 0.403 |
| 214 | 0.0067 | 0.371 |
| 215 | 0.0061 | 0.566 |
| 216 | 0.0035 | 0.604 |
| 217 | 0.0050 | 0.560 |
| 218 | 0.0070 | 0.471 |
| 219 | 0.0048 | 0.447 |
| 220 | 0.0034 | 0.328 |
| 221 | 0.0105 | 0.462 |
| 222 | 0.0099 | 0.692 |
| 223 | 0.0042 | 0.238 |
| 224 | 0.0096 | 0.280 |
| 225 | 0.0033 | 0.535 |
| 226 | 0.0034 | 0.274 |
| 227 | 0.0027 | 0.138 |
| 228 | 0.0024 | 0.392 |
| 229 | 0.0034 | 0.488 |
| 230 | 0.0051 | 0.274 |
| 231 | 0.0034 | 0.088 |
| 232 | 0.0357 | 0.697 |
| 233 | 0.0074 | 0.469 |
| 234 | 0.0044 | 0.233 |
| 234 | 0.0032 | 0.101 |
| 235 | 0.0017 | 0.263 |
| 236 | 0.0047 | 0.346 |
| 237 | 0.0031 | 0.222 |
| 238 | 0.0132 | 0.595 |
| 239 | 0.0097 | 0.379 |
| 241 | 0.0041 | 0.516 |
| 242 | 0.0019 | 0.179 |
| 243 | 0.0055 | 0.567 |
| 244 | 0.0019 | 0.156 |
| 245 | 0.0028 | 0.390 |
| 246 | 0.0055 | 0.262 |
| 247 | 0.0027 | 0.170 |
| 248 | 0.0031 | 0.176 |
| 249 | 0.0029 | 0.554 |
| 250 | 0.0063 | 0.748 |
| 251 | 0.0032 | 0.369 |
| 252 | 0.0042 | 0.173 |
| 253 | 0.0052 | 0.308 |
| 254 | 0.0025 | 0.131 |
| 255 | 0.0024 | 0.086 |
| 256 | 0.0088 | 0.587 |
| 257 | 0.0031 | 0.321 |
| 258 | 0.0049 | 0.432 |
| 259 | 0.0018 | 0.132 |
| 261 | 0.0036 | 0.126 |
| 262 | 0.0029 | 0.141 |
| 263 | 0.0042 | 0.190 |
| 264 | 0.0046 | 0.384 |
| 265 | 0.0033 | 0.217 |
| 266 | 0.0049 | 0.548 |
| 267 | 0.0074 | 0.468 |
| 268 | 0.0061 | 0.376 |
| 269 | 0.0050 | 0.445 |
| 270 | 0.0094 | 0.265 |
| 271 | 0.0043 | 0.128 |
| 272 | 0.0048 | 0.175 |
| 273 | 0.0024 | 0.764 |
| 274 | 0.0028 | 0.712 |
| 275 | 0.0031 | 0.335 |
| 276 | 0.0071 | 0.256 |
| 277 | 0.0036 | 0.180 |
| 278 | 0.0108 | 0.618 |
| 279 | 0.0040 | 0.292 |
| 280 | 0.0027 | 0.127 |
| 281 | 0.0012 | 0.354 |
| 282 | 0.0114 | 0.458 |
| 283 | 0.0096 | 0.417 |
| 284 | 0.0077 | 0.189 |
| 285 | 0.0071 | 0.512 |
| 286 | 0.0052 | 0.415 |
| 287 | 0.0062 | 0.674 |
| 288 | 0.0010 | 0.134 |
| 289 | 0.0061 | 0.502 |
| 290 | 0.0114 | 0.607 |
| 291 | 0.0070 | 0.283 |
| 292 | 0.0070 | 0.427 |
| 293 | 0.0018 | 0.310 |
| 294 | 0.0047 | 0.416 |
| 295 | 0.0048 | 0.446 |
| 296 | 0.0071 | 0.384 |
| 297 | 0.0057 | 0.535 |
| 298 | 0.0079 | 0.596 |
| 299 | 0.0017 | 0.420 |
| 300 | 0.0044 | 0.294 |
| 301 | 0.0031 | 0.190 |
| 302 | 0.0056 | 0.426 |
| 303 | 0.0133 | 0.331 |
| 304 | 0.0020 | 0.453 |
| 305 | 0.0117 | 0.647 |
| 306 | 0.0055 | 0.394 |
| 307 | 0.0099 | 0.372 |
| 308 | 0.0005 | 0.144 |
| 309 | 0.0019 | 0.061 |
| 310 | 0.0019 | 0.173 |
| 311 | 0.0024 | 0.081 |
| 312 | 0.0010 | 0.029 |
| 313 | 0.0034 | 0.073 |
| 314 | 0.0027 | 0.115 |
| 315 | 0.0039 | 0.426 |
| 316 | 0.0047 | 0.429 |
| 317 | 0.0017 | 0.374 |
| 318 | 0.0069 | 0.278 |
| 319 | 0.0030 | 0.315 |
| 320 | 0.0024 | 0.270 |
| 321 | 0.0064 | 1.145 |
| 322 | 0.0085 | 0.495 |

-continued

IRAK4 Inhibition Data

| Ex No. | IRAK4 IC$_{50}$ (μM) | Cell IC$_{50}$ (or *EC$_{50}$) (μM) |
|---|---|---|
| 323 | 0.0085 | 0.207 |
| 324 | 0.0107 | 0.190 |
| 325 | 0.0049 | 0.853 |
| 326 | 0.0129 | 0.437 |
| 327 | 0.0097 | 1.005 |
| 328 | 0.0048 | 0.491 |
| 329 | 0.0032 | 0.113 |
| 330 | 0.0022 | 0.076 |
| 331 | 0.0024 | 0.163 |
| 332 | 0.0031 | 0.791 |
| 333 | 0.0041 | 0.152 |
| 334 | 0.0045 | 0.321 |
| 335 | 0.0041 | 0.135 |
| 336 | 0.0039 | 0.466 |
| 337 | 0.0058 | 0.799 |
| 338 | 0.0171 | 0.493 |
| 339 | 0.0117 | 0.460 |
| 340 | 0.0096 | 0.419 |
| 341 | 0.0049 | 0.097 |
| 342 | 0.0033 | 0.071 |
| 343 | 0.0030 | 0.114 |
| 344 | 0.0018 | 0.038 |
| 345 | 0.0059 | 0.246 |
| 346 | 0.0025 | 0.076 |
| 347 | 0.0032 | 0.327 |
| 348 | 0.0067 | 0.562 |
| 349 | 0.0086 | 0.475 |
| 350 | 0.0027 | 0.148 |
| 351 | 0.0059 | 0.227 |
| 352 | 0.0038 | 0.245 |
| 353 | 0.0029 | 0.112 |
| 354 | 0.0044 | 0.402 |
| 355 | 0.0022 | 0.236 |
| 356 | 0.0030 | 0.281 |
| 357 | 0.0072 | 0.399 |
| 358 | 0.0024 | 0.048 |
| 359 | 0.0046 | 0.188 |
| 360 | 0.0028 | 0.073 |
| 361 | 0.0069 | 0.176 |
| 362 | 0.0029 | 0.044 |
| 363 | 0.0025 | 0.087 |
| 364 | 0.0036 | 0.092 |
| 365 | 0.0058 | 0.097 |
| 366 | 0.0093 | 0.734 |
| 367 | 0.0048 | 0.569 |
| 368 | 0.0053 | 0.445 |
| 369 | 0.0081 | 0.859 |
| 370 | 0.0041 | 0.571 |
| 371 | 0.0060 | 0.604 |
| 372 | 0.0037 | 0.383 |
| 373 | 0.0051 | 0.431 |
| 374 | 0.0031 | 0.271 |
| 375 | 0.0053 | 0.394 |
| 376 | 0.0110 | 0.312 |
| 377 | 0.0099 | 0.372 |
| 378 | 0.0048 | 0.139 |
| 379 | 0.0063 | 0.748 |
| 380 | 0.0074 | 0.468 |
| 381 | 0.0061 | 0.376 |
| 382 | 0.0063 | 0.491 |
| 383 | 0.0063 | 0.194 |
| 384 | 0.0035 | 0.180 |
| 385 | 0.0043 | 0.135 |
| 386 | 0.0201 | 0.516 |
| 387 | 0.0043 | 0.293 |
| 388 | 0.0066 | 0.234 |
| 389 | 0.0104 | 0.574 |
| 390 | 0.0030 | 0.165 |
| 391 | 0.0025 | 0.119 |
| 392 | 0.0080 | 0.297 |
| 393 | 0.0070 | 0.392 |
| 394 | 0.0102 | 0.311 |
| 395 | 0.0044 | 0.333 |
| 396 | 0.0027 | 0.351 |
| 397 | 0.0049 | 0.197 |
| 398 | 0.0035 | 0.301 |
| 399 | 0.0031 | 0.203 |
| 400 | 0.0075 | 0.119 |
| 401 | 0.0126 | 0.328 |
| 402 | 0.0090 | 0.357 |
| 403 | 0.0210 | 1.482 |
| 404 | 0.0078 | 1.014 |
| 405 | 0.0058 | 0.788 |
| 406 | 0.0118 | 1.320 |
| 407 | 0.0027 | 0.260 |
| 408 | 0.0019 | 0.209 |
| 409 | 0.0030 | 0.207 |
| 410 | 0.0032 | 0.340 |
| 411 | 0.0024 | 0.092 |
| 412 | 0.0026 | 0.109 |
| 413 | 0.0063 | 0.226 |
| 414 | 0.0134 | 0.256 |
| 415 | 0.0063 | 0.502 |
| 416 | 0.0018 | 0.255 |
| 417 | 0.0109 | 0.072 |
| 418 | 0.0012 | 0.030 |
| 419 | 0.0051 | 0.184 |
| 420 | 0.0036 | 0.184 |
| 421 | 0.0033 | 0.131 |
| 422 | 0.0113 | 0.753 |
| 423 | 0.0065 | 0.461 |
| 424 | 0.0060 | 0.597 |
| 425 | 0.0131 | 0.560 |
| 426 | 0.0063 | 0.171 |
| 427 | 0.0015 | 0.042 |
| 428 | 0.0020 | 0.052 |
| 429 | 0.0021 | 0.128 |
| 430 | 0.0016 | 0.102 |
| 431 | 0.0041 | 0.220 |
| 432 | 0.0038 | 0.503 |
| 433 | 0.0065 | 0.504 |
| 434 | 0.0065 | 0.052 |
| 435 | 0.0021 | 0.079 |
| 436 | 0.0049 | 0.346 |
| 437 | 0.0049 | 0.214 |
| 438 | 0.0116 | 0.168 |
| 439 | 0.0031 | 0.064 |
| 440 | 0.0105 | 0.330 |
| 441 | 0.0018 | 0.028 |
| 442 | 0.0056 | 0.106 |
| 443 | 0.0045 | 0.125 |
| 444 | 0.0023 | 0.055 |
| 445 | 0.0038 | 0.106 |
| 446 | 0.0106 | 0.094 |
| 447 | 0.0020 | 1.248 |
| 448 | 0.0165 | 0.047 |
| 449 | 0.0014 | 0.208 |
| 450 | 0.0017 | 0.217 |
| 451 | 0.0050 | 0.258 |
| 452 | 0.0025 | 0.239 |
| 453 | 0.0026 | 0.836 |
| 454 | 0.0028 | 0.038 |
| 455 | 0.0008 | 0.573 |
| 456 | 0.0016 | 0.336 |
| 457 | 0.0034 | 1.554 |
| 458 | 0.0019 | 0.363 |
| 459 | 0.0034 | 0.141 |
| 460 | 0.0033 | 0.553 |
| 461 | 0.0020 | 0.147 |
| 462 | 0.0017 | 0.115 |
| 463 | 0.0031 | 0.204 |
| 464 | 0.0096 | 0.843 |
| 465 | 0.0061 | 0.388 |
| 466 | 0.0027 | 0.212 |
| 467 | 0.0020 | 0.428 |
| 468 | 0.0041 | 0.246 |

-continued

IRAK4 Inhibition Data

| Ex No. | IRAK4 IC$_{50}$ (µM) | Cell IC$_{50}$ (or *EC$_{50}$) (µM) |
|---|---|---|
| 469 | 0.0031 | 0.476 |
| 470 | 0.0036 | 0.635 |
| 471 | 0.0024 | 1.202 |
| 472 | 0.0038 | 1.361 |
| 473 | 0.0015 | 0.401 |
| 474 | 0.0028 | 0.204 |
| 475 | 0.0026 | 0.564 |
| 476 | 0.0059 | 1.039 |
| 477 | 0.0100 | 0.717 |
| 478 | 0.0022 | 0.050 |
| 479 | 0.0043 | 0.473 |
| 480 | 0.0084 | 0.877* |
| 481 | 0.0036 | 0.223 |
| 482 | 0.0103 | 0.251* |
| 483 | 0.0034 | 0.463 |
| 484 | 0.0087 | 1.349 |
| 485 | 0.0078 | 0.539* |
| 486 | 0.0068 | 0.469* |
| 487 | 0.0081 | 0.632* |
| 488 | 0.0026 | 0.192* |
| 489 | 0.0082 | 0.374* |
| 490 | 0.0042 | 0.277* |
| 491 | 0.0050 | 0.281* |
| 492 | 0.0121 | 0.454* |
| 493 | 0.0043 | 0.365* |
| 494 | 0.0085 | 0.209* |
| 495 | 0.0119 | 0.447* |
| 496 | 0.0064 | 0.091* |
| 497 | 0.0152 | 0.299* |
| 498 | 0.0066 | 0.423* |
| 499 | 0.0040 | 0.072* |
| 500 | 0.0054 | 0.228* |
| 501 | 0.0045 | 0.209* |
| 502 | 0.0048 | 0.144* |
| 503 | 0.0015 | 0.077* |
| 504 | 0.0047 | 0.496 |
| 505 | 0.0042 | 0.243 |
| 506 | 0.0065 | 0.320 |
| 507 | 0.0120 | 0.523 |
| 508 | 0.0102 | 10.000 |
| 509 | 0.0095 | 1.204 |
| 510 | 0.0015 | 0.028* |
| 511 | 0.0042 | 0.611 |
| 512 | 0.0174 | 0.602 |
| 513 | 0.0094 | 1.570 |
| 514 | 0.0018 | 0.026* |
| 515 | 0.0034 | 0.450 |
| 516 | 0.0031 | 1.201 |
| 517 | 0.0060 | 1.293 |
| 518 | 0.0038 | 1.835 |
| 519 | 0.0022 | 0.634 |
| 520 | 0.0025 | 1.064 |
| 521 | 0.0085 | 2.327 |
| 522 | 0.0093 | 0.795 |
| 523 | 0.0054 | 0.365* |
| 524 | 0.0037 | 0.075* |
| 525 | 0.0015 | 0.131* |
| 526 | 0.0066 | 0.423* |
| 527 | 0.0077 | 0.32* |

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of the general formula (I) can be prepared according to the method outlined in Scheme 1. Hydrolysis of ester (1) to the acid 1.1 followed by reaction with an amine using standard amide bond forming conditions can afford the dichloro amide 1.2. Selective displacement of the C4 chloride by reacting with an amine can afford the mono-chloro product 1.3. Reaction of 1.3 with an appropriate nucleophile, such as an amine, in the presence of a catalyst, such as palladium, can afford compounds of the general formula I.

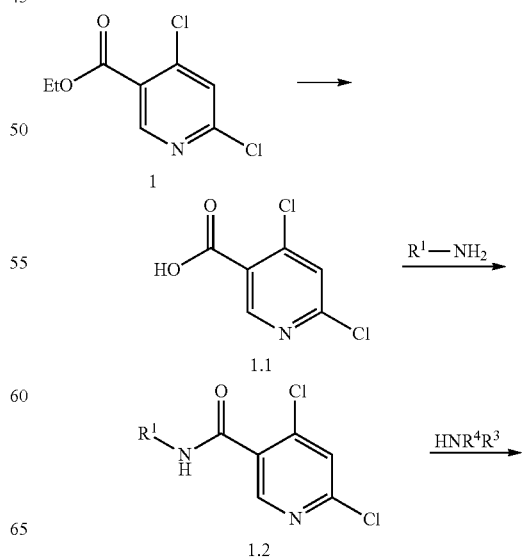

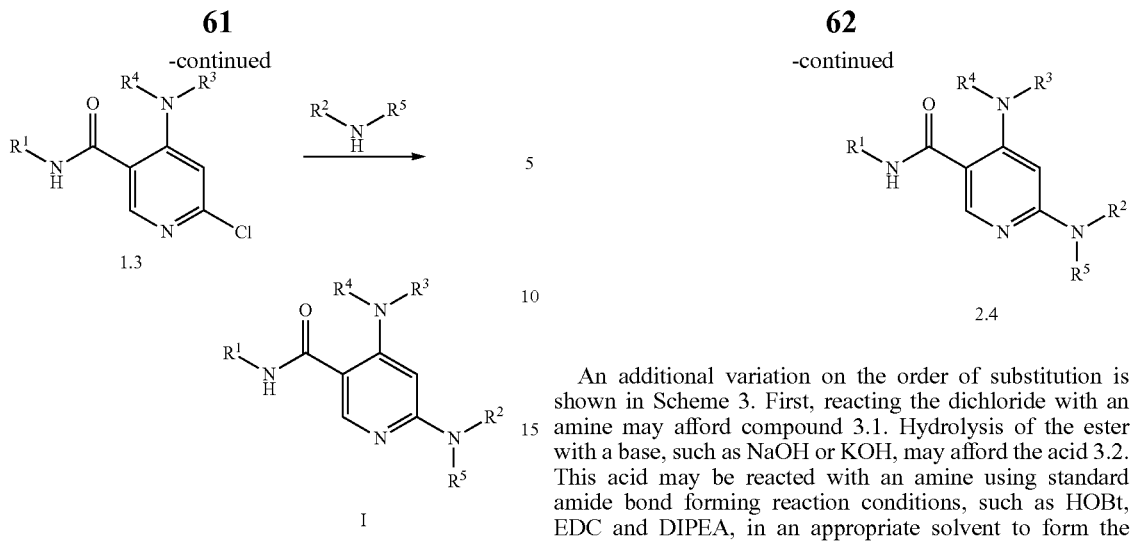

Alternatively, the order of reactions can be modified to change the overall synthesis in order to allow for variations at different positions of the molecule at different stages of the preparation. For example, in Scheme 2, the chloride 1 may be reacted with an amine first to form the monochlorinated ester 2.1. Subsequent reaction with another amine, either in the presence of a metal catalyst or thermally in the presence of acid, may form the disubstituted intermediate 2.2. Hydrolysis of the ester to acid 2.3 followed by amide bond formation can afford the final analog 2.4.

An additional variation on the order of substitution is shown in Scheme 3. First, reacting the dichloride with an amine may afford compound 3.1. Hydrolysis of the ester with a base, such as NaOH or KOH, may afford the acid 3.2. This acid may be reacted with an amine using standard amide bond forming reaction conditions, such as HOBt, EDC and DIPEA, in an appropriate solvent to form the amide 3.3, similar to amide 1.3 in Scheme 1. Subsequent aryl amine or heteroaryl amine coupling in the presence of a metal catalyst such as palladium, may afford the final compound 3.4.

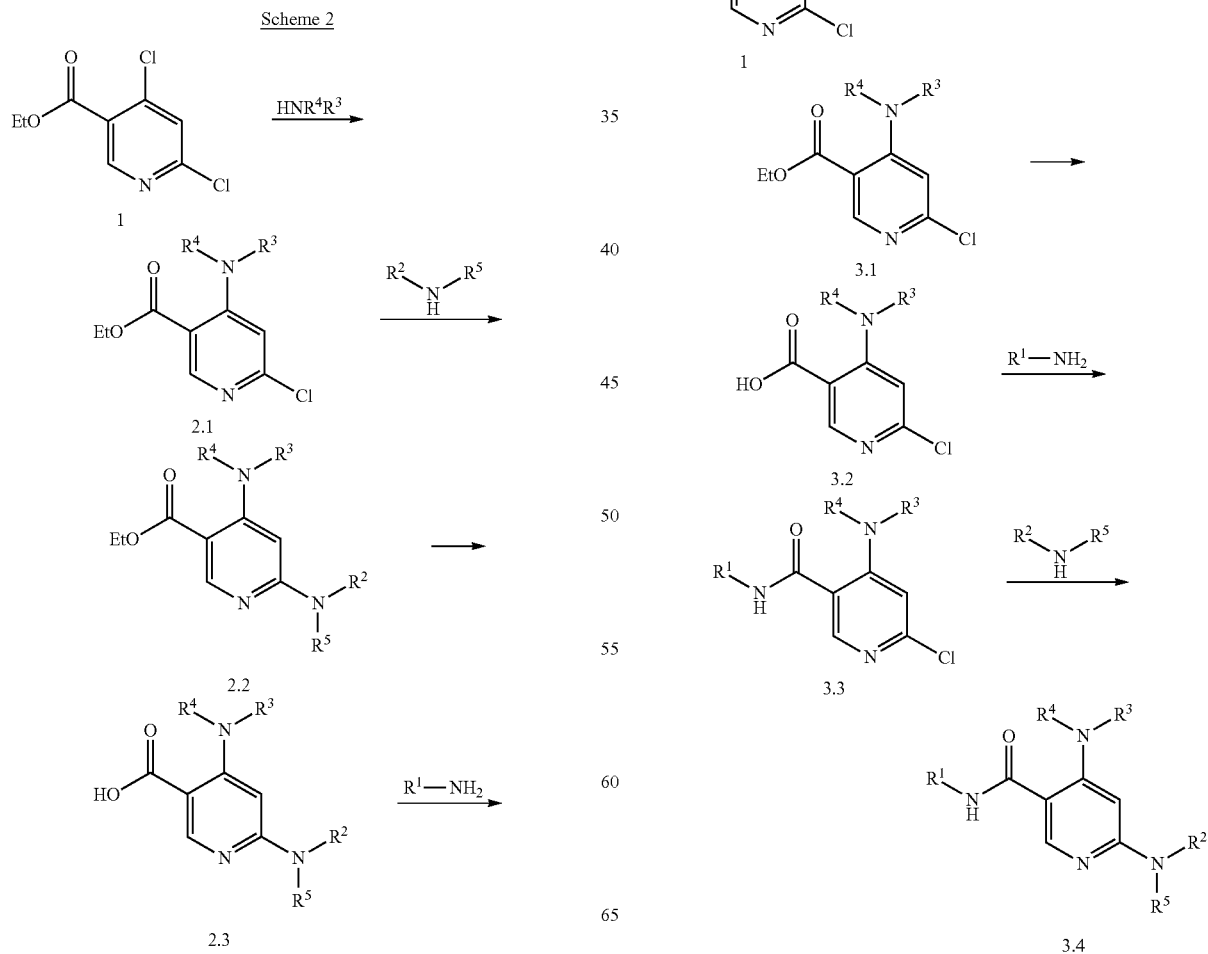

Another variation involves the synthesis of a differentially halogenated pyridine core to allow for variation of the HNR³R⁴ substituent at the last stage of the synthesis. 6-Bromo-4-choronicotinic acid may be reacted with a halogenating reagent, such as oxalyl chloride, to afford the acid chloride 4.1. This may be further reacted with an amine in the presence of a base, such as DIPEA or TEA, in an appropriate solvent, such as DCM, to afford the amide 4.2. Amide 4.2 may be reacted with another amine in the presence of a base, such as $Cs_2CO_3$ or $K_2CO_3$ and a metal catalyst, such as Pd, in a solvent to afford compound 4.3. Finally, compound 4.3 may be reacted with an amine in the presence of a base at elevated temperature to afford compound 4.4.

of amide bond forming reagents may afford compounds such as 5.3. It should be obvious to those skilled in the art that other functionalities than a carboxylate may be present for subsequent functionalization. For example, nitro groups can be converted readily to amines and subsequently functionalized, and halogens can be readily converted to aryl amines or nitriles.

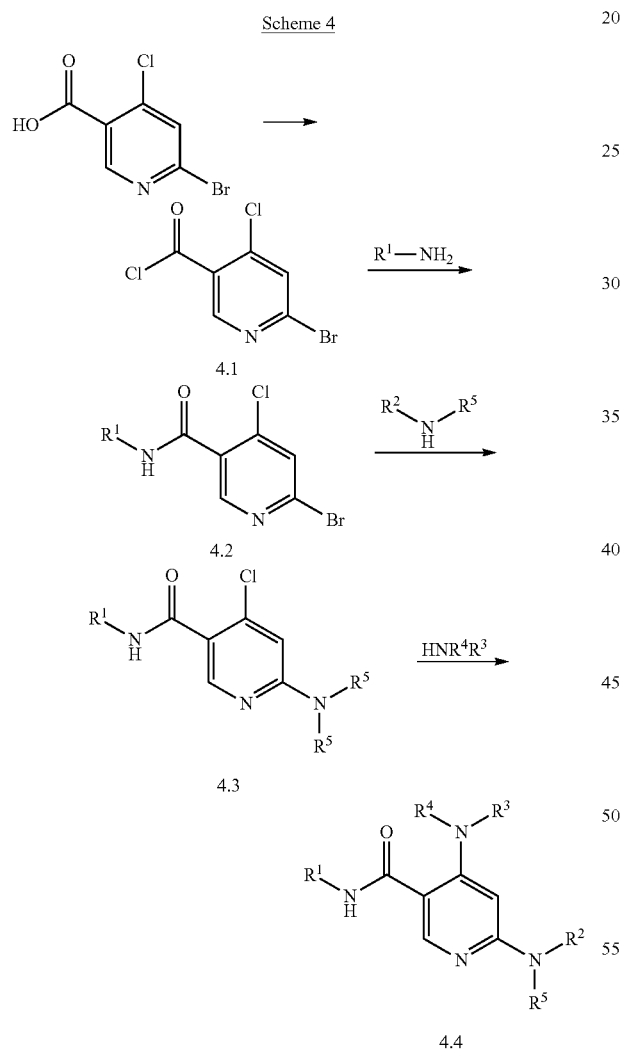

It should be also noted, and obvious to those skilled in the art, that synthetic manipulations of the incorporated R¹, R², R³, R⁴, and R⁵ groups is possible. An illustrative example is shown in Scheme 5. The butyl ester incorporated in compound 5.1 may be converted to the acid 5.2 upon treatment with an acid, such as TFA, in an appropriate solvent, such as DCM. Further reaction of 5.2 with an amine in the presence Another variation on the chemistry in Scheme 5 is outlined in Scheme 6. Alkyl groups may be functionalized, as in the alcohol 6.1, then subsequently transformed via standard chemical manipulations to compounds such as the fluoro analog 6.2. Subsequent conversion of the ester to the acid then amide and amine coupling at the remaining pyridine chloride may afford analogs such as 6.3. It should be obvious to one skilled in the art that these transformations are not limited to the example shown and can be applied to a variety of chemical substrates to afford the desired compounds.

Scheme 6

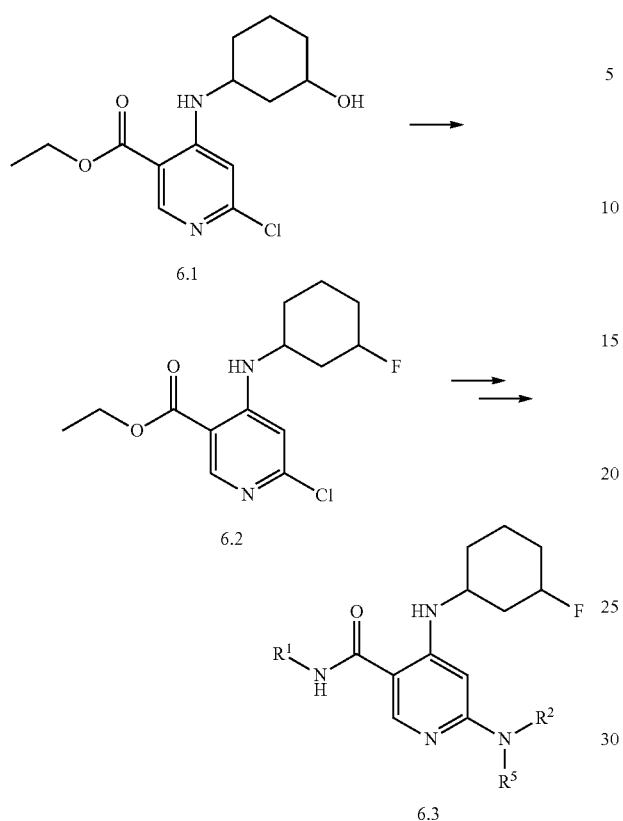

Additionally, variations to the R¹ group can be made via functionalization after incorporating onto the pyridine scaffold. For example, in Scheme 7, an appropriately protected amine is coupled to the pyridine acid via standard amide bond forming conditions to form 7.2. Compound 7.2 may be deprotected to reveal the amine 7.3 which can be reacted with a variety of reagents (acids, acid chlorides, sulfonyl chlorides, isocyanates, aldehydes, etc.) to form compounds of the general formula 7.4.

Scheme 7

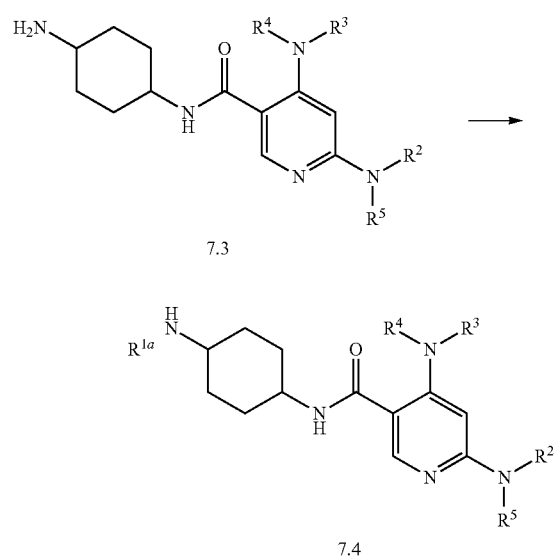

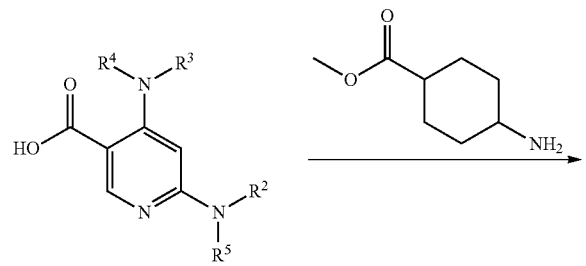

Similarly, a substituted amino ester may be coupled to the pyridine acid core to furnish the ester 8.1 which may be saponified to the acid 8.2. Subsequent reaction with amines under amide bond forming reaction conditions may form the compounds 8.3.

Scheme 8

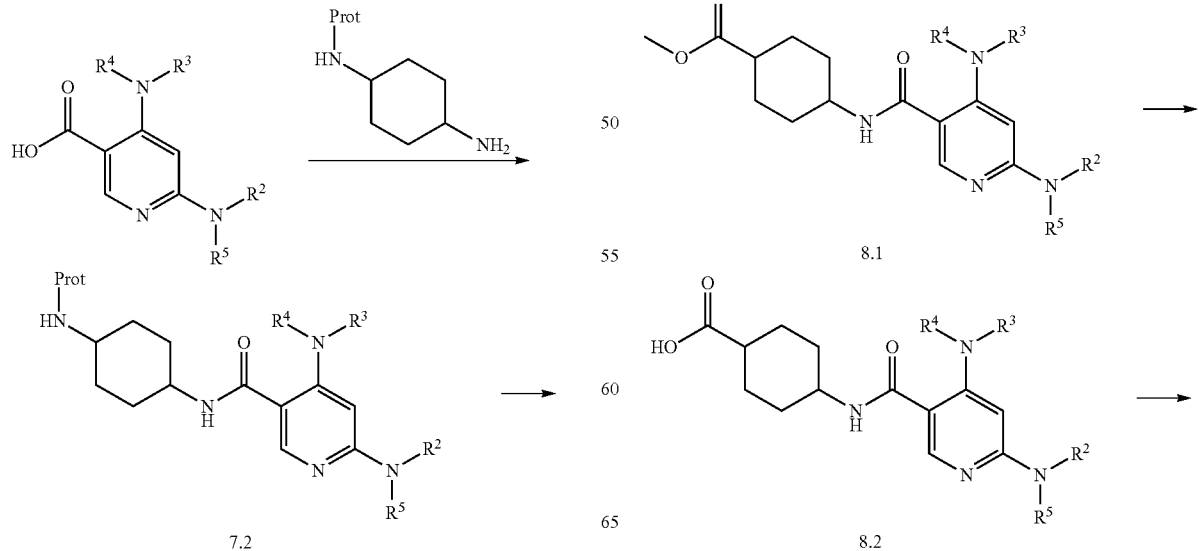

-continued

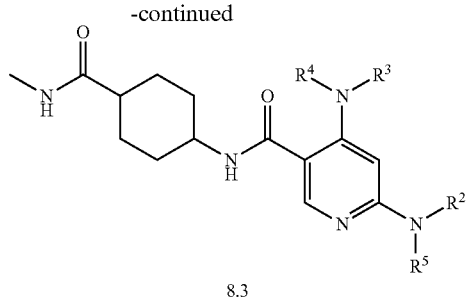

8.3

Substitution at either $R^2$ or $R^5$ may be accomplished via the methods outlined in Scheme 9. Preparation of an appropriately functionalized precursor, such as compound 9.1, and reaction with a variety of reagents, such as amines, aryl cross coupling partners, and cyanide may form compounds of the formula 9.2.

Scheme 9

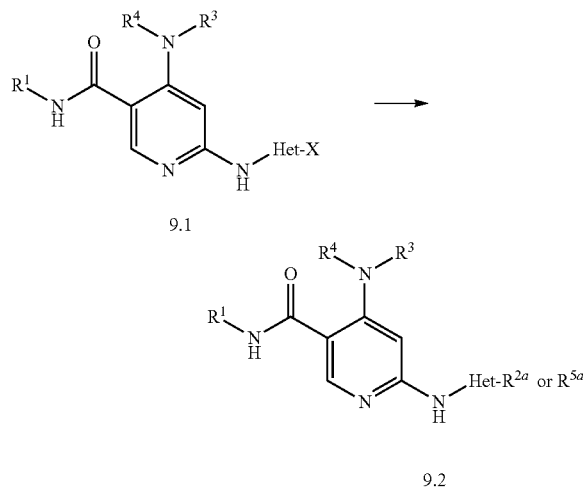

EXAMPLES

Preparation of compounds of Formula (I), and intermediates used in the preparation of compounds of Formula (I), can be prepared using procedures shown in the following Examples and related procedures. The methods and conditions used in these Examples, and the actual compounds prepared in these Examples, are not meant to be limiting, but are meant to demonstrate how the compounds of Formula (I) can be prepared. Starting materials and reagents used in these Examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters SunFire $C_{18}$, Waters XBridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

ACN=acetonitrile
brine=saturated aqueous sodium chloride
DAST=(diethylamino)sulfur trifluoride
DCM=dichloromethane
DEA=diethylamine
DIEA=N,N-diisopropylethylamine
DIPEA=N,N-diisopropylethylamine
DMAP=4-(N,N-dimethylamino)pyridine
DMF=N,N-dimethylformamide
DMSO=dimethyl sulfoxide
DPPF=1,1'-bis(diphenylphosphino)ferrocene
EDC=N-(3-dimethylaminopropyl)-N'-ethylcarbodiimide hydrochloride
EtOAc=ethyl acetate
h=hour(s)
HATU=O-(7-azabenzotriazol-1-yl)-N,N,N',N'-tetramethyluronium hexafluorophosphate
HOAT=1-hydroxy-7-azabenzotriazole
HOBT=1-hydroxybenzotriazole hydrate
LCMS=Liquid Chromatography-Mass Spectroscopy
MeOH=methanol
MTBE=methyl t-butyl ether
$NaHCO_3$ (aq)=saturated aqueous sodium bicarbonate
n-BuLi=n-butyl lithium
$NH_4OAc$=ammonium acetate
$Pd_2(dba)_3$=tris-(dibenzylideneacetone)dipalladium
$PdCl_2(dppf).CH_2Cl_2$=dichloro[1,1'-bis(diphenylphosphino)ferrocene]palladium(II) dichloromethane adduct
PyBrOP=bromotripyrrolidinophosphonium hexafluorophosphate
rt=ambient room temperature (generally about 20-25° C.)
TBAF=tetrabutylammonium fluoride
TEA=triethylamine
TFA=trifluoroacetic acid
THF=tetrahydrofuran
HPLC Conditions:
  A: XBridge Phenyl (150×4.6 mm), 3.5μ; Solvent A=5% ACN: 95% $H_2O$: 0.05% TFA pH=2.5; Solvent B=95% ACN: 5% $H_2O$: 0.05% TFA pH=2.5; gradient 0-100% B over 15 min; Flow rate: 1.0 μl/min.
  B: SunFire C18 (150×4.6 mm), 3.5μ; Solvent A=5% ACN: 95% $H_2O$: 0.05% TFA pH=2.5; Solvent B=95% ACN: 5% $H_2O$: 0.05% TFA pH=2.5; gradient 0-100% B over 30 min.
  C: Eclipse XDB C18 (150×4.6 mm) 5μ; Solvent A=20 mM $NH_4OAc$ in water; Solvent B=ACN; gradient 0-100% B over 20 min; Flow rate=1.0 mL/min.
  D: ZORBAX® SB C18, 4.6×50 mm, 5 μm; Solvent A=10% MeOH: 90% $H_2O$: 0.1% TFA; Solvent B=90% MeOH: 10% $H_2O$: 0.1% TFA; gradient 0-100% B over 2 min.
  E: SunFire C18 (150×4.6 mm), 3.5μ; Solvent A=5% ACN: 95% $H_2O$: 0.05% TFA pH=2.5; Solvent B=95% ACN: 5% $H_2O$: 0.05% TFA pH=2.5; gradient 0-100% B over 15 min.

F: Ascentis Express C18 (4.6×50) mm, 2.7 µm; Solvent A=5% ACN: 95% water: 10 mM NH₄OAc; Solvent B=95% ACN: 5% water: 10 mM NH₄OAc.gradient 0-100% B over 4 min; Flow rate=4 mL/min. Column temp=45° C.

G: BEH C18 (2.1×50) mm, 1.7 µm; Solvent A=5% ACN: 95% water: 10 mM NH₄OAc; Solvent B=95% ACN: 5% water: 10 mM NH₄OAc.gradient 0-100% B over 4 min; Flow rate=1.1 mL/min. Column temp=45-50° C.

H: CHIRALCEL®-OJ-H (250×4.6×5.0µ), CO₂-3.0 g(70%), co-solvent-30% (0.5% DEA in methanol).

I: Chiral-OD-H (250×4.6) mm 5µ Mobile Phase A: 0.2 DEA in n-hexane(85); Mobile Phase B: Ethanol(15); Flow: 1.0 ml/min.

J: XBridge Phenyl (4.6×150 mm) 3.5µ Mobile Phase A: 10 mM NH₄HCO₃ pH 9.5 adjusted using dil. NH₃; Mobile Phase B: Methanol; Flow rate: 1 ml/min K: SunFire C18 (4.6×150) mm, 3.5µ Mobile Phase A: 0.05% TFA in water:acetonitrile: 95:05; Mobile Phase B: Acetonitrile: 0.05% TFA in water: 95:05 flow: 1 ml\min time; gradient 0-100% B over 18 min.

L: XBridge (150×4.6 mm) 3.5µ SC/749 Buffer: 0.05% TFA in water pH 2.5 Mobile Phase A: Buffer:Acetonitrile (95:5) Mobile Phase B: Acetonitrile:Buffer (95:5); Flow: 1.0 ml\min % B 100 time(min) 15.

M: SunFire C18(150×4.6 mm) 3.5µ, Buffer: 0.05% TFA in water pH adjusted with 2.5 using Dil. Ammonia Solvent A: Buffer:Acetonitrile (95:5), Solvent B: Acetonitrile:Buffer (95:5), N: CHIRALPAK®-1A (250×4.6 mm) 5µ CO2-3.og (70%), co-solvent-30% Mobile Phase A: 0.5% DEA in methanol.

O: Waters Acquity UPLC BEH C18, 2.1×50 mm: Mobile Phase A: 5:95 acetonitrile:water with 0.05% TFA; Mobile Phase B: 95:5 acetonitrile:water with 0.05% TFA; Gradient: 0-100% B over 3 minutes, then a 0.75-minute hold at 100% B; Flow: 1.11 mL/min.

Example 1

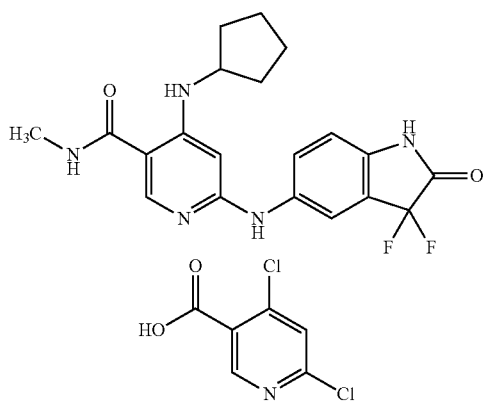

Step 1: Synthesis of 4,6-dichloronicotinic acid: Ethyl 4,6-dichloronicotinate in ethanol (20 mL) and water (10 mL) was stirred at ambient temperature. Lithium hydroxide was added to the reaction mixture and stirred at room temperature for 4 h. The solvent was concentrated under reduced pressure, diluted with EtOAc and added water. The aqueous layer was collected and acidified to pH 3-4 using citric acid. The mixture was allowed to stir for 10 min in an ice bath the precipitated product was filtered and dried under vacuum to furnish compound.

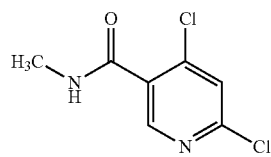

Step 2: Synthesis of 4,6-dichloro-N-methylnicotinamide: To a stirred solution of 4,6-dichloronicotinic acid (2) (10 g, 1 equiv.) in DCM (100 mL), DMF (catalytic amt.) was added at 0° C. Oxalyl chloride (14 mL, 3 equiv.) was added to the reaction mixture. The reaction was allowed to warm to ambient temperature and stirred for 30 min and was then heated at reflux for 2 h. The reaction mixture was concentrated to remove excess of oxalyl chloride and redissolved in DCM (50 mL) and cooled to −20° C. Methyl amine was added in portions to the reaction mixture and stirred at room temperature for 3 h. The reaction was quenched with water followed by NaHCO₃ solution. The layers were separated and the organic layer was dried over anhydrous sodium sulfate, filtered and concentrated to obtain the desired compound, 6-chloro-4-(isopropylamino)nicotinamide. LC/MS: ZORBAX® SB C18, 4.6×50 mm, 5 µm; Solvent A=10% MeOH: 90% H₂O: 0.1% TFA; Solvent B=90% MeOH: 10% H₂O: 0.1% TFA; gradient 0-100% B over 2 min (3 min run time); retention time: 0.874 min; LCMS (ES-API), m/z 205 (M+H).

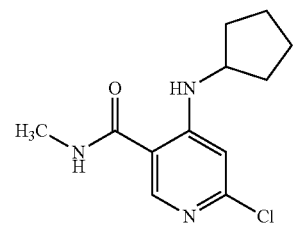 [SMILES: CNC(=O)c1cnc(Cl)cc1NC1CCCC1]

Step 3: Synthesis of 6-chloro-4-(cyclopentylamino)-N-methylnicotinamide: A stirred solution of 4,6-dichloro-N-methylnicotinamide (0.2 g, 1 equiv.), cyclopentyl amine (0.17 g, 1.1 equiv.) and N,N-diisopropylethyl amine (0.7 mL, 4 equiv.) in DMA (2 mL) was heated at 120° C. in a closed condition for 3 h. The reaction mixture was concentrated to dryness to remove excess of DMA from the reaction mass. The crude material obtained was purified by column chromatography through silica gel and EtOAc:pet ether as eluent to obtain the title compound. LC/MS: Ascentis Express C18, 5×2.1 mm, 2.7 µm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.776 min; LCMS (ES-API), m/z 252.2 (M−H).

Step 4: Synthesis of 4-(cyclopentylamino)-6-(3,3-difluoro-2-oxoindolin-5-ylamino)-N-methylnicotinamide: 6-Chloro-4-(cyclopentylamino)-N-methylnicotinamide (50 mg, 1 equiv.) and 5-amino-3,3-difluoroindolin-2-one (40 mg, 1.2 equiv.) were taken in a sealed tube and heated at 150° C. for 2 h in a closed condition. The crude material was purified by column chromatography through silica gel and MeOH: CHCl₃ as eluent to obtain 4-(cyclopentylamino)-6-(3,3-difluoro-2-oxoindolin-5-ylamino)-N-methylnicotinamide. ¹H NMR: 400 MHz, CD₃OD: δ 1.67-1.82 (m, 6H), 2.02-2.10 (m, 2H), 2.87 (s, 3H), 3.83-3.89 (m, 1H), 5.95 (s, 1H), 7.12 (d, J=8.40 Hz, 1H), 7.46-7.49 (m, 1H), 7.61 (d, J=2.00 Hz, 1H), 8.00 (s, 1H). LC/MS: Ascentis Express C18, 5×2.1 mm, 2.7 µm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.76 min; LCMS (ES-API), m/z 402.4 (M+H). HPLC: XBridge Phenyl (150×4.6 mm), 3.5μ; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μl/min; Retention time: 7.43 min.

Synthesis of 3,3-difluoro-5-nitroindolin-2-one: A solution of 5-nitroindoline-2,3-dione (i) (1 g, 1 equiv.) in DCM (10 mL) was cooled to 0° C. To the reaction mixture DAST (1.7 mL, 2.5 equiv.) was added to the reaction mixture and stirred for 16 h at ambient temperature. The reaction was quenched with 10% NaHCO₃ solution and extracted into DCM (twice). The organic layers were collected, dried over anhydrous sodium sulfate, filtered and concentrated. The crude product was purified by flash column chromatography using silica gel and EtOAc:pet ether to obtain the desired product. LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.495 min; LCMS (ES-API), m/z 213 (M−H).

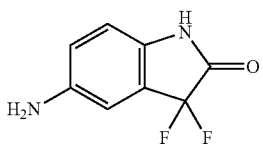 [SMILES: O=C1Nc2ccc([N+](=O)[O-])cc2C1(F)F]

Synthesis of 5-amino-3,3-difluoroindolin-2-one: A solution of 3,3-difluoro-5-nitroindolin-2-one (50 mg, 1 equiv.) in EtOAC:THF:DIPEA (16 mL:4 mL:0.1 mL) was degassed with N₂ for 5 min. Pd/C (10% w/w) (50 mg) was added to the reaction mixture in a tiny autoclave. H₂ pressure (42 psi) was applied and stirred at room temperature for 2 h. The reaction mixture was filtered through a bed of CELITE® and concentrated under reduced pressure. The crude product was purified by flash column chromatography using silica gel and EtOAc:pet ether to obtain the desired product. ¹H NMR 400 MHz, CD₃OD: δ 6.74 (d, J=8.40 Hz, 1H), 6.83 (d, J=8.40 Hz, 1H), 6.94 (d, J=2.00 Hz, 1H).

Example 2

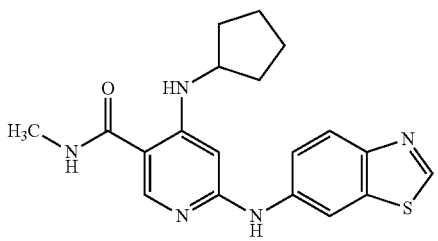 [SMILES: CNC(=O)c1cnc(Nc2ccc3ncsc3c2)cc1NC1CCCC1]

Example 2 was prepared via the method outlined for Example 1, Step 4 using 6-chloro-4-(cyclopentylamino)-N-methylnicotinamide and 6-amino benzothiazole. LCMS m/z 368.21 (M+H)⁺; ¹H NMR (400 MHz, DMSO-d₆) δ 9.45 (br s, 1H), 9.22 (s, 1H), 8.56 (br s, 2H), 8.36 (br s, 1H), 8.29 (s, 1H), 8.10-7.90 (m, 1H), 7.57 (dd, J=8.9, 2.1 Hz, 1H), 6.05 (s, 1H), 3.85-3.67 (m, 1H), 2.82-2.66 (m, 3H), 2.01 (dq, J=12.2, 6.2 Hz, 2H), 1.84-1.56 (m, 4H), 1.50 (dt, J=12.1, 5.9 Hz, 2H).

Example 3

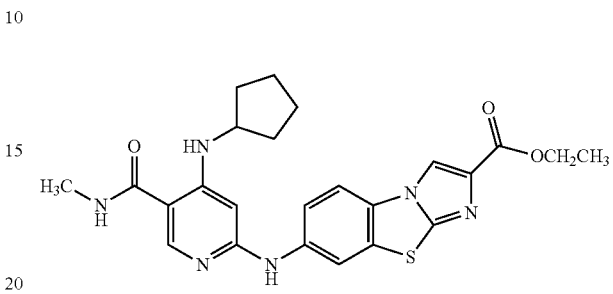

Step 1: Synthesis of ethyl 7-nitrobenzo[d]imidazo[2,1-b]thiazole-2-carboxylate: A solution of 6-nitrobenzo[d]thiazol-2-amine (3 g, 1 equiv.) in DMF (60 mL) was treated with ethyl bromopyruvate (3.3 g, 1.1 equiv.). The reaction mixture was heated at 150° C. for 24 h. The reaction mixture was cooled and diluted with water, and made basic with aqueous ammonia. The product gradually precipitated out, was filtered and dried. The crude material was purified by column chromatography to obtain ethyl 7-nitrobenzo[d]imidazo[2,1-b]thiazole-2-carboxylate.

Step 2: Synthesis of ethyl 7-aminobenzo[d]imidazo[2,1-b]thiazole-2-carboxylate: To a solution of ethyl 7-nitrobenzo[d]imidazo[2,1-b]thiazole-2-carboxylate (2 g, 1 equiv.) in ethanol: water 2:1 (30 mL), ammonium chloride (3.6 g, 10 equiv.) and iron powder (1.5 g, 4 equiv.) were added and refluxed at 80° C. for 2 h. After 2 h the reaction mixture was filtered through a bed of CELITE®. The filtrate was concentrated to the crude product which was purified by flash column chromatography using silica gel and EtOAc:pet ether as eluent to afford ethyl 7-aminobenzo[d]imidazo[2,1-b]thiazole-2-carboxylate. LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.273 min; LCMS (ES-API), m/z 2.62.2 (M+H).

Step 3: Synthesis of Example 3: Example 3 was prepared using the methods outlined for Example 1 using 6-chloro-4-(cyclopentylamino)-N-methylnicotinamide and ethyl 7-aminobenzo[d]imidazo[2,1-b]thiazole-2-carboxylate. ¹H NMR: 400 MHz, DMSO-d₆: δ 1.33 (t, J=6.80 Hz, 3H), 1.49-1.71 (m, 6H), 1.95-2.00 (m, 2H), 2.75 (d, J=4.40 Hz, 3H), 3.80-3.84 (m, 1H), 4.32 (q, J=7.20 Hz, 2H), 6.06 (s, 1H), 7.56 (d, J=8.40 Hz, 1H), 8.16-8.23 (m, 3H), 8.65 (bs, 1H), 9.06 (s, 1H), 9.16 (bs, 1H), 9.99 (bs, 1H). LC/MS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.826 min; LCMS (ES-API), m/z 479.2 (M+H). HPLC: XBridge Phenyl (150×4.6 mm), 3.5μ; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μl/min; Retention time: 7.85 min.

Example 4

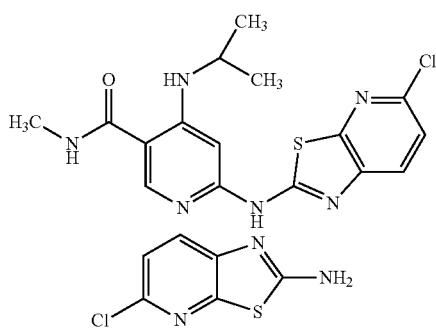

Step 1: Synthesis of 5-chlorothiazolo[5,4-b]pyridin-2-amine: To a stirred solution of 6-chloropyridin-3-amine (7.5 g, 1 equiv.) in acetic acid (35 mL) at 0° C. was added potassium thiocyanate (46 g, 8.1 equiv.) followed by dropwise addition of $Br_2$ (5 mL, 1.6 equiv.) in acetic acid (15 mL). The reaction mixture was allowed to stir at 0° C. for 2 h. The reaction mixture was then warmed to room temperature for 14 h. The reaction was quenched with ammonia solution which generated a solid precipitate. The precipitate was filtered and dried under vacuum to afford pure 5-chlorothiazolo[5,4-b]pyridin-2-amine. $^1$H NMR: 400 MHz, DMSO-$d_6$: δ 7.31 (d, J=8.40 Hz, 1H), 7.66 (d, J=8.00 Hz, 1H), 7.92 (s, 2H).

Step 2: Synthesis of 6-(5-chlorothiazolo[5,4-b]pyridin-2-ylamino)-4-(isopropylamino)-N-methylnicotinamide: Example 4 was prepared using the methods outlined for Example 1 using 6-chloro-4-(cyclopentylamino)-N-methylnicotinamide and 5-chlorothiazolo[5,4-b]pyridin-2-amine. $^1$H NMR: 400 MHz, DMSO-$d_6$: δ 1.31-1.32 (m, 6H), 2.89 (s, 3H), 3.70-3.77 (m, 1H), 6.32 (s, 1H), 7.39-7.41 (m, 1H), 7.88-7.90 (m, 1H), 8.38 (s, 1H). LC/MS: Ascentis Express C18, 5×2.1 mm, 2.7 μm; Solvent A=2% ACN: 98% $H_2O$: 10 mM $NH_4COOH$; Solvent B=98% ACN: 2% $H_2O$: 10 mM $NH_4COOH$; gradient 0-100% B over 1.5 min; retention time: 2.38 min; LCMS (ES-API), m/z 375.0 (M–H). HPLC: SunFire C18 (150×4.6 mm), 3.5μ; Solvent A=5% ACN: 95% $H_2O$: 0.05% TFA pH=2.5; Solvent B=95% ACN: 5% $H_2O$: 0.05% TFA pH=2.5; gradient 0-100% B over 30 min (36 min run time); Flow rate: 1.0 μl/min; Retention time: 12.84 min.

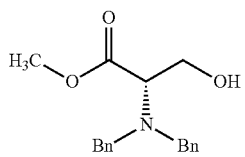 [SMILES: COC(=O)[C@H](CO)N(Cc1ccccc1)Cc1ccccc1]

Synthesis of methyl 2-(dibenzylamino)-3-hydroxypropanoate: To a solution of $K_2CO_3$ (34.8 g, 2 equiv.) in DMF (280 mL), was added L-serine methyl ester hydrochloride (1 equiv.), potassium iodide (10.8 g, 0.5 equiv.) and benzyl bromide (38 mL, 2.5 equiv.). The mixture was stirred for 16 h at room temperature. The reaction mixture was concentrated under reduced pressure to remove excess of DMF and then diluted with EtOAc. The organic layer was washed with brine and water. The organic layer was separated, dried over anhydrous sodium sulfate, filtered and concentrated. The crude material was purified by column chromatography through silica gel (EtOAC: pet ether as eluent) to afford methyl 2-(dibenzylamino)-3-hydroxypropanoate. $^1$H NMR: 400 MHz, DMSO-$d_6$: δ 2.49 (s, 1H), 3.58-3.59 (m, 1H), 3.67-3.70 (m, 2H), 3.73-3.75 (m, 2H), 3.77-3.80 (m, 3H), 3.90-3.94 (m, 2H), 7.24-7.38 (m, 10H).

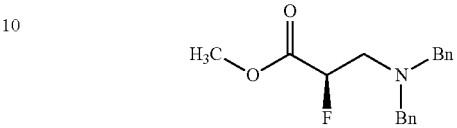

Synthesis of (R)-methyl 3-(dibenzylamino)-2-fluoropropanoate: To an ice cool solution of methyl 2-(dibenzylamino)-3-hydroxypropanoate (15 g, 1 equiv.) in THF (95 mL), DAST (13.1 mL, 1.23 equiv.) was added dropwise under $N_2$-atmosphere and the reaction mixture was stirred for 14 h at room temperature. The reaction mixture was quenched with aq. 10% $NaHCO_3$ solution at 0° C. and extracted into ethyl acetate (twice). The organic layers were collected, dried over anhydrous sodium sulfate, filtered and concentrated. The crude product was purified by flash column chromatography using silica gel and EtOAc:pet ether to afford (R)-methyl 3-(dibenzylamino)-2-fluoropropanoate. $^1$H NMR: 400 MHz, $CDCl_3$: δ 2.93-3.11 (m, 2H), 3.51-3.55 (m, 2H), 3.70 (s, 3H), 3.82-3.85 (m, 2H), 4.98-5.13 (m, 1H), 7.22-7.34 (m, 10H).

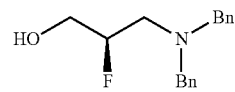

Synthesis of (S)-3-(dibenzylamino)-2-fluoropropan-1-ol: To a stirred solution of $LiBH_4$ (34.5 mL, 1.4 equiv.) in THF (300 mL), (R)-methyl 3-(dibenzylamino)-2-fluoropropanoate (15 g, 1 equiv.), in THF (150 mL), was added dropwise under $N_2$-atm. The reaction mixture was stirred for 16 h at room temperature. The reaction mixture was quenched with saturated solution of ammonium chloride at 0° C. and extracted into ethyl acetate (twice). The organic layers were collected together, dried over anhydrous sodium sulfate, filtered and concentrated. The crude product was purified by flash column chromatography using silica gel and EtOAc: pet ether to afford (R)-3-(dibenzylamino)-2-fluoropropan-1-ol.

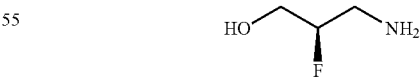

Synthesis of (R)-3-amino-2-fluoropropan-1-ol: To a degassed solution of (R)-3-(dibenzylamino)-2-fluoropropan-1-ol (2 g, 1 equiv.) in ethanol (50 mL), 10% Pd/C (0.2 equiv.) and $Pd(OH)_2$ (0.2 equiv.), were added and the reaction mixture was hydrogenated in an autoclave at 60° C. at 10 Kg (140 psi) pressure for 14 h. The reaction mixture was filtered through CELITE® and the filtrate was concentrated to afford (R)-3-amino-2-fluoropropan-1-ol.

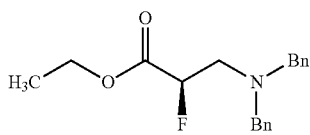 [SMILES: CCOC(=O)[C@H](F)CN(Cc1ccccc1)Cc1ccccc1]

Synthesis of (R)-ethyl 3-(dibenzylamino)-2-fluoropropanoate: Prepared according to the method as described for the synthesis of (R)-methyl 3-(dibenzylamino)-2-fluoropropanoate.

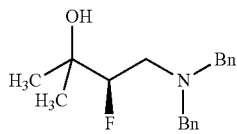 [SMILES: CC(C)(O)[C@H](F)CN(Cc1ccccc1)Cc1ccccc1]

Synthesis of (R)-4-(dibenzylamino)-3-fluoro-2-methylbutan-2-ol: To a solution of (R)-ethyl 3-(dibenzylamino)-2-fluoropropanoate (15 g, 1 equiv.) in THF (150 mL), methyl magnesium bromide (3M in diethyl ether) (15 mL, 2.5 equiv.) was added dropwise at 0° C. under $N_2$ atm. The reaction mixture was slowly allowed to attain room temperature and stirred for 1 h. The reaction mixture was quenched with saturated aqueous ammonium chloride at 0° C. and extracted into ethyl acetate (twice). The organic layers were collected, dried over anhydrous sodium sulfate, filtered and concentrated. The crude product was purified by flash column chromatography using silica gel and EtOAc: pet ether to afford (R)-4-(dibenzylamino)-3-fluoro-2-methylbutan-2-ol. $^1$H NMR: 400 MHz, DMSO-$d_6$: δ 0.92-0.92 (m, 3H), 0.98-0.98 (m, 3H), 2.53-2.94 (m, 2H), 3.51-3.81 (m, 4H), 4.34-4.46 (m, 1H), 4.80 (s, 1H), 7.22-7.40 (m, 10H).

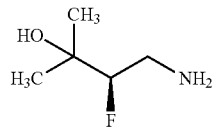

Synthesis of (R)-4-amino-3-fluoro-2-methylbutan-2-ol: (R)-4-(Dibenzylamino)-3-fluoro-2-methylbutan-2-ol was deprotected using the procedures outlined for the synthesis of (R)-3-amino-2-fluoropropan-1-ol.

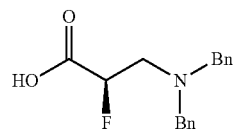 [SMILES: O=C(O)[C@H](F)CN(Cc1ccccc1)Cc1ccccc1]

Synthesis of (R)-3-(dibenzylamino)-2-fluoropropanoic acid: To a solution of (R)-ethyl 3-(dibenzylamino)-2-fluoropropanoate (5.5 g, 1 equiv.) in EtOH (30 mL), LiOH (5 equiv.) dissolved in water (30 mL) was added. The reaction mixture was stirred at room temperature for 12 h. The reaction mixture was concentrated and the residue obtained was dissolved in minimum amount of water and neutralized with 6N HCl resulting in white solid. The precipitate was filtered and dried under vacuum to afford (R)-3-(dibenzylamino)-2-fluoropropanoic acid. LC/MS: Acquity BEH C18 2.1×50 mm, 1.8μ; Solvent A=0.1% TFA in water; Solvent B=0.1% TFA in ACN; gradient 0-100% B over 2 min; retention time: 0.64 min; LCMS (ES-API), m/z 288.8 (M+H).

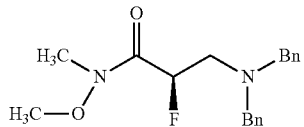

Synthesis of (R)-3-(dibenzylamino)-2-fluoro-N-methoxy-N-methylpropanamide: To a solution of (R)-3-(dibenzylamino)-2-fluoropropanoic acid (1.4 g, 1 equiv.) in DMF (5 mL), N,O-dimethylhydroxylamine.HCl (0.7 g, 1.5 equiv.), EDC.HCl (1.8 g, 2 equiv.) and DIPEA (4.5 mL, 5 equiv.) were added followed by the addition of HOBT (0.65 g, 1 equiv.). The reaction mixture was stirred at room temperature. The reaction mixture was concentrated under reduced pressure to remove excess of DMF and the residue obtained was diluted with ethyl acetate and washed with brine solution followed by water. The organic layer was collected and dried over anhydrous sodium sulfate, filtered and concentrated. The crude material was purified by flash chromatography through silica gel and EtOAC: pet ether as eluent to afford (R)-3-(dibenzylamino)-2-fluoro-N-methoxy-N-methylpropanamide. LC/MS: Acquity BEH C18 2.1×50 mm, 1.8μ; Solvent A=0.1% TFA in water; Solvent B=0.1% TFA in ACN; gradient 0-100% B over 2 min; retention time: 0.71 min; LCMS (ES-API), m/z 331.8 (M+H).

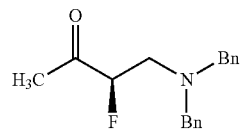

Synthesis of (R)-4-(dibenzylamino)-3-fluorobutan-2-one: A solution of (R)-3-(dibenzylamino)-2-fluoro-N-methoxy-N-methylpropanamide (0.9 g, 1 equiv.) in THF (10 mL) was cooled to 0° C. Methyl magnesium bromide (3 equiv, 3M in diethyl ether) was added to the reaction mixture. After completion of addition the reaction was warmed to room temperature and stirred for 1 h. The reaction was quenched using saturated ammonium chloride solution and extracted with ethyl acetate. The organic layer was collected and dried over anhydrous sodium sulfate, filtered and concentrated to afford the title compound (R)-4-(dibenzylamino)-3-fluorobutan-2-one. LC/MS: Acquity BEH C18 2.1×50 mm, 1.8μ; Solvent A=0.1% TFA in water; Solvent B=0.1% TFA in ACN; gradient 0-100% B over 2 min; retention time: 0.73 min; LCMS (ES-API), m/z 286.8 (M+H).

Synthesis of (R)-1-(dibenzylamino)-2-fluoro-4-methylpentan-3-one and (R)-1-cyclopropyl-3-(dibenzylamino)-2-fluoropropan-1-one: These compounds were prepared using the methods described for the synthesis of (R)-4-(dibenzylamino)-3-fluorobutan-2-one using iso-propyl or cyclopropyl Grignard reagents, respectively.

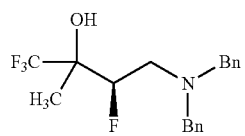 [SMILES: CC(O)([C@H](F)CN(Cc1ccccc1)Cc1ccccc1)C(F)(F)F]

Synthesis of (R)-4-(dibenzylamino)-1,1,1,3-tetrafluoro-2-methylbutan-2-ol: To a solution of (R)-4-(dibenzylamino)-3-fluorobutan-2-one (1.2 g, 1 equiv.) in THF (15 mL), CF₃TMS (3 g, 5 equiv.) was added and stirred for 30 min. The reaction mixture was cooled to 0° C. and added TBAF (1M in THF, 21 mL, 5 equiv.) dropwise to the reaction mixture. The reaction mixture was allowed to stir for 16 h at room temperature and quenched with 2 M HCl. The product was extracted into MTBE, and the organic layer was collected and dried over anhydrous sodium sulfate, filtered and concentrated. The crude material was purified by flash chromatography through silica gel and EtOAC:pet ether as eluent to afford the title compound (R)-4-(dibenzylamino)-1,1,1,3-tetrafluoro-2-methylbutan-2-ol as a mixture of diastereomers. LC/MS: Acquity BEH C18 2.1×50 mm, 1.8µ; Solvent A=0.1% TFA in water; Solvent B=0.1% TFA in ACN; gradient 0-100% B over 2 min; retention time: 0.77 min; LCMS (ES-API), m/z 356.8 (M+H).

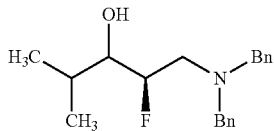 [SMILES: CC(C)C(O)[C@H](F)CN(Cc1ccccc1)Cc1ccccc1]

Synthesis of (2R)-1-(dibenzylamino)-2-fluoro-4-methylpentan-3-ol: To (R)-1-(dibenzylamino)-2-fluoro-4-methylpentan-3-one (0.9 g, 1 equiv.) in THF:MeOH (2:1) (10 mL), NaBH₄ (0.2 g, 2 equiv.) was added in portions at 0° C. and allowed to stir for 1 h. The reaction was quenched with saturated NH₄Cl solution at ambient temperature and concentrated under reduced pressure to remove excess of solvent. The residue obtained was diluted with ethyl acetate and washed with water. The organic layer was collected and dried over anhydrous sodium sulfate, filtered and concentrated. The material obtained was washed with diethyl ether and dried under vacuum to afford (2R)-1-(dibenzylamino)-2-fluoro-4-methylpentan-3-ol as a mixture of diastereomers. LC/MS: Acquity BEH C18 2.1×50 mm, 1.8µ; Solvent A=0.1% TFA in water; Solvent B=0.1% TFA in ACN; gradient 0-100% B over 2 min; retention time: 0.76 min; LCMS (ES-API), m/z 316.8 (M+H).

Synthesis of (2R)-1-cyclopropyl-3-(dibenzylamino)-2-fluoropropan-1-ol and (3R)-4-(dibenzylamino)-3-fluorobutan-2-ol: These compounds were prepared using the methods described for the synthesis of (2R)-1-(dibenzylamino)-2-fluoro-4-methylpentan-3-ol starting from (R)-1-cyclopropyl-3-(dibenzylamino)-2-fluoropropan-1-one and (R)-4-(dibenzylamino)-3-fluorobutan-2-one.

Synthesis of (3R)-2-cyclopropyl-4-(dibenzylamino)-1,1,1,3-tetrafluorobutan-2-ol: This compound was prepared using the method described for the synthesis of compound no. (R)-4-(dibenzylamino)-1,1,1,3-tetrafluoro-2-methylbutan-2-ol starting from (R)-1-cyclopropyl-3-(dibenzylamino)-2-fluoropropan-1-one.

Synthesis of (3R)-4-amino-1,1,1,3-tetrafluoro-2-methylbutan-2-ol, (2R)-1-amino-2-fluoro-4-methylpentan-3-ol, (2R)-3-amino-1-cyclopropyl-2-fluoropropan-1-ol, (3R)-4-amino-3-fluorobutan-2-ol, (3R)-4-amino-2-cyclopropyl-1,1,1,3-tetrafluorobutan-2-ol: These compounds were prepared using the benzyl deprotection method described for the synthesis of (R)-3-amino-2-fluoropropan-1-ol.

(3R)-4-Amino-1,1,1,3-tetrafluoro-2-methylbutan-2-ol: LC/MS: ELSD method. Retention time: 1.804 min; LCMS (ES-API), m/z 175.6 (M–H).

Example 5

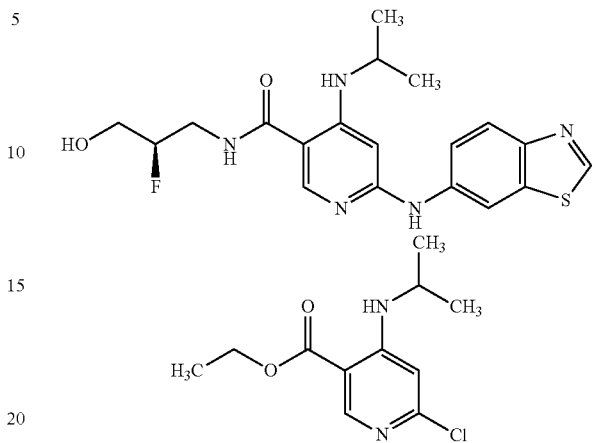

Step 1: Synthesis of ethyl 6-chloro-4-(isopropylamino)nicotinate: To a solution of ethyl 4,6-dichloronicotinate (1 g, 1 equiv.) in DMA (5 mL) was added DIPEA (3.97 mL, 5 equiv.) and propan-2-amine (0.5 g, 2 equiv.). The mixture was heated at 50° C. for 12 h. The reaction mixture was concentrated under reduced pressure to remove excess solvent. The residue was dissolved in ethyl acetate and washed water followed by brine. The organic layer was collected, dried over Na₂SO₄, filtered and concentrated to get the crude product. The product was purified by flash chromatography through silica gel (EtOAC: pet ether as eluent) to afford ethyl 6-chloro-4-(isopropylamino)nicotinate. LC/MS: Acquity BEH C18 2.1×50 mm, 1.8µ; Solvent A=0.1% TFA in water; Solvent B=0.1% TFA in ACN; gradient 0-100% B over 2 min; retention time: 0.90 min; LCMS (ES-API), m/z 243.7 (M+H).

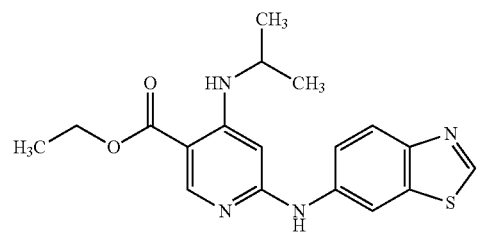 [SMILES: CCOC(=O)c1cnc(Nc2ccc3ncsc3c2)cc1NC(C)C]

Step 2: Synthesis of ethyl 6-(benzo[d]thiazol-6-ylamino)-4-(isopropylamino)nicotinate: To a solution of ethyl 6-chloro-4-(isopropylamino)nicotinate (5 g, 20.66 mmol) in dioxane (30 mL) and H₂O (5 mL) was added 6-amino benzothiazole (1 equiv.), xanthphos (0.4 equiv.) and Na₂CO₃ (4 equiv.) followed by Pd₂(dba)₃ (0.4 equiv.) to the reaction mixture and heated at 115° C. for 12 h. The reaction mass was cooled and filtered. The filtrate obtained was concentrated to provide crude material. The crude material was purified by column chromatography through silica gel (EtOAc:pet ether as eluent) to afford ethyl 6-(benzo[d]thiazol-6-ylamino)-4-(isopropylamino)nicotinate (5 g, 68% yield). LC/MS: Acquity BEH C18 2.1×50 mm, 1.8µ; Solvent A=0.1% TFA in water; Solvent B=0.1% TFA in ACN; gradient 0-100% B over 2 min; retention time: 0.78 min; LCMS (ES-API), m/z 357.8 (M+H). ¹H NMR (400 MHz CD₃OD) δ 1.20-1.32 (m, 6H), 1.34-1.41 (m, 3H), 4.27-4.36

(m, 2H), 6.02 (s, 1H), 7.51 (dd, J=2.80, 11.60 Hz, 1H), 7.95-7.98 (m, 1H), 8.33 (d, J=2.40 Hz, 1H), 8.57 (s, 1H), 9.08 (s, 1H).

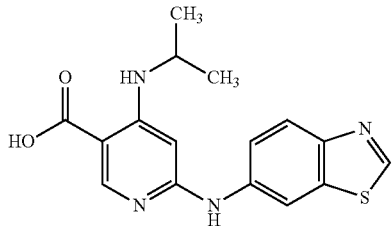 [SMILES: CC(C)Nc1cc(Nc2ccc3ncsc3c2)ncc1C(=O)O]

Step 3: Synthesis of 6-(benzo[d]thiazol-6-ylamino)-4-(isopropylamino)nicotinic acid: To a solution of ethyl 6-(benzo[d]thiazol-6-ylamino)-4-(isopropylamino)nicotinate (1 g, 1 equiv.) in ethanol:water (2:1) (10 mL) was added lithium hydroxide (5 equiv.) and stirred at room temperature for 12 h. The reaction mixture was concentrated, diluted with EtOAc and added water. The aqueous layer was collected and acidified to pH 3-4 using citric acid in ice. The acid product precipitated and was filtered and dried under vacuum to furnish 6-(benzo[d]thiazol-6-ylamino)-4-(isopropylamino)nicotinic acid. LC/MS: Acquity BEH C18 2.1×50 mm, 1.8μ; Solvent A=0.1% TFA in water; Solvent B=0.1% TFA in ACN; gradient 0-100% B over 2 min; retention time: 0.65 min; LCMS (ES-API), m/z 329.8 (M+H).

Step 4: Synthesis of (R)-6-(benzo[d]thiazol-6-ylamino)-N-(2-fluoro-3-hydroxypropyl)-4-(isopropylamino)nicotinamide: To a stirred solution of 6-(benzo[d]thiazol-6-ylamino)-4-(isopropylamino)nicotinic acid (0.2 g, 1 equiv.) and (R)-3-amino-2-fluoropropan-1-ol (1.2 equiv.) in DMF (5 mL), were added sequentially DIPEA (4 equiv.) and HATU (1 equiv.) and stirred for 4 h. The reaction mixture was concentrated under reduced pressure to remove excess of DMF. The residue obtained was partitioned between water and EtOAc. The organic layer was separated, dried over anhydrous sodium sulfate, filtered and concentrated. The product was purified by column chromatography through silica gel and MeOH: CHCl$_3$ as eluent to afford Example 5. $^1$H NMR: 400 MHz, CD$_3$OD: δ 1.28 (d, J=6.40 Hz, 6H), 1.99 (s, 2H), 3.54-3.84 (m, 5H), 4.60-4.75 (m, 1H), 6.05 (s, 1H), 7.52 (dd, J=2.40, 8.80 Hz, 1H), 7.97 (d, J=8.80 Hz, 1H), 8.26 (s, 1H), 8.36 (d, J=2.40 Hz, 1H), 9.08 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.613 min; LCMS (ES-API), m/z 404.2 (M+H). HPLC: Eclipse XDB C18 (150×4.6 mm) 5μ; Solvent A=20 mM NH$_4$OAc in water; Solvent B=ACN; gradient 0-100% B over 20 min; Flow rate=1.0 mL/min; Retention time: 7.39 min.

The Examples highlighted in Table 1 were prepared using the methods outlined for Example 5 using the appropriate starting material and amine.

TABLE 1

| Ex. No. | Structure | HPLC RT (min) | HPLC cond. | LCMS |
|---|---|---|---|---|
| 5 | 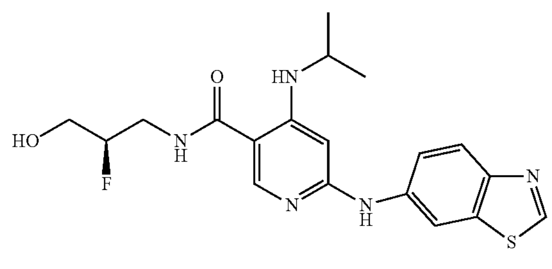 [SMILES: CC(C)Nc1cc(Nc2ccc3ncsc3c2)ncc1C(=O)NC[C@@H](F)CO] | 7.39 | C | 404.2 M + H |
| 6 | 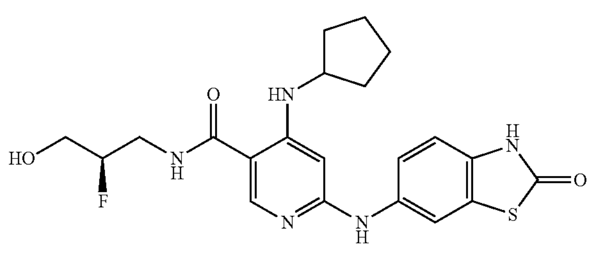 [SMILES: O=C(NC[C@@H](F)CO)c1cnc(Nc2ccc3[nH]c(=O)sc3c2)cc1NC1CCCC1] | 6.61 | A | 444.0 M − H |
| 7 | 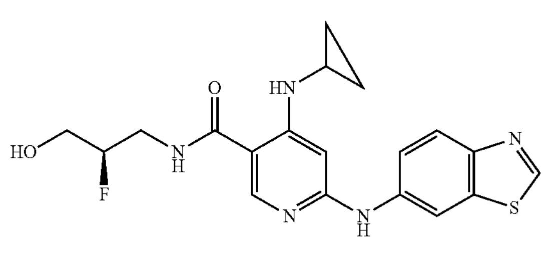 [SMILES: O=C(NC[C@@H](F)CO)c1cnc(Nc2ccc3ncsc3c2)cc1NC1CC1] | 7.23 | C | 400.0 M − H |

TABLE 1-continued

| Ex. No. | Structure | HPLC RT (min) | HPLC cond. | LCMS |
|---|---|---|---|---|
| 8 | 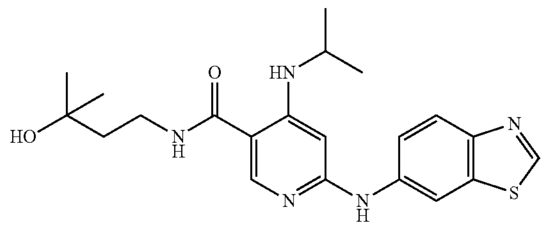 [SMILES: CC(C)Nc1cc(Nc2ccc3ncsc3c2)ncc1C(=O)NCCC(C)(C)O] | 9.21 | A | 414.2 M + H |
| 9 | 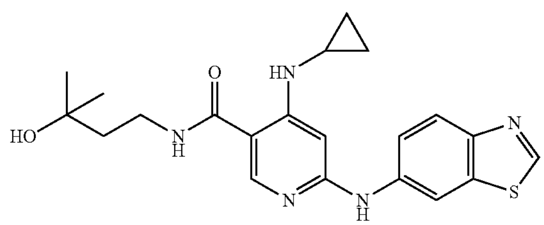 [SMILES: CC(C)(O)CCNC(=O)c1cnc(Nc2ccc3ncsc3c2)cc1NC1CC1] | 5.34 | B | 412.2 M + H |
| 10 | 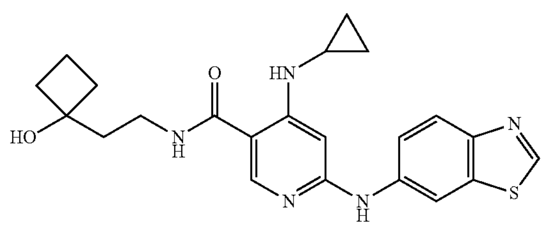 [SMILES: O=C(NCCC1(O)CCC1)c1cnc(Nc2ccc3ncsc3c2)cc1NC1CC1] | 1.35 | D | 424.2 M + H |
| 11 | 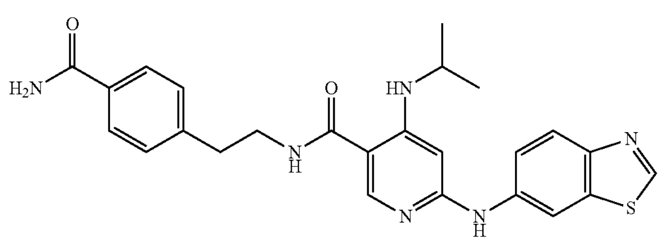 [SMILES: CC(C)Nc1cc(Nc2ccc3ncsc3c2)ncc1C(=O)NCCc1ccc(C(N)=O)cc1] | 5.92 | E | 475.2 M + H |
| 12 | 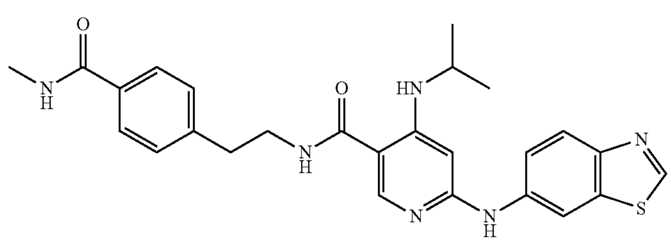 [SMILES: CNC(=O)c1ccc(CCNC(=O)c2cnc(Nc3ccc4ncsc4c3)cc2NC(C)C)cc1] | — | — | 489.0 M + H |

The Examples highlighted in Table 2 were prepared using the methods outlined for Example 5 using the appropriate starting material and amine.

TABLE 2

| Ex. No. | Structure | HPLC RT (min) | HPLC cond. | LCMS |
|---|---|---|---|---|
| 13 | 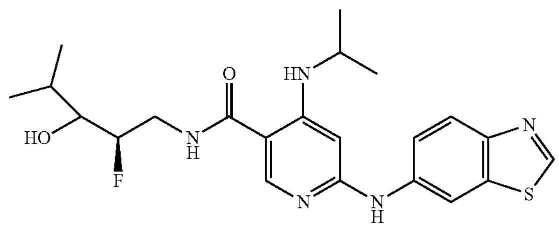 [SMILES: CC(C)Nc1cc(Nc2ccc3ncsc3c2)ncc1C(=O)NC[C@@H](F)C(O)C(C)C] | 9.28 | C | 446.2 M + H |
| 14 | 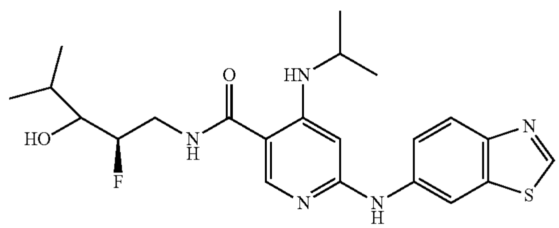 [SMILES: CC(C)Nc1cc(Nc2ccc3ncsc3c2)ncc1C(=O)NC[C@@H](F)C(O)C(C)C] | 9.75 | C | 446.2 M + H |
| 15 | 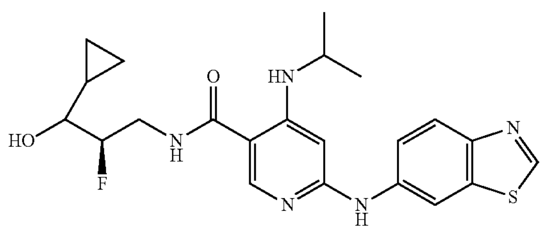 [SMILES: CC(C)Nc1cc(Nc2ccc3ncsc3c2)ncc1C(=O)NC[C@@H](F)C(O)C1CC1] | 6.30 | E | 444.2 M + H |
| 16 | 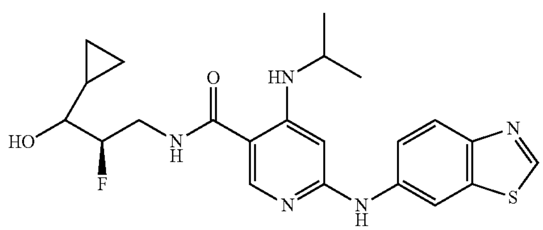 [SMILES: CC(C)Nc1cc(Nc2ccc3ncsc3c2)ncc1C(=O)NC[C@@H](F)C(O)C1CC1] | 6.36 | E | 444.2 M + H |
| 17 | 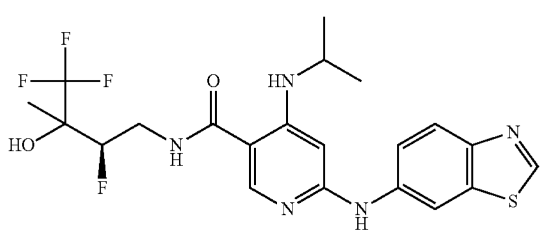 [SMILES: CC(C)Nc1cc(Nc2ccc3ncsc3c2)ncc1C(=O)NC[C@@H](F)C(C)(O)C(F)(F)F] | 6.69 | E | 486.2 M + H |
| 18 | 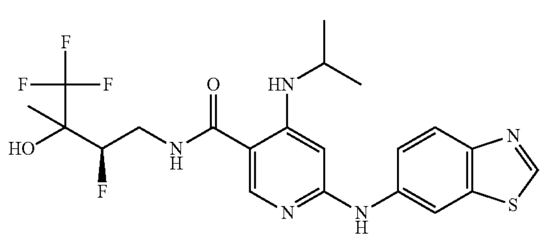 [SMILES: CC(C)Nc1cc(Nc2ccc3ncsc3c2)ncc1C(=O)NC[C@@H](F)C(C)(O)C(F)(F)F] | 6.81 | E | 486.2 M + H |

TABLE 2-continued
| Ex. No. | Structure | HPLC RT (min) | HPLC cond. | LCMS |
|---|---|---|---|---|
| 19 | 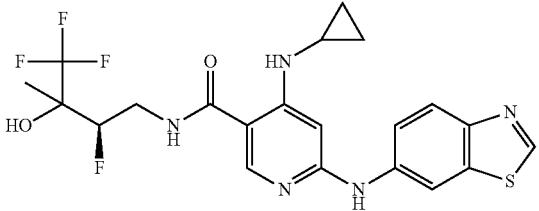 [SMILES: CC(O)([C@H](F)CNC(=O)c1cnc(Nc2ccc3ncsc3c2)cc1NC1CC1)C(F)(F)F] | 6.56 | E | 484.0 M + H |
| 20 | 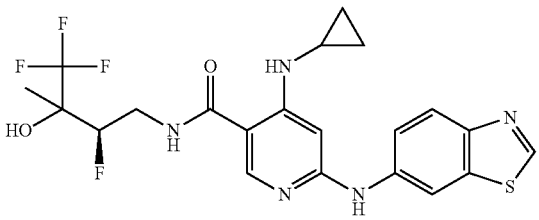 [SMILES: CC(O)([C@H](F)CNC(=O)c1cnc(Nc2ccc3ncsc3c2)cc1NC1CC1)C(F)(F)F] | 6.80 | E | 484.0 M + H |
| 22 | 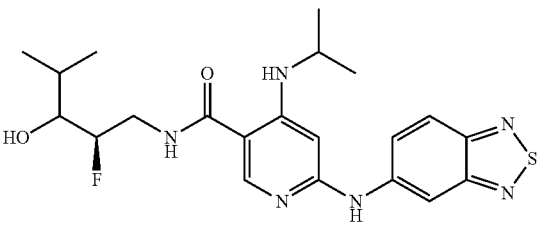 [SMILES: CC(C)Nc1cc(Nc2ccc3nsnc3c2)ncc1C(=O)NC[C@@H](F)C(O)C(C)C] | 7.11 | E | 445.2 M − H |
| 23 | 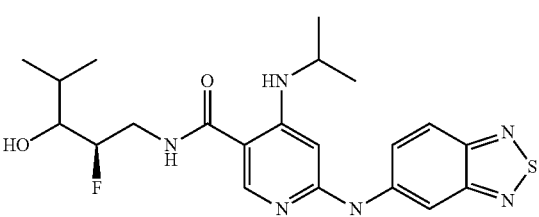 | 6.92 | E | 445.2 M − H |
| 24 | 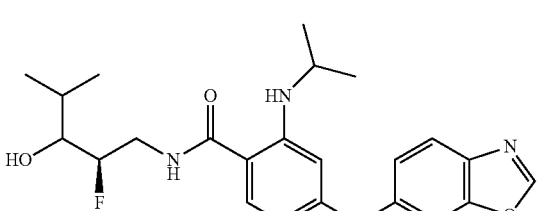 | 6.27 | E | 430.2 M + H |
| 25 | 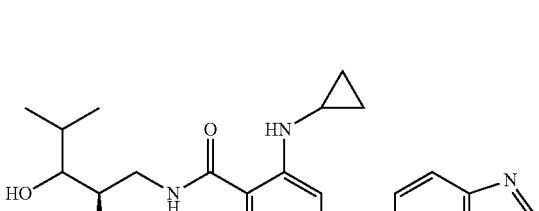 | 11.02 | A | 444.2 M + H |

TABLE 2-continued

| Ex. No. | Structure | HPLC RT (min) | HPLC cond. | LCMS |
|---|---|---|---|---|
| 26 | 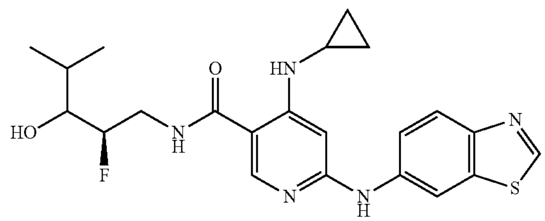 [SMILES: CC(C)C(O)[C@H](F)CNC(=O)c1cnc(Nc2ccc3ncsc3c2)cc1NC1CC1] | 10.57 | A | 444.2 M + H |
| 27 | 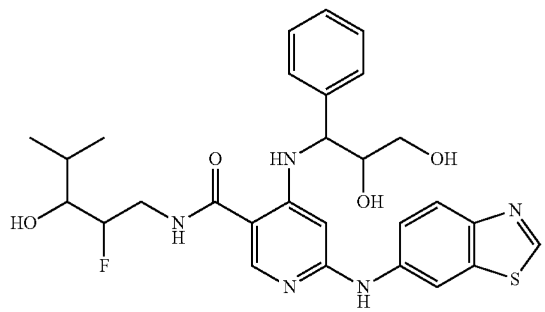 [SMILES: CC(C)C(O)C(F)CNC(=O)c1cnc(Nc2ccc3ncsc3c2)cc1NC(c1ccccc1)C(O)CO] | 5.86 | E | 554.2 M + H |
| 28 | 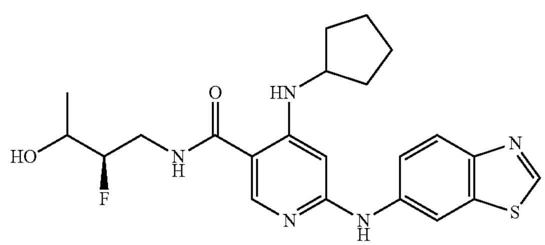 [SMILES: CC(O)[C@H](F)CNC(=O)c1cnc(Nc2ccc3ncsc3c2)cc1NC1CCCC1] | 6.10 | E | 444.2 M + H |
| 29 | 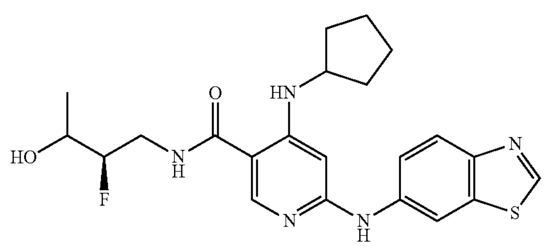 [SMILES: CC(O)[C@H](F)CNC(=O)c1cnc(Nc2ccc3ncsc3c2)cc1NC1CCCC1] | 6.04 | E | 444.2 M + H |
| 30 | 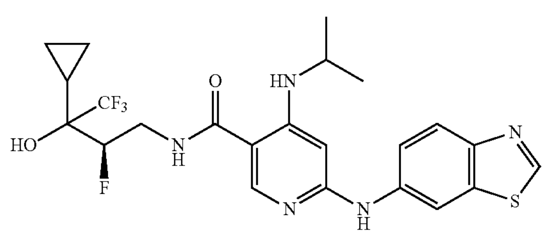 [SMILES: CC(C)Nc1cc(Nc2ccc3ncsc3c2)ncc1C(=O)NC[C@@H](F)C(O)(C1CC1)C(F)(F)F] | 7.21 | E | 512.2 M + H |
| 31 | 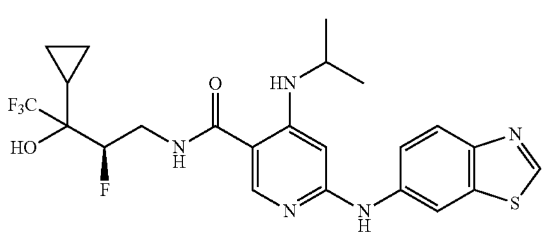 [SMILES: CC(C)Nc1cc(Nc2ccc3ncsc3c2)ncc1C(=O)NC[C@@H](F)C(O)(C1CC1)C(F)(F)F] | 7.27 | E | 512.2 M + H |

TABLE 2-continued

| Ex. No. | Structure | HPLC RT (min) | HPLC cond. | LCMS |
|---|---|---|---|---|
| 32 | 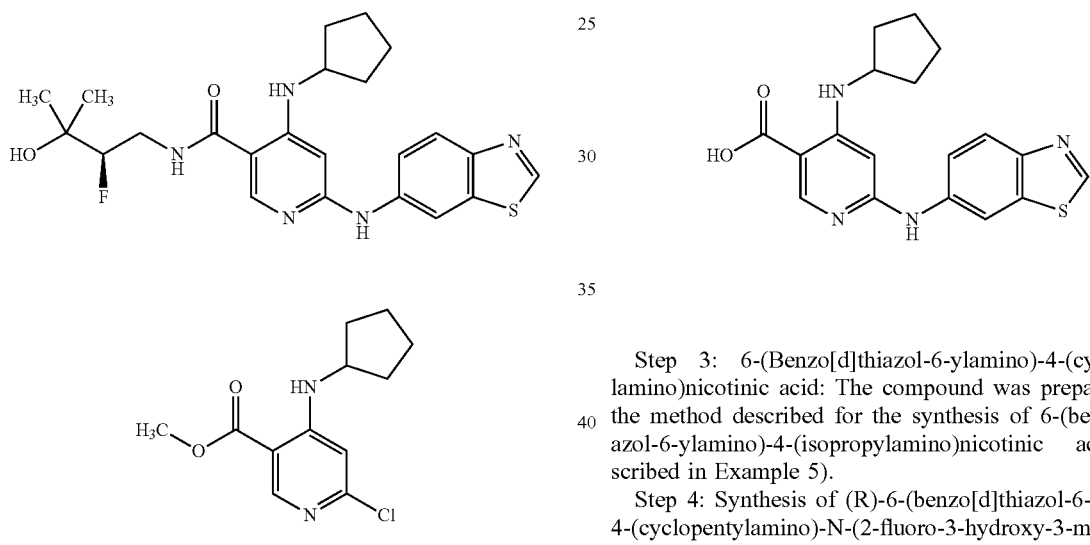 | 8.17 | A | 582.2 M + H |

Example 33 thiazol-6-ylamino)-4-(isopropylamino)nicotinate starting from methyl 6-chloro-4-(cyclopentylamino)nicotinate.

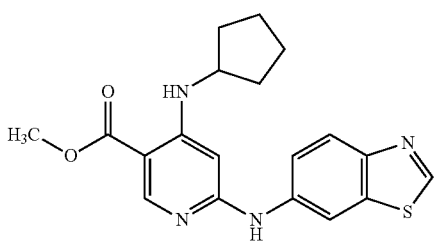 [SMILES: COC(=O)c1cnc(Nc2ccc3ncsc3c2)cc1NC1CCCC1]

Step 1: Methyl 6-chloro-4-(cyclopentylamino)nicotinate: The compound was prepared using the method described for the synthesis of ethyl 6-chloro-4-(isopropylamino)nicotinate starting from methyl 4,6-dichloronicotinate.

Step 2: Methyl 6-(benzo[d]thiazol-6-ylamino)-4-(cyclopentylamino)nicotinate: The compound was prepared using the method described for the synthesis of ethyl 6-(benzo[d]

Step 3: 6-(Benzo[d]thiazol-6-ylamino)-4-(cyclopentylamino)nicotinic acid: The compound was prepared using the method described for the synthesis of 6-(benzo[d]thiazol-6-ylamino)-4-(isopropylamino)nicotinic acid (described in Example 5).

Step 4: Synthesis of (R)-6-(benzo[d]thiazol-6-ylamino)-4-(cyclopentylamino)-N-(2-fluoro-3-hydroxy-3-methylbutyl)nicotinamide: Example 33 was prepared from 6-(Benzo[d]thiazol-6-ylamino)-4-(cyclopentylamino)nicotinic acid and (R)-4-amino-3-fluoro-2-methylbutan-2-ol (15) using the coupling procedure outlined for the preparation of Example 5: $^1$H NMR: 400 MHz, CD$_3$OD: δ 1.24-1.31 (m, 6H), 1.57-1.62 (m, 2H), 1.67-1.82 (m, 4H), 2.03-2.08 (m, 2H), 3.44-3.50 (m, 1H), 3.78-3.87 (m, 2H), 4.33-4.47 (m, 1H), 6.07 (s, 1H), 7.52 (dd, J=2.00, 8.80 Hz, 1H), 7.97 (d, J=8.80 Hz, 1H), 8.25 (s, 1H), 8.36 (d, J=2.00 Hz, 1H), 9.07 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.809 min; LCMS (ES-API), m/z 458.0 (M+H). HPLC: SunFire C18 (150×4.6 mm), 3.5μ; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μl/min; Retention time: 6.25 min.

The Examples highlighted in Table 3 below were prepared according to the methods outlined for Example 33, substituting where appropriate, alternate amines to properly prepare the desired Example.

TABLE 3

| Ex. No. | Structure | HPLC RT (min) | HPLC cond. | LCMS (M + H)+ |
|---|---|---|---|---|
| 33 | 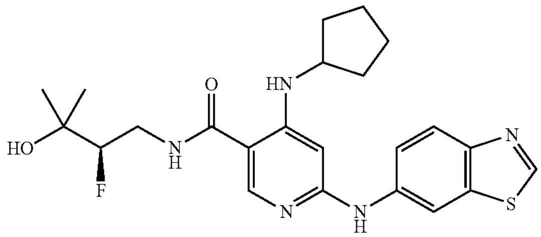 [SMILES: CC(C)(O)[C@H](F)CNC(=O)c1cnc(Nc2ccc3ncsc3c2)cc1NC1CCCC1] | 6.24 | E | 458.0 |
| 34 | 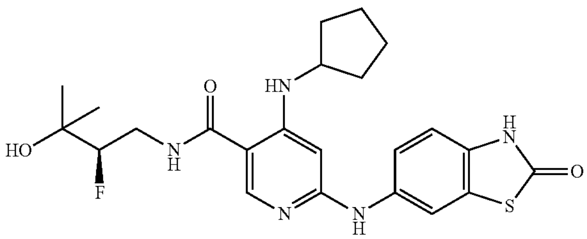 [SMILES: CC(C)(O)[C@H](F)CNC(=O)c1cnc(Nc2ccc3[nH]c(=O)sc3c2)cc1NC1CCCC1] | 7.31 | A | 472.0 M − H |
| 35 | 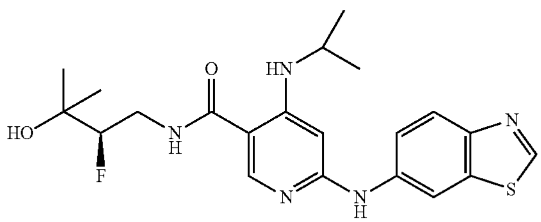 [SMILES: CC(C)Nc1cc(Nc2ccc3ncsc3c2)ncc1C(=O)NC[C@@H](F)C(C)(C)O] | 5.62 | E | 432.2 |
| 36 | 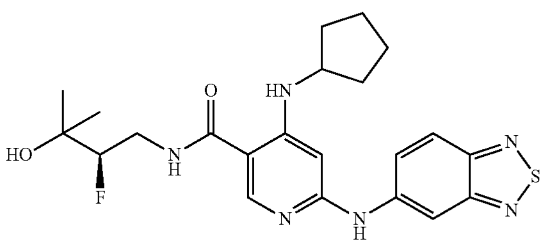 [SMILES: CC(C)(O)[C@H](F)CNC(=O)c1cnc(Nc2ccc3nsnc3c2)cc1NC1CCCC1] | 6.93 | B | 459.0 |
| 37 | 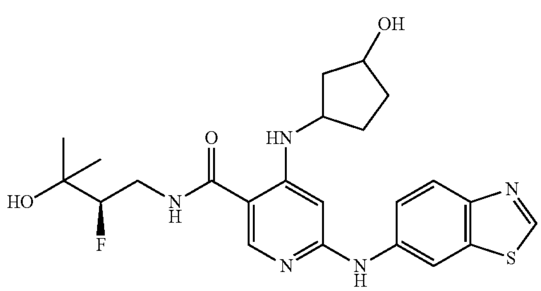 [SMILES: CC(C)(O)[C@H](F)CNC(=O)c1cnc(Nc2ccc3ncsc3c2)cc1NC1CCC(O)C1] | 9.43 | B | 474.0 |
| 38 | 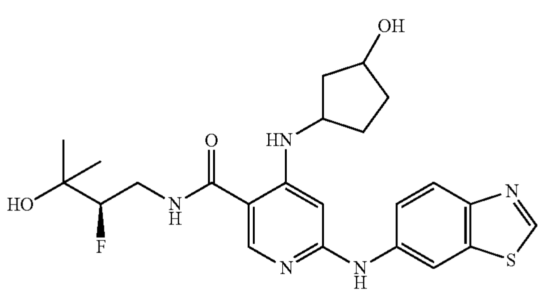 [SMILES: CC(C)(O)[C@H](F)CNC(=O)c1cnc(Nc2ccc3ncsc3c2)cc1NC1CCC(O)C1] | 9.77 | B | 474.0 |

TABLE 3-continued

| Ex. No. | Structure | HPLC RT (min) | HPLC cond. | LCMS (M + H)+ |
|---|---|---|---|---|
| 39 | 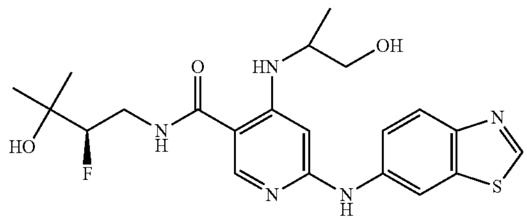 [SMILES: CC(CO)Nc1cc(Nc2ccc3ncsc3c2)ncc1C(=O)NC[C@@H](F)C(C)(C)O] | 9.37 | B | 448.2 |
| 40 | 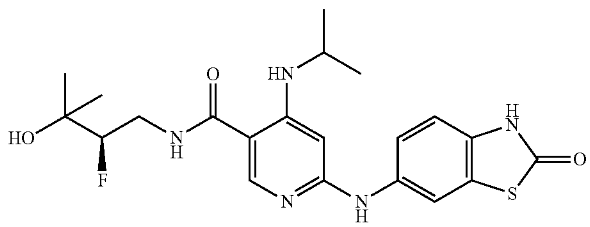 [SMILES: CC(C)Nc1cc(Nc2ccc3[nH]c(=O)sc3c2)ncc1C(=O)NC[C@@H](F)C(C)(C)O] | 5.69 | E | 446.2 M − H |
| 41 | 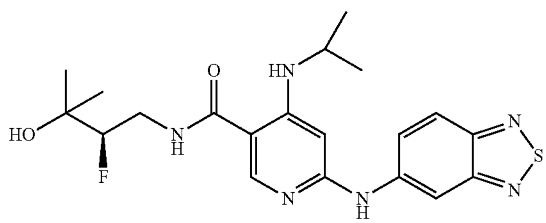 [SMILES: CC(C)Nc1cc(Nc2ccc3nsnc3c2)ncc1C(=O)NC[C@@H](F)C(C)(C)O] | 7.82 | A | 433.2 |
| 42 | 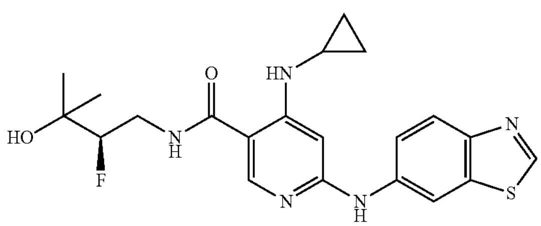 [SMILES: CC(C)(O)[C@H](F)CNC(=O)c1cnc(Nc2ccc3ncsc3c2)cc1NC1CC1] | 11.32 | B | 430.2 |
| 43 | 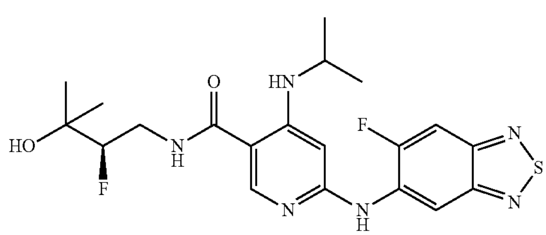 [SMILES: CC(C)Nc1cc(Nc2cc3nsnc3cc2F)ncc1C(=O)NC[C@@H](F)C(C)(C)O] | 6.28 | E | 450.14 |
| 44 | 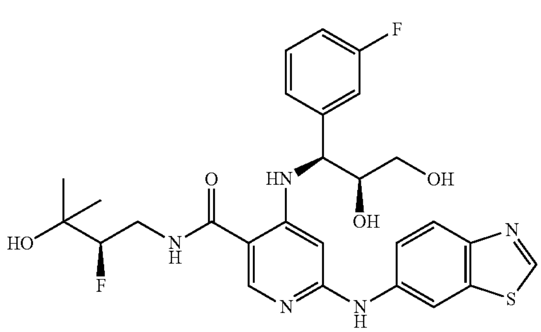 [SMILES: CC(C)(O)[C@H](F)CNC(=O)c1cnc(Nc2ccc3ncsc3c2)cc1N[C@@H](c1cccc(F)c1)[C@H](O)CO] | 5.39 | E | 559.2 |

TABLE 3-continued

| Ex. No. | Structure | HPLC RT (min) | HPLC cond. | LCMS (M + H)+ |
|---|---|---|---|---|
| 45 | 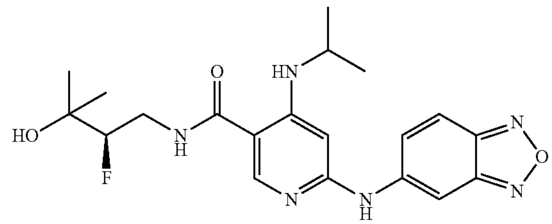 [SMILES: CC(C)Nc1cc(Nc2ccc3nonc3c2)ncc1C(=O)NC[C@@H](F)C(C)(C)O] | 7.76 | A | 417.2 |
| 46 | 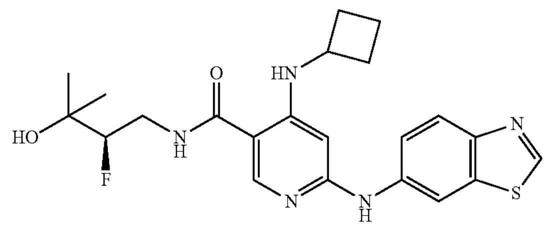 [SMILES: CC(C)(O)[C@H](F)CNC(=O)c1cnc(Nc2ccc3ncsc3c2)cc1NC1CCC1] | 7.02 | A (30 min gradient) | 445.2 |
| 47 | 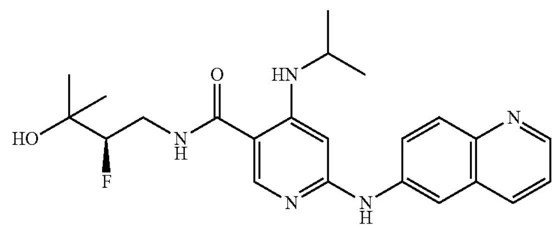 [SMILES: CC(C)Nc1cc(Nc2ccc3ncccc3c2)ncc1C(=O)NC[C@@H](F)C(C)(C)O] | 8.47 | E | 424.2 M − H |
| 48 | 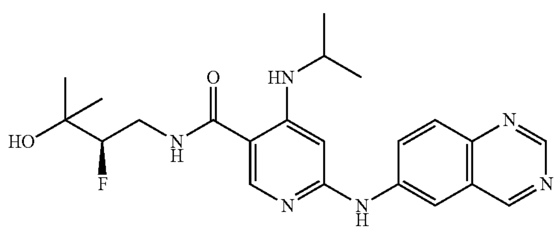 [SMILES: CC(C)Nc1cc(Nc2ccc3ncncc3c2)ncc1C(=O)NC[C@@H](F)C(C)(C)O] | 9.44 | A | 427.2 |
| 49 | 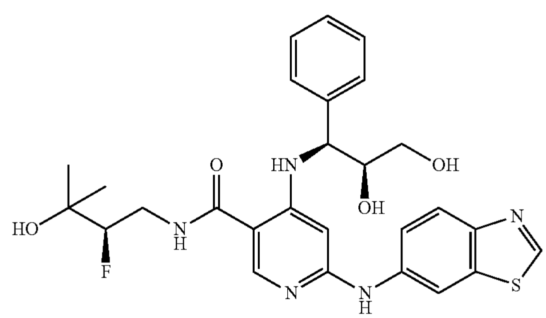 [SMILES: CC(C)(O)[C@H](F)CNC(=O)c1cnc(Nc2ccc3ncsc3c2)cc1N[C@@H](c1ccccc1)[C@H](O)CO] | 5.23 | E | 540.2 |
| 50 | 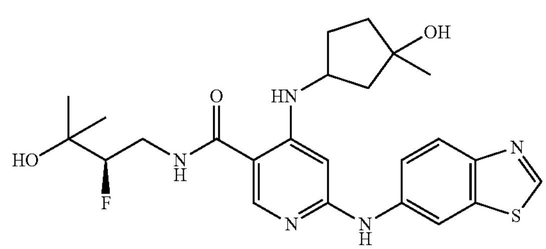 [SMILES: CC1(O)CCC(Nc2cc(Nc3ccc4ncsc4c3)ncc2C(=O)NC[C@@H](F)C(C)(C)O)C1] | 5.23 | E | 488.2 |

TABLE 3-continued

| Ex. No. | Structure | HPLC RT (min) | HPLC cond. | LCMS (M + H)+ |
|---|---|---|---|---|
| 51 | 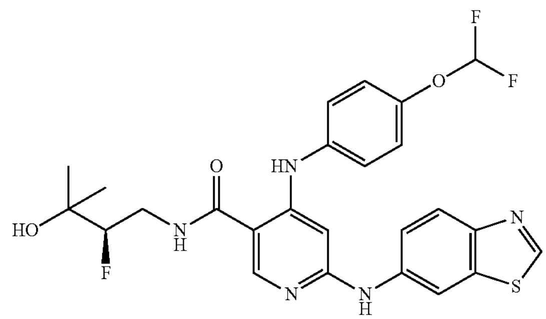 [SMILES: CC(C)(O)[C@H](F)CNC(=O)c1cnc(Nc2ccc3ncsc3c2)cc1Nc1ccc(OC(F)F)cc1] | 6.84 | E | 532.2 |
| 52 | 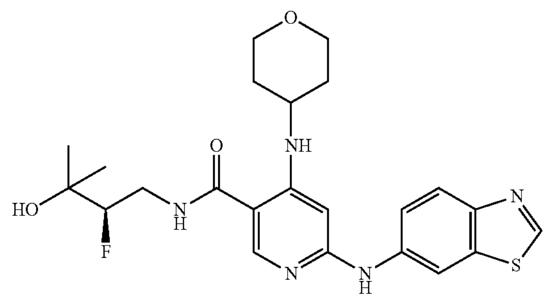 [SMILES: CC(C)(O)[C@H](F)CNC(=O)c1cnc(Nc2ccc3ncsc3c2)cc1NC1CCOCC1] | 5.74 | E | 474.2 |
| 53 | 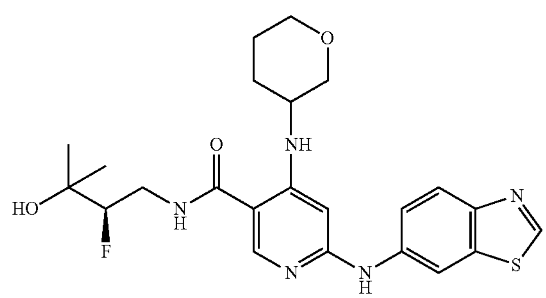 [SMILES: CC(C)(O)[C@H](F)CNC(=O)c1cnc(Nc2ccc3ncsc3c2)cc1NC1CCCOC1] | 5.53 | E | 474.2 |
| 54 | 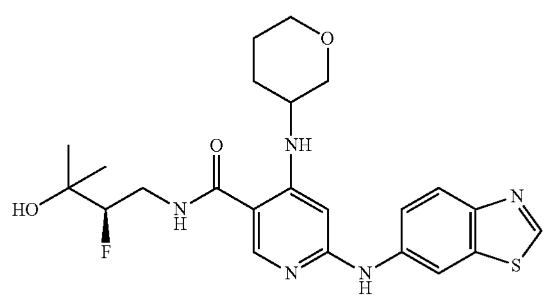 [SMILES: CC(C)(O)[C@H](F)CNC(=O)c1cnc(Nc2ccc3ncsc3c2)cc1NC1CCCOC1] | 5.52 | E | 474.2 |
| 55 | 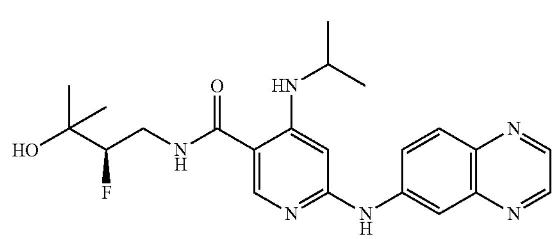 [SMILES: CC(C)Nc1cc(Nc2ccc3nccnc3c2)ncc1C(=O)NC[C@@H](F)C(C)(C)O] | 5.24 | E | 427.2 |

TABLE 3-continued

| Ex. No. | Structure | HPLC RT (min) | HPLC cond. | LCMS (M + H)+ |
|---------|-----------|---------------|------------|---------------|
| 56 | 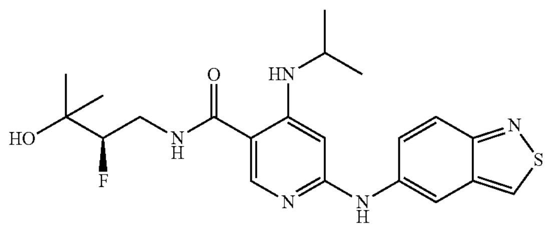 [SMILES: CC(C)Nc1cc(Nc2ccc3nscc3c2)ncc1C(=O)NC[C@@H](F)C(C)(C)O] | 6.06 | E | 430.2 M − H |
| 57 | 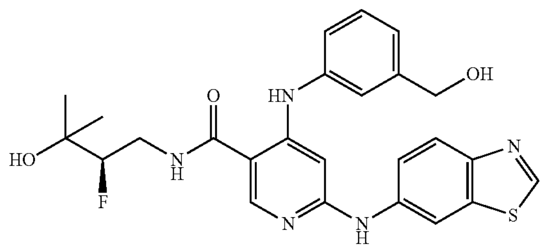 [SMILES: CC(C)(O)[C@H](F)CNC(=O)c1cnc(Nc2ccc3ncsc3c2)cc1Nc1cccc(CO)c1] | 7.33 | C | 496.2 |
| 58 | 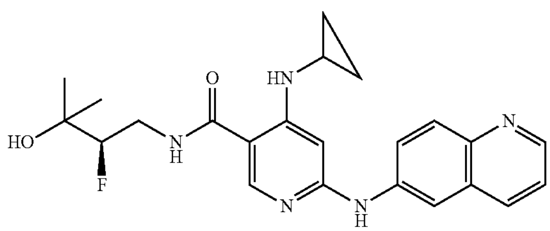 [SMILES: CC(C)(O)[C@H](F)CNC(=O)c1cnc(Nc2ccc3ncccc3c2)cc1NC1CC1] | 8.43 | E | 424.2 |
| 59 | 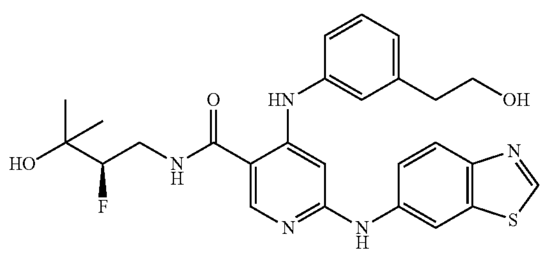 [SMILES: CC(C)(O)[C@H](F)CNC(=O)c1cnc(Nc2ccc3ncsc3c2)cc1Nc1cccc(CCO)c1] | 5.54 | E | 510.2 |
| 61 | 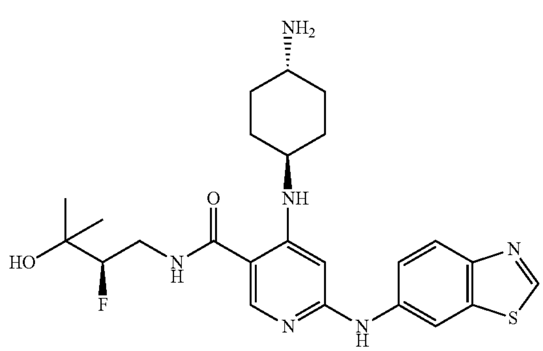 [SMILES: CC(C)(O)[C@H](F)CNC(=O)c1cnc(Nc2ccc3ncsc3c2)cc1N[C@H]1CC[C@H](N)CC1] | 6.99 | B | 487.2 |

TABLE 3-continued
| Ex. No. | Structure | HPLC RT (min) | HPLC cond. | LCMS (M + H)+ |
|---|---|---|---|---|
| 62 | 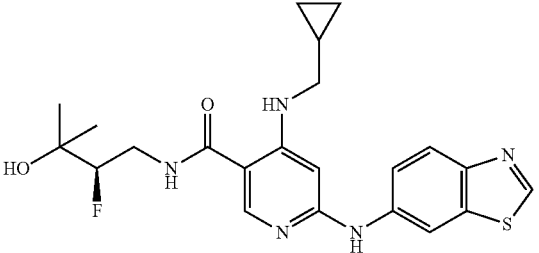 [SMILES: CC(C)(O)[C@H](F)CNC(=O)c1cnc(Nc2ccc3ncsc3c2)cc1NCC1CC1] | 8.48 | C | 442.2 M − H |
| 63 | 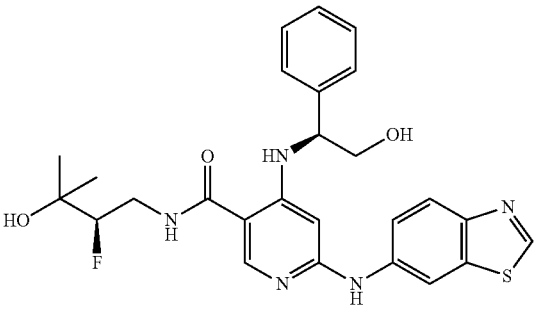 [SMILES: CC(C)(O)[C@H](F)CNC(=O)c1cnc(Nc2ccc3ncsc3c2)cc1N[C@H](CO)c1ccccc1] | 6.51 | A | 510.2 |
| 64 | 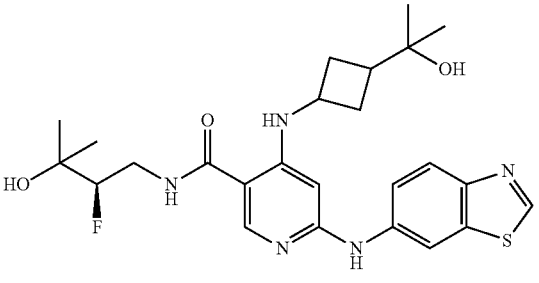 [SMILES: CC(C)(O)C1CC(Nc2cc(Nc3ccc4ncsc4c3)ncc2C(=O)NC[C@@H](F)C(C)(C)O)C1] | 7.34 | B | 502.2 |
| 65 | 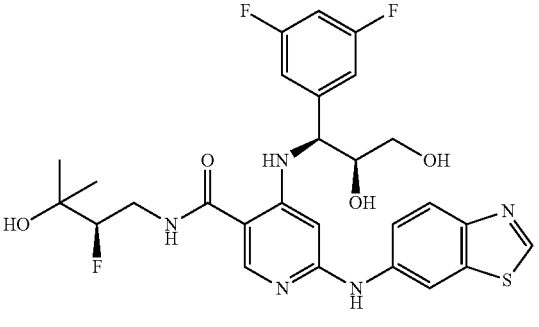 | 7.95 | C | 576.2 |
| 66 | 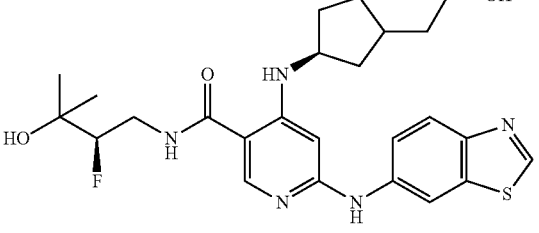 | 5.48 | E | 502.2 |

US 9,546,153 B2
103                                                                                                                                                                    104
TABLE 3-continued
| Ex. No. | Structure | HPLC RT (min) | HPLC cond. | LCMS (M + H)+ |
|---|---|---|---|---|
| 67 | 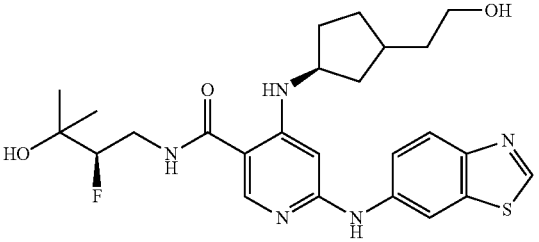 [SMILES: CC(C)(O)[C@H](F)CNC(=O)c1cnc(Nc2ccc3ncsc3c2)cc1N[C@H]1CCC(CCO)C1] | 5.13 | E | 502.2 |
| 68 | 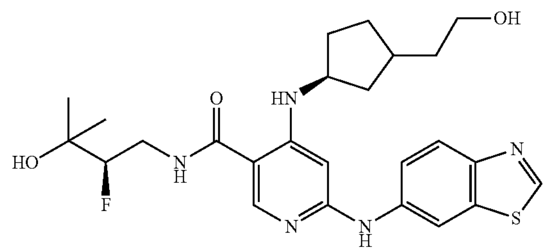 [SMILES: CC(C)(O)[C@H](F)CNC(=O)c1cnc(Nc2ccc3ncsc3c2)cc1N[C@H]1CCC(CCO)C1] | 5.18 | E | 502.2 |
| 69 | 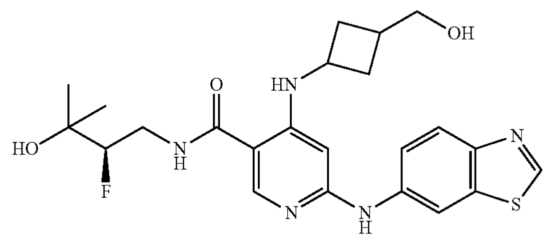 [SMILES: CC(C)(O)[C@H](F)CNC(=O)c1cnc(Nc2ccc3ncsc3c2)cc1NC1CC(CO)C1] | 8.66 | B | 474.2 |
| 70 | 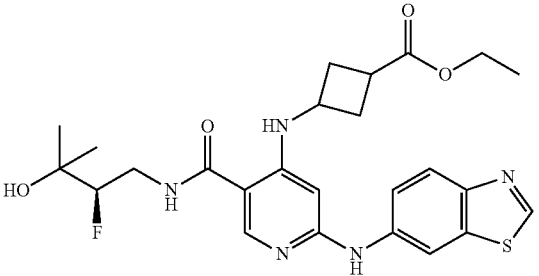 [SMILES: CCOC(=O)C1CC(Nc2cc(Nc3ccc4ncsc4c3)ncc2C(=O)NC[C@@H](F)C(C)(C)O)C1] | 5.82 | E | 516.2 |
| 71 | 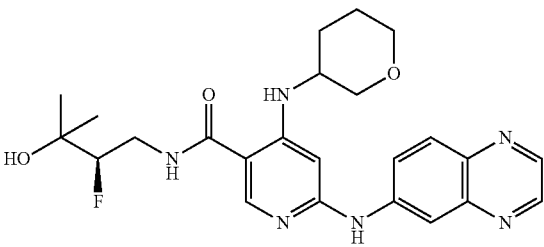 [SMILES: CC(C)(O)[C@H](F)CNC(=O)c1cnc(Nc2ccc3nccnc3c2)cc1NC1CCCOC1] | 5.30 | B | 469.2 |
| 72 | 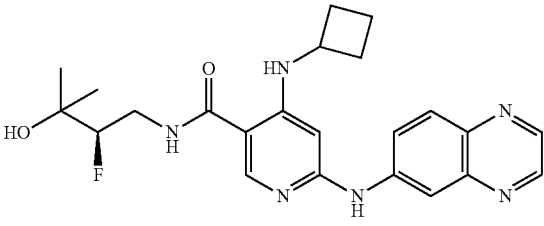 [SMILES: CC(C)(O)[C@H](F)CNC(=O)c1cnc(Nc2ccc3nccnc3c2)cc1NC1CCC1] | 7.95 | C | 436.2 |

TABLE 3-continued
| Ex. No. | Structure | HPLC RT (min) | HPLC cond. | LCMS (M + H)+ |
|---|---|---|---|---|
| 73 | 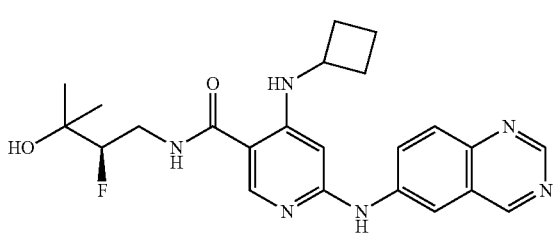 [SMILES: CC(C)(O)[C@H](F)CNC(=O)c1cnc(Nc2ccc3ncncc3c2)cc1NC1CCC1] | 7.00 | C | 439.2 |
| 74 | 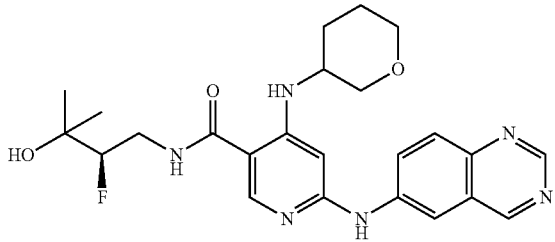 [SMILES: CC(C)(O)[C@H](F)CNC(=O)c1cnc(Nc2ccc3ncncc3c2)cc1NC1CCCOC1] | 11.29 | J | 467.2 |
| 75 | 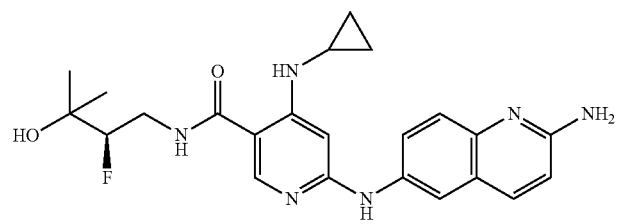 [SMILES: CC(C)(O)[C@H](F)CNC(=O)c1cnc(Nc2ccc3nc(N)ccc3c2)cc1NC1CC1] | 10.09 | E | 439.2 |
| 76 | 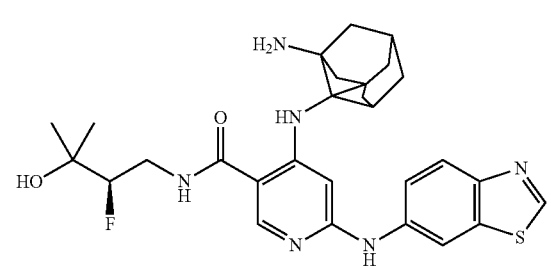 [SMILES: CC(C)(O)[C@H](F)CNC(=O)c1cnc(Nc2ccc3ncsc3c2)cc1NC12C3CC4CC1(N)CC2(C4)C3] | 8.29 | B | 539.2 |
| 77 | 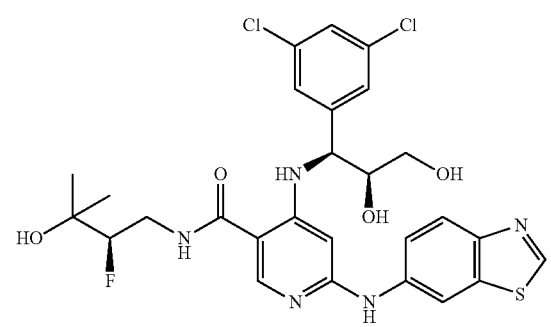 [SMILES: CC(C)(O)[C@H](F)CNC(=O)c1cnc(Nc2ccc3ncsc3c2)cc1N[C@@H](c1cc(Cl)cc(Cl)c1)[C@H](O)CO] | 5.89 | E | 610.5 M + 2H |

TABLE 3-continued

| Ex. No. | Structure | HPLC RT (min) | HPLC cond. | LCMS (M + H)+ |
|---|---|---|---|---|
| 78 | 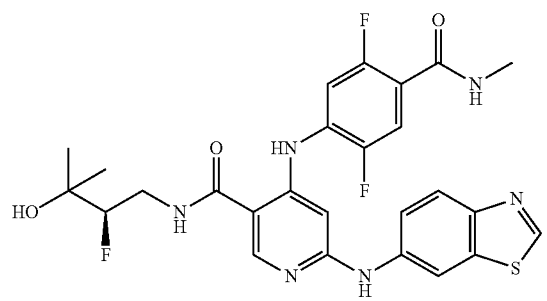 [SMILES: CNC(=O)c1cc(F)c(Nc2cc(Nc3ccc4ncsc4c3)ncc2C(=O)NC[C@@H](F)C(C)(C)O)cc1F] | 6.19 | A | 559.2 |
| 79 | 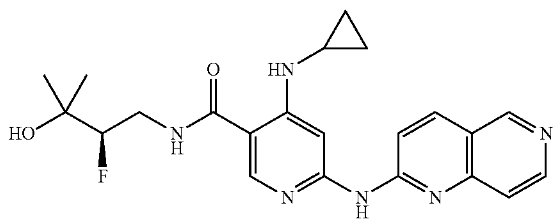 [SMILES: CC(C)(O)[C@H](F)CNC(=O)c1cnc(Nc2ccc3cnccc3n2)cc1NC1CC1] | 8.66 | A | 425.2 |
| 80 | 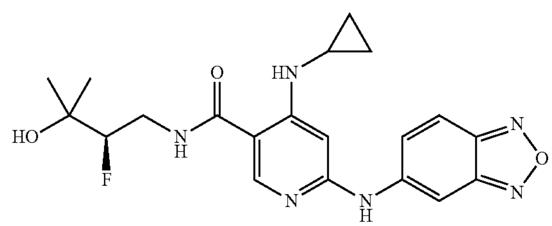 [SMILES: CC(C)(O)[C@H](F)CNC(=O)c1cnc(Nc2ccc3nonc3c2)cc1NC1CC1] | 6.85 | A | 413.2 M − H |
| 81 | 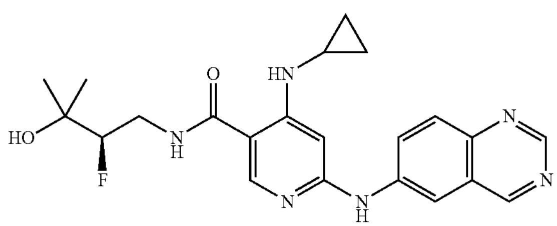 [SMILES: CC(C)(O)[C@H](F)CNC(=O)c1cnc(Nc2ccc3ncncc3c2)cc1NC1CC1] | 7.95 | C | 423.2 M − H |
| 82 | 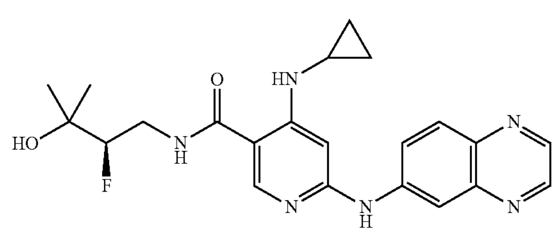 [SMILES: CC(C)(O)[C@H](F)CNC(=O)c1cnc(Nc2ccc3nccnc3c2)cc1NC1CC1] | 5.14 | E | 425.2 |
| 83 | 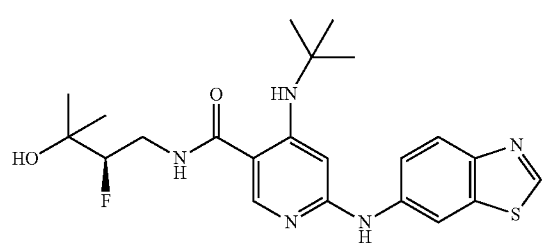 [SMILES: CC(C)(C)Nc1cc(Nc2ccc3ncsc3c2)ncc1C(=O)NC[C@@H](F)C(C)(C)O] | 6.19 | E | 446.2 |

TABLE 3-continued

| Ex. No. | Structure | HPLC RT (min) | HPLC cond. | LCMS (M + H)+ |
|---|---|---|---|---|
| 84 | 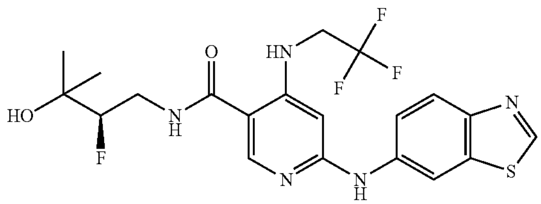 [SMILES: CC(C)(O)[C@H](F)CNC(=O)c1cnc(Nc2ccc3ncsc3c2)cc1NCC(F)(F)F] | 5.84 | E | 470.0 M − H |
| 85 | 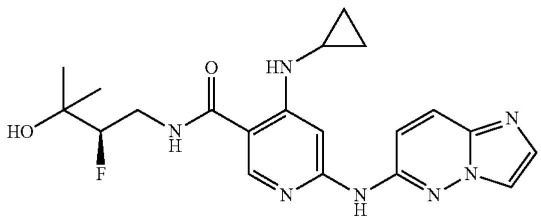 [SMILES: CC(C)(O)[C@H](F)CNC(=O)c1cnc(Nc2ccc3nccn3n2)cc1NC1CC1] | 5.95 | K | 414.2 |
| 86 | 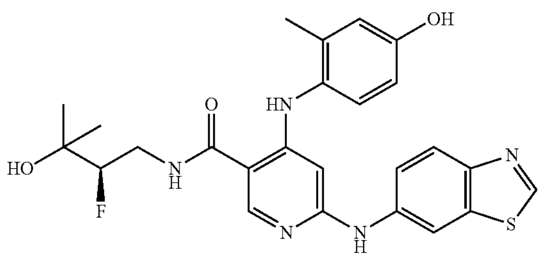 [SMILES: Cc1cc(O)ccc1Nc1cc(Nc2ccc3ncsc3c2)ncc1C(=O)NC[C@@H](F)C(C)(C)O] | 5.55 | E | 496.2 |
| 87 | 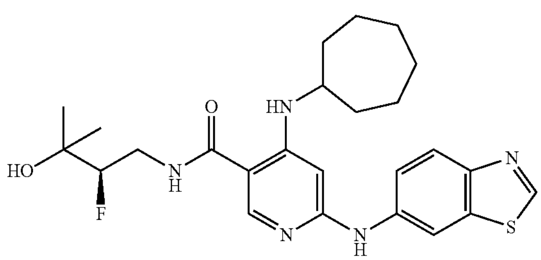 [SMILES: CC(C)(O)[C@H](F)CNC(=O)c1cnc(Nc2ccc3ncsc3c2)cc1NC1CCCCCC1] | 7.36 | E | 486.2 |
| 88 | 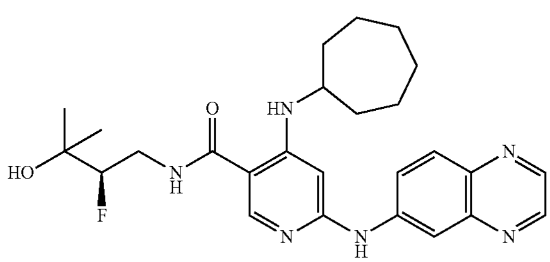 [SMILES: CC(C)(O)[C@H](F)CNC(=O)c1cnc(Nc2ccc3nccnc3c2)cc1NC1CCCCCC1] | 6.87 | E | 481.2 |
| 89 | 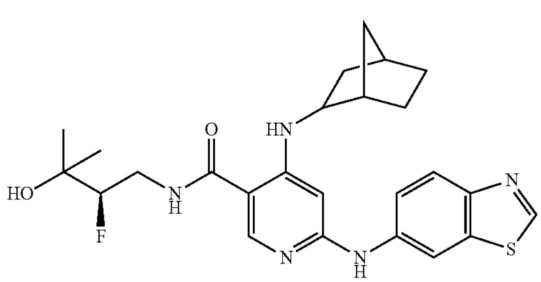 [SMILES: CC(C)(O)[C@H](F)CNC(=O)c1cnc(Nc2ccc3ncsc3c2)cc1NC1CC2CCC1C2] | 6.75 | E | 484.2 |

TABLE 3-continued

| Ex. No. | Structure | HPLC RT (min) | HPLC cond. | LCMS (M + H)+ |
|---|---|---|---|---|
| 90 | 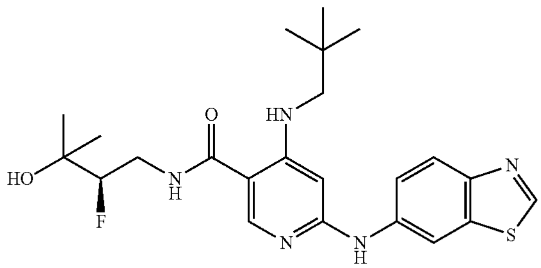 [SMILES: CC(C)(C)CNc1cc(Nc2ccc3ncsc3c2)ncc1C(=O)NC[C@@H](F)C(C)(C)O] | 5.6 | E | 456.2 |
| 91 | 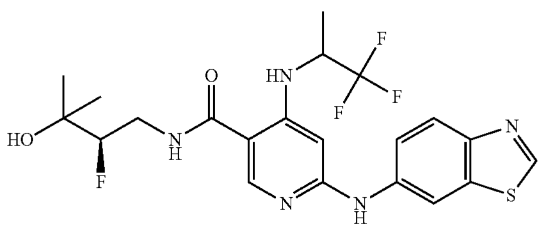 [SMILES: CC(Nc1cc(Nc2ccc3ncsc3c2)ncc1C(=O)NC[C@@H](F)C(C)(C)O)C(F)(F)F] | 6.34 | E | 486.2 |
| 92 | 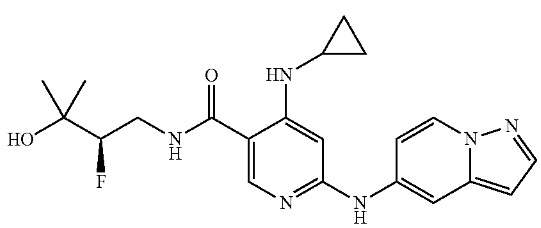 | 6.35 | A | 413.2 |
| 93 | 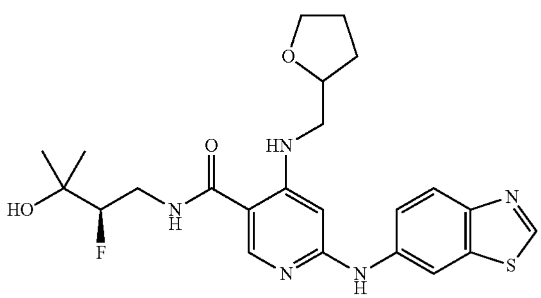 [SMILES: CC(C)(O)[C@H](F)CNC(=O)c1cnc(Nc2ccc3ncsc3c2)cc1NCC1CCCO1] | 5.70 | E | 474.2 |
| 94 | 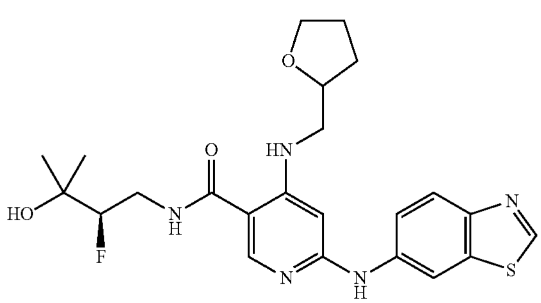 [SMILES: CC(C)(O)[C@H](F)CNC(=O)c1cnc(Nc2ccc3ncsc3c2)cc1NCC1CCCO1] | 5.70 | E | 474.2 |

TABLE 3-continued

| Ex. No. | Structure | HPLC RT (min) | HPLC cond. | LCMS (M + H)+ |
|---|---|---|---|---|
| 95 | 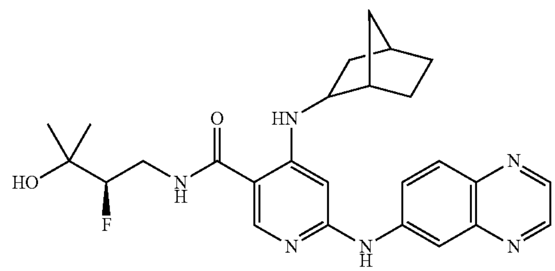 [SMILES: CC(C)(O)[C@H](F)CNC(=O)c1cnc(Nc2ccc3nccnc3c2)cc1NC1CC2CCC1C2] | 6.79 | E | 479.2 |
| 96 | 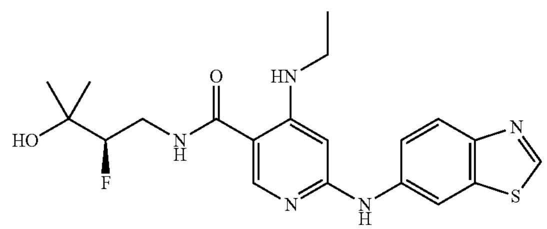 [SMILES: CCNc1cc(Nc2ccc3ncsc3c2)ncc1C(=O)NC[C@@H](F)C(C)(C)O] | 1.91 | F | 418.0 |
| 97 | 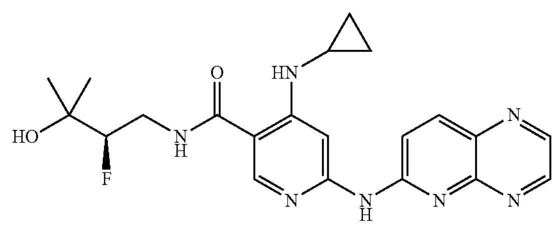 [SMILES: CC(C)(O)[C@H](F)CNC(=O)c1cnc(Nc2ccc3nccnc3n2)cc1NC1CC1] | 5.15 | E | 426.2 |
| 98 | 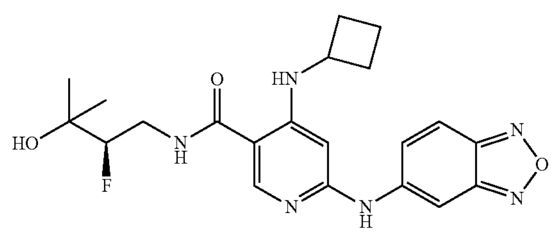 [SMILES: CC(C)(O)[C@H](F)CNC(=O)c1cnc(Nc2ccc3nonc3c2)cc1NC1CCC1] | 6.90 | E | 429.2 |
| 99 | 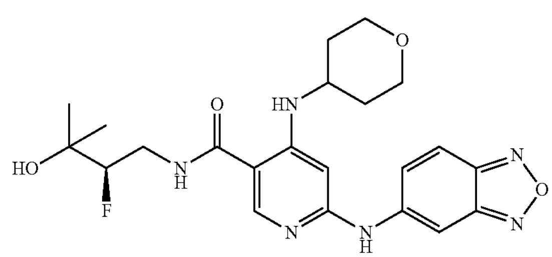 [SMILES: CC(C)(O)[C@H](F)CNC(=O)c1cnc(Nc2ccc3nonc3c2)cc1NC1CCOCC1] | 5.89 | E | 457.2 M − H |
| 100 | 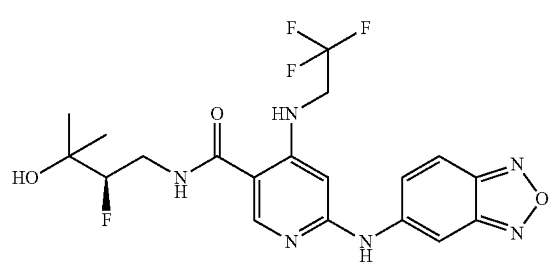 [SMILES: CC(C)(O)[C@H](F)CNC(=O)c1cnc(Nc2ccc3nonc3c2)cc1NCC(F)(F)F] | 7.65 | A | 457.2 |

TABLE 3-continued

| Ex. No. | Structure | HPLC RT (min) | HPLC cond. | LCMS (M + H)+ |
|---|---|---|---|---|
| 101 | 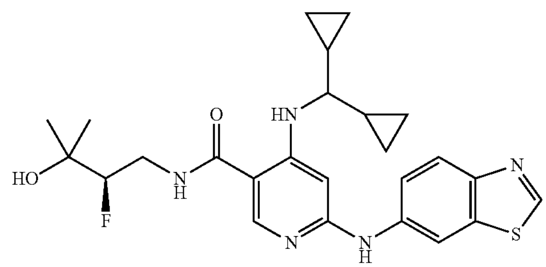 [SMILES: CC(C)(O)[C@H](F)CNC(=O)c1cnc(Nc2ccc3ncsc3c2)cc1NC(C1CC1)C1CC1] | 7.83 | A | 484.2 |
| 102 | 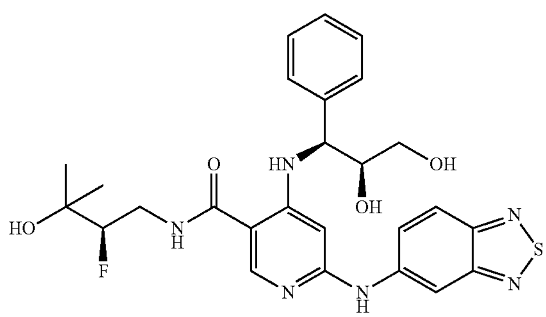 [SMILES: CC(C)(O)[C@H](F)CNC(=O)c1cnc(Nc2ccc3nsnc3c2)cc1N[C@@H](c1ccccc1)[C@H](O)CO] | 5.69 | E | 541.0 |
| 103 | 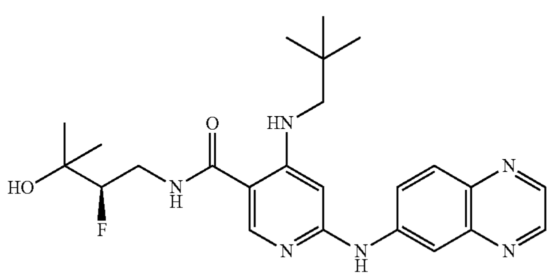 [SMILES: CC(C)(C)CNc1cc(Nc2ccc3nccnc3c2)ncc1C(=O)NC[C@@H](F)C(C)(C)O] | 6.46 | E | 455.3 |
| 104 | 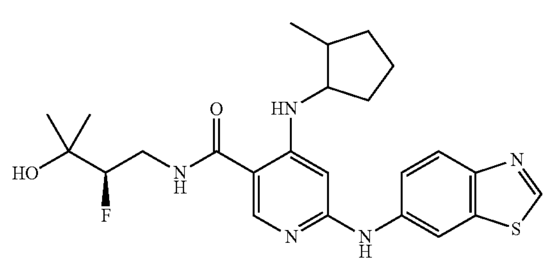 [SMILES: CC1CCCC1Nc1cc(Nc2ccc3ncsc3c2)ncc1C(=O)NC[C@@H](F)C(C)(C)O] | 5.66 | M | 472.2 |
| 105 | 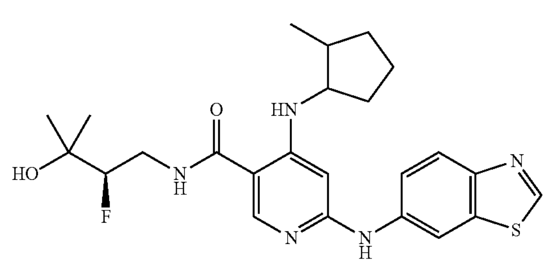 [SMILES: CC1CCCC1Nc1cc(Nc2ccc3ncsc3c2)ncc1C(=O)NC[C@@H](F)C(C)(C)O] | 7.69 | L | 472.2 |

TABLE 3-continued

| Ex. No. | Structure | HPLC RT (min) | HPLC cond. | LCMS (M + H)+ |
|---|---|---|---|---|
| 106 | 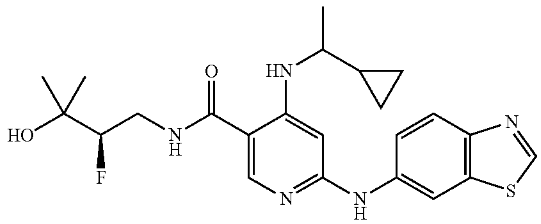 [SMILES: CC(Nc1cc(Nc2ccc3ncsc3c2)ncc1C(=O)NC[C@@H](F)C(C)(C)O)C1CC1] | 15.3 and 18.3 | I | 458 |
| 107 | 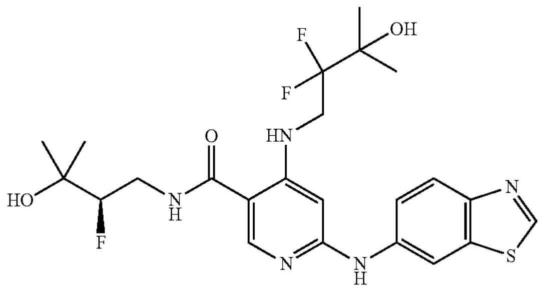 [SMILES: CC(C)(O)[C@H](F)CNC(=O)c1cnc(Nc2ccc3ncsc3c2)cc1NCC(F)(F)C(C)(C)O] | 5.42 | B | 512.2 |
| 108 | 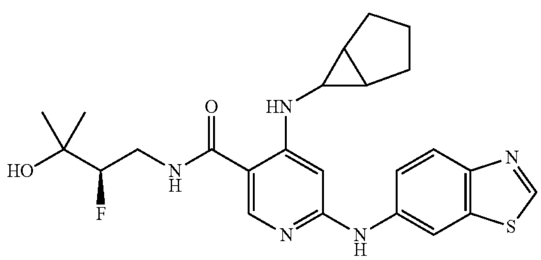 [SMILES: CC(C)(O)[C@H](F)CNC(=O)c1cnc(Nc2ccc3ncsc3c2)cc1NC1C2CCCC21] | 6.42 | E | 470.4 |
| 109 | 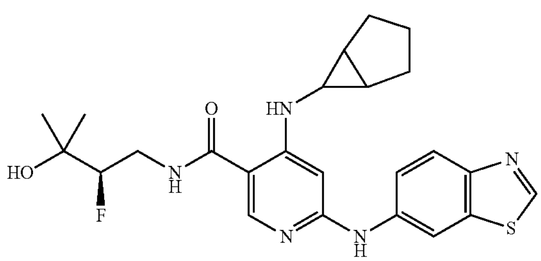 [SMILES: CC(C)(O)[C@H](F)CNC(=O)c1cnc(Nc2ccc3ncsc3c2)cc1NC1C2CCCC21] | 6.54 | E | 470.4 |
| 110 | 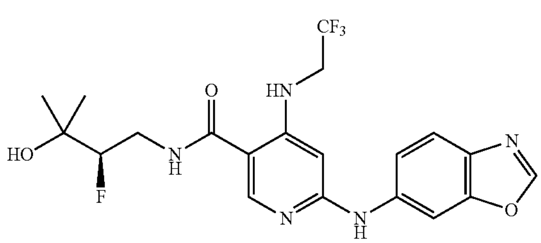 [SMILES: CC(C)(O)[C@H](F)CNC(=O)c1cnc(Nc2ccc3ncoc3c2)cc1NCC(F)(F)F] | 5.60 | E | 456.2 |
| 111 | 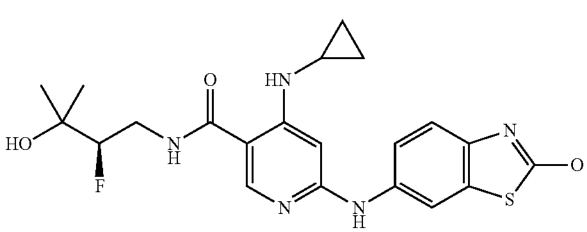 [SMILES: CC(C)(O)[C@H](F)CNC(=O)c1cnc(Nc2ccc3nc(O)sc3c2)cc1NC1CC1] | 5.47 | K | 431.5 |

TABLE 3-continued
| Ex. No. | Structure | HPLC RT (min) | HPLC cond. | LCMS (M + H)+ |
|---|---|---|---|---|
| 112 | 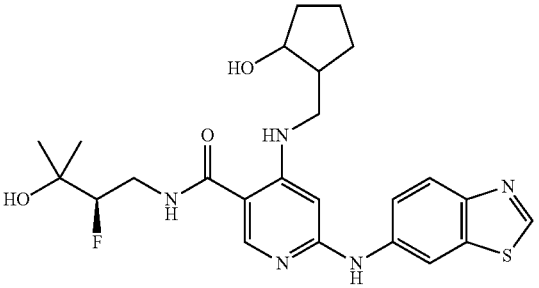 [SMILES: CC(C)(O)[C@H](F)CNC(=O)c1cnc(Nc2ccc3ncsc3c2)cc1NCC1CCCC1O] | 8.32 | G | 487 |
| 113 | 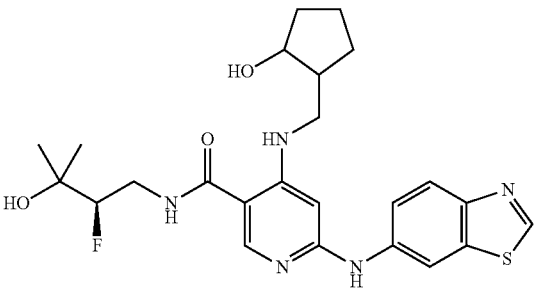 [SMILES: CC(C)(O)[C@H](F)CNC(=O)c1cnc(Nc2ccc3ncsc3c2)cc1NCC1CCCC1O] | 17.23 | G | 487 |
| 114 | 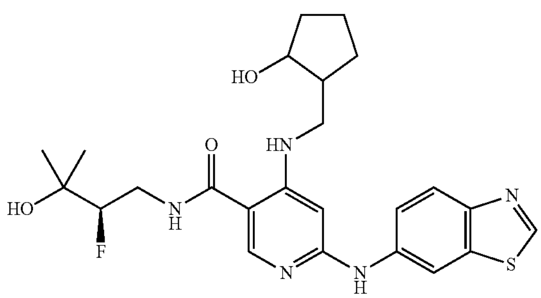 [SMILES: CC(C)(O)[C@H](F)CNC(=O)c1cnc(Nc2ccc3ncsc3c2)cc1NCC1CCCC1O] | 6.07 | G | 487 |
| 115 | 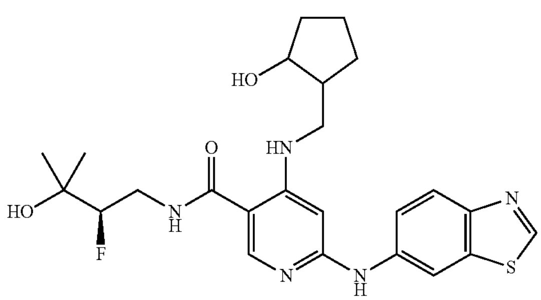 [SMILES: CC(C)(O)[C@H](F)CNC(=O)c1cnc(Nc2ccc3ncsc3c2)cc1NCC1CCCC1O] | 9.78 | G | 487 |
| 116 | 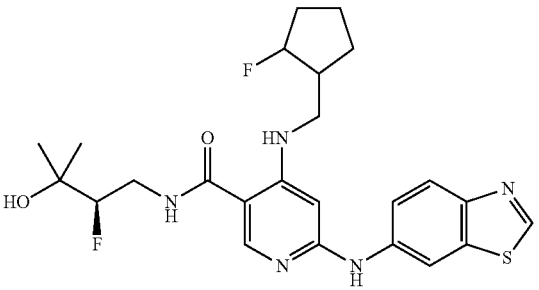 [SMILES: CC(C)(O)[C@H](F)CNC(=O)c1cnc(Nc2ccc3ncsc3c2)cc1NCC1CCCC1F] | 9.09 | G | 489 |

TABLE 3-continued

| Ex. No. | Structure | HPLC RT (min) | HPLC cond. | LCMS (M + H)+ |
|---|---|---|---|---|
| 117 | 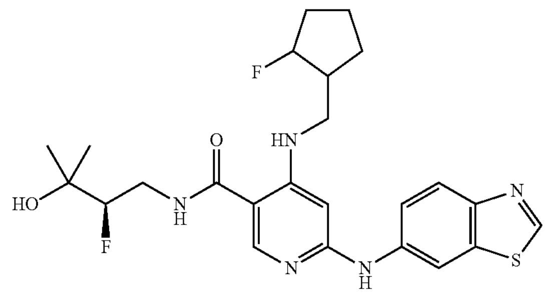 [SMILES: CC(C)(O)[C@H](F)CNC(=O)c1cnc(Nc2ccc3ncsc3c2)cc1NCC1CCCC1F] | 9.29 and 10.39 | G | 489 |
| 118 | 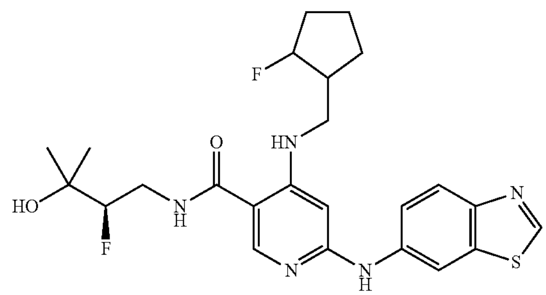 [SMILES: CC(C)(O)[C@H](F)CNC(=O)c1cnc(Nc2ccc3ncsc3c2)cc1NCC1CCCC1F] | 11.35 | G | 489 |
| 119 | 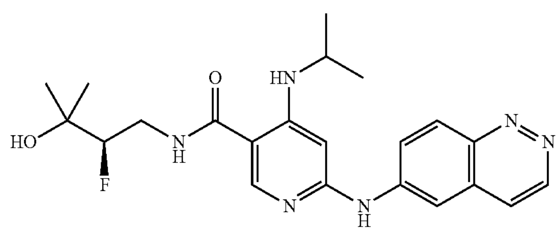 [SMILES: CC(C)Nc1cc(Nc2ccc3nnccc3c2)ncc1C(=O)NC[C@@H](F)C(C)(C)O] | 9.3 | B | 427.4 |
| 120 | 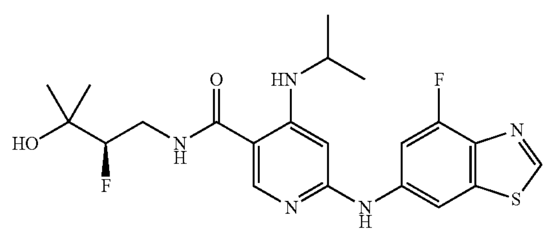 [SMILES: CC(C)Nc1cc(Nc2cc(F)c3ncsc3c2)ncc1C(=O)NC[C@@H](F)C(C)(C)O] | 5.87 | E | 450.3 |
| 121 | 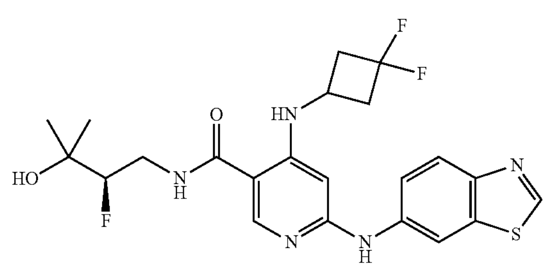 [SMILES: CC(C)(O)[C@H](F)CNC(=O)c1cnc(Nc2ccc3ncsc3c2)cc1NC1CC(F)(F)C1] | 6.21 | E | 480.2 |
| 122 | 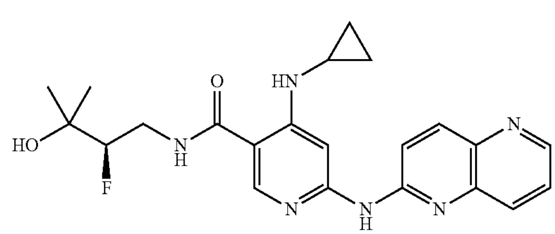 | 7.07 | A | 425 |

TABLE 3-continued

| Ex. No. | Structure | HPLC RT (min) | HPLC cond. | LCMS (M + H)+ |
|---|---|---|---|---|
| 123 | 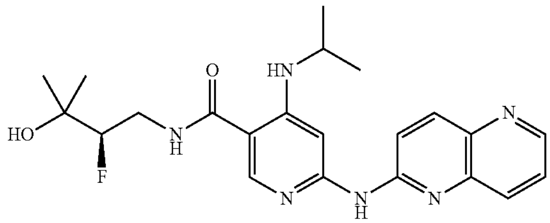 | 5.68 | A | 427.3 |
| 124 | 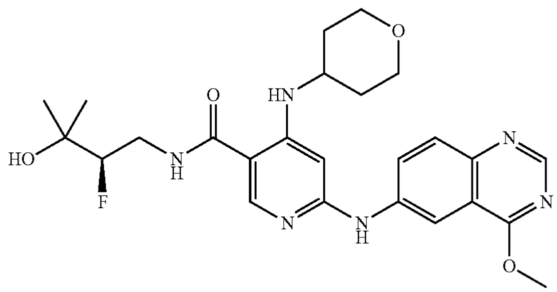 [SMILES: COc1ncnc2ccc(Nc3cc(NC4CCOCC4)c(C(=O)NC[C@@H](F)C(C)(C)O)cn3)cc12] | 5.04 | E | 499.2 |
| 125 | 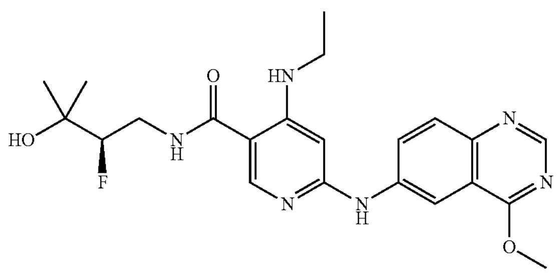 [SMILES: CCNc1cc(Nc2ccc3ncnc(OC)c3c2)ncc1C(=O)NC[C@@H](F)C(C)(C)O] | 5.23 | E | 443.2 |
| 126 | 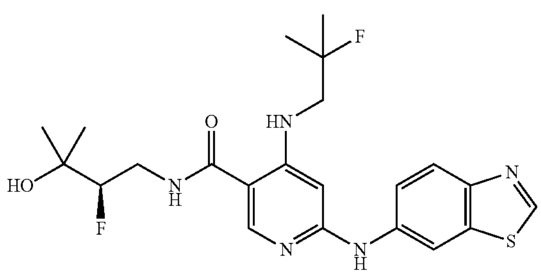 [SMILES: CC(C)(F)CNc1cc(Nc2ccc3ncsc3c2)ncc1C(=O)NC[C@@H](F)C(C)(C)O] | 1.77 | A | 464.2 |
| 127 | 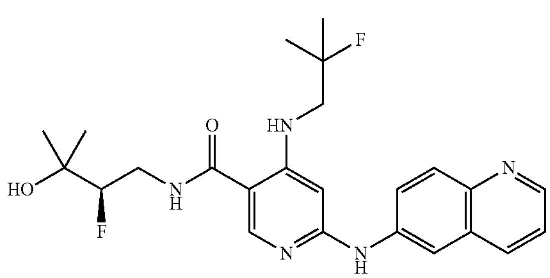 [SMILES: CC(C)(F)CNc1cc(Nc2ccc3ncccc3c2)ncc1C(=O)NC[C@@H](F)C(C)(C)O] | 9.32 | E | 458.2 |

TABLE 3-continued

| Ex. No. | Structure | HPLC RT (min) | HPLC cond. | LCMS (M + H)+ |
|---|---|---|---|---|
| 128 | 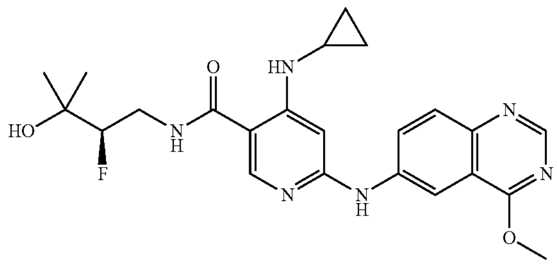 [SMILES: COc1ncnc2ccc(Nc3cc(NC4CC4)c(C(=O)NC[C@@H](F)C(C)(C)O)cn3)cc12] | 5.37 | A | 455.2 |
| 129 | 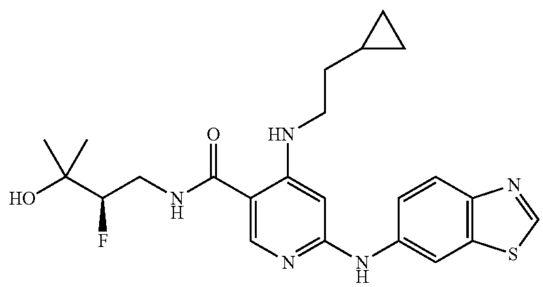 [SMILES: CC(C)(O)[C@H](F)CNC(=O)c1cnc(Nc2ccc3ncsc3c2)cc1NCCC1CC1] | 1.92 | A | 458.2 |
| 130 | 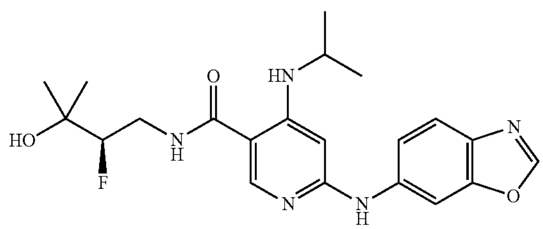 [SMILES: CC(C)Nc1cc(Nc2ccc3ncoc3c2)ncc1C(=O)NC[C@@H](F)C(C)(C)O] | 6.02 | E | 416.2 |
| 131 | 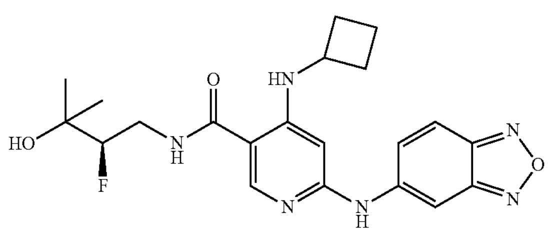 [SMILES: CC(C)(O)[C@H](F)CNC(=O)c1cnc(Nc2ccc3nonc3c2)cc1NC1CCC1] | 6.25 | E | 417.2 |
| 132 | 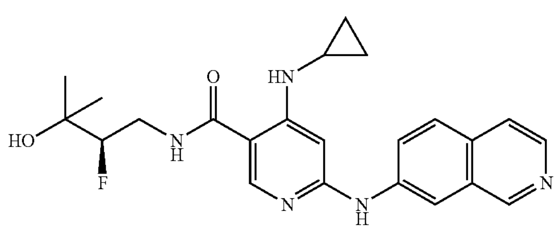 [SMILES: CC(C)(O)[C@H](F)CNC(=O)c1cnc(Nc2ccc3ccncc3c2)cc1NC1CC1] | 8.18 | B | 423.5 |
| 133 | 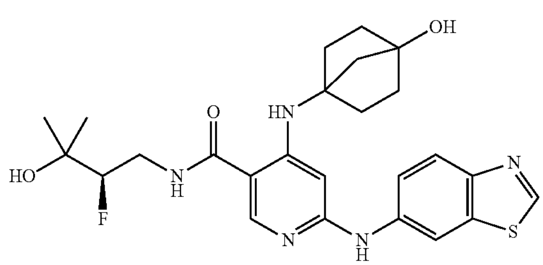 [SMILES: CC(C)(O)[C@H](F)CNC(=O)c1cnc(Nc2ccc3ncsc3c2)cc1NC12CCC(O)(CC1)C2] | 1.12 | G | 500.2 |

TABLE 3-continued

| Ex. No. | Structure | HPLC RT (min) | HPLC cond. | LCMS (M + H)+ |
|---|---|---|---|---|
| 134 | 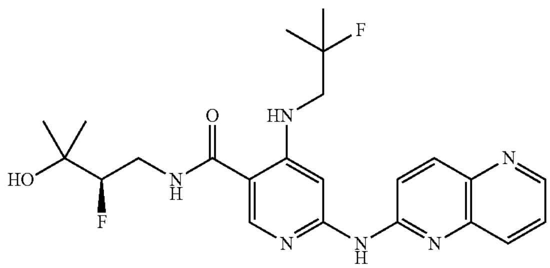 [SMILES: CC(C)(F)CNc1cc(Nc2ccc3ncccc3n2)ncc1C(=O)NC[C@@H](F)C(C)(C)O] | 5.86 | A | 459 |
| 135 | 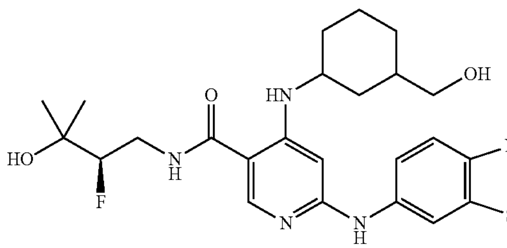 | 5.19 | M | 486.4 |
| 136 | 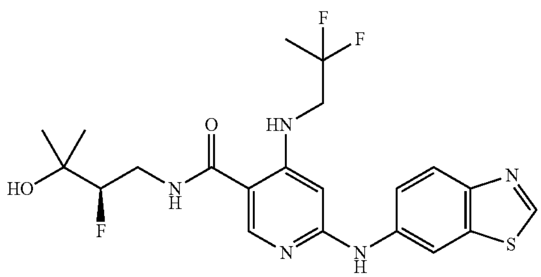 [SMILES: CC(F)(F)CNc1cc(Nc2ccc3ncsc3c2)ncc1C(=O)NC[C@@H](F)C(C)(C)O] | 6.78 | A | 469.8 |
| 137 | 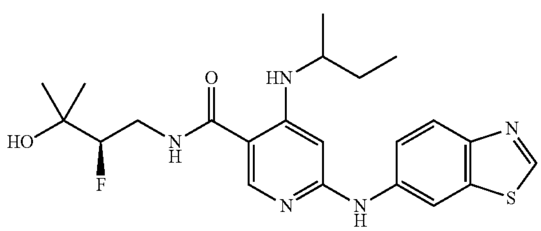 [SMILES: CCC(C)Nc1cc(Nc2ccc3ncsc3c2)ncc1C(=O)NC[C@@H](F)C(C)(C)O] | 6.08 | B | 446.2 |
| 138 | 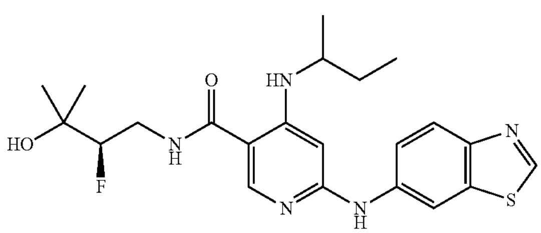 [SMILES: CCC(C)Nc1cc(Nc2ccc3ncsc3c2)ncc1C(=O)NC[C@@H](F)C(C)(C)O] | 6.09 | B | 446.2 |
| 139 | 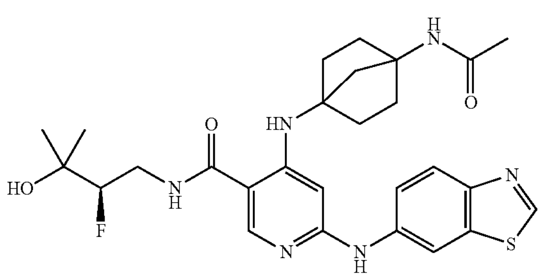 [SMILES: CC(=O)NC12CCC(Nc3cc(Nc4ccc5ncsc5c4)ncc3C(=O)NC[C@@H](F)C(C)(C)O)(CC1)C2] | 1.14 | G | 541.2 |

TABLE 3-continued

| Ex. No. | Structure | HPLC RT (min) | HPLC cond. | LCMS (M + H)+ |
|---|---|---|---|---|
| 140 | 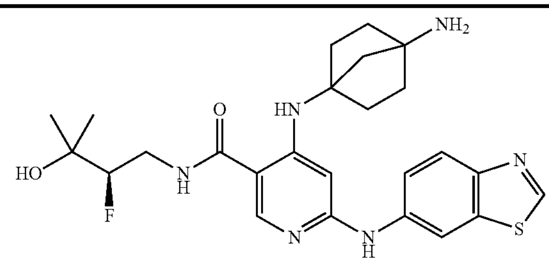 | 1.01 | G | 499.2 |
| 141 | 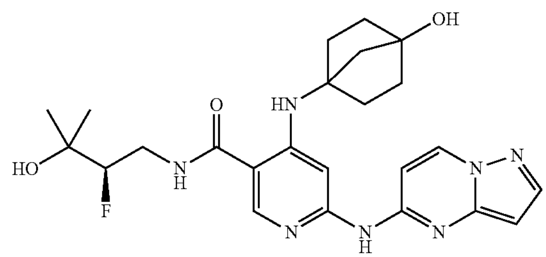 [SMILES: CC(C)(O)[C@H](F)CNC(=O)c1cnc(Nc2ccn3nccc3n2)cc1NC12CCC(O)(CC1)C2] | 1.15 | G | 484.5 |
| 142 | 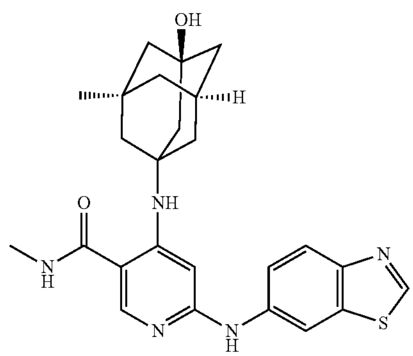 [SMILES: CNC(=O)c1cnc(Nc2ccc3ncsc3c2)cc1NC12C[C@H]3C[C@@](C)(C1)C[C@](O)(C3)C2] | 2.62 | F | 450.1 |

Example 143

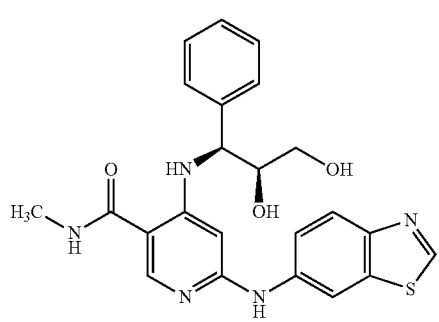 [SMILES: CNC(=O)c1cnc(Nc2ccc3ncsc3c2)cc1N[C@@H](c1ccccc1)[C@H](O)CO]

Prepared according to the general methods outlined for Examples 1 and 5 starting from (2S,3S)-3-amino-3-phenyl-propane-1,2-diol. LCMS 450.12; HPLC RT 8.82 min, XBridge C18 (150×4.6 mm), 3.5µ; Solvent A=10% MeOH: 90% H₂O: 0.1% TFA; Solvent B=90% MeOH: 10% H₂O: 0.0% TFA; gradient 0-100% B over 15 min; Flow rate: 1.0 mL/min.

Example 144

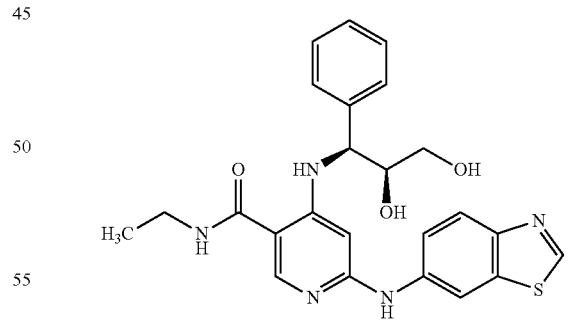

Prepared according to the general methods outlined for Examples 1 and 5 starting from (2S,3S)-3-amino-3-phenyl-propane-1,2-diol. LCMS: 464.17; HPLC rt 9.39 min, XBridge C18 (150×4.6 mm), 3.5µ; Solvent A=10% MeOH: 90% H₂O: 0.1% TFA; Solvent B=90% MeOH: 10% H₂O: 0.0% TFA; gradient 0-100% B over 15 min; Flow rate: 1.0 mL/min. ¹H NMR (400 MHz, methanol-d₄) δ 9.43-9.29 (m, 1H), 8.16-8.01 (m, 2H), 7.81 (d, J=2.0 Hz, 1H), 7.41-7.17

(m, 7H), 5.96-5.72 (m, 1H), 4.62 (d, J=4.3 Hz, 1H), 4.06-3.81 (m, 1H), 3.58-3.35 (m, 3H), 1.27 (t, J=7.3 Hz, 3H).

Example 145

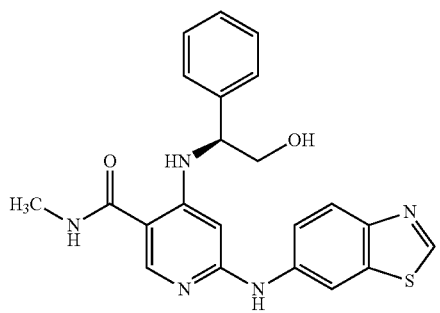 [SMILES: CNC(=O)c1cnc(Nc2ccc3ncsc3c2)cc1N[C@H](CO)c1ccccc1]

Prepared according to the general methods outlined for Examples 1 and 5 starting from (S)-2-amino-2-phenylethanol. LCMS 420.14; HPLC rt 9.71 min, XBridge C18 (150×4.6 mm), 3.5μ; Solvent A=10% MeOH: 90% H$_2$O: 0.1% TFA; Solvent B=90% MeOH: 10% H$_2$O: 0.0% TFA; gradient 0-100% B over 15 min; Flow rate: 1.0 mL/min.

Example 147

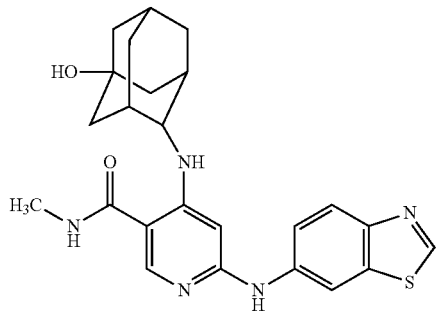 [SMILES: CNC(=O)c1cnc(Nc2ccc3ncsc3c2)cc1NC1C2CC3CC1CC(O)(C3)C2]

Prepared according to the general methods outlined for Examples 1 and 5 starting from (±)-4-aminoadamantan-1-ol to afford after chiral HPLC Example 146 (Isomer B). LCMS: 450.15; HPLC rt 10.44 min; XBridge C18 (150×4.6 mm), 3.5μ; Solvent A=10% MeOH: 90% H$_2$O: 0.1% TFA; Solvent B=90% MeOH: 10% H$_2$O: 0.0% TFA; gradient 0-100% B over 15 min; Flow rate: 1.0 mL/min.

Example 148

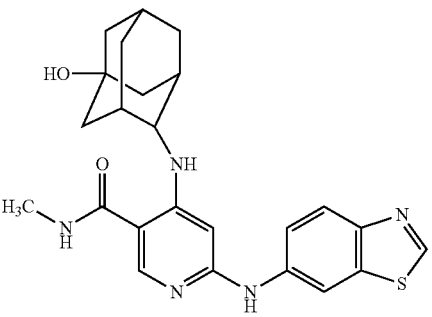 [SMILES: CNC(=O)c1cnc(Nc2ccc3ncsc3c2)cc1NC1C2CC3CC1CC(O)(C3)C2]

Prepared according to the general methods outlined for Examples 1 and 5 starting from (±)-4-aminoadamantan-1-ol to afford after chiral HPLC Example 147 (Isomer A. LCMS 450.22; HPLC rt 9.81 min; XBridge C18 (150×4.6 mm), 3.5μ; Solvent A=10% MeOH: 90% H$_2$O: 0.1% TFA; Solvent B=90% MeOH: 10% H$_2$O: 0.0% TFA; gradient 0-100% B over 15 min; Flow rate: 1.0 mL/min.

Example 149

Example 149 was prepared from 6-(benzo[d]thiazol-6-ylamino)-4-(cyclopentylamino)nicotinic acid and 2-(1-methylpyrrolidin-2-yl)ethanamine using the procedure outlined in Example 5, Step 4.

Synthesis of Examples 150 to 158, Table 4, were prepared according to the procedures referenced above.

TABLE 4

| Ex. No. | Structure | HPLC RT (min) | HPLC cond. | LCMS |
|---|---|---|---|---|
| 149 | 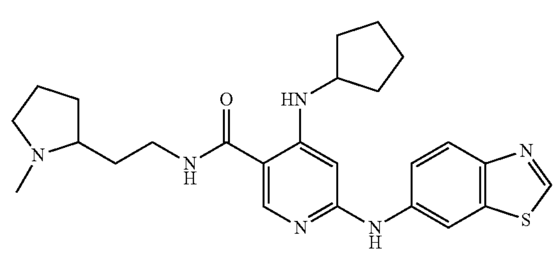 [SMILES: CN1CCCC1CCNC(=O)c1cnc(Nc2ccc3ncsc3c2)cc1NC1CCCC1] | 1.82 | F | 465.2 |

TABLE 4-continued

| Ex. No. | Structure | HPLC RT (min) | HPLC cond. | LCMS |
|---|---|---|---|---|
| 150 | 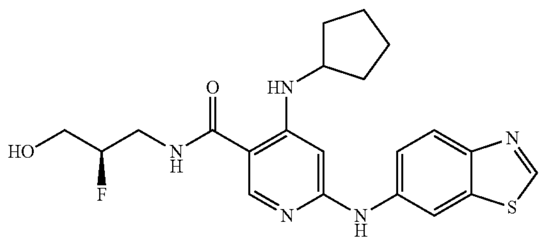 [SMILES: O=C(NC[C@@H](F)CO)c1cnc(Nc2ccc3ncsc3c2)cc1NC1CCCC1] | 6.09 | E | 430.2 |
| 151 | 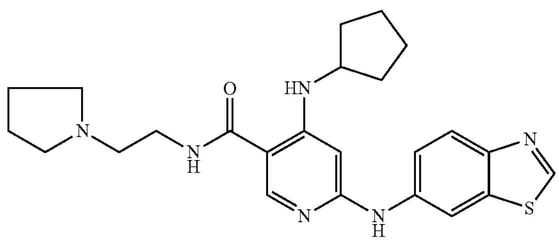 [SMILES: O=C(NCCN1CCCC1)c1cnc(Nc2ccc3ncsc3c2)cc1NC1CCCC1] | 1.83 | F | 451.2 |
| 152 | 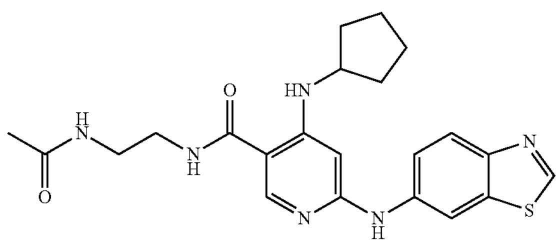 [SMILES: CC(=O)NCCNC(=O)c1cnc(Nc2ccc3ncsc3c2)cc1NC1CCCC1] | 1.87 | F | 439.2 |
| 153 | 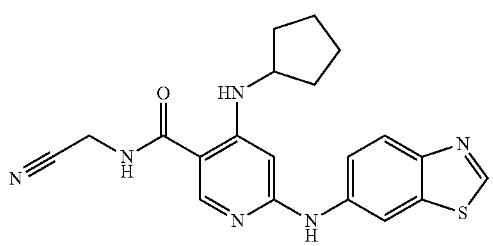 [SMILES: N#CCNC(=O)c1cnc(Nc2ccc3ncsc3c2)cc1NC1CCCC1] | 2.19 | F | 393.2 |
| 154 | 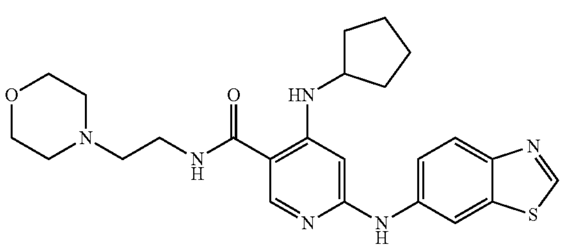 [SMILES: O=C(NCCN1CCOCC1)c1cnc(Nc2ccc3ncsc3c2)cc1NC1CCCC1] | 2.08 | F | 467.2 |
| 155 | 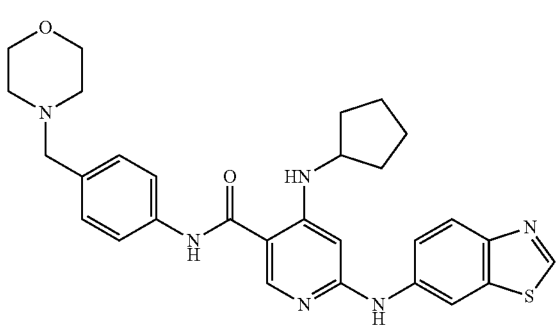 [SMILES: O=C(Nc1ccc(CN2CCOCC2)cc1)c1cnc(Nc2ccc3ncsc3c2)cc1NC1CCCC1] | 2.49 | F | 555.2 |

TABLE 4-continued

| Ex. No. | Structure | HPLC RT (min) | HPLC cond. | LCMS |
|---|---|---|---|---|
| 156 | 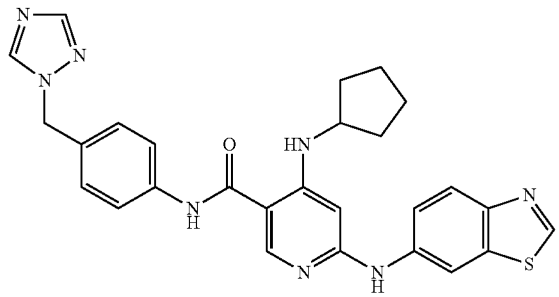 [SMILES: O=C(Nc1ccc(Cn2cncn2)cc1)c1cnc(Nc2ccc3ncsc3c2)cc1NC1CCCC1] | 2.28 | F | 511.2 |
| 157 | 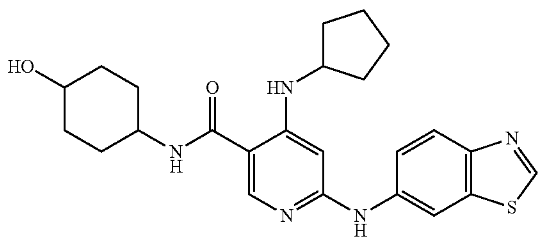 [SMILES: O=C(NC1CCC(O)CC1)c1cnc(Nc2ccc3ncsc3c2)cc1NC1CCCC1] | 2.03 | F | 452.2 |
| 158 | 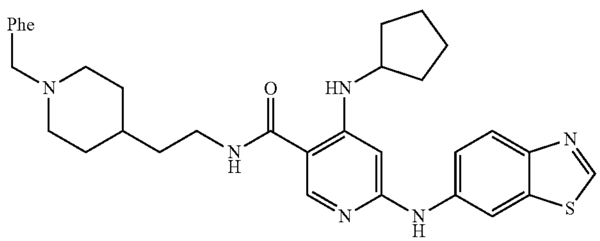 | 2.50 | F | 555.2 |

Example 159

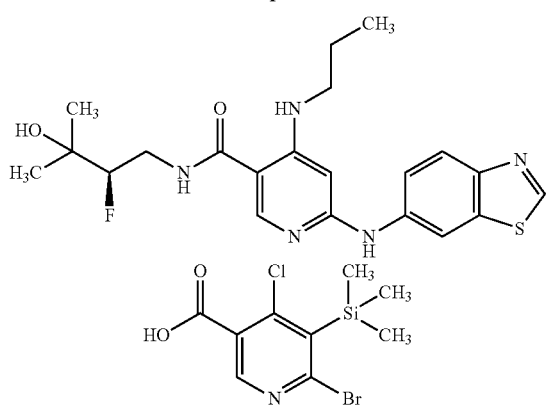

Step 1: A solution of 2,2,6,6-tetramethylpiperidine (23.5 g, 160 mmol) in (THF 250 mL) was cooled to −78° C. under a nitrogen atmosphere. Butyl lithium (9.7 g, 151 mmol) was added dropwise and then allowed to stir at 0° C. for 45 min. The LTMP solution was then cooled to −78° C. and treated dropwise with a solution of 2-bromo-4-fluoro-3-(trimethylsilyl)pyridine (20 g, 76 mmol) in THF (50 mL). The reaction mixture was stirred at −78° C. for 3.5 h and then quenched with dry ice under a nitrogen atmosphere. The reaction mixture was acidified with 5% $H_2SO_4$ solution and the aqueous layer was extracted twice with EtOAc. The separated organic layer was dried ($Na_2SO_4$) and concentrated to afford the crude product (6-chloro-4-fluoro-5-(trimethylsilyl)nicotinic acid (18.7 g, 80% yield) as a brown oil. This crude product was used directly in the next step. $^1$H NMR (400 MHz, $CDCl_3$) δ 8.66 (s, 1H), 0.59 (s, 9H).

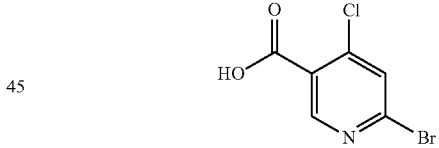

Step 2: To solution of 6-chloro-4-bromo-5-(trimethylsilyl)nicotinic acid (4 g, 13 mmol) in MeOH (100 mL) and was added $K_2CO_3$ (4 g, 29 mmol). The reaction mixture was stirred at rt for 2 h. The reaction mixture was slowly added to ice then acidified with 10% $H_2SO_4$. The aqueous layer was extracted twice with EtOAc (50 mL). The separated organic layer was dried ($Na_2SO_4$) and concentrated to afford the crude product 6-chloro-4-bromonicotinic acid (2.3 g, 75% yield). LCMS m/z 233.9 (M)$^+$; $^1$H NMR (400 MHz, DMSO-$d_6$) δ 14.05 (br s, 1H), 8.77 (s, 1H), 8.06 (s, 1H).

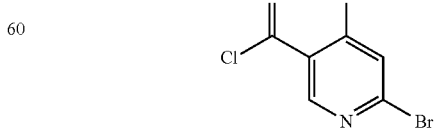

Step 3: A suspension of 6-bromo-4-chloronicotinic acid (5 g, 21.15 mmol) in DCM (75 mL) was cooled to 0° C. Oxalyl chloride (3.70 ml, 42.3 mmol) was added and the reaction mixture was heated at 50° C. for 1 h. The reaction mixture was cooled to rt and the excess oxalyl chloride and DCM was removed by distillation to obtain the acid chloride as a brown oil which was used directly in the next step.

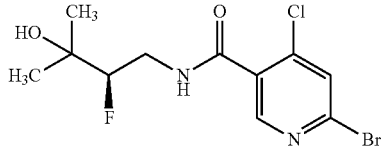 [SMILES: CC(C)(O)[C@H](F)CNC(=O)c1cnc(Br)cc1Cl]

Step 4: (R)-4-Amino-3-fluoro-2-methylbutan-2-ol (2.82 g, 23.26 mmol) in DCM (25 mL) was added TEA (8.84 mL, 63.4 mmol) at 0° C. The acid chloride prepared above was dissolved in DCM (75 mL) and added dropwise at 0° C. to the amine solution. The reaction mixture was stirred for 30 min and allowed to warm to RT for 30 min. The reaction mixture was diluted with DCM (150 mL) and washed with water and brine. The organic layer was dried over $Na_2SO_4$, filtered and concentrated to give (R)-6-bromo-4-chloro-N-(2-fluoro-3-hydroxy-3-methylbutyl)nicotinamide (2.7 g, 7.95 mmol, 37.6% yield) as a brown oil. The residue was purified via column chromatography (pet ether:EA, 15-20%). $^1$H NMR (400 MHz, DMSO-$d_6$) δ 8.90 (t, J=5.6 Hz, 1H), 8.47 (s, 1H), 7.91 (s, 1H), 4.84 (s, 1H), 4.31 (ddd, J=49.6, 8.4, 2.0 Hz, 1H), 3.77 (ddd, J=38.4, 14.8, 6.0 Hz, 1H), 3.69 (m, 1H), 1.17 (s, sH), 1.15 (s, 3H).

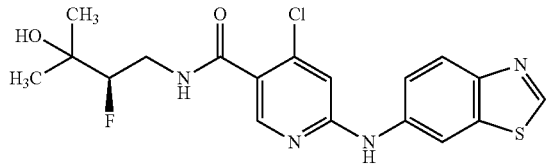 [SMILES: CC(C)(O)[C@H](F)CNC(=O)c1cnc(Nc2ccc3ncsc3c2)cc1Cl]

Step 5: (R)-6-Bromo-4-chloro-N-(2-fluoro-3-hydroxy-3-methylbutyl)nicotinamide (3.2 g, 9.42 mmol), benzo[d]thiazol-6-amine (1.84 g, 12.25 mmol), dioxane (20 mL), and $Cs_2CO_3$ (6.14 g, 18.85 mmol) was charged into 80 mL microwave vial and was degassed for 5 min with argon. DPPF (0.522 g, 0.942 mmol) was added and again it was degassed for 5 min followed by $PdCl_2$ (dppf) (0.689 g, 0.942 mmol) and further degassed for 15 min. The vial was heated in microwave at 100° C. for 3 h. The reaction was diluted with EA and washed with water and brine. The organic layer and dried with sodium sulfate, concentrated the crude residue was purified with column by using 80% EA to afford (R)-6-(benzo[d]thiazol-6-ylamino)-4-chloro-N-(2-fluoro-3-hydroxy-3-methylbutyl)nicotinamide (1.1 g, 28% yield). LCMS m/z 409.0 (M+H)'; $^1$H NMR (400 MHz, DMSO-$d_6$) δ 9.72 (s, 1H), 9.21 (s, 1H), 8.67 (d, J=2.0 Hz, 1H), 8.58 (t, J=5.6 Hz, 1H), 8.29 (s, 1H), 8.01 (d, J=8.8 Hz, 1H), 7.61 (dd, J=8.8, 6.8 Hz, 1H), 6.96 (s, 1H), 4.82 (s, 1H), 4.32 (dd, J=49.2, 9.2 Hz, 1H), 3.69 (m, 1H), 1.17 (m, 6H).

Step 6: General Procedure: In a microwave vial (R)-6-(benzo[d]thiazol-6-ylamino)-4-chloro-N-(2-fluoro-3-hydroxy-3-methylbutyl)nicotinamide (20 mg, 0.05 mmol), butyl amine (0.1 mmol), $K_2CO_3$ (20 mg, 0.15 mmol) and DMF (0.5 mL) was stirred for 12 hr at 120° C. The reaction was cooled and the product was purified directly via reverse phase prep HPLC using the following conditions: Column: XBridge prep OBD C18, 19×100 mm, 5 μm, Mobile Phases: A=10 mM ammonium acetate in water, B=Acetonitrile, 15 mL/min flow, 20 min gradient. Accordingly, 5.7 mg (29% yield) of Example 159 were isolated.

The Examples described in Table 5 were prepared according to the method outlined for Example 159.

TABLE 5

| Ex. No. | Structure | HPLC RT (min) | HPLC cond. | LCMS |
|---|---|---|---|---|
| 159 | [Abs] | 1.98 | F | 432.0 |
| 160 | [Abs] | 2.16 | F | 446.2 |

TABLE 5-continued

| Ex. No. | Structure | | HPLC RT (min) | HPLC cond. | LCMS |
|---|---|---|---|---|---|
| 161 | 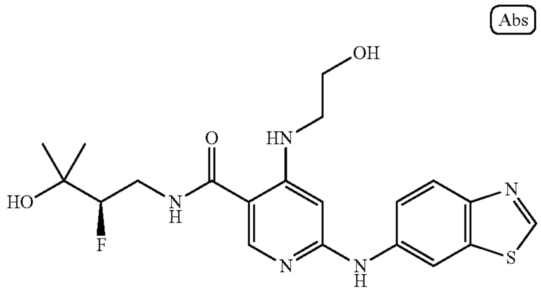 [SMILES: CC(C)(O)[C@H](F)CNC(=O)c1cnc(Nc2ccc3ncsc3c2)cc1NCCO] | Abs | 1.43 | F | 434.0 |
| 162 | 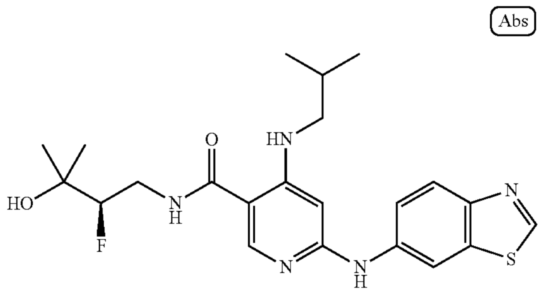 [SMILES: CC(C)CNc1cc(Nc2ccc3ncsc3c2)ncc1C(=O)NC[C@@H](F)C(C)(C)O] | Abs | 2.24 | F | 446.0 |
| 163 | 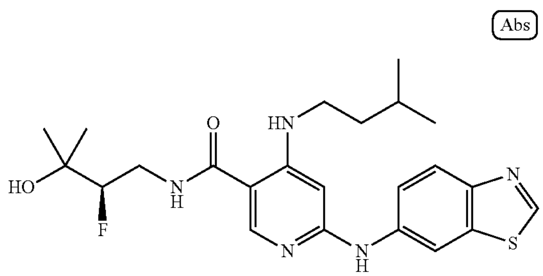 [SMILES: CC(C)CCNc1cc(Nc2ccc3ncsc3c2)ncc1C(=O)NC[C@@H](F)C(C)(C)O] | Abs | 2.40 | F | 460.2 |
| 164 | 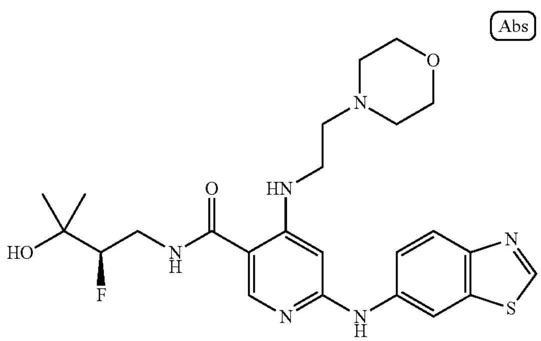 [SMILES: CC(C)(O)[C@H](F)CNC(=O)c1cnc(Nc2ccc3ncsc3c2)cc1NCCN1CCOCC1] | Abs | 1.67 | F | 503.0 |
| 165 | 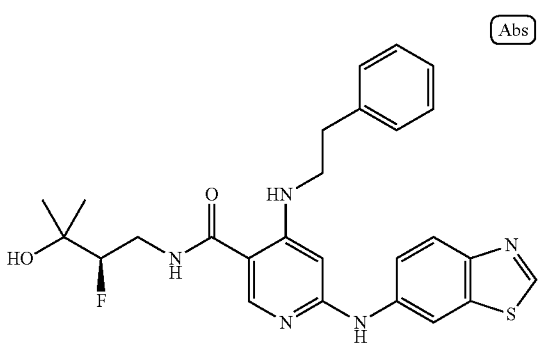 [SMILES: CC(C)(O)[C@H](F)CNC(=O)c1cnc(Nc2ccc3ncsc3c2)cc1NCCc1ccccc1] | Abs | 2.32 | F | 494.2 |

141
142
TABLE 5-continued
| Ex. No. | Structure | | HPLC RT (min) | HPLC cond. | LCMS |
|---|---|---|---|---|---|
| 166 | 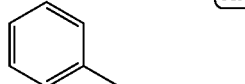 | Abs | 2.15 | G | 494.3 |
| 167 | 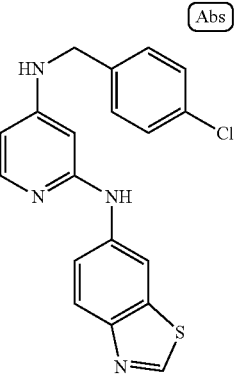 | Abs | 2.20 | G | 514.3 |
| 168 | 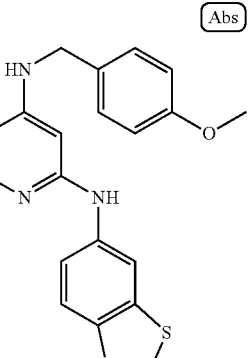 | Abs | 1.99 | G | 510.3 |
Example 169
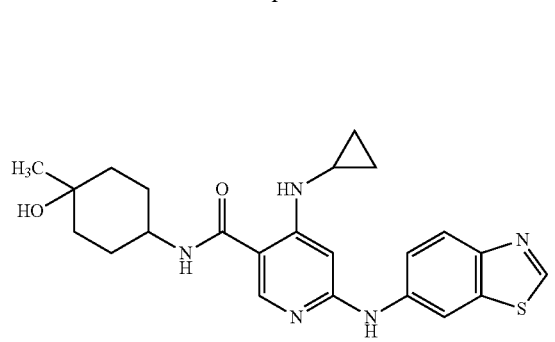
-continued
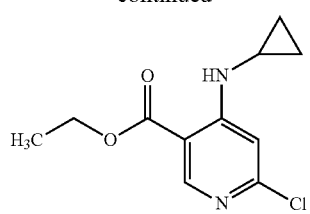
Step 1: To a solution of ethyl 4,6-dichloronicotinate (50 g, 227 mmol) in DMA (500 mL) was added DIPEA (39.7 mL, 227 mmol) and cyclopropyl amine (17.6 mL, 250 mmol). The mixture was then heated at 90° C. for 5 h. The reaction mixture was quenched into crushed ice with stirring. The resulting slurry was stirred and filtered to afford the crude product (42 g, 91% yield) which was used without further purification. LCMS m/z 241.1 (M+H)+. $^1$H NMR (400 MHz, DMSO-d$_6$) δ 8.54 (s, 1H), 8.09 (s, 1H), 7.03 (s, 1H), 4.29 (q, J=7.2 Hz, 2H), 2.61 (m, 1H), 1.31 (t, J=7.2 Hz, 3H), 0.86 (m, 2H), 0.58 (m, 2H).

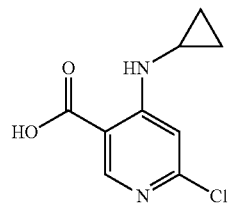 [SMILES: O=C(O)c1cnc(Cl)cc1NC1CC1]

Step 2: To a solution of ethyl 6-chloro-4-(cyclopropylamino)nicotinate (2 g, 8.31 mmol) in EtOH (14 mL), was added LiOH.H$_2$O (1.02 g, 25 mmol) and water (6 mL, 8.31 mmol). The reaction mixture was stirred at rt for 1 h. The solvents were removed in vacuo and the pH adjusted to 3-4 with 1.5 N HCl. The resulting solid was filtered and dried to afford 6-chloro-4-(cyclopropylamino)nicotinic acid (1.5 g, 82% yield) as a white solid. LCMS m/z 213.2 (M+H)+.

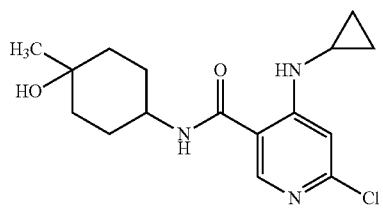 [SMILES: CC1(O)CCC(NC(=O)c2cnc(Cl)cc2NC2CC2)CC1]

Step 3: To a stirred solution of 6-chloro-4-(cyclopropylamino)nicotinic acid (0.30 g, 1.4 mmol) in DMF (5 mL) was added HATU (0.644 g, 1.7 mmol), DIPEA (0.74 mL, 4.23 mmol) and (1R,4R)-4-amino-1-methylcyclohexanol (0.219 g, 1.693 mmol). The mixture was stirred for 3 hours at room temperature. The DMF was evaporated from the reaction mixture and the residue was partitioned with water and EtOAc. The organic layer was washed with cold water (3 times). The organic layer was dried over Na$_2$SO$_4$ and concentrated under vacuum to get crude compound which was then purified by flash column chromatography (10% MeOH/DCM) to afford 6-chloro-4-(cyclopropylamino)-N-(4-hydroxy-4-methylcyclohexyl)nicotinamide (310 mg, 63% yield). LCMS m/z 324.2 (M+H)+.

Step 4: A solution of 6-chloro-4-(cyclopropylamino)-N-(4-hydroxy-4-methylcyclohexyl)nicotinamide (0.100 g, 0.309 mmol) in dioxane (10 mL) was added benzo[d]thiazol-6-amine (0.056 g, 0.37 mmol), Xantphos (0.071 g, 0.124 mmol) and sodium carbonate (0.131 g, 1.24 mmol). The solution was purged with N$_2$ for 10 mins. Tris(dibenzylideneacetone)dipalladium (0) (0.113 g, 0.124 mmol) was added and the mixture purged with N$_2$ for an additional 10 min. The reaction mixture was heated at 110° C. for 18 h. The mixture was cooled to rt and diluted with EtOAc. The mixture was filtered through CELITE® and concentrated to a residue which was purified via preparative HPLC to afford 6-(benzo[d]thiazol-6-ylamino)-4-(cyclopropylamino)-N-(4-hydroxy-4-methylcyclohexyl)nicotinamide (7 mg, 5% yield).

The Examples in the table below were prepared in an analogous fashion to Example 169, substituting where appropriate, alternate amines in the synthetic sequence. Additionally, the methods outlined for Example 5 may be employed to prepare Examples in this table, substituting where appropriate, alternate amines in the synthetic sequence.

TABLE 6

| Ex. No. | Structure | HPLC RT (min) | HPLC cond. | LCMS (M + H)+ |
|---|---|---|---|---|
| 169 | 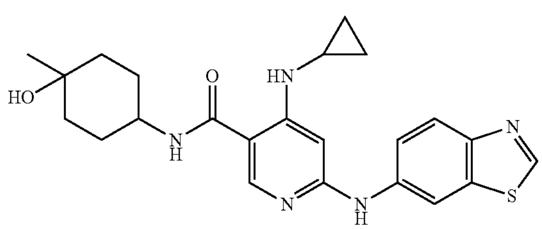 [SMILES: CC1(O)CCC(NC(=O)c2cnc(Nc3ccc4ncsc4c3)cc2NC2CC2)CC1] | 6.19 | E | 438.0 |
| 170 | 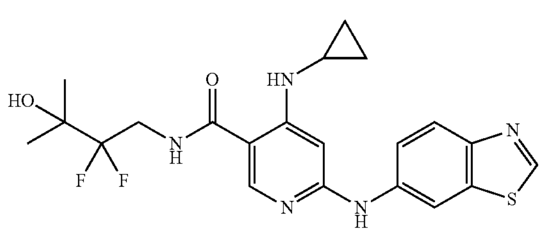 [SMILES: CC(C)(O)C(F)(F)CNC(=O)c1cnc(Nc2ccc3ncsc3c2)cc1NC1CC1] | 6.8 | A | 448.5 |

TABLE 6-continued

| Ex. No. | Structure | HPLC RT (min) | HPLC cond. | LCMS (M + H)+ |
|---|---|---|---|---|
| 171 | 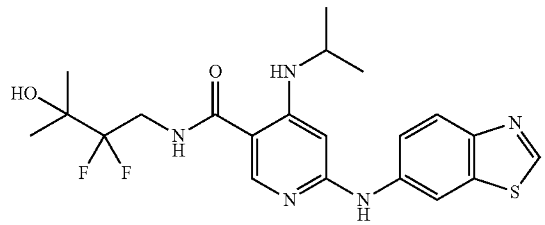 [SMILES: CC(C)Nc1cc(Nc2ccc3ncsc3c2)ncc1C(=O)NCC(F)(F)C(C)(C)O] | 5.72 | E | 450.2 M + H |
| 172 | 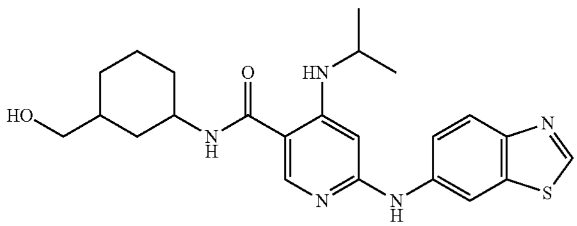 [SMILES: CC(C)Nc1cc(Nc2ccc3ncsc3c2)ncc1C(=O)NC1CCCC(CO)C1] | 1.62 | H | 440.6 |
| 173 | 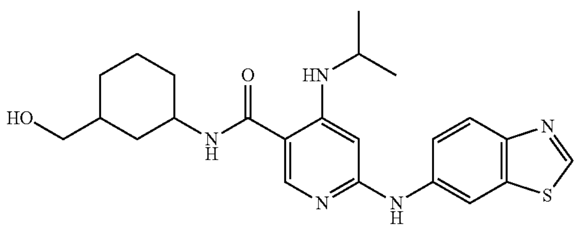 [SMILES: CC(C)Nc1cc(Nc2ccc3ncsc3c2)ncc1C(=O)NC1CCCC(CO)C1] | 3.94 | H | 440.6 |
| 174 | 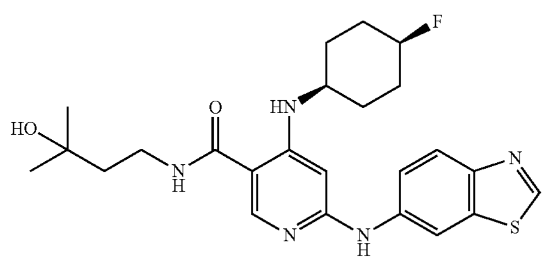 [SMILES: CC(C)(O)CCNC(=O)c1cnc(Nc2ccc3ncsc3c2)cc1N[C@H]1CC[C@@H](F)CC1] | 1.31 | G | 471.6 (M+) |
| 175 | 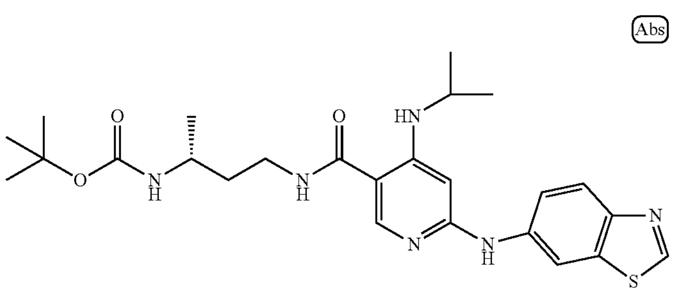 [SMILES: CC(C)Nc1cc(Nc2ccc3ncsc3c2)ncc1C(=O)NCC[C@@H](C)NC(=O)OC(C)(C)C] | 0.84 | G | 499.3 |
| 176 | 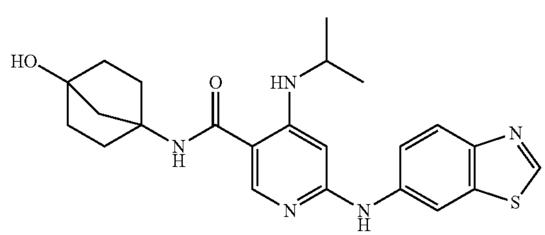 [SMILES: CC(C)Nc1cc(Nc2ccc3ncsc3c2)ncc1C(=O)NC12CCC(O)(CC1)C2] | 1.42 | G | 438.3 |

TABLE 6-continued

| Ex. No. | Structure | HPLC RT (min) | HPLC cond. | LCMS (M + H)+ |
|---|---|---|---|---|
| 177 | 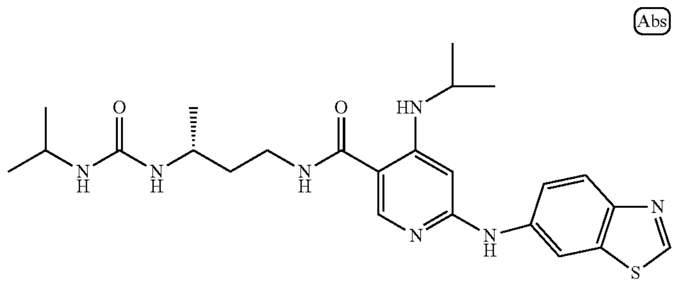 [SMILES: CC(C)NC(=O)N[C@H](C)CCNC(=O)c1cnc(Nc2ccc3ncsc3c2)cc1NC(C)C] | 1.48 | G | 484.2 |
| 178 | 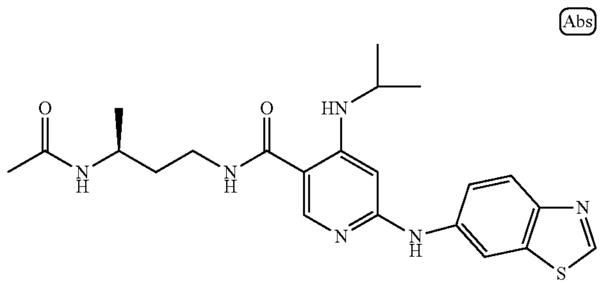 [SMILES: CC(=O)N[C@@H](C)CCNC(=O)c1cnc(Nc2ccc3ncsc3c2)cc1NC(C)C] | 1.32 | G | 441.2 |
| 179 | 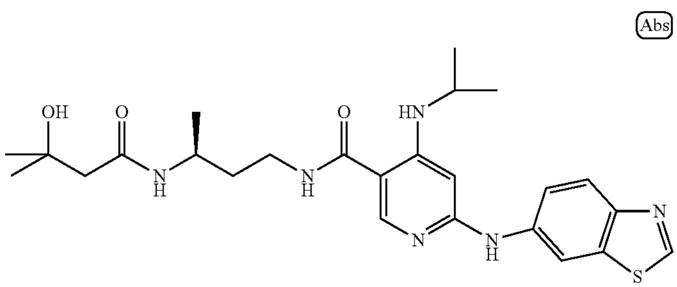 [SMILES: CC(C)Nc1cc(Nc2ccc3ncsc3c2)ncc1C(=O)NCC[C@H](C)NC(=O)CC(C)(C)O] | 1.38 | G | 499.3 |
| 180 | 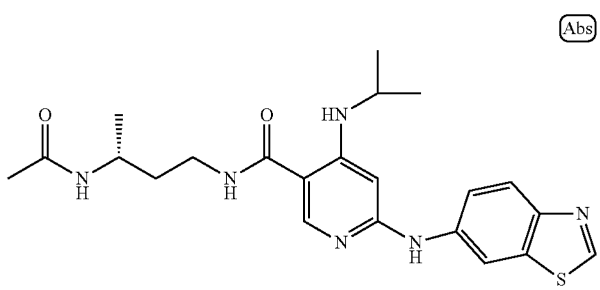 [SMILES: CC(=O)N[C@H](C)CCNC(=O)c1cnc(Nc2ccc3ncsc3c2)cc1NC(C)C] | 1.33 | G | 441.1 |
| 181 | 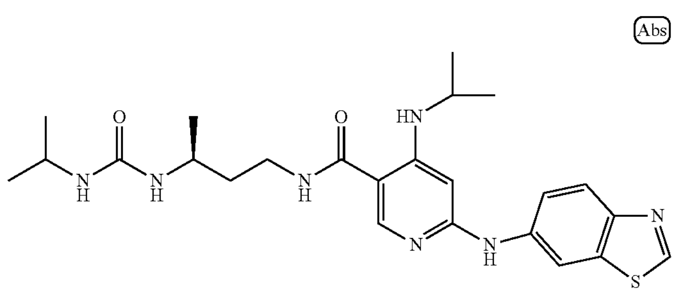 [SMILES: CC(C)NC(=O)N[C@@H](C)CCNC(=O)c1cnc(Nc2ccc3ncsc3c2)cc1NC(C)C] | 1.49 | G | 484.2 |

TABLE 6-continued
| Ex. No. | Structure | HPLC RT (min) | HPLC cond. | LCMS (M + H)+ |
|---|---|---|---|---|
| 182 |  Abs | 1.24 | G | 511.6 |
| 183 |  Abs | 1.46 | G | 485.2 |
| 184 |  Abs | 1.67 | G | 495.2 |
| 185 |  Abs | 1.22 | O | 503.2 |
| 186 |  Abs | 1.22 | O | 531.2 |

TABLE 6-continued
| Ex. No. | Structure | HPLC RT (min) | HPLC cond. | LCMS (M + H)+ |
|---|---|---|---|---|
| 187 | 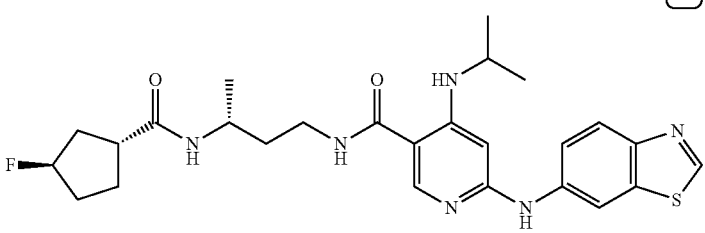 | 1.35 | G | 513.2 |
| 188 | 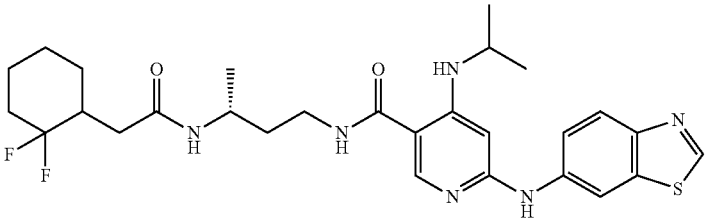 [SMILES: CC(C)Nc1cc(Nc2ccc3ncsc3c2)ncc1C(=O)NCC[C@@H](C)NC(=O)CC1CCCCC1(F)F] | 1.79 | G | 559.3 |
| 189 | 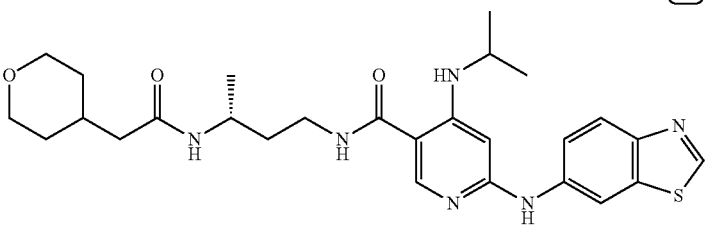 | 1.21 | O | 525.2 |
| 190 | 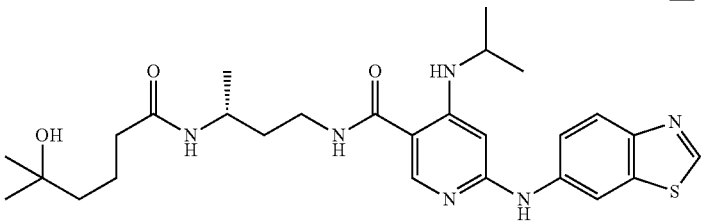 | 1.42 | G | 527.2 |
| 191 | 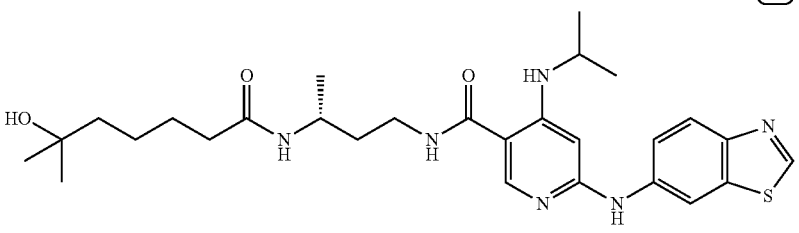 | 1.48 | G | 541.3 |
| 192 | 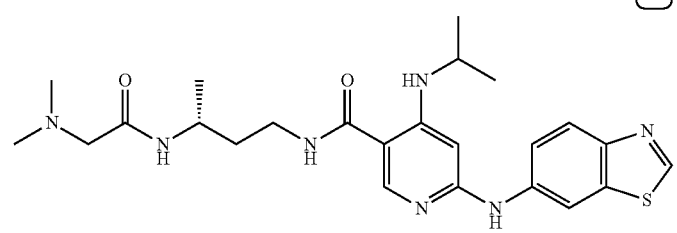 | 0.97 | O | 484.2 |

TABLE 6-continued
| Ex. No. | Structure | HPLC RT (min) | HPLC cond. | LCMS (M + H)+ |
|---|---|---|---|---|
| 193 | 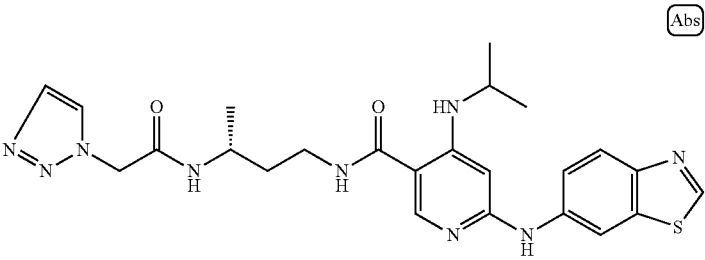 [SMILES: CC(C)Nc1cc(Nc2ccc3ncsc3c2)ncc1C(=O)NCC[C@@H](C)NC(=O)Cn1ccnn1] | 1.10 | O | 508.2 |
| 194 | 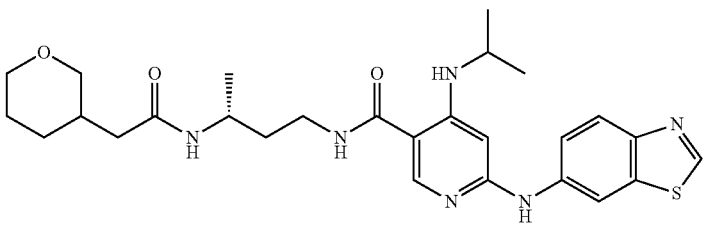 [SMILES: CC(C)Nc1cc(Nc2ccc3ncsc3c2)ncc1C(=O)NCC[C@@H](C)NC(=O)CC1CCCOC1] | 1.14 | O | 525.2 |
| 195 | 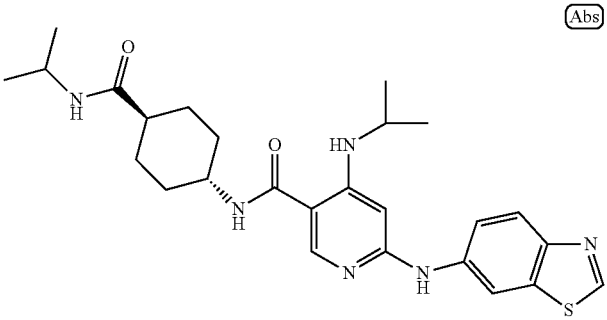 [SMILES: CC(C)Nc1cc(Nc2ccc3ncsc3c2)ncc1C(=O)N[C@H]1CC[C@H](C(=O)NC(C)C)CC1] | 1.33 | G | 495.2 |
| 196 | 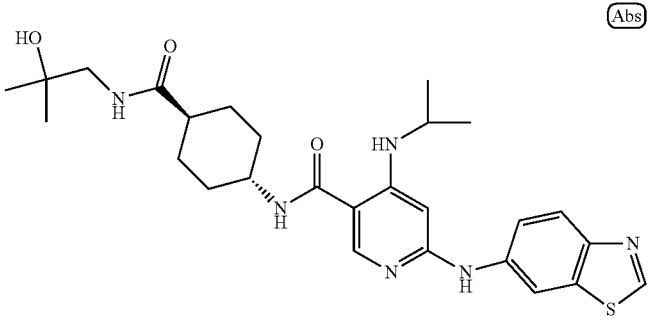 [SMILES: CC(C)Nc1cc(Nc2ccc3ncsc3c2)ncc1C(=O)N[C@H]1CC[C@H](C(=O)NCC(C)(C)O)CC1] | 1.22 | G | 525.2 |
| 197 | 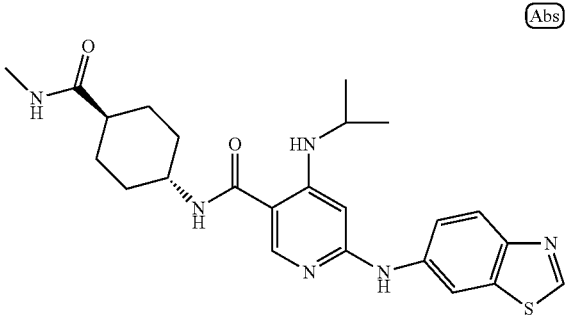 [SMILES: CNC(=O)[C@H]1CC[C@H](NC(=O)c2cnc(Nc3ccc4ncsc4c3)cc2NC(C)C)CC1] | 1.20 | G | 466.4 |

TABLE 6-continued
| Ex. No. | Structure | HPLC RT (min) | HPLC cond. | LCMS (M + H)+ |
|---|---|---|---|---|
| 198 | 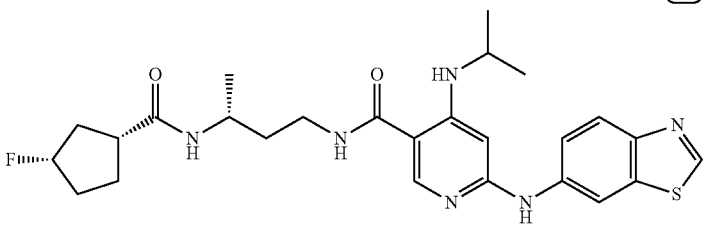 | 1.59 | G | 513.2 |
| 199 | 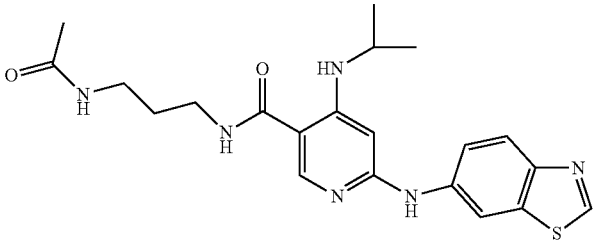 [SMILES: CC(=O)NCCCNC(=O)c1cnc(Nc2ccc3ncsc3c2)cc1NC(C)C] | 1.26 | O | 427.1 |
| 200 | 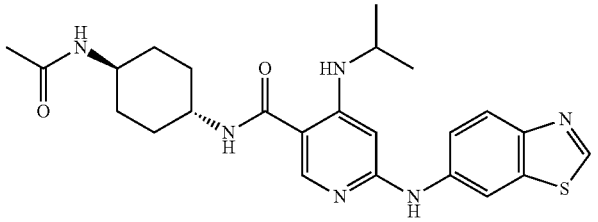 [SMILES: CC(=O)N[C@H]1CC[C@H](NC(=O)c2cnc(Nc3ccc4ncsc4c3)cc2NC(C)C)CC1] | 1.22 | G | 467.2 |
| 201 | 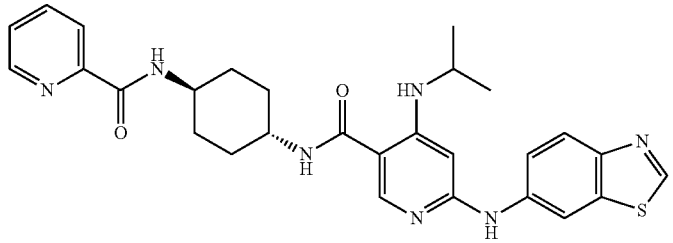 [SMILES: CC(C)Nc1cc(Nc2ccc3ncsc3c2)ncc1C(=O)N[C@H]1CC[C@H](NC(=O)c2ccccn2)CC1] | 1.45 | G | 530.2 |
| 202 | 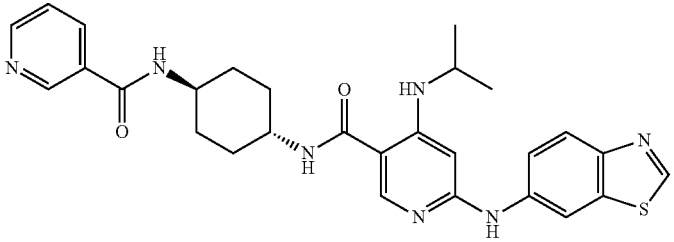 [SMILES: CC(C)Nc1cc(Nc2ccc3ncsc3c2)ncc1C(=O)N[C@H]1CC[C@H](NC(=O)c2cccnc2)CC1] | 1.26 | G | 530.2 |
| 203 | 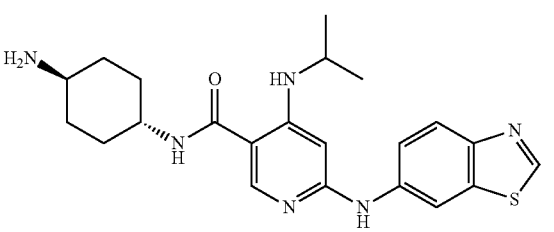 [SMILES: CC(C)Nc1cc(Nc2ccc3ncsc3c2)ncc1C(=O)N[C@H]1CC[C@H](N)CC1] | 1.24 | G | 425.1 |

TABLE 6-continued

| Ex. No. | Structure | HPLC RT (min) | HPLC cond. | LCMS (M + H)+ |
|---|---|---|---|---|
| 204 | 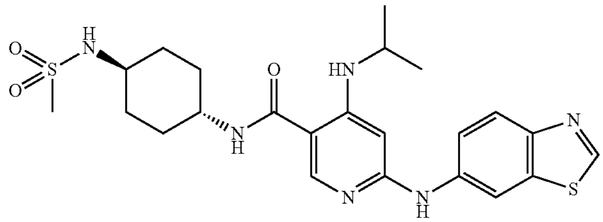 [SMILES: CC(C)Nc1cc(Nc2ccc3ncsc3c2)ncc1C(=O)N[C@H]1CC[C@H](NS(C)(=O)=O)CC1] | 1.28 | G | 503.2 |
| 205 | 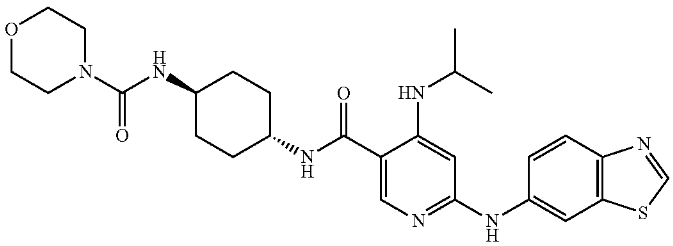 [SMILES: CC(C)Nc1cc(Nc2ccc3ncsc3c2)ncc1C(=O)N[C@H]1CC[C@H](NC(=O)N2CCOCC2)CC1] | 1.16 | G | 538.3 |
| 206 | 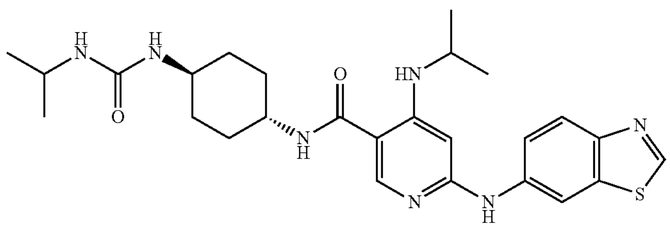 [SMILES: CC(C)NC(=O)N[C@H]1CC[C@H](NC(=O)c2cnc(Nc3ccc4ncsc4c3)cc2NC(C)C)CC1] | 1.55 | G | 510.3 |
| 207 | 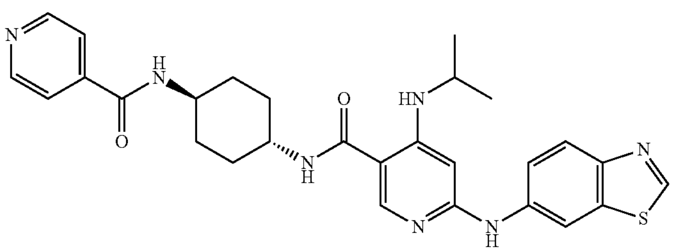 [SMILES: CC(C)Nc1cc(Nc2ccc3ncsc3c2)ncc1C(=O)N[C@H]1CC[C@H](NC(=O)c2ccncc2)CC1] | 1.26 | G | 530.2 |
| 208 | (Abs) | 1.50 | G | 532.3 |
| 209 | 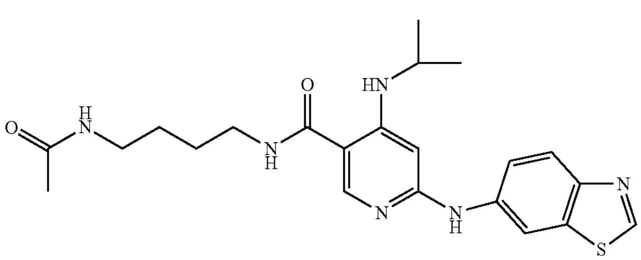 [SMILES: CC(=O)NCCCCNC(=O)c1cnc(Nc2ccc3ncsc3c2)cc1NC(C)C] | 1.17 | G | 441.2 |

TABLE 6-continued

| Ex. No. | Structure | HPLC RT (min) | HPLC cond. | LCMS (M + H)+ |
|---|---|---|---|---|
| 210 | 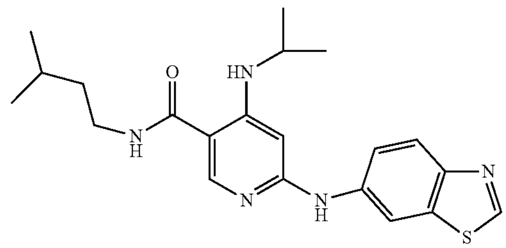 [SMILES: CC(C)CCNC(=O)c1cnc(Nc2ccc3ncsc3c2)cc1NC(C)C] | 1.64 | G | 397.5 |
| 211 | 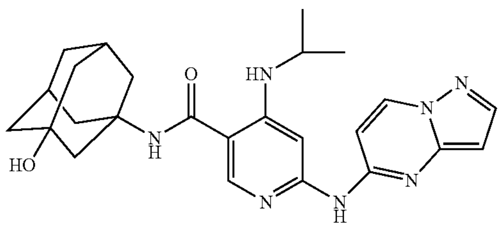 [SMILES: CC(C)Nc1cc(Nc2ccn3nccc3n2)ncc1C(=O)NC12CC3CC(CC(O)(C3)C1)C2] | 1.55 | G | 463.2 |
| 212 | 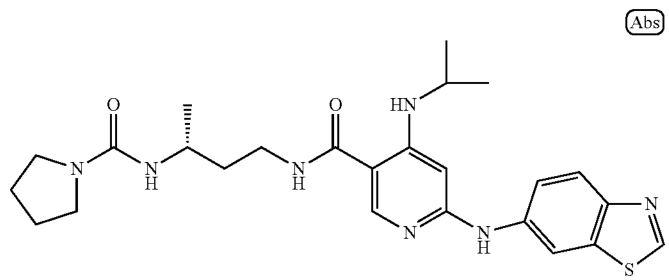 [SMILES: CC(C)Nc1cc(Nc2ccc3ncsc3c2)ncc1C(=O)NCC[C@@H](C)NC(=O)N1CCCC1] | 1.33 | G | 496.2 |
| 213 | 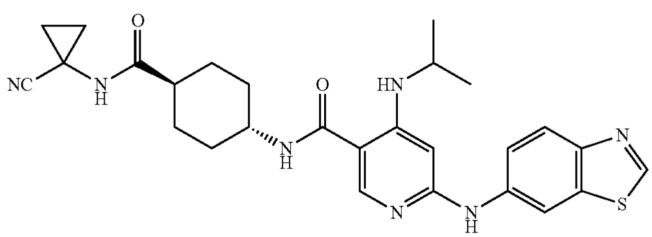 [SMILES: CC(C)Nc1cc(Nc2ccc3ncsc3c2)ncc1C(=O)N[C@H]1CC[C@H](C(=O)NC2(C#N)CC2)CC1] | 1.29 | G | 518.2 |
| 214 | 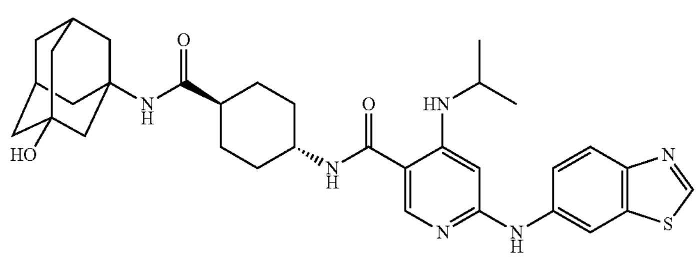 [SMILES: CC(C)Nc1cc(Nc2ccc3ncsc3c2)ncc1C(=O)N[C@H]1CC[C@H](C(=O)NC23CC4CC(CC(O)(C4)C2)C3)CC1] | 1.36 | G | 603.3 |
| 215 | 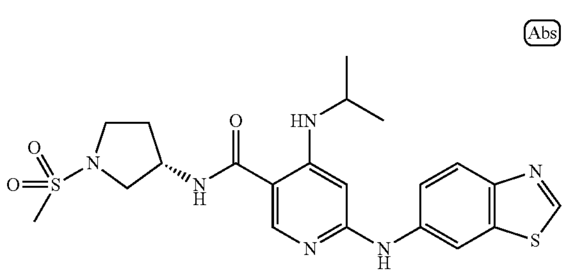 [SMILES: CC(C)Nc1cc(Nc2ccc3ncsc3c2)ncc1C(=O)N[C@H]1CCN(S(C)(=O)=O)C1] | 1.42 | G | 475.1 |

TABLE 6-continued

| Ex. No. | Structure | HPLC RT (min) | HPLC cond. | LCMS (M + H)+ |
|---|---|---|---|---|
| 216 | 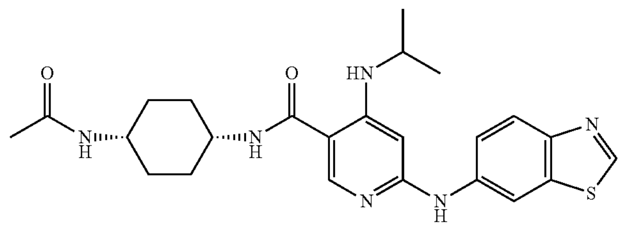 [SMILES: CC(=O)N[C@H]1CC[C@@H](NC(=O)c2cnc(Nc3ccc4ncsc4c3)cc2NC(C)C)CC1] | 1.38 | G | 467.2 |
| 217 | 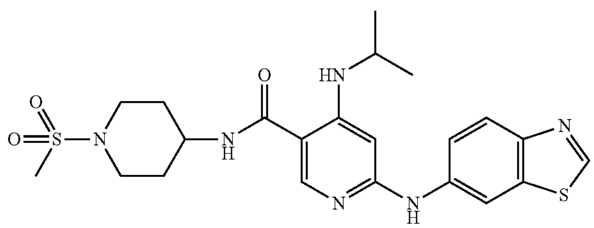 [SMILES: CC(C)Nc1cc(Nc2ccc3ncsc3c2)ncc1C(=O)NC1CCN(S(C)(=O)=O)CC1] | 1.46 | G | 489.2 |
| 218 | 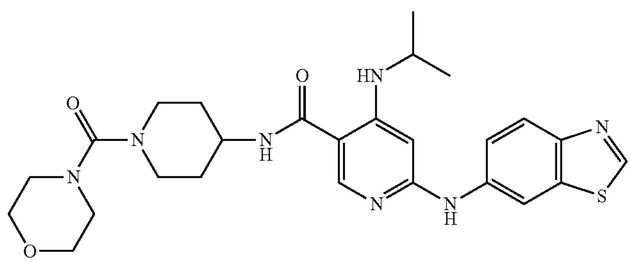 [SMILES: CC(C)Nc1cc(Nc2ccc3ncsc3c2)ncc1C(=O)NC1CCN(C(=O)N2CCOCC2)CC1] | 1.44 | G | 524.2 |
| 219 | 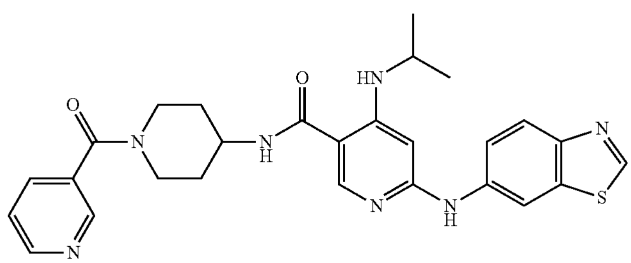 [SMILES: CC(C)Nc1cc(Nc2ccc3ncsc3c2)ncc1C(=O)NC1CCN(C(=O)c2cccnc2)CC1] | 1.40 | G | 516.2 |
| 220 | 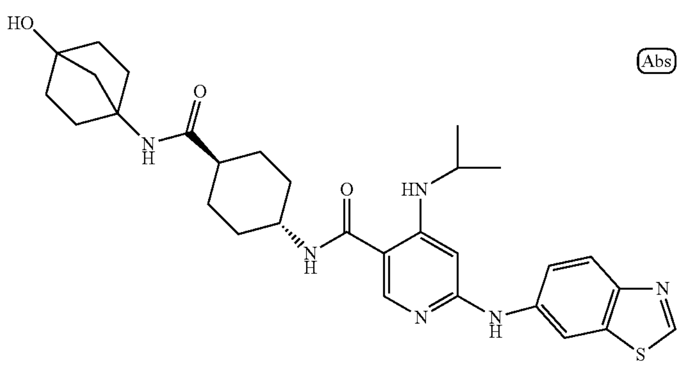 [SMILES: CC(C)Nc1cc(Nc2ccc3ncsc3c2)ncc1C(=O)N[C@H]1CC[C@H](C(=O)NC23CCC(O)(CC2)C3)CC1] | 1.25 | G | 563.2 |

TABLE 6-continued

| Ex. No. | Structure | HPLC RT (min) | HPLC cond. | LCMS (M + H)+ |
|---|---|---|---|---|
| 221 | 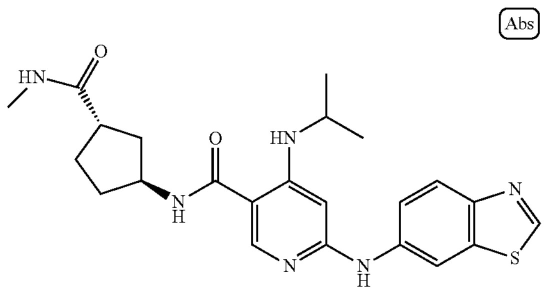 [SMILES: CNC(=O)[C@H]1CC[C@H](NC(=O)c2cnc(Nc3ccc4ncsc4c3)cc2NC(C)C)C1] | 1.22 | O | 453.1 |
| 222 | 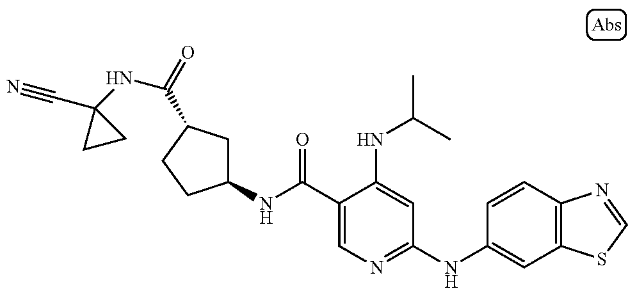 [SMILES: CC(C)Nc1cc(Nc2ccc3ncsc3c2)ncc1C(=O)N[C@H]1CC[C@H](C(=O)NC2(C#N)CC2)C1] | 1.13 | O | 504.2 |
| 223 | 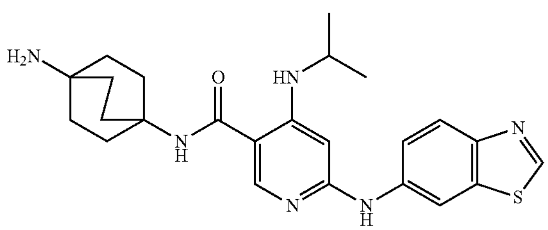 [SMILES: CC(C)Nc1cc(Nc2ccc3ncsc3c2)ncc1C(=O)NC12CCC(N)(CC1)CC2] | 1.12 | G | 451.0 |
| 224 | 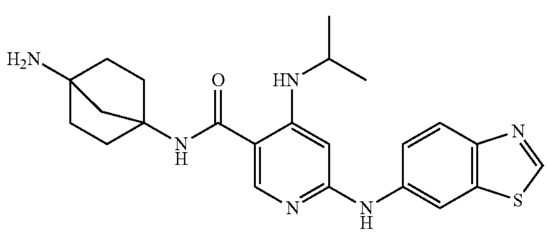 [SMILES: CC(C)Nc1cc(Nc2ccc3ncsc3c2)ncc1C(=O)NC12CCC(N)(CC1)C2] | 1.12 | G | 437.2 |
| 225 | 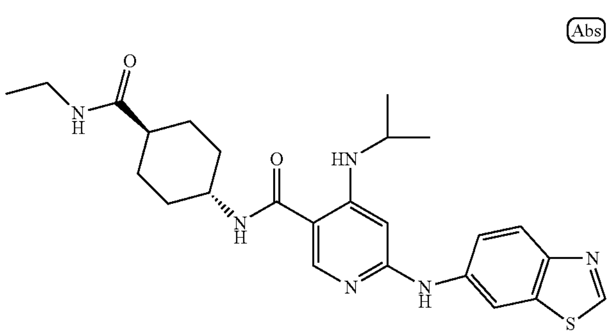 [SMILES: CCNC(=O)[C@H]1CC[C@H](NC(=O)c2cnc(Nc3ccc4ncsc4c3)cc2NC(C)C)CC1] | 1.29 | G | 481.2 |

TABLE 6-continued

| Ex. No. | Structure | HPLC RT (min) | HPLC cond. | LCMS (M + H)+ |
|---|---|---|---|---|
| 226 | 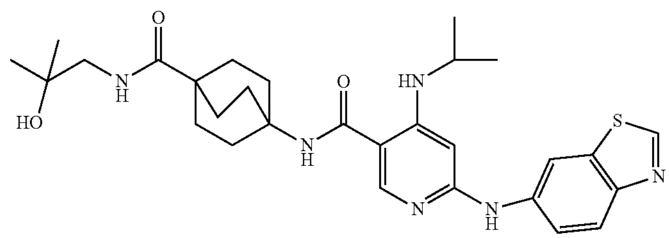 [SMILES: CC(C)Nc1cc(Nc2ccc3ncsc3c2)ncc1C(=O)NC12CCC(C(=O)NCC(C)(C)O)(CC1)CC2] | 1.31 | G | 551.2 |
| 227 | [Abs] | 1.30 | G | 493.2 |
| 228 | [Abs] | 1.32 | G | 453.2 |
| 229 | 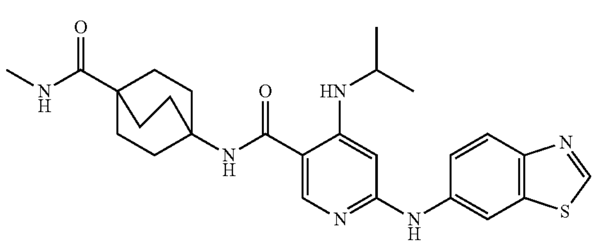 [SMILES: CNC(=O)C12CCC(NC(=O)c3cnc(Nc4ccc5ncsc5c4)cc3NC(C)C)(CC1)CC2] | 1.49 | G | 493.2 |
| 230 | 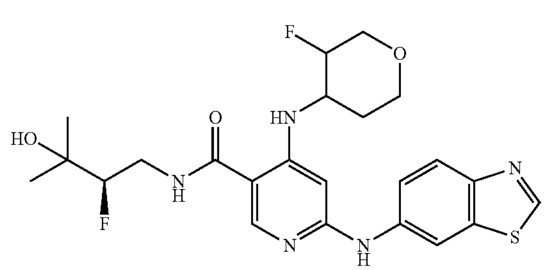 [SMILES: CC(C)(O)[C@H](F)CNC(=O)c1cnc(Nc2ccc3ncsc3c2)cc1NC1CCOCC1F] | 5.32 | B | 492.5 |

TABLE 6-continued
| Ex. No. | Structure | HPLC RT (min) | HPLC cond. | LCMS (M + H)+ |
|---|---|---|---|---|
| 231 | 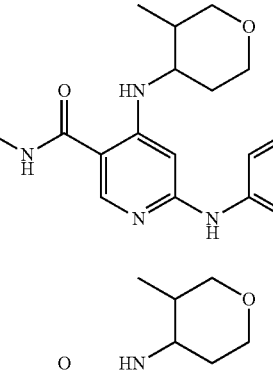 | 5.49 | B | 492.5 |
| 232 | 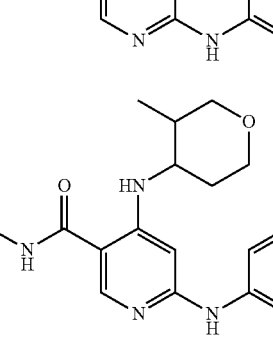 | 5.5 | B | 488.2 |
| 233 | 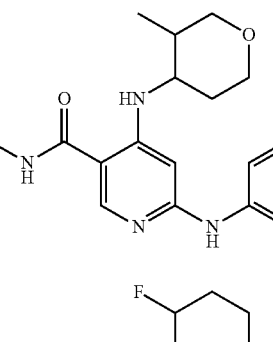 | 5.62 | B | 488.2 |
| 234 | 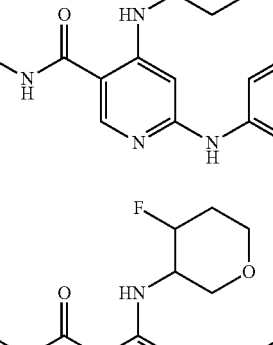 | 5.51 | B | 488.2 |
| 235 | 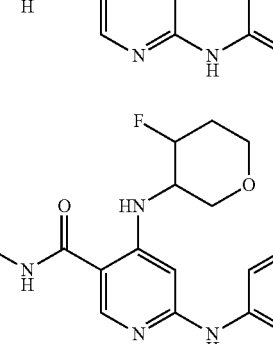 | 6.35 | A | 492.2 |
| 236 | 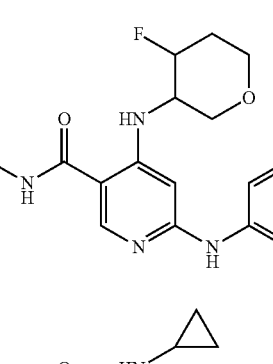 | 5.21 | E | 414.3 |

TABLE 6-continued

| Ex. No. | Structure | HPLC RT (min) | HPLC cond. | LCMS (M + H)+ |
|---|---|---|---|---|
| 237 | 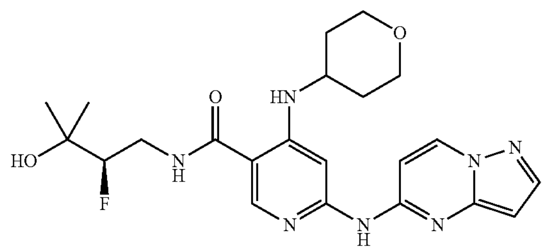 [SMILES: CC(C)(O)[C@H](F)CNC(=O)c1cnc(Nc2ccn3nccc3n2)cc1NC1CCOCC1] | 6.82 | A | 458 |
| 238 | 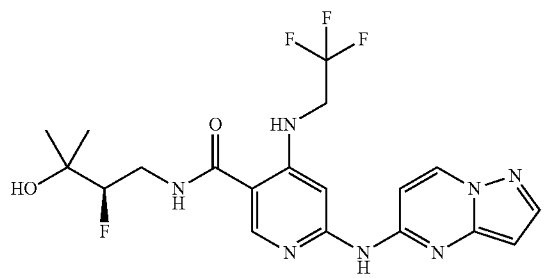 [SMILES: CC(C)(O)[C@H](F)CNC(=O)c1cnc(Nc2ccn3nccc3n2)cc1NCC(F)(F)F] | 5.4 | B | 455.4 |
| 239 | 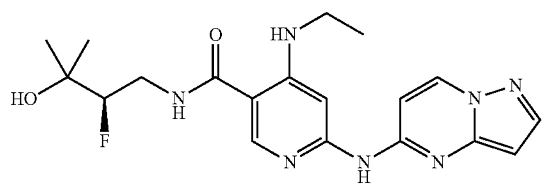 [SMILES: CCNc1cc(Nc2ccn3nccc3n2)ncc1C(=O)NC[C@@H](F)C(C)(C)O] | 5.06 | B | 401.4 |
| 240 | 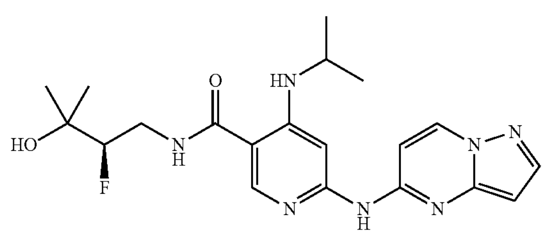 [SMILES: CC(C)Nc1cc(Nc2ccn3nccc3n2)ncc1C(=O)NC[C@@H](F)C(C)(C)O] | 5.53 | E | 416.36 |
| 241 | 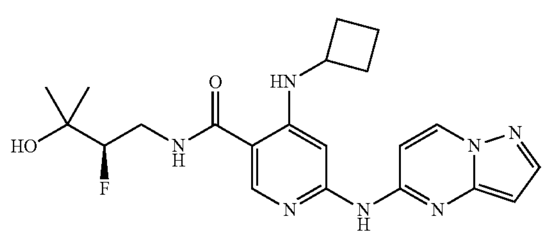 [SMILES: CC(C)(O)[C@H](F)CNC(=O)c1cnc(Nc2ccn3nccc3n2)cc1NC1CCC1] | 5.95 | E | 428.39 |
| 242 | 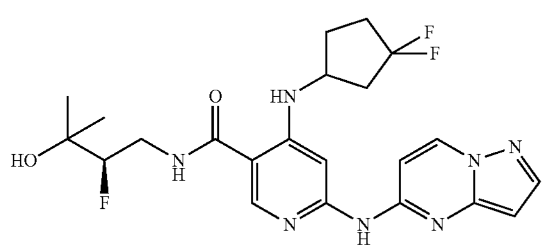 [SMILES: CC(C)(O)[C@H](F)CNC(=O)c1cnc(Nc2ccn3nccc3n2)cc1NC1CCC(F)(F)C1] | 5.89 | B | 478.2 |

TABLE 6-continued
| Ex. No. | Structure | HPLC RT (min) | HPLC cond. | LCMS (M + H)+ |
|---|---|---|---|---|
| 243 | 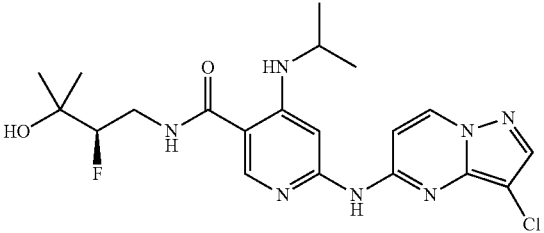 | 6.70 | A | 450.31 |
| 244 | 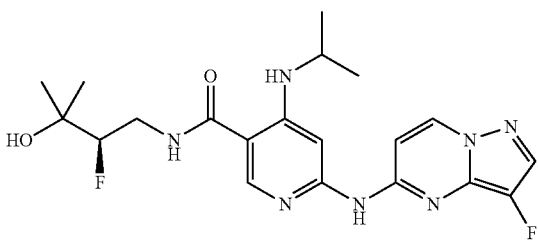 | 6.22 | A | 434.25 |
| 245 | 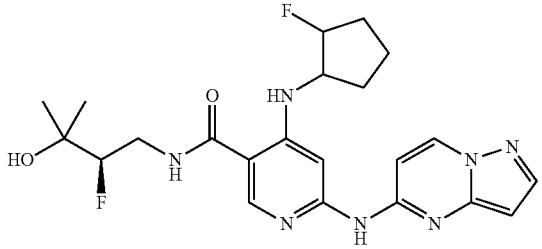 [SMILES: CC(C)(O)[C@H](F)CNC(=O)c1cnc(Nc2ccn3nccc3n2)cc1NC1CCCC1F] | 9.87 | N | 460 |
| 246 | 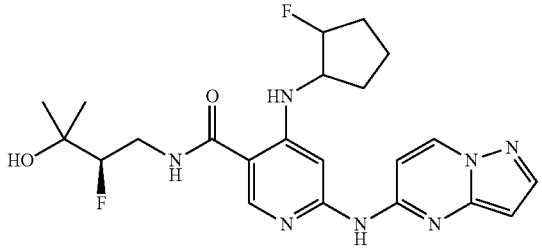 [SMILES: CC(C)(O)[C@H](F)CNC(=O)c1cnc(Nc2ccn3nccc3n2)cc1NC1CCCC1F] | 12.5 | N | 460 |
| 247 | 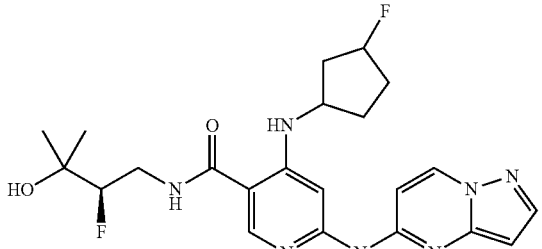 | 6.08 | A | 460.2 |

TABLE 6-continued

| Ex. No. | Structure | HPLC RT (min) | HPLC cond. | LCMS (M + H)+ |
|---|---|---|---|---|
| 248 | 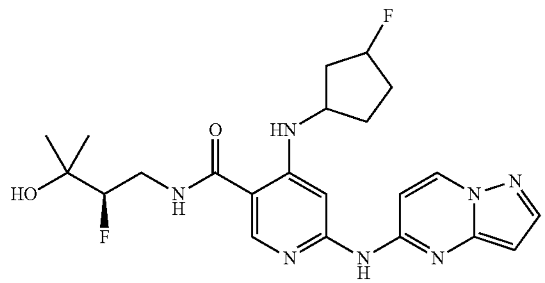 | 6.05 | A | 460.2 |
| 249 | 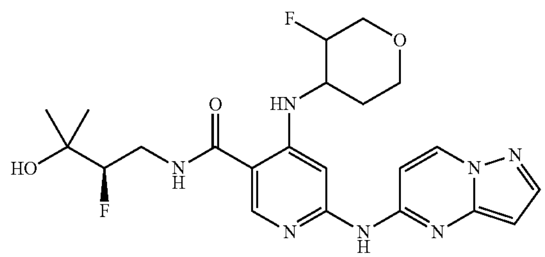 [SMILES: CC(C)(O)[C@H](F)CNC(=O)c1cnc(Nc2ccn3nccc3n2)cc1NC1CCOCC1F] | 9.64 | B | 476.39 |
| 250 | 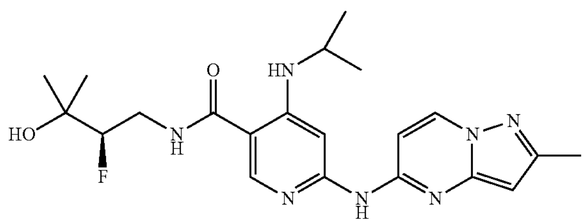 [SMILES: Cc1cc2nc(Nc3cc(NC(C)C)c(C(=O)NC[C@@H](F)C(C)(C)O)cn3)ccn2n1] | 5.5 | B | 429.4 |
| 251 | 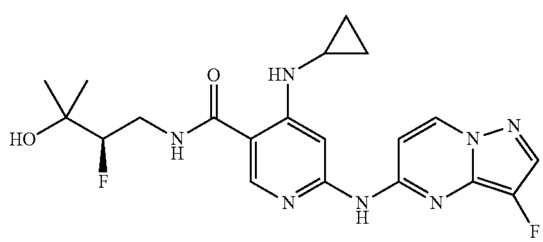 [SMILES: CC(C)(O)[C@H](F)CNC(=O)c1cnc(Nc2ccn3ncc(F)c3n2)cc1NC1CC1] | 5.31 | M | 432.28 |
| 252 | 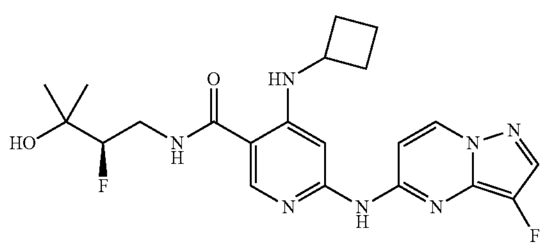 [SMILES: CC(C)(O)[C@H](F)CNC(=O)c1cnc(Nc2ccn3ncc(F)c3n2)cc1NC1CCC1] | 6.55 | A | 446.27 |
| 253 | 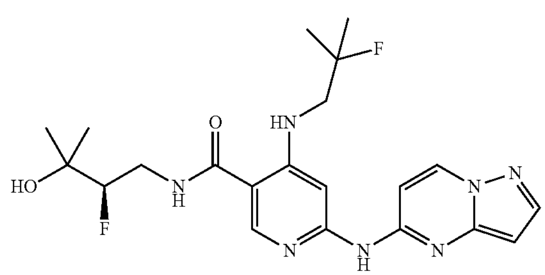 [SMILES: CC(C)(F)CNc1cc(Nc2ccn3nccc3n2)ncc1C(=O)NC[C@@H](F)C(C)(C)O] | 6.20 | A | 448.28 |

TABLE 6-continued

| Ex. No. | Structure | HPLC RT (min) | HPLC cond. | LCMS (M + H)+ |
|---|---|---|---|---|
| 254 | 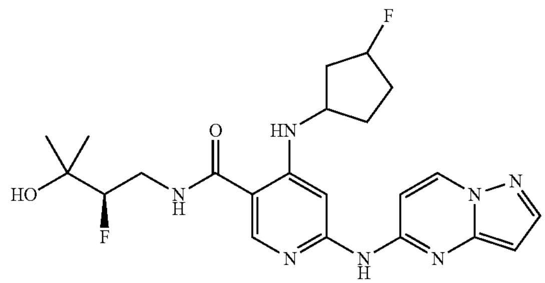 [SMILES: CC(C)(O)[C@H](F)CNC(=O)c1cnc(Nc2ccn3nccc3n2)cc1NC1CCC(F)C1] | 11.02 | B | 460.2 |
| 255 | 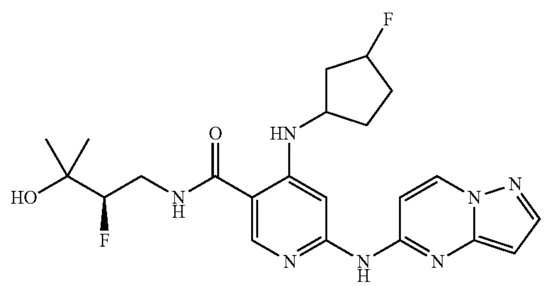 [SMILES: CC(C)(O)[C@H](F)CNC(=O)c1cnc(Nc2ccn3nccc3n2)cc1NC1CCC(F)C1] | 11.01 | B | 460.2 |
| 256 | 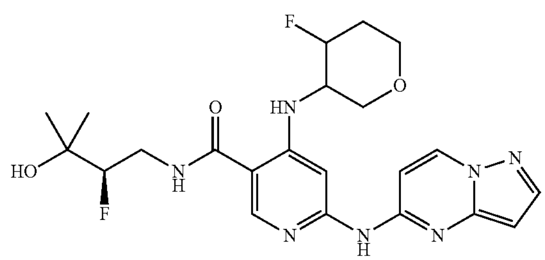 | 5.80 | A | 476.2 |
| 257 | 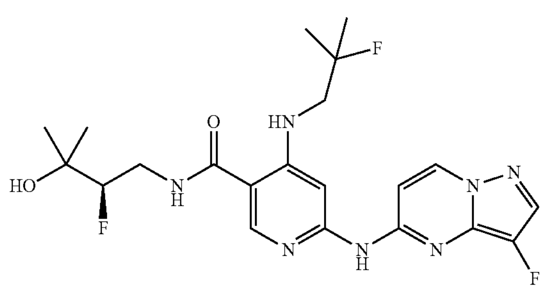 [SMILES: CC(C)(F)CNc1cc(Nc2ccn3ncc(F)c3n2)ncc1C(=O)NC[C@@H](F)C(C)(C)O] | 6.00 | E | 466.37 |
| 258 | 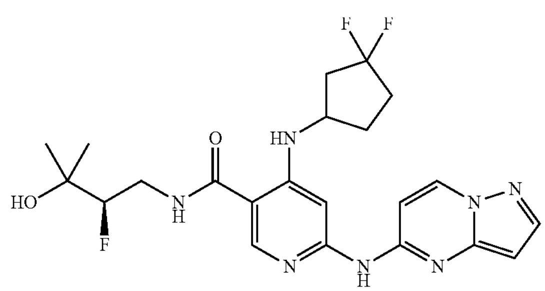 [SMILES: CC(C)(O)[C@H](F)CNC(=O)c1cnc(Nc2ccn3nccc3n2)cc1NC1CCC(F)(F)C1] | 11.36 | B | 478.2 |

TABLE 6-continued

| Ex. No. | Structure | HPLC RT (min) | HPLC cond. | LCMS (M + H)+ |
|---|---|---|---|---|
| 259 | 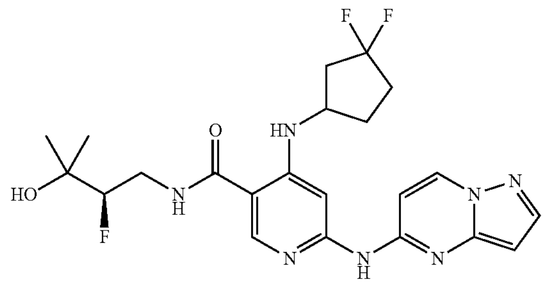 [SMILES: CC(C)(O)[C@H](F)CNC(=O)c1cnc(Nc2ccn3nccc3n2)cc1NC1CCC(F)(F)C1] | 11.37 | B | 478.2 |
| 261 | 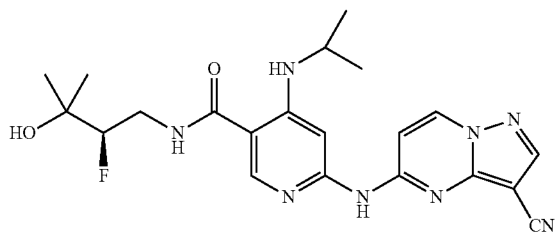 [SMILES: CC(C)Nc1cc(Nc2ccn3ncc(C#N)c3n2)ncc1C(=O)NC[C@@H](F)C(C)(C)O] | 5.94 | E | 441.5 |
| 262 | 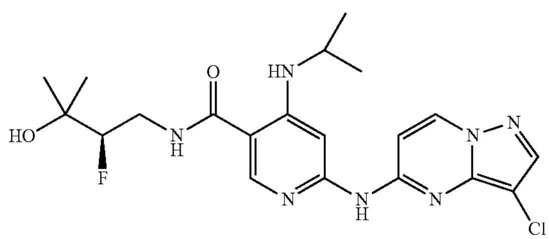 [SMILES: CC(C)Nc1cc(Nc2ccn3ncc(Cl)c3n2)ncc1C(=O)NC[C@@H](F)C(C)(C)O] | 6.37 | E | 450.0 |
| 263 | 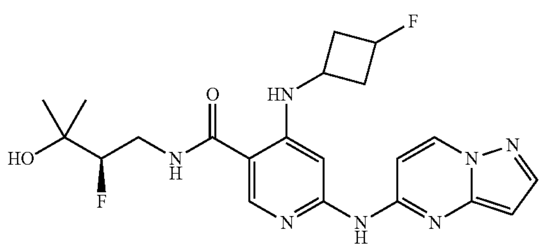 [SMILES: CC(C)(O)[C@H](F)CNC(=O)c1cnc(Nc2ccn3nccc3n2)cc1NC1CC(F)C1] | 18.21 | N | 446 |
| 264 | 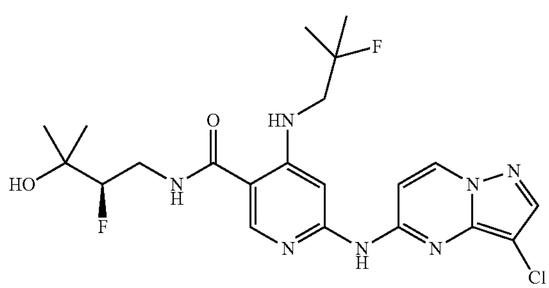 [SMILES: CC(C)(F)CNc1cc(Nc2ccn3ncc(Cl)c3n2)ncc1C(=O)NC[C@@H](F)C(C)(C)O] | 7.04 | A | 482.33 |
| 265 | 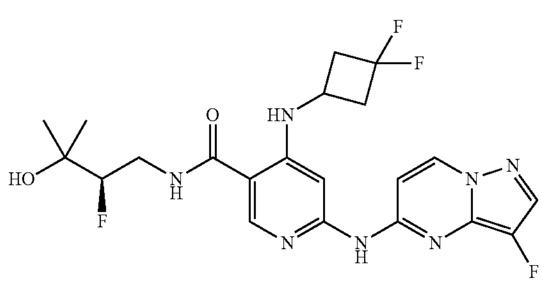 [SMILES: CC(C)(O)[C@H](F)CNC(=O)c1cnc(Nc2ccn3ncc(F)c3n2)cc1NC1CC(F)(F)C1] | 7.07 | A | 482.36 |

TABLE 6-continued

| Ex. No. | Structure | HPLC RT (min) | HPLC cond. | LCMS (M + H)+ |
|---|---|---|---|---|
| 266 | 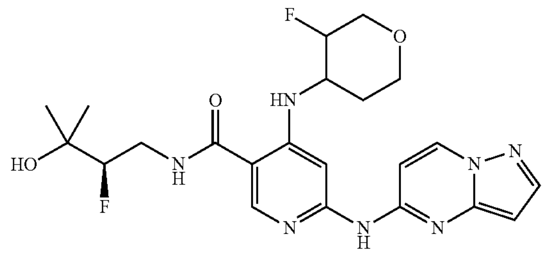 [SMILES: CC(C)(O)[C@H](F)CNC(=O)c1cnc(Nc2ccn3nccc3n2)cc1NC1CCOCC1F] | 9.22 | B | 476 |
| 267 | 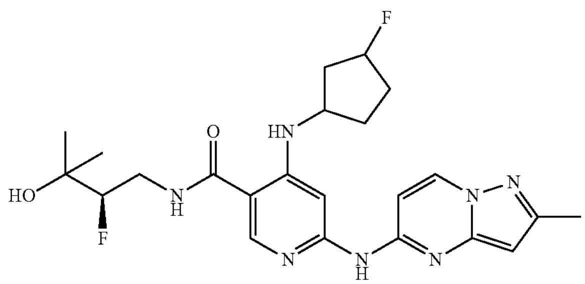 [SMILES: Cc1cc2nc(Nc3cc(NC4CCC(F)C4)c(C(=O)NC[C@@H](F)C(C)(C)O)cn3)ccn2n1] | 5.98 | E | 474.44 |
| 268 | 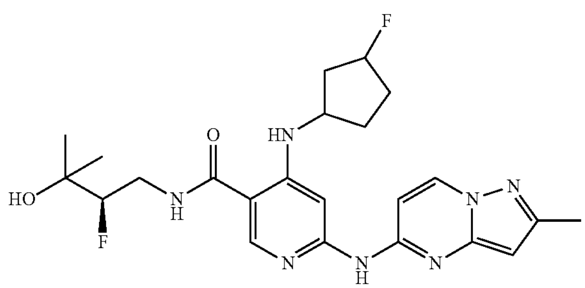 [SMILES: Cc1cc2nc(Nc3cc(NC4CCC(F)C4)c(C(=O)NC[C@@H](F)C(C)(C)O)cn3)ccn2n1] | 5.98 | E | 474.44 |
| 269 | 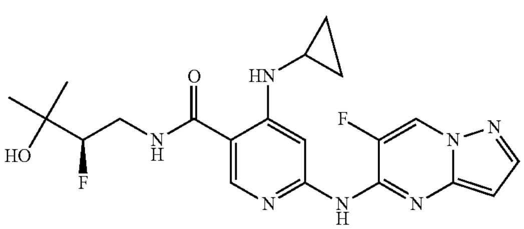 [SMILES: CC(C)(O)[C@H](F)CNC(=O)c1cnc(Nc2nc3ccnn3cc2F)cc1NC1CC1] | 5.57 | A | 433.4 |
| 270 | 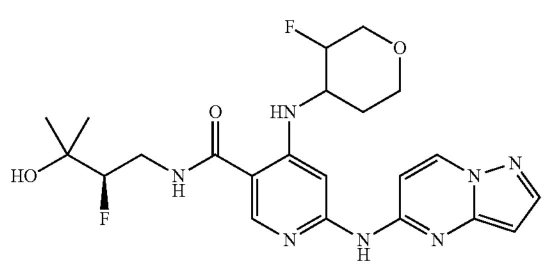 | 5.74 | A | 476.2 |

TABLE 6-continued

| Ex. No. | Structure | HPLC RT (min) | HPLC cond. | LCMS (M + H)+ |
|---|---|---|---|---|
| 271 | 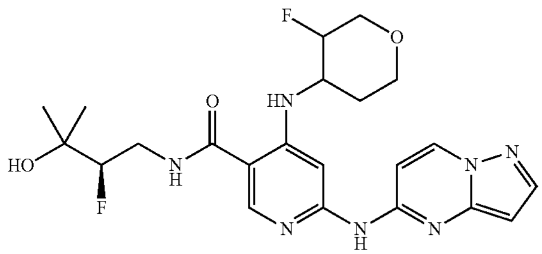 | 5.72 | A | 476.2 |
| 272 | 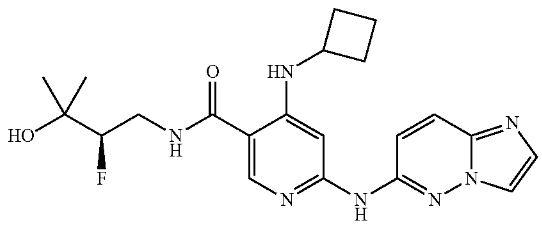 [SMILES: CC(C)(O)[C@H](F)CNC(=O)c1cnc(Nc2ccc3nccn3n2)cc1NC1CCC1] | 9.10 | A | 428.2 |
| 273 | 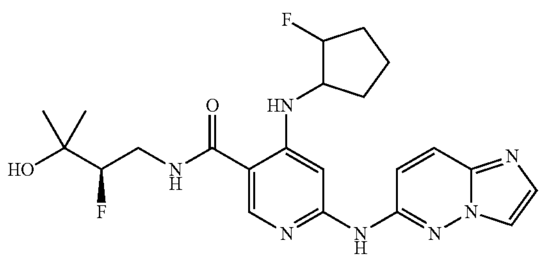 [SMILES: CC(C)(O)[C@H](F)CNC(=O)c1cnc(Nc2ccc3nccn3n2)cc1NC1CCCC1F] | 8.69 | E | 460.2 |
| 274 | 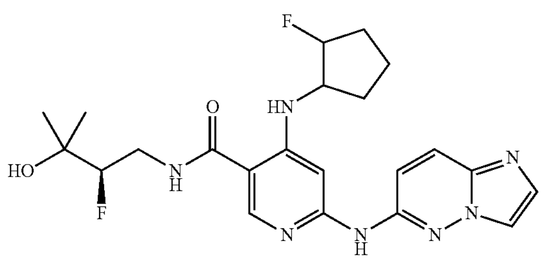 [SMILES: CC(C)(O)[C@H](F)CNC(=O)c1cnc(Nc2ccc3nccn3n2)cc1NC1CCCC1F] | 8.69 | E | 460.2 |
| 275 | 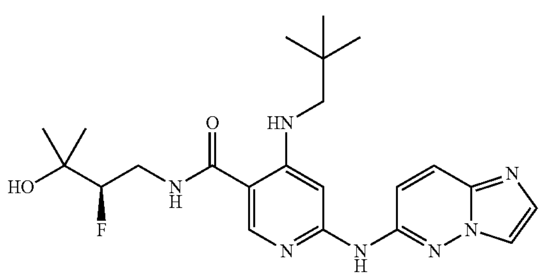 [SMILES: CC(C)(C)CNc1cc(Nc2ccc3nccn3n2)ncc1C(=O)NC[C@@H](F)C(C)(C)O] | 9.02 | E | 444 |
| 276 | 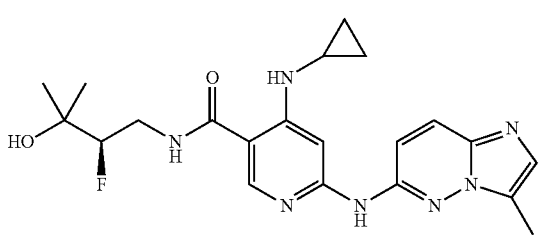 [SMILES: Cc1cnc2ccc(Nc3cc(NC4CC4)c(C(=O)NC[C@@H](F)C(C)(C)O)cn3)nn12] | 7.44 | K | 428.2 |

TABLE 6-continued

| Ex. No. | Structure | HPLC RT (min) | HPLC cond. | LCMS (M + H)+ |
|---|---|---|---|---|
| 277 | 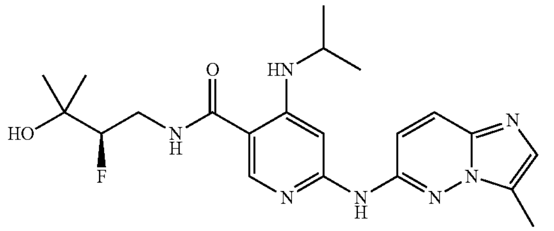 [SMILES: Cc1cnc2ccc(Nc3cc(NC(C)C)c(C(=O)NC[C@@H](F)C(C)(C)O)cn3)nn12] | 8.08 | K | 430.5 |
| 278 | 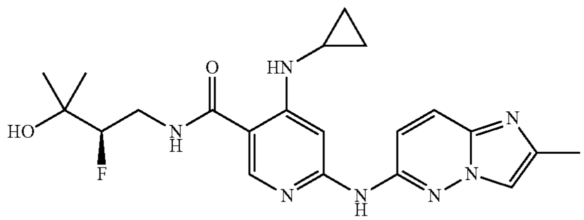 [SMILES: Cc1cn2nc(Nc3cc(NC4CC4)c(C(=O)NC[C@@H](F)C(C)(C)O)cn3)ccc2n1] | 7.65 | K | 428.6 |
| 279 | 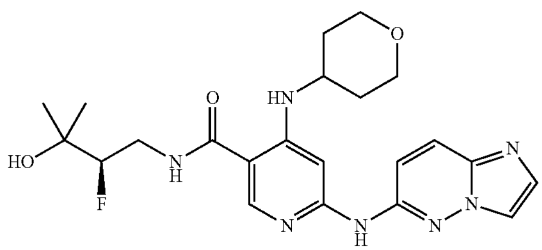 [SMILES: CC(C)(O)[C@H](F)CNC(=O)c1cnc(Nc2ccc3nccn3n2)cc1NC1CCOCC1] | 6.19 | C | 457.9 |
| 280 | 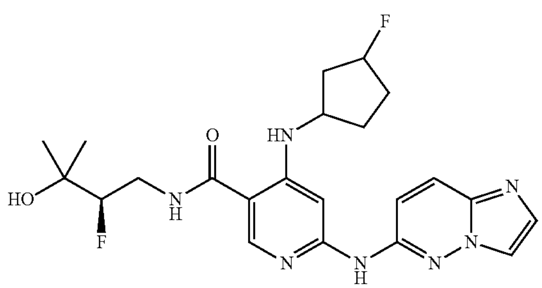 [SMILES: CC(C)(O)[C@H](F)CNC(=O)c1cnc(Nc2ccc3nccn3n2)cc1NC1CCC(F)C1] | 9.23 | B | 460.2 |
| 281 | 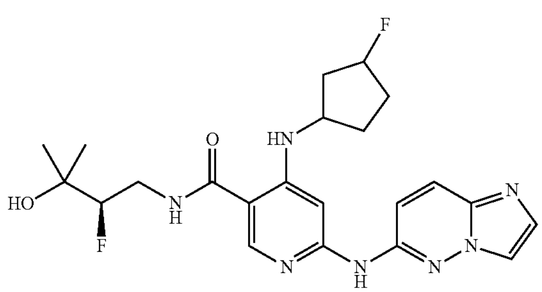 [SMILES: CC(C)(O)[C@H](F)CNC(=O)c1cnc(Nc2ccc3nccn3n2)cc1NC1CCC(F)C1] | 8.16 | B | 460.2 |
| 282 | 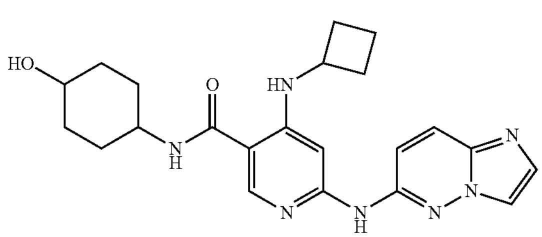 [SMILES: O=C(NC1CCC(O)CC1)c1cnc(Nc2ccc3nccn3n2)cc1NC1CCC1] | 7.48 | E | 422.2 |

TABLE 6-continued

| Ex. No. | Structure | HPLC RT (min) | HPLC cond. | LCMS (M + H)+ |
|---|---|---|---|---|
| 283 | 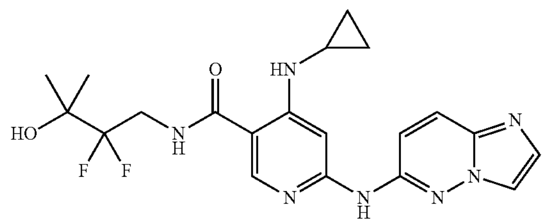 [SMILES: CC(C)(O)C(F)(F)CNC(=O)c1cnc(Nc2ccc3nccn3n2)cc1NC1CC1] | 7.33 | C | 432 |
| 284 | 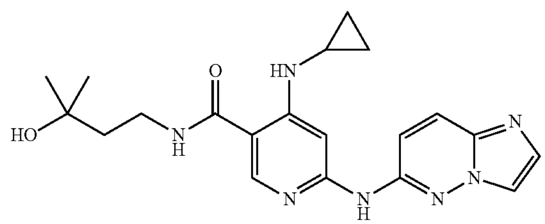 [SMILES: CC(C)(O)CCNC(=O)c1cnc(Nc2ccc3nccn3n2)cc1NC1CC1] | 7.43 | C | 410 |
| 285 | 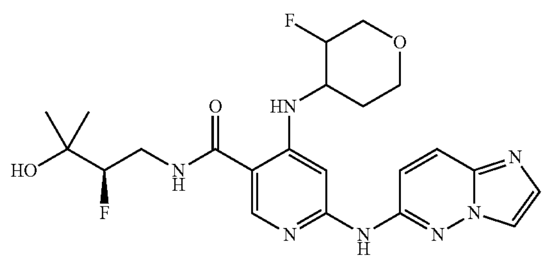 [SMILES: CC(C)(O)[C@H](F)CNC(=O)c1cnc(Nc2ccc3nccn3n2)cc1NC1CCOCC1F] | 7.35 | B | 476 |
| 286 | 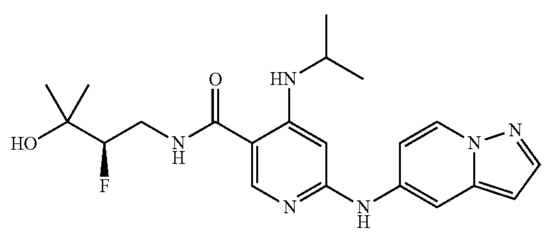 [SMILES: CC(C)Nc1cc(Nc2ccn3nccc3c2)ncc1C(=O)NC[C@@H](F)C(C)(C)O] | 5.83 | E | 415.2 |
| 287 | 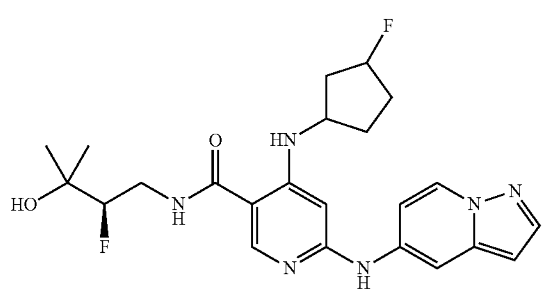 | 6.63 | A | 459.2 |
| 288 | 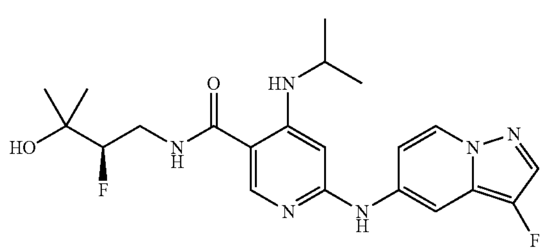 [SMILES: CC(C)Nc1cc(Nc2ccn3ncc(F)c3c2)ncc1C(=O)NC[C@@H](F)C(C)(C)O] | 6.64 | A | 433.2 |

TABLE 6-continued

| Ex. No. | Structure | HPLC RT (min) | HPLC cond. | LCMS (M + H)+ |
|---|---|---|---|---|
| 289 | 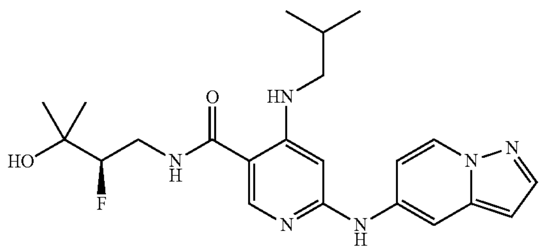 [SMILES: CC(C)CNc1cc(Nc2ccn3nccc3c2)ncc1C(=O)NC[C@@H](F)C(C)(C)O] | 1.53 | D | 429.2 |
| 290 | 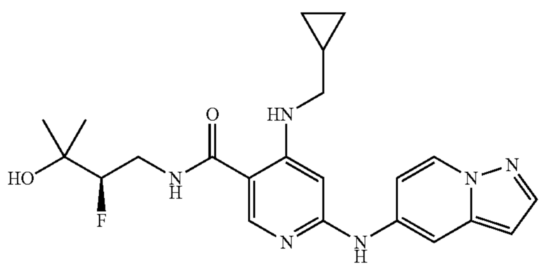 [SMILES: CC(C)(O)[C@H](F)CNC(=O)c1cnc(Nc2ccn3nccc3c2)cc1NCC1CC1] | 1.41 | D | 427.2 |
| 291 | 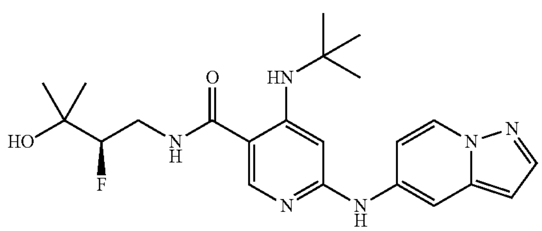 [SMILES: CC(C)(C)Nc1cc(Nc2ccn3nccc3c2)ncc1C(=O)NC[C@@H](F)C(C)(C)O] | 1.46 | D | 429.2 |
| 292 | 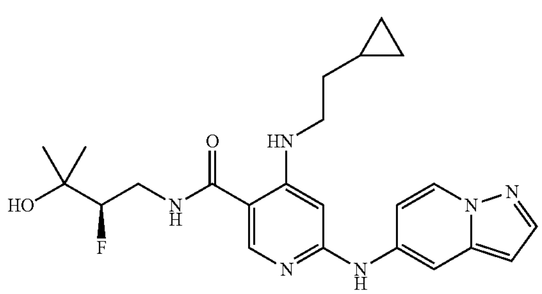 [SMILES: CC(C)(O)[C@H](F)CNC(=O)c1cnc(Nc2ccn3nccc3c2)cc1NCCC1CC1] | 1.52 | D | 441.2 |
| 293 | 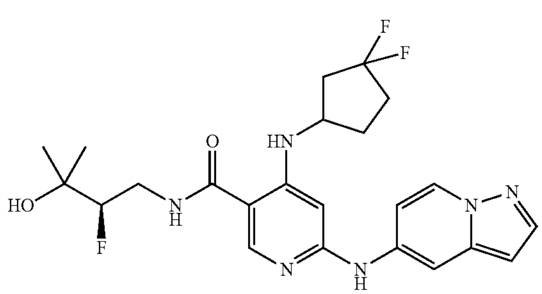 [SMILES: CC(C)(O)[C@H](F)CNC(=O)c1cnc(Nc2ccn3nccc3c2)cc1NC1CCC(F)(F)C1] | 6.98 | A | 477.2 |

US 9,546,153 B2
189 190
TABLE 6-continued
| Ex. No. | Structure | HPLC RT (min) | HPLC cond. | LCMS (M + H)+ |
|---|---|---|---|---|
| 294 | 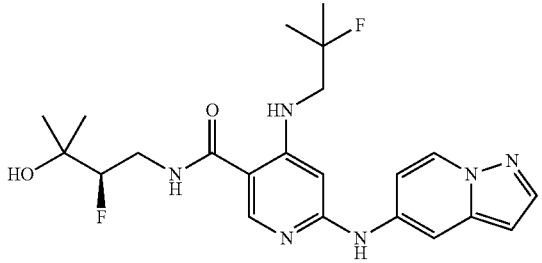 [SMILES: CC(C)(F)CNc1cc(Nc2ccn3nccc3c2)ncc1C(=O)NC[C@@H](F)C(C)(C)O] | 6.31 | D | 447.2 |
| 295 | 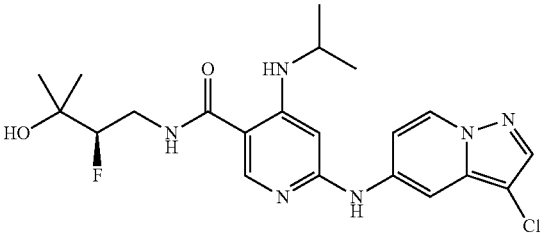 [SMILES: CC(C)Nc1cc(Nc2ccn3ncc(Cl)c3c2)ncc1C(=O)NC[C@@H](F)C(C)(C)O] | 7.31 | A | 449.2 |
| 296 | 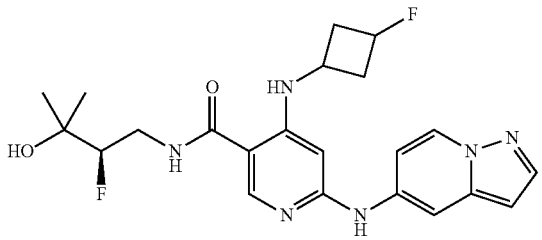 [SMILES: CC(C)(O)[C@H](F)CNC(=O)c1cnc(Nc2ccn3nccc3c2)cc1NC1CC(F)C1] | 5.67 | H | 445 |
| 297 | 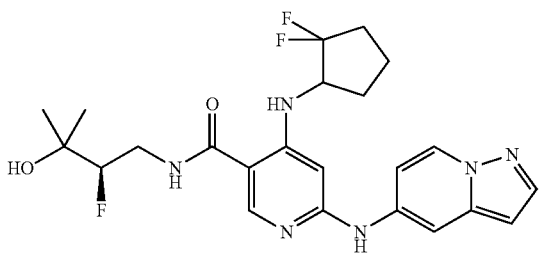 [SMILES: CC(C)(O)[C@H](F)CNC(=O)c1cnc(Nc2ccn3nccc3c2)cc1NC1CCCC1(F)F] | 6.22 | B | 477.2 |
| 298 | 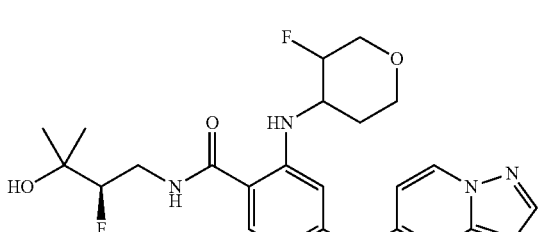 | 5.94 | A | 475.2 |
| 299 | 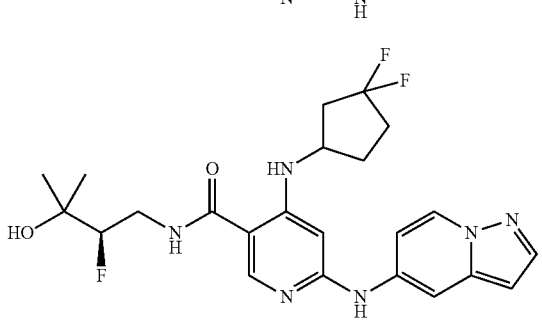 | 5.60 | B | 477.2 |

TABLE 6-continued

| Ex. No. | Structure | HPLC RT (min) | HPLC cond. | LCMS (M + H)+ |
|---|---|---|---|---|
| 300 | 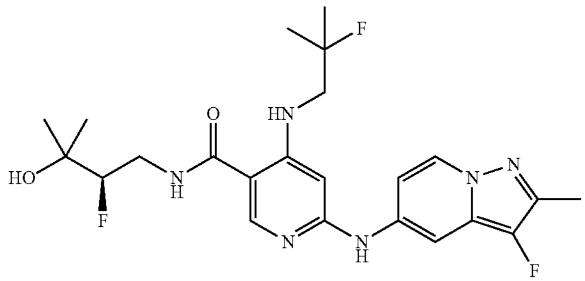 [SMILES: Cc1nn2ccc(Nc3cc(NCC(C)(C)F)c(C(=O)NC[C@@H](F)C(C)(C)O)cn3)cc2c1F] | 7.27 | A | 479.2 |
| 301 | 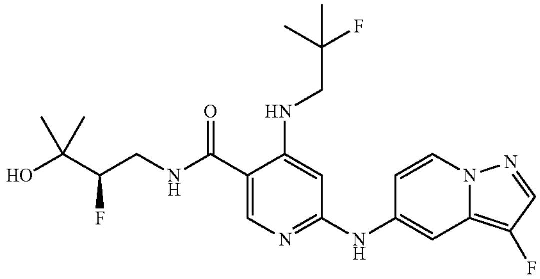 [SMILES: CC(C)(F)CNc1cc(Nc2ccn3ncc(F)c3c2)ncc1C(=O)NC[C@@H](F)C(C)(C)O] | 7.11 | A | 465.2 |
| 302 | 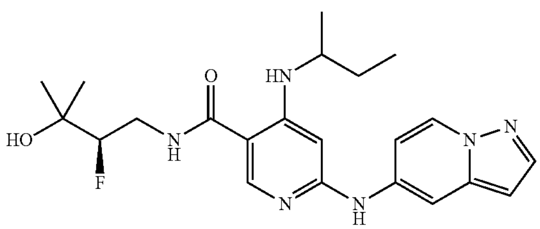 [SMILES: CCC(C)Nc1cc(Nc2ccn3nccc3c2)ncc1C(=O)NC[C@@H](F)C(C)(C)O] | 5.89 | B | 429.2 |
| 308 | 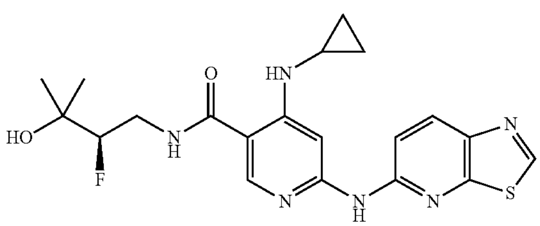 [SMILES: CC(C)(O)[C@H](F)CNC(=O)c1cnc(Nc2ccc3ncsc3n2)cc1NC1CC1] | 5.32 | E | 431.2 |
| 309 | 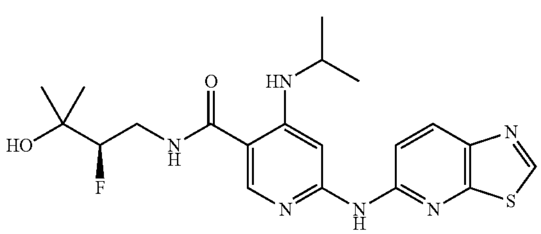 | 5.594 | E | 433.1 |
| 310 | 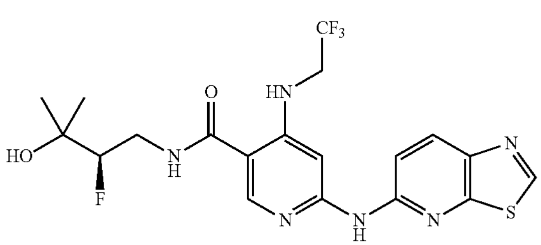 [SMILES: CC(C)(O)[C@H](F)CNC(=O)c1cnc(Nc2ccc3ncsc3n2)cc1NCC(F)(F)F] | 5.540 | E | 473.1 |

TABLE 6-continued

| Ex. No. | Structure | HPLC RT (min) | HPLC cond. | LCMS (M + H)+ |
|---|---|---|---|---|
| 311 | 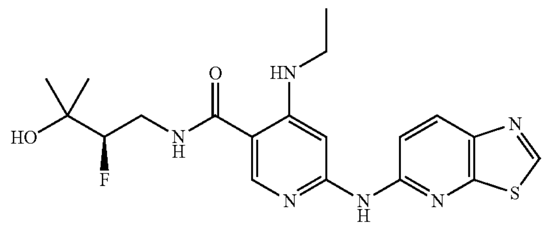 [SMILES: CCNc1cc(Nc2ccc3ncsc3n2)ncc1C(=O)NC[C@@H](F)C(C)(C)O] | 5.17 | E | 419.2 |
| 312 | 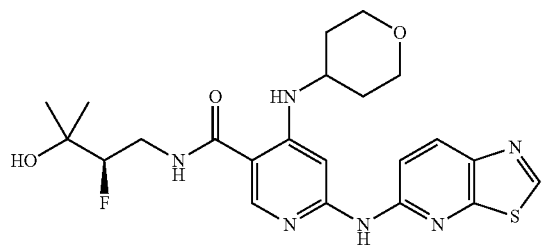 [SMILES: CC(C)(O)[C@H](F)CNC(=O)c1cnc(Nc2ccc3ncsc3n2)cc1NC1CCOCC1] | 5.59 | A | 475.2 |
| 313 | 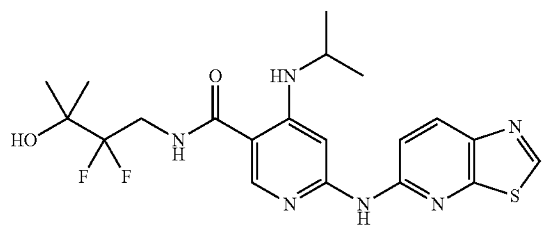 [SMILES: CC(C)Nc1cc(Nc2ccc3ncsc3n2)ncc1C(=O)NCC(F)(F)C(C)(C)O] | 6.64 | A | 451.2 |
| 314 | 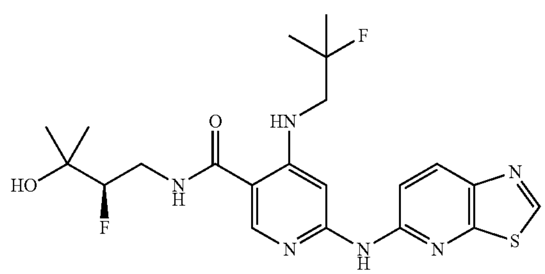 [SMILES: CC(C)(F)CNc1cc(Nc2ccc3ncsc3n2)ncc1C(=O)NC[C@@H](F)C(C)(C)O] | 5.75 | A | 465.2 |
| 315 | 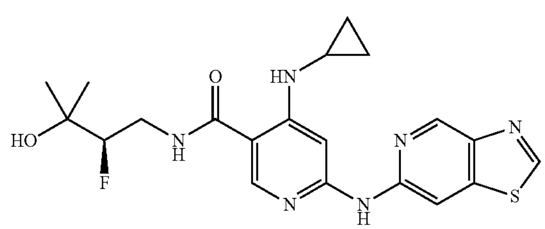 | 6.21 | A | 431 |
| 316 | 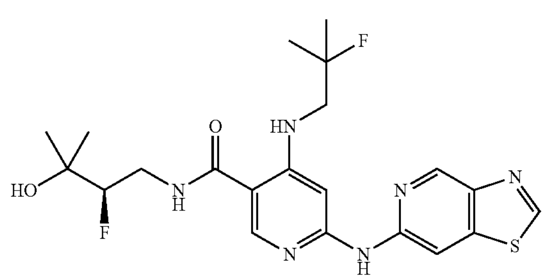 [SMILES: CC(C)(F)CNc1cc(Nc2cc3scnc3cn2)ncc1C(=O)NC[C@@H](F)C(C)(C)O] | 5.86 | E | 465.2 |

TABLE 6-continued

| Ex. No. | Structure | HPLC RT (min) | HPLC cond. | LCMS (M + H)+ |
|---|---|---|---|---|
| 317 | 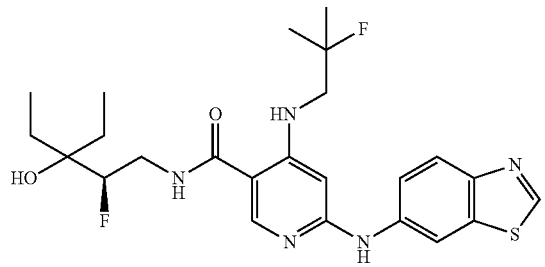 [SMILES: CCC(O)(CC)[C@H](F)CNC(=O)c1cnc(Nc2ccc3ncsc3c2)cc1NCC(C)(C)F] | 6.61 | E | 492.2 |

Example 318

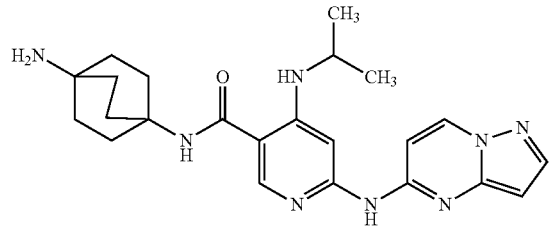 [SMILES: CC(C)Nc1cc(Nc2ccn3nccc3n2)ncc1C(=O)NC12CCC(N)(CC1)CC2]

A solution of 4-(isopropylamino)-6-(pyrazolo[1,5-a]pyrimidin-5-ylamino)nicotinic acid (10 mg, 0.032 mmol), PYBOP (16.66 mg, 0.032 mmol), DIPEA (0.017 mL, 0.096 mmol) and bicyclo[2.2.2]octane-1,4-diamine (4.49 mg, 0.032 mmol) in DMF (1 mL) at 25° C. was stirred for 1 h. An additional batch of bicyclo[2.2.2]octane-1,4-diamine (4.49 mg, 0.032 mmol) was added and the reaction stirred for 1 h. The product was isolated directly via preparative HPLC to afford N-(4-aminobicyclo[2.2.2]octan-1-yl)-4-(isopropylamino)-6-(pyrazolo[1,5-a]pyrimidin-5-ylamino) nicotinamide (3.1 mg, 21% yield). LCMS m/z 435.2 (M+)+; HPLC rt 1.11, Condition G.

Example 319

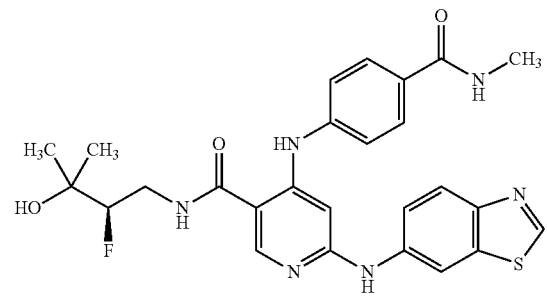

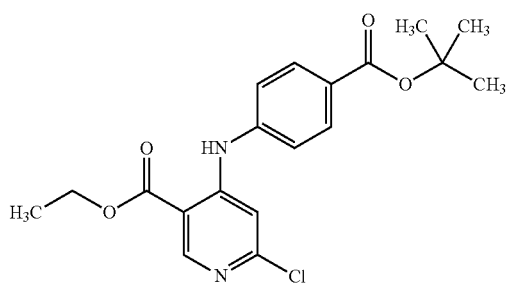

Step 1: Synthesis of ethyl 4-(4-(tert-butoxycarbonyl)phenylamino)-6-chloronicotinate: Followed the same method outlined for the synthesis of Example 5, Step 1 using ethyl 4,6-dichloronicotinate and tert-butyl 4-aminobenzoate. LC/MS: PUROSPHER® Star RP-18, 4×55 mm, 3 μm; Solvent A=10% ACN: 90% $H_2O$: 20 mM $NH_4OAc$; Solvent B=90% ACN: 10% $H_2O$: 20 mM $NH_4COOAc$; gradient 0-100% B over 1.5 min (3.2 min run time); retention time: 2.525 min; LCMS (ES-API), m/z 377.0 (M+H).

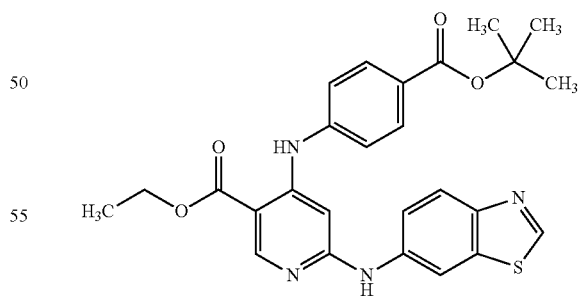

Step 2: Synthesis of ethyl 6-(benzo[d]thiazol-6-ylamino)-4-(4-(tert-butoxycarbonyl)phenylamino)nicotinate: Followed the same method outlined for the synthesis of Example 5, Step 2 using ethyl 4-(4-(tert-butoxycarbonyl) phenylamino)-6-chloronicotinate and benzo[d]thiazol-6-amine.

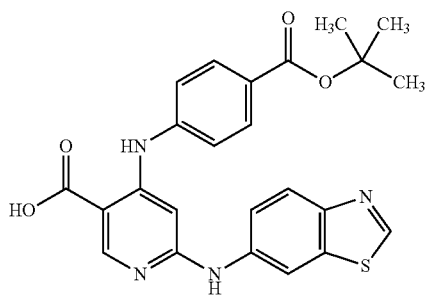 [SMILES: CC(C)(C)OC(=O)c1ccc(Nc2cc(Nc3ccc4ncsc4c3)ncc2C(=O)O)cc1]

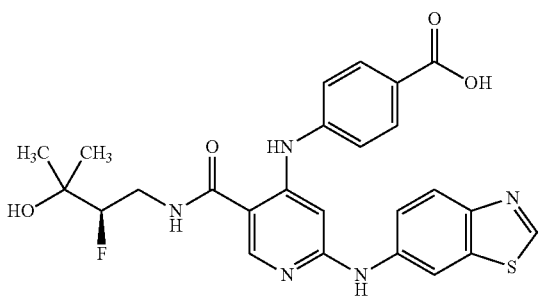

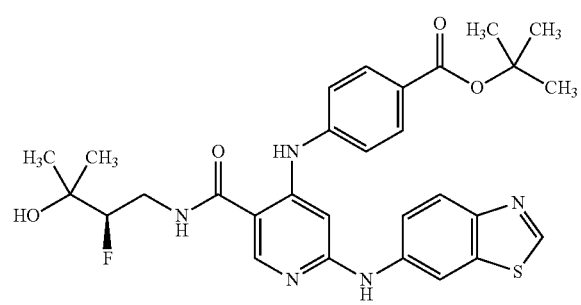 [SMILES: CC(C)(C)OC(=O)c1ccc(Nc2cc(Nc3ccc4ncsc4c3)ncc2C(=O)NC[C@@H](F)C(C)(C)O)cc1]

Step 3: Synthesis of 6-(benzo[d]thiazol-6-ylamino)-4-(4-(tert-butoxycarbonyl)phenylamino)nicotinic acid: Followed the same method as mentioned for the synthesis of Example 5, Step 3 using ethyl 6-(benzo[d]thiazol-6-ylamino)-4-(4-(tert-butoxycarbonyl)phenylamino)nicotinate.

Step 4: Synthesis of tert-butyl 4-(2-(benzo[d]thiazol-6-ylamino)-5-(2-fluoro-3-hydroxy-3-methylbutylcarbamoyl)pyridin-4-ylamino)benzoate: A stirred solution 6-(benzo[d]thiazol-6-ylamino)-4-((4-(tert-butoxycarbonyl)phenyl)amino)nicotinic acid (0.4 g, 0.865 mmol), DIPEA (0.76 mL, 4.3 mmol), HATU (0.33 g, 0.87 mmol) in DMF (10 mL) was added (R)-4-amino-3-fluoro-2-methylbutan-2-ol (0.105 g, 0.87 mmol). The reaction was stirred at rt for 4 h. The mixture was concentrated and the crude product was dissolved in ethyl acetate (30 mL), washed with water (15 mL), brine (15 mL), dried and concentrated. The product was purified by column chromatography (12 g REDISEP® column) eluting chloroform/methanol(0-10%) to afford tert-butyl 4-((2-(benzo[d]thiazol-6-ylamino)-5-((2-fluoro-3-hydroxy-3-methylbutyl)carbamoyl)pyridin-4-yl)amino)benzoate (0.3 g, 61.3% yield) as a brown solid. LCMS (ES-API), m/z 566.0 (M+H).

Step 5: Synthesis of 4-(2-(benzo[d]thiazol-6-ylamino)-5-(2-fluoro-3-hydroxy-3-methylbutylcarbamoyl)pyridin-4-ylamino)benzoic acid: A solution of tert-butyl 4-(2-(benzo[d]thiazol-6-ylamino)-5-(2-fluoro-3-hydroxy-3-methylbutylcarbamoyl)pyridin-4-ylamino)benzoate (200 mg) in DCM (10 mL) was cooled to 0° C. TFA (5 mL) was added dropwise to the reaction mixture and warmed to ambient temperature. The reaction mixture was then heated at 50° C. for 4 h. After completion of 4 h the reaction mixture was purified in reverse phase (60:40:ACN/NH$_4$OAc) to afford the title compound. LC/MS: PUROSPHER® Star RP-18, 4×55 mm, 3 µm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.117 min; LCMS (ES-API), m/z 510.2 (M+H).

Step 6: Synthesis of (R)-6-(benzo[d]thiazol-6-ylamino)-N-(2-fluoro-3-hydroxy-3-methylbutyl)-4-(4-(methylcarbamoyl)phenylamino)nicotinamide: Followed the same method as mentioned for the synthesis of Example 5, Step 4 (amide coupling) using 4-(2-(benzo[d]thiazol-6-ylamino)-5-(2-fluoro-3-hydroxy-3-methylbutylcarbamoyl)pyridin-4-ylamino)benzoic acid and methyl amine. $^1$H NMR: 400 MHz, DMSO-d$_6$: δ 1.18-1.19 (m, 6H), 2.80 (d, J=4.40 Hz, 3H), 3.39-3.46 (m, 1H), 3.67-3.83 (m, 1H), 4.31-4.46 (m, 1H), 4.84 (s, 1H), 6.73 (s, 1H), 7.35-7.37 (m, 2H), 7.57 (dd, J=2.00, 8.80 Hz, 1H), 7.88-7.91 (m, 2H), 7.96-7.98 (m, 1H), 8.37-8.38 (m, 1H), 8.57 (s, 1H), 8.65 (d, J=2.00 Hz, 1H), 8.71 (t, J=5.60 Hz, 1H), 9.18 (s, 1H), 9.42 (s, 1H), 10.49 (s, 1H). LC/MS: PUROSPHER® Star RP-18, 4×55 mm, 3 µm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.346 min; LCMS (ES-API), m/z 523.2 (M+H). HPLC: SunFire C18 (150×4.6 mm), 3.5µ; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 µl/min; Retention time: 5.02 min.

The Examples in the table below were prepared in an analogous fashion to Example 319, substituting where appropriate, alternate amines in the synthetic sequence.

TABLE 6

| Ex. No. | Structure | HPLC RT (min) | HPLC cond. | LCMS (M + H)+ |
|---|---|---|---|---|
| 319 | 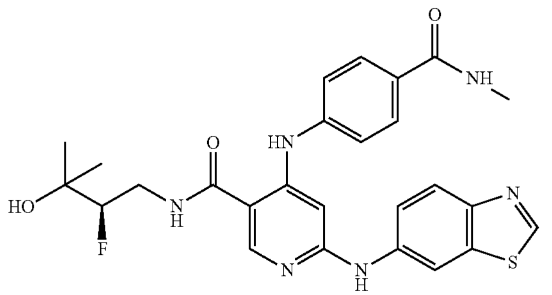 [SMILES: CNC(=O)c1ccc(Nc2cc(Nc3ccc4ncsc4c3)ncc2C(=O)NC[C@@H](F)C(C)(C)O)cc1] | 5.02 | E | 523.2 |
| 320 | 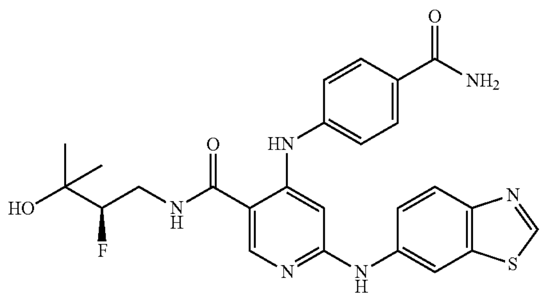 [SMILES: CC(C)(O)[C@H](F)CNC(=O)c1cnc(Nc2ccc3ncsc3c2)cc1Nc1ccc(C(N)=O)cc1] | 5.05 | A | 509.2 |
| 321 | 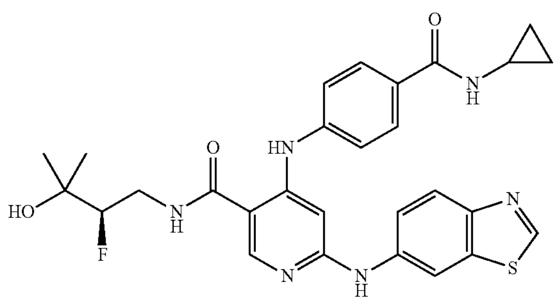 [SMILES: CC(C)(O)[C@H](F)CNC(=O)c1cnc(Nc2ccc3ncsc3c2)cc1Nc1ccc(C(=O)NC2CC2)cc1] | 5.49 | E | 549.2 |
| 322 | 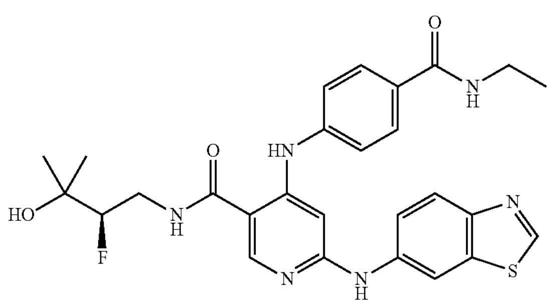 [SMILES: CCNC(=O)c1ccc(Nc2cc(Nc3ccc4ncsc4c3)ncc2C(=O)NC[C@@H](F)C(C)(C)O)cc1] | 5.42 | E | 537.2 |
| 323 | 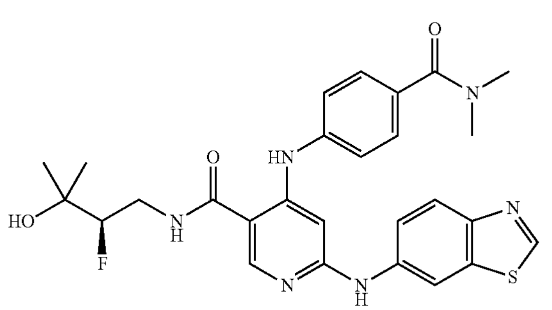 [SMILES: CN(C)C(=O)c1ccc(Nc2cc(Nc3ccc4ncsc4c3)ncc2C(=O)NC[C@@H](F)C(C)(C)O)cc1] | 5.24 | E | 535.2 M − H |

TABLE 6-continued

| Ex. No. | Structure | HPLC RT (min) | HPLC cond. | LCMS (M + H)+ |
|---|---|---|---|---|
| 324 | 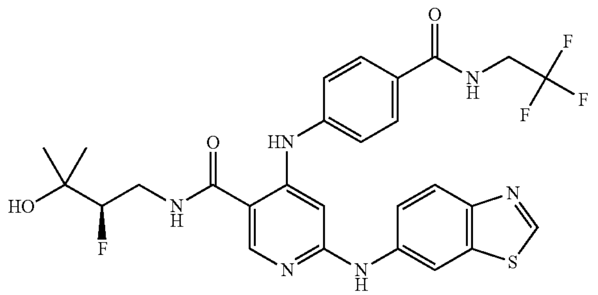 [SMILES: CC(C)(O)[C@H](F)CNC(=O)c1cnc(Nc2ccc3ncsc3c2)cc1Nc1ccc(C(=O)NCC(F)(F)F)cc1] | 8.46 | C | 591.2 |
| 325 | 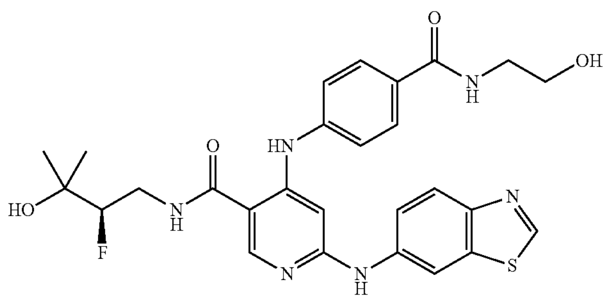 [SMILES: CC(C)(O)[C@H](F)CNC(=O)c1cnc(Nc2ccc3ncsc3c2)cc1Nc1ccc(C(=O)NCCO)cc1] | 9.19 | B | 553.2 |
| 326 | 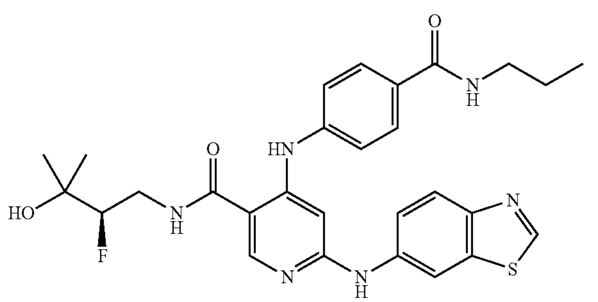 [SMILES: CCCNC(=O)c1ccc(Nc2cc(Nc3ccc4ncsc4c3)ncc2C(=O)NC[C@@H](F)C(C)(C)O)cc1] | 8.00 | C | 551.2 |

Example 327

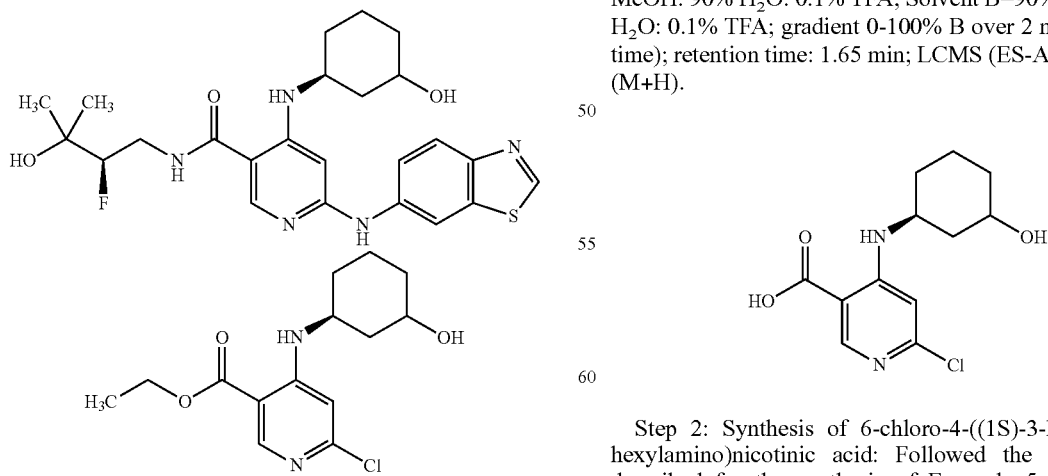

Step 1: Synthesis of ethyl 6-chloro-4-(3-hydroxycyclohexylamino)nicotinate: Followed the same method outlined for the synthesis of Example 5, Step 1 using ethyl 4,6-dichloronicotinate and (3S)-3-aminocyclohexanol. LC/MS: ZORBAX® SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.65 min; LCMS (ES-API), m/z 299.0 (M+H).

Step 2: Synthesis of 6-chloro-4-((1S)-3-hydroxycyclohexylamino)nicotinic acid: Followed the same method described for the synthesis of Example 5, Step 3 using 6-chloro-4-(3-hydroxycyclohexylamino)nicotinate. LC/MS: ZORBAX® SB C18, 4.6×50 mm, 5 μm; Solvent A=10% MeOH: 90% H$_2$O: 0.1% TFA; Solvent B=90% MeOH: 10%

H₂O: 0.1% TFA; gradient 0-100% B over 2 min (3 min run time); retention time: 1.095 min; LCMS (ES-API), m/z 271.0 (M+H).

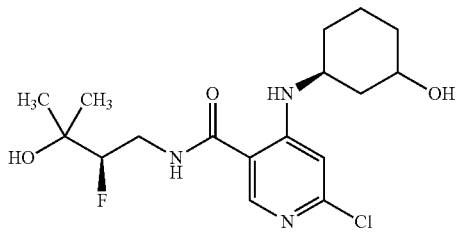 [SMILES: CC(C)(O)[C@H](F)CNC(=O)c1cnc(Cl)cc1N[C@H]1CCCC(O)C1]

Step 3: Synthesis of 6-chloro-N-(2-fluoro-3-hydroxy-3-methylbutyl)-4-((1S)-3-hydroxycyclohexylamino)nicotinamide: Followed the method described for the synthesis of Example 5, Step 4, using (R)-4-amino-3-fluoro-2-methylbutan-2-ol and 6-chloro-4-((1S)-3-hydroxycyclohexylamino) nicotinic acid.

Step 4: Synthesis of 6-(benzo[d]thiazol-6-ylamino)-N—((R)-2-fluoro-3-hydroxy-3-methylbutyl)-4-(3-hydroxycyclohexylamino)nicotinamide: Followed the method described for the synthesis of Example 5, Step 2, using 6-chloro-N-(2-fluoro-3-hydroxy-3-methylbutyl)-4-((1S)-3-hydroxycyclohexylamino)nicotinamide and benzo[d]thiazol-6-amine. ¹H NMR: 400 MHz, DMSO-d₆: δ 1.01-1.82 (m, 9H), 1.72-1.77 (m, 1H), 1.83-1.86 (m, 1H), 1.94-1.99 (m, 1H), 2.20-2.23 (m, 1H), 2.90-2.91 (m, 1H), 3.34 (1H, merged with water peak), 3.48-3.54 (m, 1H), 3.60-3.73 (m, 1H), 4.26-4.41 (m, 1H), 4.67 (d, J=4.80 Hz, 1H), 4.79 (s, 1H), 6.05 (s, 1H), 7.57 (dd, J=2.00, 9.00 Hz, 1H), 7.93-7.95 (m, 1H), 8.29 (d, J=7.60 Hz, 1H), 8.37-8.40 (m, 2H), 8.65 (d, J=2.00 Hz, 1H), 9.14 (s, 1H), 9.22 (s, 1H). LC/MS: ZORBAX® SB C18, 4.6×50 mm, 5 μm; Solvent A=10% MeOH: 90% H₂O: 0.1% TFA; Solvent B=90% MeOH: 10% H₂O: 0.1% TFA; gradient 0-100% B over 2 min (3 min run time); retention time: 1.412 min; LCMS (ES-API), m/z 488.2 (M+H). HPLC: XBridge Phenyl (150×4.6 mm), 3.5μ; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μl/min; Retention time: 5.69 min.

Example 328

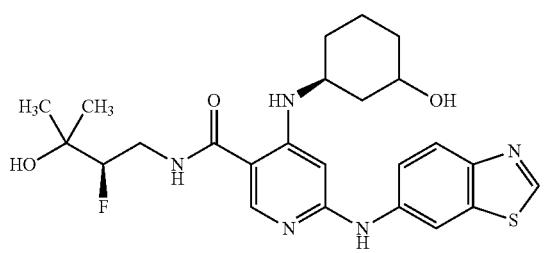 [SMILES: CC(C)(O)[C@H](F)CNC(=O)c1cnc(Nc2ccc3ncsc3c2)cc1N[C@H]1CCCC(O)C1]

The other alcohol diastereomer was isolated as Example 328: ¹H NMR: 400 MHz, DMSO-d₆: δ 1.01-1.82 (m, 8H), 1.72-1.77 (m, 1H), 1.83-1.86 (m, 1H), 1.94-1.99 (m, 1H), 2.20-2.23 (m, 1H), 2.90-2.91 (m, 1H), 3.48-3.54 (m, 1H), 3.60-3.64 (m, 1H), 3.69-3.73 (m, 1H), 4.26-4.41 (m, 1H), 4.67 (d, J=4.80 Hz, 1H), 4.79 (s, 1H), 6.05 (s, 1H), 7.57 (dd, J=2.00, 9.00 Hz, 1H), 7.93-7.95 (m, 1H), 8.29 (d, J=7.60 Hz, 1H), 8.37-8.40 (m, 2H), 8.65 (d, J=2.00 Hz, 1H), 9.14 (s, 1H), 9.22 (s, 1H). LC/MS: ZORBAX® SB C18, 4.6×50 mm, 5 μm; Solvent A=10% MeOH: 90% H₂O: 0.1% TFA; Solvent B=90% MeOH: 10% H₂O: 0.1% TFA; gradient 0-100% B over 2 min (3 min run time); retention time: 1.403 min; LCMS (ES-API), m/z 488.2 (M+H). HPLC: XBridge Phenyl (150×4.6 mm), 3.5μ; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.00/min; Retention time: 6.06 min.

Example 329

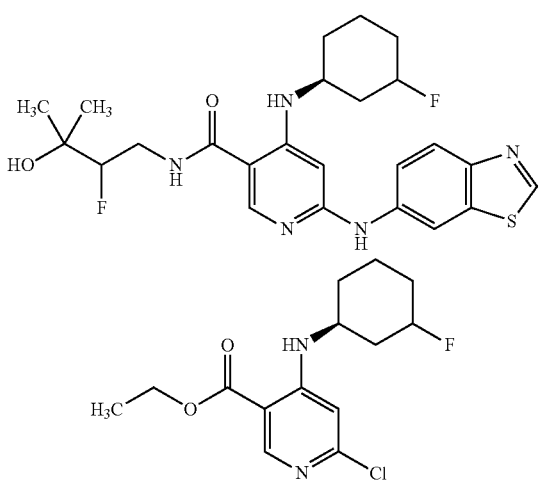

Step 1: Synthesis of ethyl 6-chloro-4-((1S)-3-fluorocyclohexylamino)nicotinate: A solution of ethyl 6-chloro-4-((3-hydroxycyclohexyl)amino)nicotinate (0.3 g, 1 equiv.) in DCM (10 mL) was cooled to −78° C. and stirred for 5 min. Xtal-Fluoro-E (1.2 equiv.) was added to the reaction mixture. After completion of addition the reaction was stirred for 5 min. The reaction mixture was quenched with saturated solution of NH₄Cl at −78° C. and extracted with DCM (twice). The organic layers were collected together, dried over anhydrous sodium sulfate and concentrated. The crude material obtained was purified via column chromatography (EtOAc:pet ether) to afford ethyl 6-chloro-4-((1S)-3-fluorocyclohexylamino)nicotinate. LC/MS: ZORBAX® SB C18, 4.6×50 mm, 5 μm; Solvent A=10% MeOH: 90% H₂O: 0.1% TFA; Solvent B=90% MeOH: 10% H₂O: 0.1% TFA; gradient 0-100% B over 2 min (3 min run time); retention time: 1.981 min; LCMS (ES-API), m/z 301 (M+H).

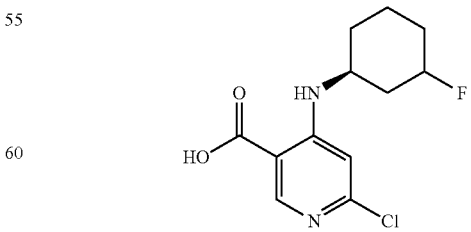

Step 2: Synthesis of 6-chloro-4-((1S)-3-fluorocyclohexylamino)nicotinic acid: Followed the same method described for the synthesis of Example 5, Step 3 using 6-chloro-4-

((1S)-3-fluorocyclohexylamino)nicotinate. LC/MS: ZORBAX® SB C18, 4.6×50 mm, 5 μm; Solvent A=10% MeOH: 90% H₂O: 0.1% TFA; Solvent B=90% MeOH: 10% H₂O: 0.1% TFA; gradient 0-100% B over 2 min (3 min run time); retention time: 1.393 min; LCMS (ES-API), m/z 273.0 (M+H).

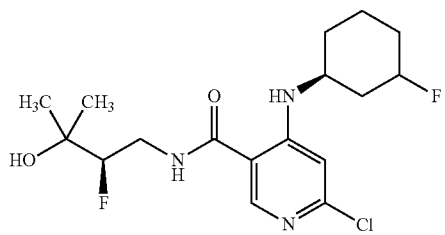 [SMILES: CC(C)(O)[C@H](F)CNC(=O)c1cnc(Cl)cc1N[C@H]1CCCC(F)C1]

Step 3: Synthesis of 6-chloro-N-(2-fluoro-3-hydroxy-3-methylbutyl)-4-((1S)-3-fluorocyclohexylamino)nicotinamide: Followed the method described for the synthesis of Example 5, Step 4, using (R)-4-amino-3-fluoro-2-methylbutan-2-ol and 6-chloro-4-((1S)-3-fluorocyclohexylamino)nicotinic acid.

Step 4: Synthesis of 6-(benzo[d]thiazol-6-ylamino)-N-(2-fluoro-3-hydroxy-3-methylbutyl)-4-(3-fluorocyclohexylamino)nicotinamide: Followed the method described for the synthesis of Example 5, Step 2, using 6-chloro-N-(2-fluoro-3-hydroxy-3-methylbutyl)-4-((1S)-3-fluorocyclohexylamino)nicotinamide and benzo[d]thiazol-6-amine. ¹H NMR: 400 MHz, DMSO-d₆: δ 1.16-1.17 (m, 6H), 1.55-1.91 (m, 9H), 3.36-3.40 (m, 2H), 3.61-3.73 (m, 1H), 4.26-4.41 (m, 1H), 4.76-4.88 (m, 2H), 6.07 (s, 1H), 7.55-7.58 (m, 1H), 7.93-7.96 (m, 1H), 8.42-8.45 (m, 3H), 8.64-8.66 (m, 1H), 9.15 (s, 1H), 9.23 (s, 1H). LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.658 min; LCMS (ES-API), m/z 490.2 (M+H). HPLC: SunFire C18 (150×4.6 mm), 3.5μ; Solvent A=5% ACN: 95% H₂O: 0.05% TFA pH=2.5; Solvent B=95% ACN: 5% H₂O: 0.05% TFA pH=2.5; gradient 0-100% B over 30 min (36 min run time); Flow rate: 1.0 μl/min; Retention time: 6.395 min.

Example 330

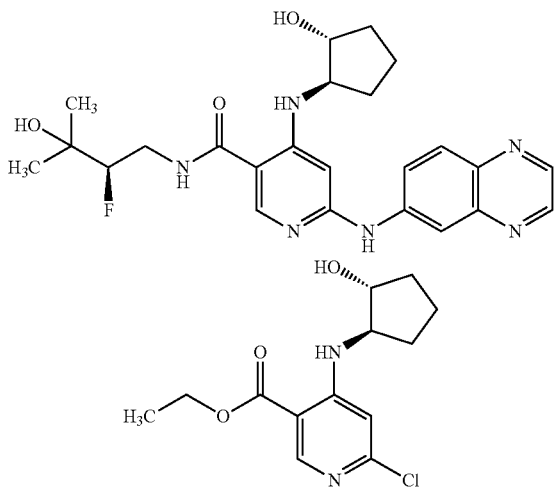

Step 1: Synthesis of ethyl 6-chloro-4-((1R,2R)-2-hydroxycyclopentylamino)nicotinate): Followed the same method outlined for the synthesis of Example 5, Step 1 using ethyl 4,6-dichloronicotinate and (1R,2R)-2-aminocyclopentanol. LC/MS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.786 min; LCMS (ES-API), m/z 285.2 (M+H).

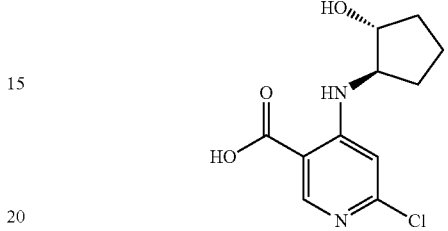

Step 2: Ethyl 6-chloro-4-(((1R,2R)-2-hydroxycyclopentyl)amino)nicotinate (1.3 g, 4.57 mmol) in THF (10 mL), MeOH (4 mL) and water (2 mL) was added LiOH (0.328 g, 13.7 mmol) and stirred at rt for 18 h. The organic layer was evaporated and the pH of the crude mixture was adjusted to 6 with 1.5N HCl to precipitate the crude acid. The solids were filtered and dried under vacuum to afford 6-chloro-4-(((1R,2R)-2-hydroxycyclopentyl)amino)nicotinic acid (0.95 mg, 81% yield). LCMS (ES-API), m/z 257.4 (M+H).

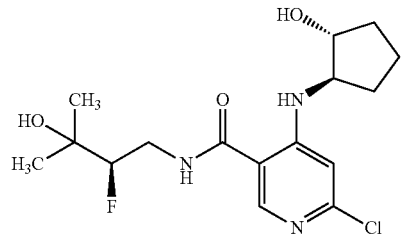 [SMILES: CC(C)(O)[C@H](F)CNC(=O)c1cnc(Cl)cc1N[C@@H]1CCC[C@H]1O]

Step 3: A solution of 6-chloro-4-(((1R,2R)-2-hydroxycyclopentyl)amino)nicotinic acid (900 mg, 3.51 mmol) in DMF (10 mL) and (R)-4-amino-3-fluoro-2-methylbutan-2-ol (425 mg, 3.51 mmol) was added HATU (1333 mg, 3.51 mmol) and DIPEA (0.612 mL, 3.51 mmol). The reaction mixture was allowed to stir for 18 h at rt. The DMF was removed under vacuum and the crude mass was diluted with water and extracted with ethylacetate. The ethylacetate layer was washed with NaHCO₃, then dried and concentrated to give 1.4 g crude mass which was purified by column chromatography (CHCl₃:MeOH:9.5/0.5) to provide the product. LCMS m/z 360.5 (M+H).

Step 4: Followed the method described for the synthesis of Example 5, Step 2, using 6-chloro-N—((R)-2-fluoro-3-hydroxy-3-methylbutyl)-4-(((1R,2R)-2-hydroxycyclopentyl)amino)nicotinamide and quinazolin-6-amine. ¹H NMR: 400 MHz, DMSO-d₆: δ 1.16-1.17 (m, 6H), 1.39-1.44 (m, 1H), 1.54-1.87 (m, 5H), 2.17-2.21 (m, 1H), 3.35-3.39 (m, 1H), 3.50-3.52 (m, 1H), 3.55-3.65 (m, 1H), 3.91-3.94 (m, 1H), 4.27-4.42 (m, 1H), 4.81 (d, J=0.80 Hz, 1H), 4.97-4.98 (m, 1H), 6.24 (s, 1H), 7.90-7.92 (m, 1H), 8.03-8.05 (m, 1H), 8.40-8.42 (m, 1H), 8.48-8.50 (m, 2H), 8.62 (d, J=2.40 Hz, 1H), 9.09 (s, 1H), 9.39 (s, 1H), 9.57 (s, 1H). LC/MS: PUROSPHER® Star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.658 min; LCMS (ES-API), m/z 469.2 (M+H). HPLC: Eclipse XDB C18 (150×4.6 mm) 5μ; Solvent A=20 mM NH$_4$OAc in water; Solvent B=ACN; gradient 0-100% B over 20 min; Flow rate=1.0 ml/min; Retention time: 7.946 min.

The Examples in Table 7 may be prepared according to the general methods outlined for the preparation of Example 330 above.

TABLE 7

| Ex. No. | Structure | HPLC RT (min) | HPLC cond. | LCMS (M + H) |
|---|---|---|---|---|
| 330 | 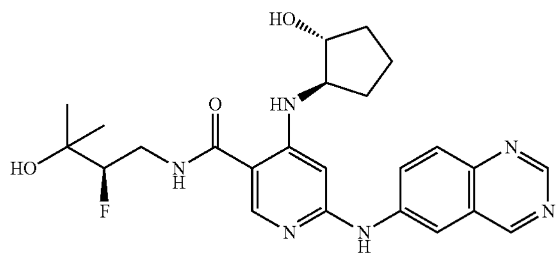 [SMILES: CC(C)(O)[C@H](F)CNC(=O)c1cnc(Nc2ccc3ncncc3c2)cc1N[C@@H]1CCC[C@H]1O] | 7.95 | C | 469.2 |
| 331 | 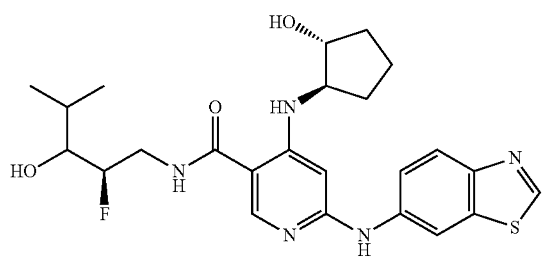 [SMILES: CC(C)C(O)[C@H](F)CNC(=O)c1cnc(Nc2ccc3ncsc3c2)cc1N[C@@H]1CCC[C@H]1O] | 7.79 | C | 488.2 |
| 332 | 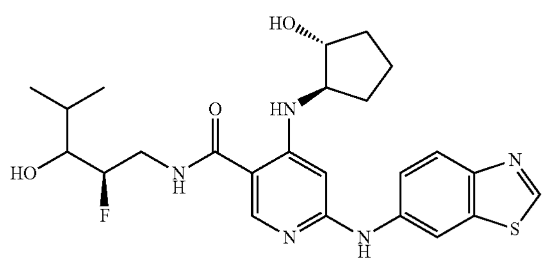 [SMILES: CC(C)C(O)[C@H](F)CNC(=O)c1cnc(Nc2ccc3ncsc3c2)cc1N[C@@H]1CCC[C@H]1O] | 8.21 | C | 488.2 |
| 333 | 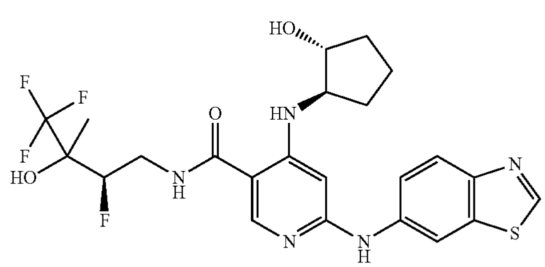 [SMILES: CC(O)([C@H](F)CNC(=O)c1cnc(Nc2ccc3ncsc3c2)cc1N[C@@H]1CCC[C@H]1O)C(F)(F)F] | 6.14 | E | 528.2 |
| 334 | 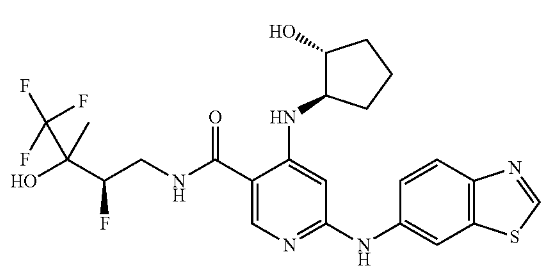 [SMILES: CC(O)([C@H](F)CNC(=O)c1cnc(Nc2ccc3ncsc3c2)cc1N[C@@H]1CCC[C@H]1O)C(F)(F)F] | 6.25 | E | 528.2 |

TABLE 7-continued

| Ex. No. | Structure | HPLC RT (min) | HPLC cond. | LCMS (M + H) |
|---|---|---|---|---|
| 335 | 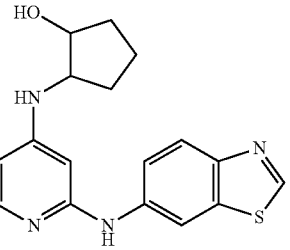 | 10.36 | B | 474.0 |
| 336 | 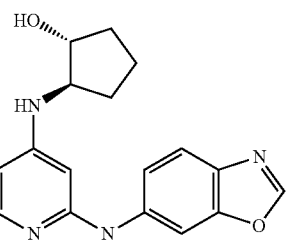 | 5.02 | E | 456.2 |
| 337 | 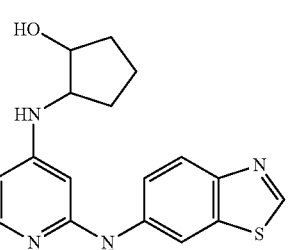 | 9.31 | B | 446.0 |
| 338 | 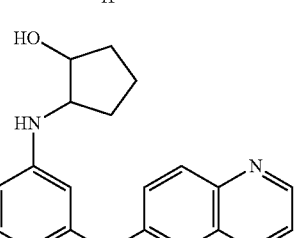 | 4.87 | E | 469.2 |

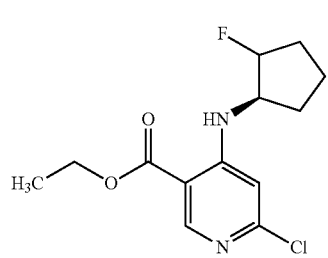 [SMILES: CCOC(=O)c1cnc(Cl)cc1N[C@@H]1CCCC1F]

Synthesis of ethyl 6-chloro-4-((1R)-2-fluorocyclopentylamino)nicotinate: A solution of ethyl 6-chloro-4-(((2S)-2-hydroxycyclopentyl)amino)nicotinate (1.0 g, 1 equiv.) in DCM (15 mL) was cooled to 0° C. DAST (0.7 mL, 1.5 equiv.) was added dropwise. The reaction mixture was stirred overnight at room temperature. The reaction mixture was again cooled to 0° C. and quenched with 10% NaHCO₃ solution. The product was extracted in DCM. The aqueous layer was washed with DCM (twice). The organic extracts were combined, dried over anhydrous sodium sulfate, filtered and concentrated. The crude product was purified by flash column chromatography using silica gel and EtOAc: pet ether to obtain the desired product. LC/MS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 2.013 min; LCMS (ES-API), m/z 287.2 (M+H).

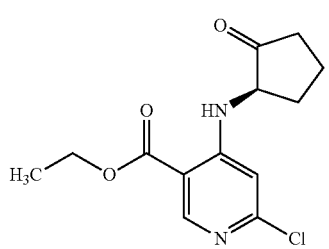 [SMILES: CCOC(=O)c1cnc(Cl)cc1N[C@@H]1CCCC1=O]

Synthesis of (R)-ethyl 6-chloro-4-(2-oxocyclopentylamino)nicotinate: A solution of ethyl 6-chloro-4-(((2S)-2-hydroxycyclopentyl)amino)nicotinate (0.5 g, 1 equiv.) in DCM (20 mL) was added Dess-Martin Periodinane (2.98 g, 4 equiv.) and the reaction mixture was stirred at room temperature for 10 min. The reaction mixture was concentrated and the residue was dissolved in ethyl acetate and filtered through a bed of CELITE®. The filtrate was concentrated. The crude product was purified by flash column chromatography using silica gel and EtOAc:pet ether to obtain the desired product. LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.863 min; LCMS (ES-API), m/z 283.2 (M+H).

Synthesis of (R)-ethyl 6-chloro-4-(2,2-difluorocyclopentylamino)nicotinate: Ethyl 6-chloro-4-((2-oxocyclopentyl)amino)nicotinate (0.57 g, 1 equiv.) in DCM (10 mL) was cooled to 0° C. DAST (0.67 mL, 2.5 equiv.) was added dropwise to the reaction mixture and allowed to overnight at room temperature. The reaction mixture was diluted with DCM, quenched with 10% NaHCO$_3$ at 0° C. The organic layer was collected, dried over anhydrous sodium sulfate, filtered and concentrated. The crude product was purified by flash column chromatography using silica gel and EtOAc: pet ether to obtain the desired product. LC/MS: PUROSPHER® Star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 2.017 min; LCMS (ES-API), m/z 305 (M+H).

Examples containing fluoro-cyclopentyl substitutions, as highlighted in Table 8, can be prepared from ethyl 6-chloro-4-((1R)-2-fluorocyclopentylamino)nicotinate or (R)-ethyl 6-chloro-4-(2,2-difluorocyclopentylamino)nicotinate using variations of the previously described methods. Individual stereoisomers can be prepared independently or separated later in the synthetic sequence via chiral chromatography.

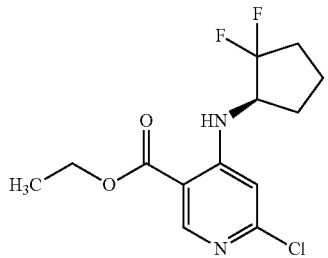 [SMILES: CCOC(=O)c1cnc(Cl)cc1N[C@@H]1CCCC1(F)F]

TABLE 8

| Ex. No. | Structure | HPLC RT (min) | HPLC cond. | LCMS (M + H) |
|---|---|---|---|---|
| 339 | 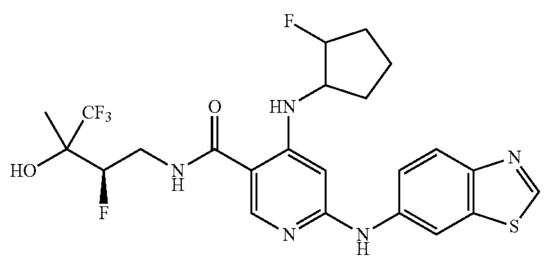 [SMILES: CC(O)([C@H](F)CNC(=O)c1cnc(Nc2ccc3ncsc3c2)cc1NC1CCCC1F)C(F)(F)F] | 6.88 | E | 530.2 |
| 340 | 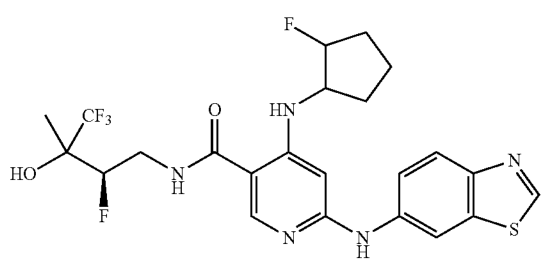 [SMILES: CC(O)([C@H](F)CNC(=O)c1cnc(Nc2ccc3ncsc3c2)cc1NC1CCCC1F)C(F)(F)F] | 6.76 | E | 530.2 |
| 341 | 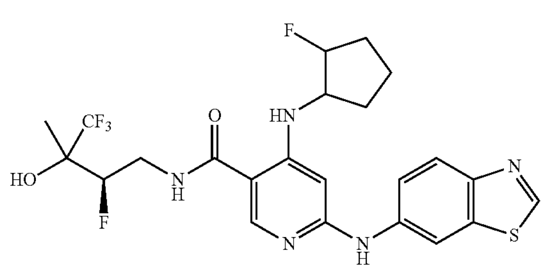 [SMILES: CC(O)([C@H](F)CNC(=O)c1cnc(Nc2ccc3ncsc3c2)cc1NC1CCCC1F)C(F)(F)F] | 6.87 | E | 530.2 |

TABLE 8-continued
| Ex. No. | Structure | | HPLC RT (min) | HPLC cond. | LCMS (M + H) |
|---|---|---|---|---|---|
| 342 | 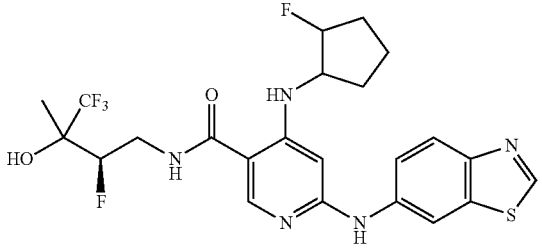 [SMILES: CC(O)([C@H](F)CNC(=O)c1cnc(Nc2ccc3ncsc3c2)cc1NC1CCCC1F)C(F)(F)F] | | 6.75 | E | 530.2 |
| 343 | 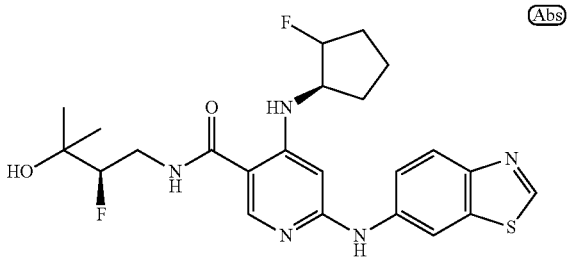 [SMILES: CC(C)(O)[C@H](F)CNC(=O)c1cnc(Nc2ccc3ncsc3c2)cc1N[C@@H]1CCCC1F] | (Abs) | 10.24 | A 30 min gradient | 476.2 |
| 344 | 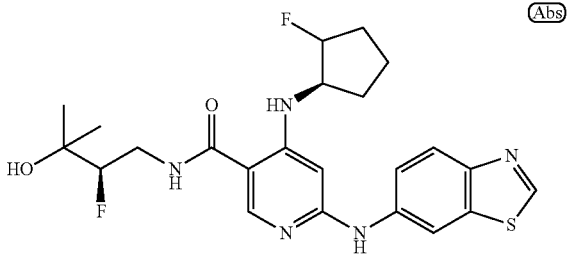 [SMILES: CC(C)(O)[C@H](F)CNC(=O)c1cnc(Nc2ccc3ncsc3c2)cc1N[C@@H]1CCCC1F] | (Abs) | 10.15 | A 30 min gradient | 476.2 |
| 345 | 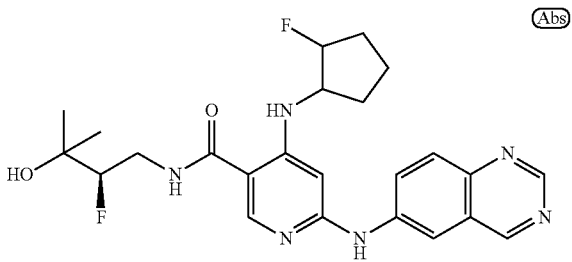 [SMILES: CC(C)(O)[C@H](F)CNC(=O)c1cnc(Nc2ccc3ncncc3c2)cc1NC1CCCC1F] | (Abs) | 7.91 | C | 469.2 |
| 346 | 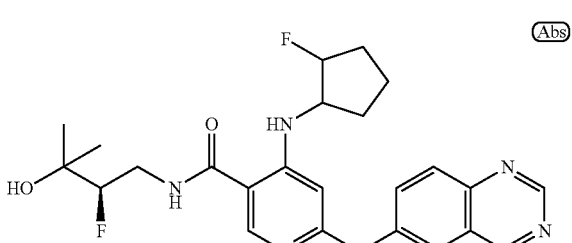 | (Abs) | 7.90 | C | 469.2 |

TABLE 8-continued

| Ex. No. | Structure | | HPLC RT (min) | HPLC cond. | LCMS (M + H) |
|---|---|---|---|---|---|
| 347 | 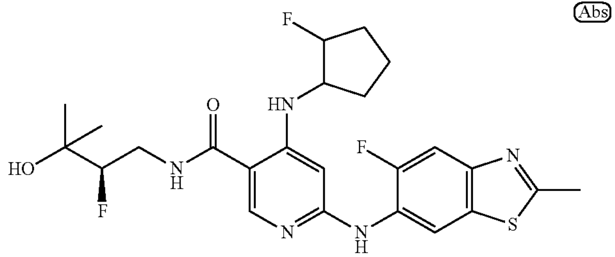 [SMILES: Cc1nc2cc(F)c(Nc3cc(NC4CCCC4F)c(C(=O)NC[C@@H](F)C(C)(C)O)cn3)cc2s1] | (Abs) | 6.25 | E | 508.2 |
| 348 | 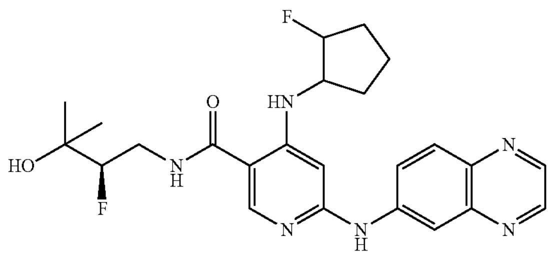 [SMILES: CC(C)(O)[C@H](F)CNC(=O)c1cnc(Nc2ccc3nccnc3c2)cc1NC1CCCC1F] | | 7.95 | C | 471.2 |
| 349 | 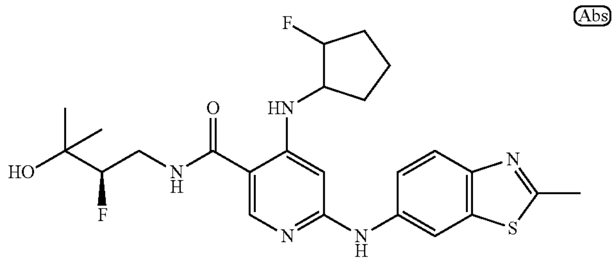 [SMILES: Cc1nc2ccc(Nc3cc(NC4CCCC4F)c(C(=O)NC[C@@H](F)C(C)(C)O)cn3)cc2s1] | (Abs) | 7.68 | A | 490.2 |
| 350 | 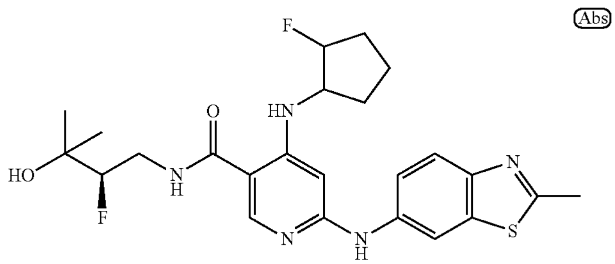 [SMILES: Cc1nc2ccc(Nc3cc(NC4CCCC4F)c(C(=O)NC[C@@H](F)C(C)(C)O)cn3)cc2s1] | (Abs) | 7.62 | A | 490.2 |
| 351 | 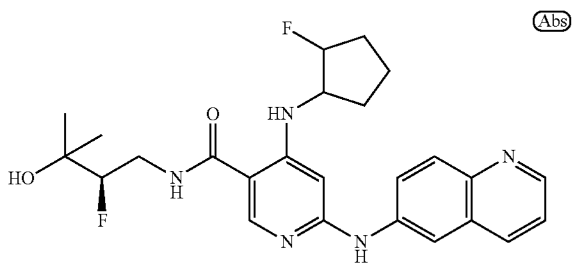 [SMILES: CC(C)(O)[C@H](F)CNC(=O)c1cnc(Nc2ccc3ncccc3c2)cc1NC1CCCC1F] | (Abs) | 4.77 | E | 470.2 |

TABLE 8-continued
| Ex. No. | Structure | HPLC RT (min) | HPLC cond. | LCMS (M + H) |
|---|---|---|---|---|
| 352 | 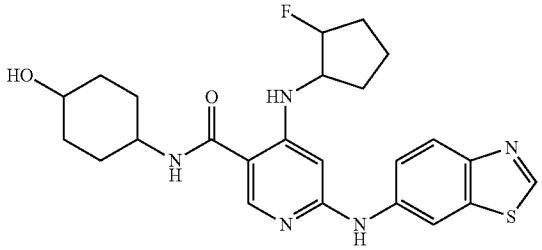 [SMILES: O=C(NC1CCC(O)CC1)c1cnc(Nc2ccc3ncsc3c2)cc1NC1CCCC1F] | 5.41 | B | 470.2 |
| 353 | 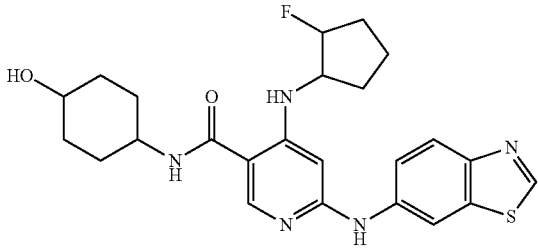 [SMILES: O=C(NC1CCC(O)CC1)c1cnc(Nc2ccc3ncsc3c2)cc1NC1CCCC1F] | 5.42 | B | 470.2 |
| 354 | 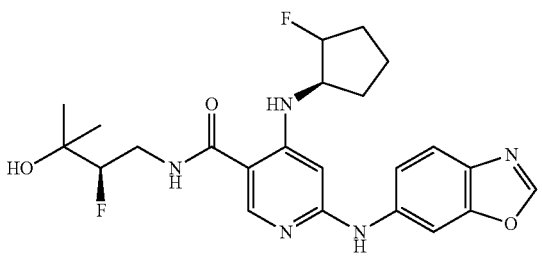 [SMILES: CC(C)(O)[C@H](F)CNC(=O)c1cnc(Nc2ccc3ncoc3c2)cc1N[C@@H]1CCCC1F] | 5.77 | E | 460.2 |
| 355 | 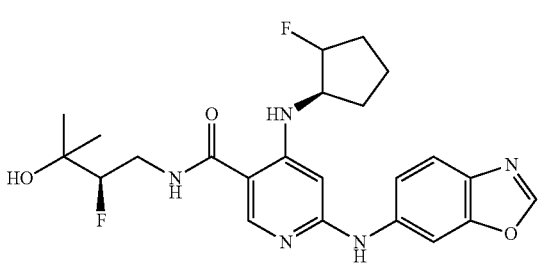 [SMILES: CC(C)(O)[C@H](F)CNC(=O)c1cnc(Nc2ccc3ncoc3c2)cc1N[C@@H]1CCCC1F] | 5.76 | E | 460.2 |
| 356 | 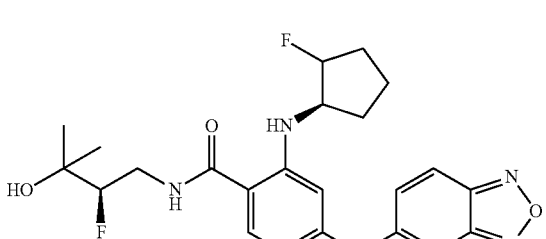 | 6.92 | E | 461.2 |
| 357 | 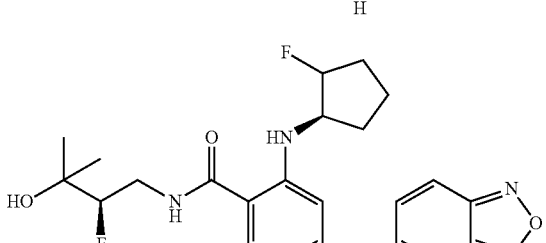 | 7.84 | A | 461.2 |

TABLE 8-continued

| Ex. No. | Structure | HPLC RT (min) | HPLC cond. | LCMS (M + H) |
|---|---|---|---|---|
| 358 | 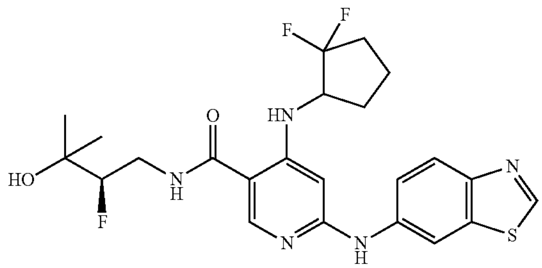 [SMILES: CC(C)(O)[C@H](F)CNC(=O)c1cnc(Nc2ccc3ncsc3c2)cc1NC1CCCC1(F)F] | 9.10 | E | 494.2 |
| 359 | 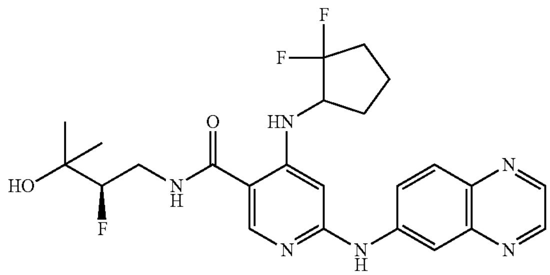 [SMILES: CC(C)(O)[C@H](F)CNC(=O)c1cnc(Nc2ccc3nccnc3c2)cc1NC1CCCC1(F)F] | 5.83 | B 30 min gradient | 489.2 |
| 360 | (Abs) | 5.17 | B 30 min gradient | 488.2 |

Example 339

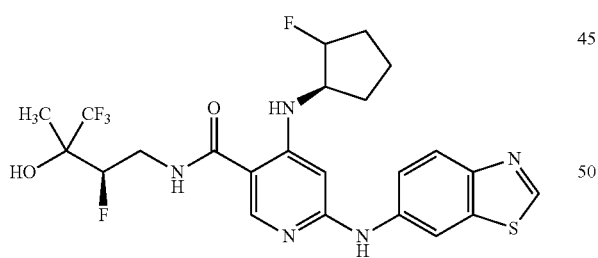

¹H NMR: 400 MHz, CD₃OD: δ 1.27-1.33 (m, 4H), 1.42-1.45 (m, 4H), 1.61-1.66 (m, 2H), 1.87-2.01 (m, 5H), 2.33-2.35 (m, 1H), 3.55-3.61 (m, 2H), 3.85-3.98 (m, 2H), 4.83-4.85 (m, 1H), 4.99-0.00 (m, 1H), 6.22 (s, 1H), 7.53-7.55 (m, 1H), 7.92-7.97 (m, 1H), 8.31 (s, 1H), 8.39 (d, J=2.00 Hz, 1H), 9.08 (s, 1H). LC/MS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 2.38 min; LCMS (ES-API), m/z 530.2 (M+H). HPLC: SunFire C18 (150×4.6 mm), 3.5μ; Solvent A=5% ACN: 95% H₂O: 0.05% TFA pH=2.5; Solvent B=95% ACN: 5% H₂O: 0.05% TFA pH=2.5; gradient 0-100% B over 30 min (36 min run time); Flow rate: 1.0 μl/min; Retention time: 6.878 min.

Example 340

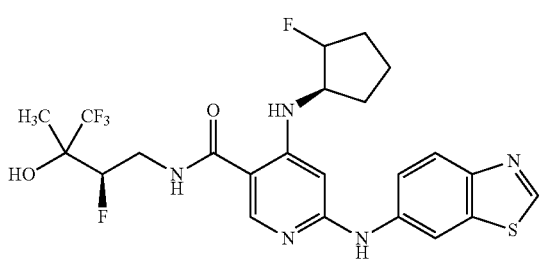 [SMILES: CC(O)([C@H](F)CNC(=O)c1cnc(Nc2ccc3ncsc3c2)cc1N[C@@H]1CCCC1F)C(F)(F)F]

¹H NMR: 400 MHz, CD₃OD: δ 1.27-1.34 (m, 7H), 1.42-1.45 (m, 3H), 1.61-1.66 (m, 2H), 1.86-2.03 (m, 2H), 2.32-2.37 (m, 1H), 3.50-3.90 (m, 2H), 3.90-3.95 (m, 1H), 4.62-4.99 (m, 1H), 5.02-0.00 (m, 1H), 6.22 (s, 1H), 7.53-7.55 (m, 1H), 7.92-7.98 (m, 1H), 8.31 (s, 1H), 8.38 (d, J=2.00 Hz, 1H), 9.09 (s, 1H). LC/MS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 2.38 min; LCMS (ES-API), m/z 530.2 (M+H). HPLC: SunFire C18 (150×4.6 mm), 3.5μ; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 μl/min; Retention time: 6.759 min.

Example 341

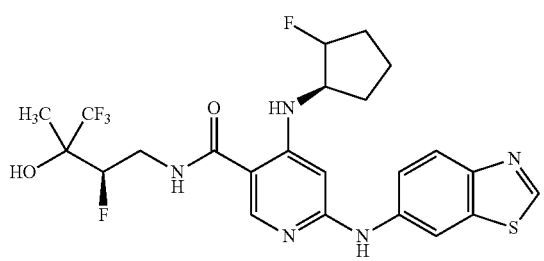 [SMILES: CC(O)([C@H](F)CNC(=O)c1cnc(Nc2ccc3ncsc3c2)cc1N[C@@H]1CCCC1F)C(F)(F)F]

$^1$Hi NMR: 400 MHz, CD$_3$OD: δ 1.45-1.45 (m, 3H), 1.61-1.66 (m, 1H), 1.83-2.03 (m, 5H), 2.33-2.35 (m, 1H), 3.55-3.61 (m, 1H), 3.85-3.98 (m, 2H), 4.70-4.85 (m, 1H), 5.00-5.01 (m, 1H), 6.22 (s, 1H), 7.53-7.55 (m, 1H), 7.96-7.98 (m, 1H), 8.30 (s, 1H), 8.38 (d, J=2.00 Hz, 1H), 9.09 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 2.38 min; LCMS (ES-API), m/z 530.2 (M+H). HPLC: SunFire C18 (150×4.6 mm), 3.5μ; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 μl/min; Retention time: 6.87 min.

Example 342

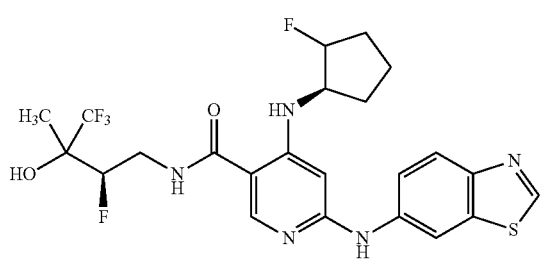 [SMILES: CC(O)([C@H](F)CNC(=O)c1cnc(Nc2ccc3ncsc3c2)cc1N[C@@H]1CCCC1F)C(F)(F)F]

$^1$H NMR: 400 MHz, CD$_3$OD: δ 1.42-1.45 (m, 3H), 1.61-1.66 (m, 1H), 1.86-2.04 (m, 5H), 2.32-2.37 (m, 1H), 3.48-3.69 (m, 2H), 3.90-3.95 (m, 3H), 4.62-4.89 (m, 1H), 4.99-5.00 (m, 1H), 6.22 (s, 1H), 7.53-7.55 (m, 1H), 7.97-7.99 (m, 1H), 8.30 (s, 1H), 8.37 (d, J=2.00 Hz, 1H), 9.10 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 2.38 min; LCMS (ES-API), m/z 530.2 (M+H). HPLC: SunFire C18 (150×4.6 mm), 3.5μ; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 μl/min; Retention time: 6.752 min.

Example 358

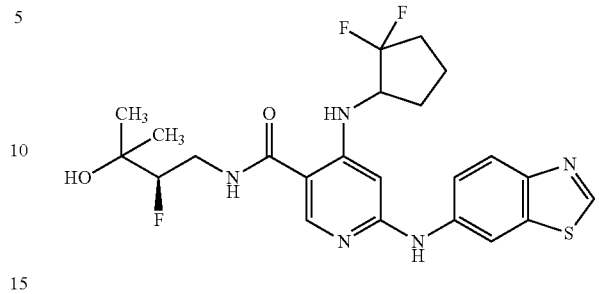

$^1$H NMR: 400 MHz, CD$_3$OD: δ 1.30 (d, J=1.60 Hz, 6H), 1.68-1.73 (m, 1H), 1.81-1.97 (m, 2H), 2.16-2.26 (m, 2H), 2.35-2.39 (m, 1H), 3.46-3.50 (m, 1H), 3.84-3.92 (m, 1H), 3.95-4.05 (m, 1H), 4.34-4.94 (m, 1H), 6.19 (s, 1H), 7.52 (dd, J=2.00, 8.80 Hz, 1H), 7.97 (d, J=8.80 Hz, 1H), 8.31 (s, 1H), 8.37-8.37 (m, 1H), 9.09 (s, 1H). LC/MS: PUROSPHER® Star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.604 min; LCMS (ES-API), m/z 494.2 (M+H). HPLC: SunFire C18 (150×4.6 mm), 3.5μ; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.00/min; Retention time: 9.10 min.

Example 359

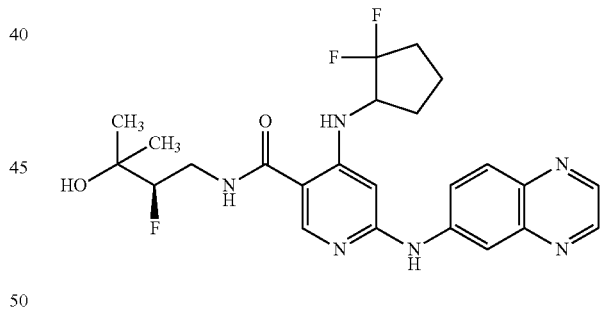

$^1$H NMR: 400 MHz, DMSO-d$_6$: δ 1.30-1.31 (m, 6H), 1.68-1.99 (m, 4H), 2.18-2.28 (m, 2H), 2.39-2.43 (m, 1H), 3.42-3.52 (m, 1H), 3.81-3.83 (m, 1H), 4.02-4.13 (m, 1H), 4.30-4.50 (m, 1H), 6.30 (s, 1H), 7.90-7.90 (m, 2H), 8.36-8.42 (m, 1H), 8.55-8.56 (m, 1H), 8.68 (d, J=2.00 Hz, 1H), 8.76 (d, J=2.00 Hz, 1H). LC/MS: PUROSPHER® Star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.658 min; LCMS (ES-API), m/z 489.2 (M+H). HPLC: SunFire C18 (150×4.6 mm), 3.5μ; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 μl/min; Retention time: 5.831 min.

Example 360

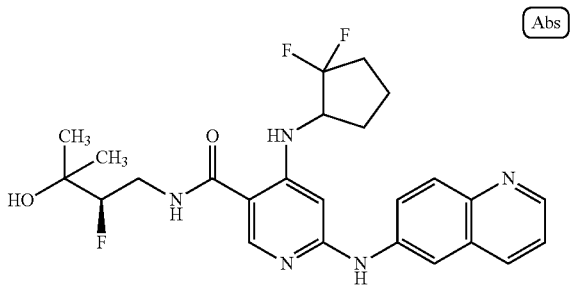 [SMILES: CC(C)(O)[C@H](F)CNC(=O)c1cnc(Nc2ccc3ncccc3c2)cc1NC1CCCC1(F)F]

¹H NMR: 400 MHz, DMSO-d₆: δ 1.31-1.31 (m, 6H), 1.70-1.95 (m, 3H), 2.01-2.10 (m, 1H), 2.18-2.41 (m, 3H), 3.44-3.52 (m, 1H), 3.81-3.90 (m, 1H), 4.03-4.07 (m, 1H), 4.36-4.48 (m, 1H), 6.28 (s, 1H), 7.47-7.50 (m, 1H), 7.79-7.82 (m, 1H), 7.94-7.96 (m, 1H), 8.18-8.24 (m, 2H), 8.36 (s, 1H), 8.68-8.69 (m, 1H). LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.658 min; LCMS (ES-API), m/z 488.2 (M+H). HPLC: SunFire C18 (150×4.6 mm), 3.5μ; Solvent A=5% ACN: 95% H₂O: 0.05% TFA pH=2.5; Solvent B=95% ACN: 5% H₂O: 0.05% TFA pH=2.5; gradient 0-100% B over 30 min (36 min run time); Flow rate: 1.0 μl/min; Retention time: 5.165 min.

Example 361

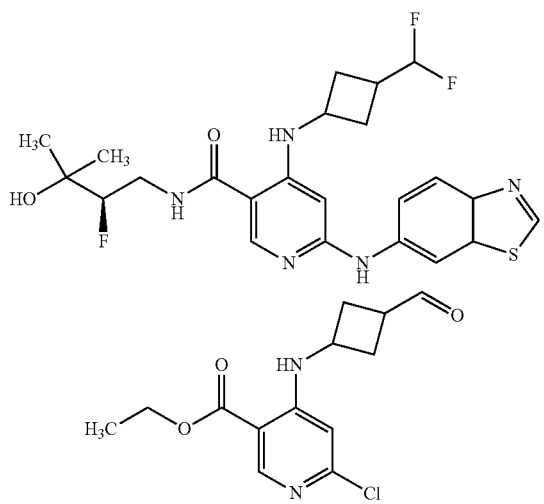

Step 1: Synthesis of ethyl 6-chloro-4-(3-formylcyclobutylamino)nicotinate: To a solution of ethyl 6-chloro-4-((3-(hydroxymethyl)cyclobutyl)amino)nicotinate (0.6 g, 1 equiv.) in DCM (35 mL) was added Dess-Martin Periodinane (3.57 g, 4 equiv.) at 0° C. and the reaction was stirred at room temperature for 30 min. The reaction mixture was concentrated. The residue was dissolved in ethyl acetate, filtered through a CELITE® bed, and washed with ethyl acetate. The filtrate was collected and washed with 10% NaHCO₃ solution. The organic layer was collected, dried over anhydrous sodium sulfate, filtered and concentrated. The crude material was purified by flash chromatography using EtOAc:pet ether as eluent to afford ethyl 6-chloro-4-(3-formylcyclobutylamino) nicotinate. LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.54 min; LCMS (ES-API), m/z 281.2 (M−H).

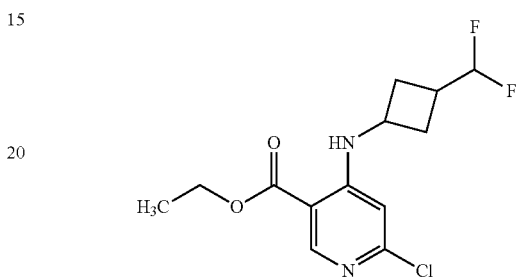

Step 2: Synthesis of ethyl 6-chloro-4-(3-(difluoromethyl)cyclobutylamino)nicotinate: A solution of ethyl 6-chloro-4-((3-formylcyclobutyl)amino)nicotinate (0.11 g, 0.389 mmol) in DCM (5 mL) was cooled to −10° C. DAST (0.103 mL, 0.78 mmol) was added dropwise to the reaction mixture and stirred at room temperature for 5 h. The reaction mixture was quenched with sat NaHCO₃ sol. at 0° C. The product was extracted into DCM and the organic extracts collected, dried over anhydrous sodium sulfate, filtered and concentrated. The crude material was purified by flash chromatography using EtOAc:pet ether as eluent to afford ethyl 6-chloro-4-(3-(difluoromethyl)cyclobutylamino)nicotinate. LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.975 min; LCMS (ES-API), m/z 305.0 (M+H).

Step 3: Synthesis of 4-(3-(difluoromethyl)cyclobutylamino)-6-(3a,27a-dihydrobenzo[d]thiazol-6-ylamino)-N-(2-fluoro-3-hydroxy-3-methylbutyl)nicotinamide: This Example was prepared according to the general method outlined for the synthesis of Example 5, Steps 2 to 4 using benzo[d]thiazol-6-amine and (R)-3-amino-2-fluoropropan-1-ol. ¹H NMR: 400 MHz, DMSO-d₆: δ 1.30-1.30 (m, 6H), 1.97-2.08 (m, 4H), 2.55-2.61 (m, 4H), 3.21-3.25 (m, 2H), 3.38-3.41 (m, 1H), 3.80-3.94 (m, 3H), 4.34-4.49 (m, 1H), 5.88 (s, 1H), 5.95 (s, 1H), 7.51-7.53 (m, 1H), 7.96-7.98 (m, 1H), 8.28 (s, 1H), 8.38 (d, J=2.00 Hz, 1H), 9.08 (s, 1H). LC/MS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 2.38 min; LCMS (ES-API), m/z 492.0 (M−H). HPLC: SunFire C18 (150×4.6 mm), 3.5μ; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μl/min; Retention time: 6.291 min.

Example 362

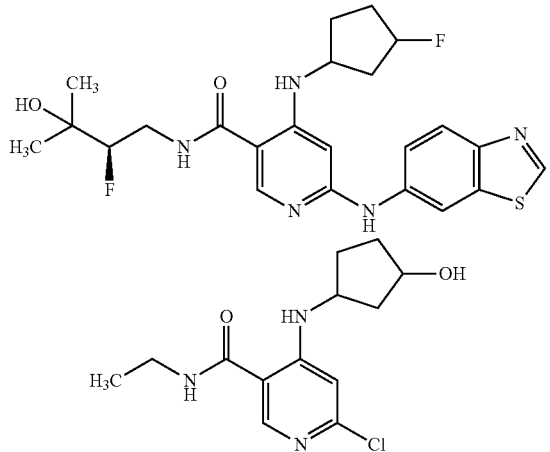

Step 1: Synthesis of ethyl 6-chloro-4-((1S)-3-hydroxycyclopentylamino)nicotinate: This intermediate was prepared from 3-aminocyclopentanol and ethyl 4,6-dichloronicotinate following the standard procedures outlined in Example 5. LC/MS: Acquity BEH C18 2.1×50 mm, 1.8μ; Solvent A=0.1% TFA in water; Solvent B=0.1% TFA in ACN; gradient 0-100% B over 2 min; retention time: 0.70 min; LCMS (ES-API), m/z 285.1 (M+H).

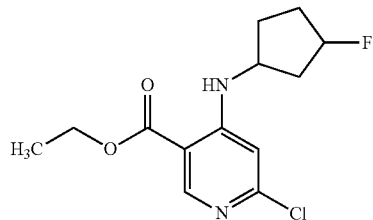 [SMILES: CCOC(=O)c1cnc(Cl)cc1NC1CCC(F)C1]

Step 2: Synthesis of ethyl 6-chloro-4-((1S)-3-fluorocyclopentylamino)nicotinate: This intermediate was prepared from the reaction of ethyl 6-chloro-4-(3-hydroxycyclopentylamino)nicotinate and DAST according to the methods outlined for the preparation of ethyl 6-chloro-4-((1R)-2-fluorocyclopentylamino)nicotinate. LC/MS: XBridge Phe 8, 4.6×30 mm, 3.5 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.165 min; LCMS (ES-API), m/z 287.0 (M+H).

Step 3: Synthesis of 6-(benzo[d]thiazol-6-ylamino)-N-(2-fluoro-3-hydroxy-3-methylbutyl)-4-(3-fluorocyclopentylamino)nicotinamide (diastereomer 1): This Example was prepared according to the general method outlined for the synthesis of Example 5, Steps 2 to 4 using benzo[d]thiazol-6-amine and (R)-3-amino-2-fluoropropan-1-ol. The individual diastereomers were separated via preparative chiral HPLC. $^1$H NMR: 400 MHz, DMSO-d$_6$: δ 1.29-1.33 (m, 6H), 1.61 (s, 2H), 1.84-1.92 (m, 1H), 1.94-1.98 (m, 1H), 2.17-2.22 (m, 3H), 3.05-3.14 (m, 2H), 3.43-3.51 (m, 1H), 3.73-3.90 (m, 3H), 4.30-4.50 (m, 1H), 5.10-5.35 (m, 1H), 6.05 (s, 1H), 7.52 (dd, J=2.00, 8.80 Hz, 1H), 7.96-7.98 (m, 1H), 8.26 (s, 1H), 8.38 (d, J=2.00 Hz, 1H), 9.07 (s, 1H). LC/MS: PUROSPHER® Star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.658 min; LCMS (ES-API), m/z 476.2 (M+H). HPLC: SunFire C18 (150×4.6 mm), 3.5μ; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μl/min; Retention time: 5.904 min.

Example 363

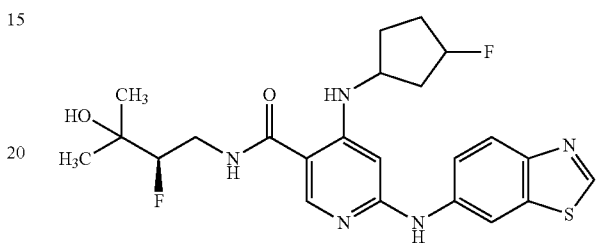

Synthesis of 6-(benzo[d]thiazol-6-ylamino)-N-(2-fluoro-3-hydroxy-3-methylbutyl)-4-(3-fluorocyclopentylamino)nicotinamide (diastereomer 2): $^1$H NMR: 400 MHz, DMSO-d$_6$: δ 1.29-1.34 (m, 6H), 1.83-1.98 (m, 2H), 2.17-2.22 (m, 2H), 3.06 (q, J=21.60 Hz, 2H), 3.40-3.45 (m, 1H), 3.79-3.90 (m, 3H), 4.30-4.50 (m, 1H), 5.10-5.35 (m, 1H), 6.05 (s, 1H), 7.52 (dd, J=2.40, 8.60 Hz, 1H), 7.96-7.98 (m, 1H), 8.26 (s, 1H), 8.37 (d, J=2.00 Hz, 1H), 9.08 (s, 1H). LC/MS: PUROSPHER® Star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.658 min; LCMS (ES-API), m/z 476.2 (M+H). HPLC: SunFire C18 (150×4.6 mm), 3.5μ; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μl/min; Retention time: 5.906 min.

Example 364

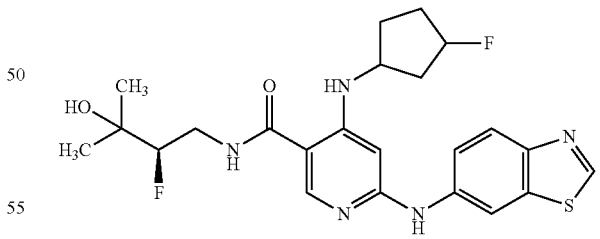

Synthesis of 6-(benzo[d]thiazol-6-ylamino)-N-(2-fluoro-3-hydroxy-3-methylbutyl)-4-(3-fluorocyclopentylamino)nicotinamide (diastereomer 3): $^1$H NMR: 400 MHz, DMSO-d$_6$: δ 1.29-1.34 (m, 6H), 1.62-2.00 (m, 3H), 2.17-2.30 (m, 1H), 2.31-2.33 (m, 2H), 2.35-2.55 (m, 2H), 3.44-3.50 (m, 1H), 3.78-3.87 (m, 1H), 4.05-4.09 (m, 1H), 4.33-4.48 (m, 1H), 5.13-5.35 (m, 1H), 6.09 (s, 1H), 7.52-7.55 (m, 1H), 7.96-7.99 (m, 1H), 8.40 (d, J=2.00 Hz, 1H), 9.08 (s, 1H). LC/MS: PUROSPHER® Star RP-18, 4×55 mm, 3 μm;

Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.658 min; LCMS (ES-API), m/z 476.2 (M+H). HPLC: XBridge (150×4.6 mm), 3.5μ; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μl/min; Retention time: 7.099 min.

Example 365

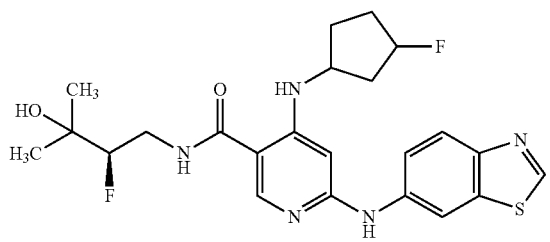 [SMILES: CC(C)(O)[C@H](F)CNC(=O)c1cnc(Nc2ccc3ncsc3c2)cc1NC1CCC(F)C1]

Synthesis of 6-(benzo[d]thiazol-6-ylamino)-N-(2-fluoro-3-hydroxy-3-methylbutyl)-4-(3-fluorocyclopentylamino) nicotinamide (diastereomer 4): ¹H NMR: 400 MHz, DMSO-d₆: δ 1.24-1.29 (m, 6H), 1.30-1.40 (m, 3H), 1.64-1.90 (m, 1H), 1.97-2.26 (m, 2H), 2.28-2.47 (m, 1H), 2.49-2.54 (m, 1H), 3.03-3.09 (m, 2H), 3.40-3.50 (m, 1H), 3.65-3.95 (m, 1H), 4.01-4.12 (m, 1H), 4.30-4.50 (m, 1H), 5.15-5.35 (m, 1H), 6.10 (s, 1H), 6.75 (s, 1H), 7.52-7.55 (m, 1H), 8.03-8.05 (m, 1H), 8.32 (d, J=2.00 Hz, 1H), 9.15 (s, 1H). LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.658 min; LCMS (ES-API), m/z 476.2 (M+H). HPLC: XBridge (150× 4.6 mm), 3.5μ; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μl/min; Retention time: 7.119 min.

Example 366

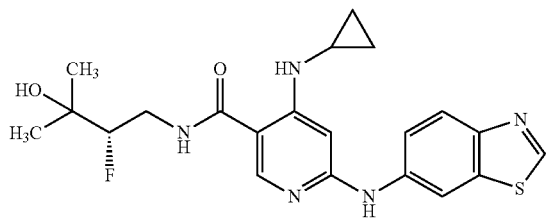 [SMILES: CC(C)(O)[C@@H](F)CNC(=O)c1cnc(Nc2ccc3ncsc3c2)cc1NC1CC1]

A solution of (S)-6-chloro-4-(cyclopropylamino)-N-(2-fluoro-3-hydroxy-3-methylbutyl)nicotinamide (110 mg, 0.348 mmol) in dioxane (11 mL) was added benzo[d] thiazol-6-amine (62.8 mg, 0.418 mmol) and water (2 mL). The mixture was purged with nitrogen, then added Xantphos (81 mg, 0.4 mmol), sodium carbonate (148 mg, 1.4 mmol) and purged again with nitrogen. Pd₂(dba)₃ (128 mg, 0.139 mmol) was added and then purged with nitrogen for 5 min. The reaction was sealed and heated at 110° C. for 18 h. After cooling, the mixture was concentrated, dissolved in 10% MeOH/CHCl₃, filtered through a CELITE® bed and concentrated to obtain a brown solid. The product was purified via preparative TLC to afford (S)-6-(benzo[d]thiazol-6-ylamino)-4-(cyclopropylamino)-N-(2-fluoro-3-hydroxy-3-methylbutyl)nicotinamide (22 mg, 15% yield). LCMS (ES-API), m/z 430.3 (M+H); ¹H NMR: 400 MHz, DMSO-d₆: δ 9.35 (s, 1H), 9.16 (s, 1H), 8.66 (d, J=2.0 Hz, 1H), 8.41 (m, 1H), 8.33 (m, 1H), 7.95 (d, J=8.8 Hz, 1H), 7.61 (dd, J=9.2, 2.4 Hz, 1H), 6.42 (s, 1H), 4.80 (s, 1H), 4.26 (dd, J=8.8, 2.0 Hz, 1H), 3.63 (m, 1H), 3.36 (m, 1H), 1.67 (2s, 6H), 0.78 (m, 2H), 0.56 (m, 2H); HPLC: Retention time: 5.70 min., Condition B.

Example 367

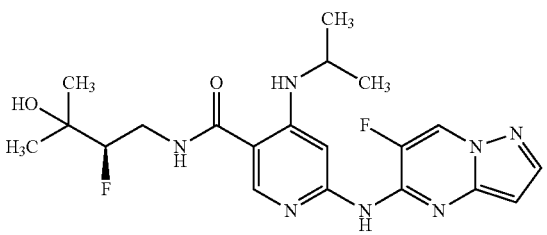 [SMILES: CC(C)Nc1cc(Nc2nc3ccnn3cc2F)ncc1C(=O)NC[C@@H](F)C(C)(C)O]

A solution of (R)-6-chloro-N-(2-fluoro-3-hydroxy-3-methylbutyl)-4-(isopropylamino)nicotinamide (2 g, 6.29 mmol) in 1,4-dioxane (50 mL)) was added 6-fluoropyrazolo[1,5-a]pyrimidin-5-amine (0.957 g, 6.29 mmol) and Xantphos (1.457 g, 2.52 mmol) and degassed for 10 min. Cesium carbonate (8.20 g, 25.2 mmol) was added and degassed for 10 min then added Pd₂(dba)₃ (2.305 g, 2.52 mmol) and degassed for 15 min then sealed and heated at 150° C. for 16 h. The reaction was cooled and filtered through CELITE®. The solvents were removed in vacuo. The residue was purified by column chromatography (methanol 4%/chloroform) and the product fractions collected and concentrated. Further purification via prep HPLC afforded (R)—N-(2-fluoro-3-hydroxy-3-methylbutyl)-6-((6-fluoropyrazolo[1,5-a]pyrimidin-5-yl)amino)-4-(isopropylamino)nicotinamide (1.2 g, 44% yield) as an off-white solid. LCMS (ES-API), m/z 434.2 (M+H); ¹H NMR: 400 MHz, DMSO-d₆: δ 9.56 (s, 1H), 9.27 (d, J=6.0 Hz, 1H), 8.57 (t, J=5.2 Hz, 1H), 8.50 (d, J=6.8 Hz, 1H), 8.47 (s, 1H), 8.00 (d, J=2.4 Hz, 1H), 7.81 (s, 1H), 6.31 (d, J=2.0 Hz, 1H), 4.81 (s, 1H), 4.35 (dd, J=2.0, 49 Hz, 1H), 3.70 (m, 2H), 3.38 (m, 1H), 1.29 (d, J=6.0 Hz, 2H), 1.16 (m, 2H); HPLC: Retention time: 11.24 min., Condition B.

TABLE 8

| Ex. No. | Structure | HPLC RT (min) | HPLC cond. | LCMS (M + H) |
|---|---|---|---|---|
| 368 | 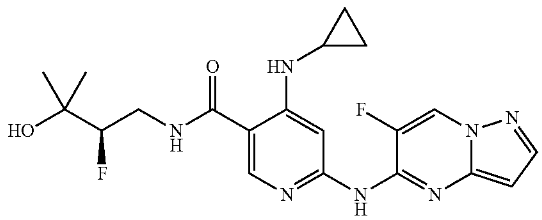 [SMILES: CC(C)(O)[C@H](F)CNC(=O)c1cnc(Nc2nc3ccnn3cc2F)cc1NC1CC1] | 5.30 | E | 432.2 |
| 369 | 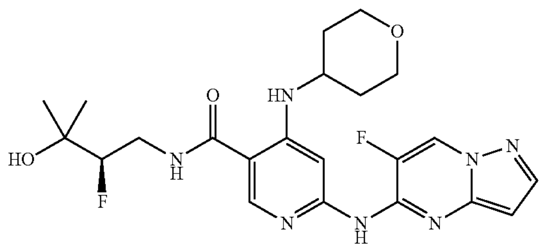 [SMILES: CC(C)(O)[C@H](F)CNC(=O)c1cnc(Nc2nc3ccnn3cc2F)cc1NC1CCOCC1] | 9.49 | E | 476.2 |

The Examples in Table 9 were prepared according to the multiple procedures previously described, substituting where appropriate, various amines to provide the described Examples.

TABLE 9

| Ex. No. | Structure | HPLC RT (min) | HPLC cond. | LCMS (M + H) |
|---|---|---|---|---|
| 370 | 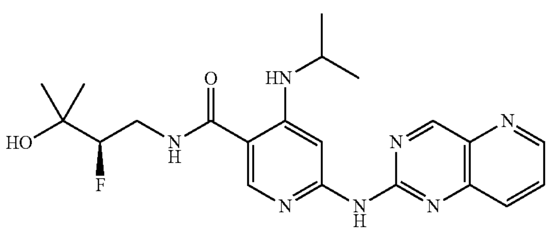 [SMILES: CC(C)Nc1cc(Nc2ncc3ncccc3n2)ncc1C(=O)NC[C@@H](F)C(C)(C)O] | 1.38 | G | 428.2 |
| 371 | 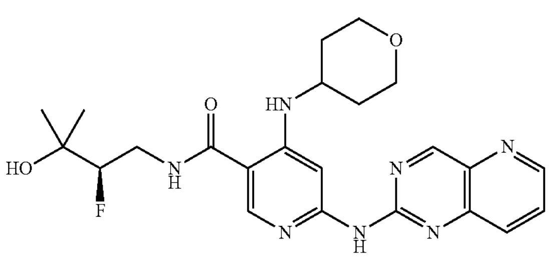 [SMILES: CC(C)(O)[C@H](F)CNC(=O)c1cnc(Nc2ncc3ncccc3n2)cc1NC1CCOCC1] | 1.15 | G | 470.5 |
| 372 | 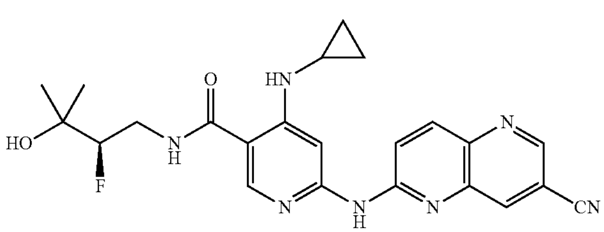 [SMILES: CC(C)(O)[C@H](F)CNC(=O)c1cnc(Nc2ccc3ncc(C#N)cc3n2)cc1NC1CC1] | 7.07 | A | 452.2 |

TABLE 9-continued
| Ex. No. | Structure | HPLC RT (min) | HPLC cond. | LCMS (M + H) |
|---|---|---|---|---|
| 373 | 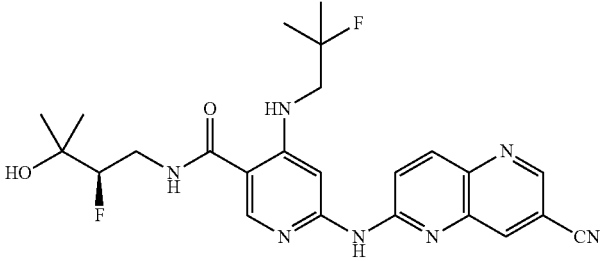 [SMILES: CC(C)(F)CNc1cc(Nc2ccc3ncc(C#N)cc3n2)ncc1C(=O)NC[C@@H](F)C(C)(C)O] | 5.95 | E | 483.8 |
| 374 | 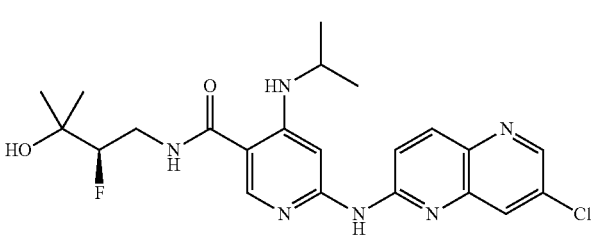 [SMILES: CC(C)Nc1cc(Nc2ccc3ncc(Cl)cc3n2)ncc1C(=O)NC[C@@H](F)C(C)(C)O] | 6.25 | E | 461.2 |
| 379 | 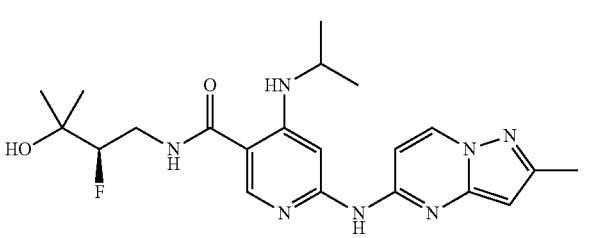 [SMILES: Cc1cc2nc(Nc3cc(NC(C)C)c(C(=O)NC[C@@H](F)C(C)(C)O)cn3)ccn2n1] | 5.53 | E | 430.2 |
| 380 Diastereomer 1 | 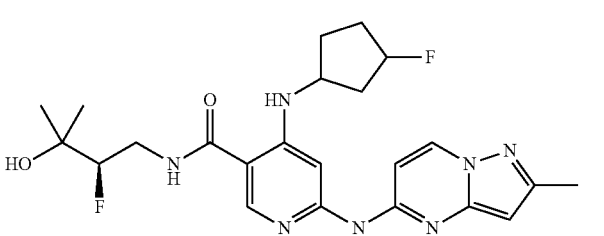 | 5.98 | E | 472.3 (M − H) |
| 381 Diastereomer 2 | 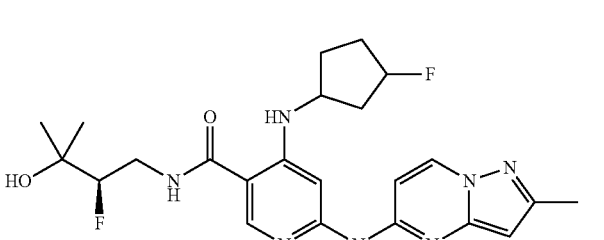 | 5.98 | E | 474.4 |
| 382 | 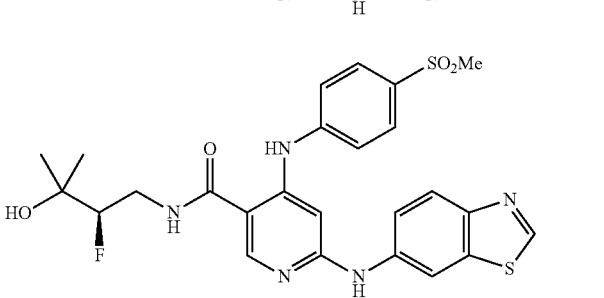 | 1.32 | G | 544.1 |

TABLE 9-continued

| Ex. No. | Structure | HPLC RT (min) | HPLC cond. | LCMS (M + H) |
|---|---|---|---|---|
| 383 | 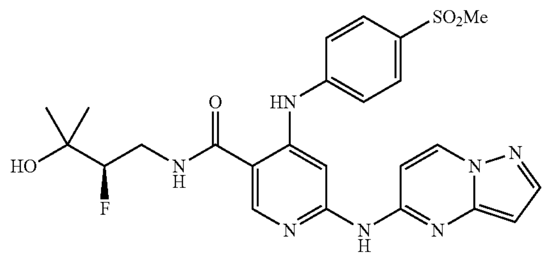 [SMILES: CC(C)(O)[C@H](F)CNC(=O)c1cnc(Nc2ccn3nccc3n2)cc1Nc1ccc(S(C)(=O)=O)cc1] | 1.12 | G | 526.2 (M − H) |
| 384 | 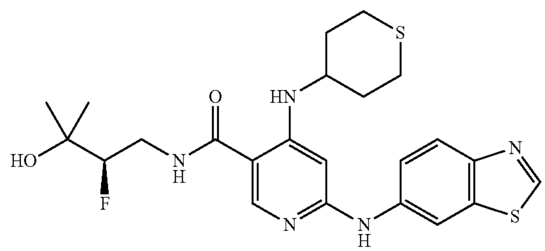 [SMILES: CC(C)(O)[C@H](F)CNC(=O)c1cnc(Nc2ccc3ncsc3c2)cc1NC1CCSCC1] | 1.33 | G | 490.1 |
| 385 | 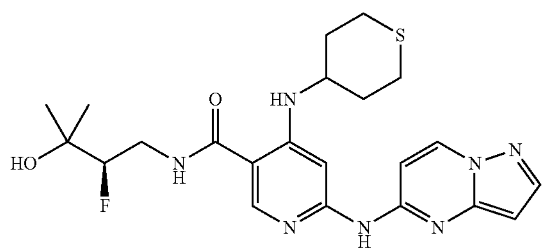 | 1.29 | G | 474.2 |

Synthesis of Various Intermediates:

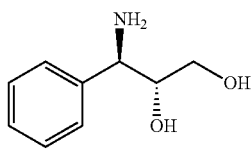 [SMILES: N[C@H](c1ccccc1)[C@@H](O)CO]

Step 1: Synthesis of ((2S,3S)-3-phenyloxiran-2-yl)methanol: (−)-DIPT (0.524 g, 0.075 equiv.) was dissolved in DCM (250 mL) and cooled to −30° C. Molecular sieves (1.6 g), titanium (IV) isopropoxide (0.437 mL, 0.05 equiv.) and t-butyl hydroperoxide (TBHP in decane) (5.78 mL, 2 equiv.) were added sequentially. The mixture was allowed to stir for 1 h, (E)-3-phenylprop-2-en-1-ol (4 g, 1 equiv.) in DCM (10 mL) was added to the reaction mixture and stirred for 3 h at −30° C. The reaction was quenched with 8 mL of 10% aqueous NaOH solution followed by brine solution. The reaction was allowed to warm to 10° C. and stirred for 10 min at 10° C. Anhydrous sodium sulfate (2 g) and CELITE® (2 g) were added to the reaction mixture and stirred for another 50 min. The reaction mixture was then filtered through a pad of CELITE®. The residue was washed with ether and the filtrate was concentrated. The crude product was purified by flash column chromatography using ethyl acetate:pet.ether as eluent to afford ((2S,3S)-3-phenyloxiran-2-yl)methanol. $^1$H NMR: 400 MHz, CDCl$_3$: δ 1.19-1.29 (m, 1H), 4.33 (t, J=4.80 Hz, 2H), 6.34-6.41 (m, 1H), 6.61-6.65 (m, 1H), 7.23-7.27 (m, 1H), 7.30-7.38 (m, 4H).

Step 2: Synthesis of (2R,3R)-3-amino-3-phenylpropane-1,2-diol: To a solution of ((2S,3S)-3-phenyloxiran-2-yl) methanol (0.5 g, 1 equiv.) in 2-propanol (5 mL) was added aqueous NH$_4$OH (10 mL). The reaction mixture was heated at 84° C. for 12 h. The reaction mixture was concentrated and the crude material was azeotroped with toluene (3×30 mL) to afford (2R,3R)-3-amino-3-phenylpropane-1,2-diol. The compound was taken to next step without purification.

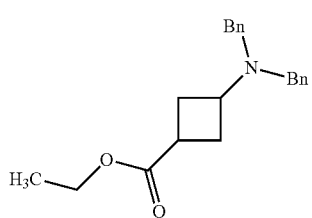 [SMILES: CCOC(=O)C1CC(N(Cc2ccccc2)Cc2ccccc2)C1]

Synthesis of ethyl 3-(dibenzylamino)cyclobutanecarboxylate: Ethyl 3-oxocyclobutanecarboxylate (5.0 g, 1 equiv.) was dissolved in a mixture of 10% aqueous acetic acid (25 mL) and THF (25 mL). Sodium triacetoxyborohydride (14.9 g, 2 equiv.) and dibenzylamine (6.94 g, 1 equiv.) were added sequentially. The reaction mixture was stirred for 14 h at room temperature. The reaction mixture was then concentrated to remove the excess solvent and the residue was dissolved in DCM, washed with water followed by 10% aq NaHCO$_3$ and brine solution. The organic layer was collected and dried over anhydrous sodium sulfate, filtered and concentrated. The crude product was purified by flash chromatography using silica gel and EtOAc:pet ether as eluent to obtain the required product. ¹H NMR 400 MHz, CD₃OD: δ 1.22-1.26 (m, 3H), 2.03-2.12 (m, 2H), 2.19-2.26 (m, 2H), 2.69-2.71 (m, 1H), 3.11-3.15 (m, 1H), 3.51 (d, J=2.40 Hz, 4H), 4.11 (q, J=7.20 Hz, 2H), 7.22-7.34 (m, 10H).

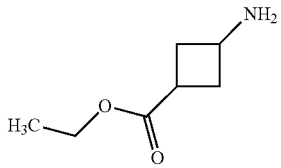

Synthesis of ethyl 3-aminocyclobutanecarboxylate: Ethyl 3-(dibenzylamino)cyclobutane carboxylate (1.0 g, 1 equiv.) dissolved in a mixture of ethanol (48 mL), water (3 mL) and acetic acid (0.2 mL) was degassed with N₂. To the reaction mixture 10% Pd/C (0.5 g, 1.1 equiv.) was added in an inert condition. The reaction mixture was hydrogenated in an autoclave at 42 psi at rt for 18 h. The reaction mixture was filtered through CELITE® and concentrated to obtain ethyl 3-aminocyclobutanecarboxylate. ¹H NMR 400 MHz, CD₃OD: δ 1.29-1.30 (m, 3H), 2.23-2.29 (m, 2H), 2.56-2.63 (m, 2H), 2.96-3.01 (m, 1H), 3.63-3.67 (m, 1H), 4.16 (q, J=7.20 Hz, 2H).

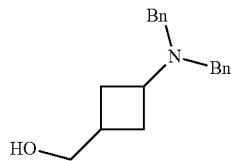

Synthesis of (3-(dibenzylamino)cyclobutyl)methanol: A solution of ethyl 3-(dibenzylamino)cyclobutanecarboxylate (4.0 g, 1 equiv.) in THF (50 mL) was cooled to −10° C. Lithium borohydride (0.404 g, 1.5 equiv.) was added to the reaction mixture in portions. After the addition was complete the reaction was allowed to warm to room temperature and stirred for 18 h. The reaction mixture was diluted with ethyl acetate, cooled to 0° C. and quenched using a saturated solution of NH₄Cl. The organic layer was collected and dried over anhydrous sodium sulfate, filtered and concentrated. The crude product was purified by flash chromatography using silica gel and EtOAc:pet ether as eluent to obtain the required product (3-(dibenzylamino)cyclobutyl) methanol. LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.955 min; LCMS (ES-API), m/z 282.2 (M+H).

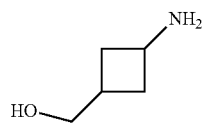

Synthesis of (3-aminocyclobutyl)methanol: Using the reduction procedure described for the preparation of ethyl 3-aminocyclobutanecarboxylate, (3-aminocyclobutyl) methanol was obtained from (3-(dibenzylamino)cyclobutyl) methanol. ¹H NMR 400 MHz, CD₃OD: δ 3.61-3.66 (m, 1H), 3.55 (d, J=5.20 Hz, 2H), 3.33-3.34 (m, 2H), 2.40-2.47 (m, 2H), 2.22-2.38 (m, 2H), 1.92-1.98 (m, 3H).

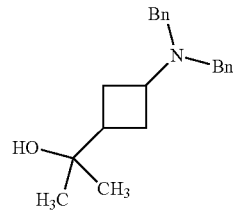

Synthesis of 2-(3-(dibenzylamino)cyclobutyl)propan-2-ol: Ethyl 3-(dibenzylamino)cyclobutanecarboxylate (1.5 g, 4.6 mmol) was dissolved in THF (30 mL) and cooled to −50° C. Methyl magnesium bromide (1.6 mL, 13.9 mmol) was added dropwise and the mixture was stirred at rt for 20 h. TLC indicated partial conversion. The reaction mixture was again cooled to −15° C. and an additional 3 eq of methyl magnesium bromide (1.603 mL, 13.91 mmol) was added and the reaction mixture was stirred at rt for 3 h. The reaction mixture was cooled to 0° C. and quenched with sat NH₄Cl solution. The aqueous layer was extracted with ethylacetate (3 times) and the combined organic extracts were dried over Na₂SO₄, filtered and concentrated to obtain a liquid as the crude product. The crude product was purified by column chromatography (EA/pet ether 15%) to obtain 2-(3-(dibenzylamino)cyclobutyl)propan-2-ol (1.4 g, 88% yield) as a colorless liquid. LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 2.201 min; LCMS (ES-API), m/z 310.2 (M+H).

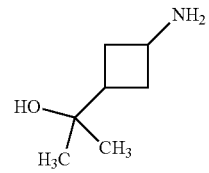

Synthesis of 2-(3-aminocyclobutyl)propan-2-ol: 2-(3-(Dibenzylamino)cyclobutyl)propan-2-ol (1.6 g, 5.17 mmol) was dissolved in ethanol (45 mL) and added 10% Pd—C (0.8 g, 7.52 mmol), AcOH (4.8 mL) and water (0.32 mL) was added. The reaction mixture was than hydrogenated in an autoclave at 3 kg psi for 18 h. The reaction mixture was filtered through CELITE®, washed with MeOH, and concentrated to obtain a colorless liquid as the product (0.63 g, 94% yield). LCMS m/z 130.1 (M+H); ¹H NMR 400 MHz, CD₃OD: δ 3.53-3.57 (m, 1H), 2.29-2.35 (m, 2H), 2.13-2.20 (m, 1H), 2.02-2.07 (m, 2H), 1.12-1.18 (m, 6H).

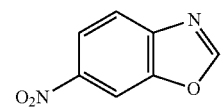

Synthesis of 6-nitrobenzo[d]oxazole: To a stirred solution of 2-amino-5-nitrophenol (0.5 g, 1 equiv.) in triethyl orthoformate (2.7 mL, 5 equiv.), was added p-toluene sulfonic acid monohydrate (0.031 g, 0.5 equiv.). The mixture was heated at 80° C. for 1 h. The reaction mixture was then cooled to 0° C. and the formed precipitate was filtered and washed with ice cooled ether and water. The solid material was dried in vacuum to afford 6-nitrobenzo[d]oxazole (0.38 g, 72% yield). $^1$H NMR: 400 MHz, DMSO-$d_6$: δ 9.12 (s, 1H), 8.79 (s, 1H), 8.34 (d, J=8.40 Hz, 1H), 8.07 (d, J=8.80 Hz, 1H).

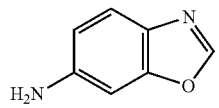 [SMILES: O=[N+]([O-])c1ccc2ncoc2c1]

Synthesis of benzo[d]oxazol-6-amine: A solution of 6-nitrobenzo[d]oxazole (0.5 g, 1 equiv.) in toluene (10 mL) was degassed with $N_2$ for 5 min. Pd/C (10% w/w) (0.324 g, 1 equiv.) was added to the reaction mixture and stirred under $H_2$ atmosphere at room temperature for 14 h. After complete consumption of starting material the reaction mixture was filtered through CELITE® and washed with 1:1:EtOAc: MeOH. The filtrate was evaporated under vacuum to afford benzo[d]oxazol-6-amine (0.31 g, 77% yield). $^1$H NMR: 400 MHz, DMSO-$d_6$: δ 8.32 (s, 1H), 7.39 (d, J=8.80 Hz, 1H), 6.79 (d, J=2.00 Hz, 1H), 6.64 (dd, J=2.00, 8.40 Hz, 1H), 5.35 (s, 2H).

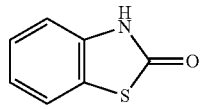

Synthesis of benzo[d]thiazol-2(3H)-one: To a stirred solution of CDI (2.59 g, 1 equiv.) in THF (8 mL), was added 2-aminobenzenethiol (2 g, 1 equiv.) in THF (8 mL) dropwise at 0° C. The reaction mixture was allowed to stir at room temperature for 12 h. The reaction mixture was then diluted with ethyl acetate and washed with 1.5N HCl followed by 10% $NaHCO_3$ solution and brine. The organic layer was collected, dried over anhydrous sodium sulfate, filtered and concentrated. The crude material obtained was purified by column chromatography using silica gel and EtOAc:pet ether as eluent to afford benzo[d]thiazol-2(3H)-one. LC/MS: XBridge Phe 8, 4.6×30 mm, 3.5 µm; Solvent A=2% ACN: 98% $H_2O$: 10 mM $NH_4COOH$; Solvent B=98% ACN: 2% $H_2O$: 10 mM $NH_4COOH$; gradient 0-100% B over 1.5 min (3.2 min run time); retention time: 1.329 min; LCMS (ES-API), m/z 150.0 (M–H).

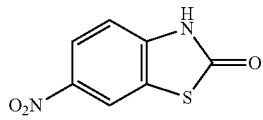

Synthesis of 6-nitrobenzo[d]thiazol-2(3H)-one: To a stirred solution of benzo[d]thiazol-2(3H)-one (0.150 g, 1 equiv.) in acetic acid (1 mL), was added $HNO_3$ (0.1 mL) at −10° C. and stirred for 1 h. The reaction mixture was warmed to room temperature at which time the product precipitated. The product was filtered and dried under vacuum to afford 6-nitrobenzo[d]thiazol-2(3H)-one. $^1$H NMR 400 MHz, DMSO-$d_6$: δ 8.66 (d, J=2.40 Hz, 1H), 8.20 (dd, J=2.40, 8.80 Hz, 1H), 7.30 (d, J=8.80 Hz, 1H).

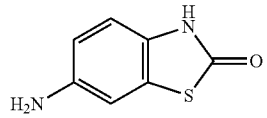

Synthesis of 6-aminobenzo[d]thiazol-2(3H)-one: To a solution of 6-nitrobenzo[d]thiazol-2(3H)-one (0.13 g, 1 equiv.) in ethanol (6 mL): water (3 mL), were added ammonium chloride (0.36 g, 10 equiv.) and iron powder (0.15 g, 4 equiv.). The reaction mixture was heated at 80° C. for 2 h. After cooling the reaction mixture was filtered through a bed of CELITE®. The filtrate was concentrated and the crude product was purified by flash column chromatography using silica gel and EtOAc:pet ether as eluent to afford 6-aminobenzo[d]thiazol-2(3H)-one. LC/MS: XBridge Phe 8, 4.6×30 mm, 3.5 µm; Solvent A=2% ACN: 98% $H_2O$: 10 mM $NH_4COOH$; Solvent B=98% ACN: 2% $H_2O$: 10 mM $NH_4COOH$; gradient 0-100% B over 1.5 min (3.2 min run time); retention time: 1.052 min; LCMS (ES-API), m/z 165.0 (M–H).

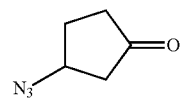

Synthesis of 3-azidocyclopentanone: A solution of cyclopent-2-enone (10 g, 1 equiv.) in DCM (100 mL) and AcOH (35 mL, 5 equiv.) at 0° C. was added trimethyl silyl azide (81 mL, 5 equiv.) followed of TEA (3.4 mL, 0.2 equiv.). The reaction mixture was allowed to stir overnight at room temperature. After complete consumption of the starting material, the reaction was quenched by adding water. The product was extracted into DCM (twice) and the organic layer was collected, dried over anhydrous sodium sulfate, filtered and concentrated to give crude 3-azidocyclopentanone. GCMS: 125 (M): Retention time: 4.445 min.

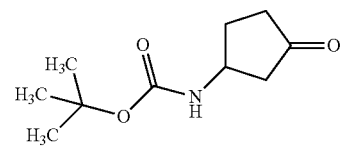

Synthesis of tert-butyl 3-oxocyclopentylcarbamate: A solution of 3-azidocyclopentanone (10 g, 1 equiv.) in EtOAc (80 mL) was added $Boc_2O$ (22.3 mL, 1.2 equiv.). The solution was degassed with $N_2$ followed by addition of Pd/C (0.850 g, 0.1 equiv.). The reaction mixture was stirred overnight at ambient temperature under $H_2$ atm (14 psi). The reaction mixture was filtered through CELITE® and the CELITE® bed washed thoroughly with ethyl acetate. The filtrate was concentrated. The residue was triturated with ether:hexane:1:1, filtered and dried to give tert-butyl (3-oxocyclopentyl)carbamate. LC/MS: Ascentis Express C18, 5×2.1 mm, 2.7 µm; Solvent A=2% ACN: 98% $H_2O$: 10 mM $NH_4COOH$; Solvent B=98% ACN: 2% $H_2O$: 10 mM NH₄COOH; gradient 0-100% B over 1.5 min; retention time: 1.6 min; LCMS (ES-API), m/z 200.9 (M+H).

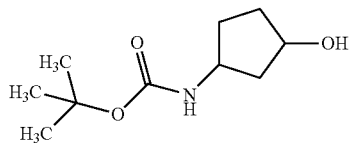

Synthesis of tert-butyl 3-hydroxycyclopentylcarbamate: A solution of tert-butyl(3-oxocyclopentyl)carbamate (2.0 g, 1 equiv.) in MeOH (20 mL) at 0° C. was added NaBH₄ (0.760 g, 2 equiv.). The reaction mixture was stirred for 1 h at room temperature. Methanol was removed under reduced pressure, and the residue was quenched with saturated NH₄Cl and extracted with EtOAc (twice). The organic layer was washed with water and brine, dried over anhydrous sodium sulfate and concentrated. The crude material obtained was purified by column chromatography using silica gel and EtOAc:pet ether as eluent to afford tert-butyl 3-hydroxycyclopentylcarbamate. LC/MS: Ascentis Express C18, 5×2.1 mm, 2.7 µm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.6 min; LCMS (ES-API), m/z 201.9 (M+H).

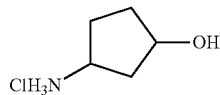

Synthesis of 3-aminocyclopentanol): A solution of tert-butyl(3-hydroxycyclopentyl)carbamate (1.6 g, 1 equiv.) in DCM (2 mL) was cooled to 0° C. 4 M HCl in dioxane (6 mL) was added to the reaction mixture and stirred for 1 h. Dioxane was removed under vacuum to give 3-aminocyclopentanol hydrochloride. ¹H NMR 400 MHz, DMSO-d₆: δ 8.02-8.19 (m, 1H), 4.12-4.23 (m, 2H), 3.43-3.58 (m, 1H), 2.04-2.10 (m, 1H), 1.88-1.94 (m, 2H), 1.66-1.75 (m, 2H), 1.49-1.60 (m, 1H).

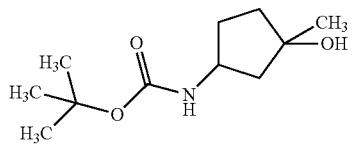

Synthesis of tert-butyl 3-hydroxy-3-methylcyclopentylcarbamate: A solution of tert-butyl(3-oxocyclopentyl)carbamate (0.25 g, 1 equiv.) in THF (10 mL) was cooled to 0° C. Methyl magnesium bromide (3 M in THF) (0.449 g, 3 equiv.) was added and stirred at room temperature for 4 h. After completion of 4 h, the reaction mixture was quenched using sat. NH₄Cl solution (20 mL) at 0° C. and stirred at room temperature for 10 min. The product was extracted into ethyl acetate (twice) and the combined organic layers were dried over anhydrous sodium sulfate and concentrated. The crude product was purified by flash column chromatography using silica gel and EtOAc:pet ether to afford tert-butyl (3-hydroxy-3-methylcyclopentyl)carbamate. ¹H NMR: 400 MHz, DMSO-d₆: δ 7.19 (bs, 1H), 4.42 (s, 1H), 3.72-3.85 (m, 1H), 2.08-2.16 (m, 2H), 1.77-1.99 (m, 2H), 1.50-1.66 (m, 2H), 1.33-1.45 (m, 9H), 1.16-1.21 (m, 3H).

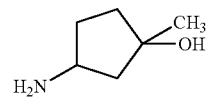

Synthesis of 3-amino-1-methylcyclopentanol: A solution of tert-butyl (3-hydroxy-3-methylcyclopentyl)carbamate (0.12 g) in DCM (10 mL) was treated with methanol hydrochloride (10 mL) at 0° C. The reaction mixture was stirred at room temperature for 4 h. After complete consumption of the starting material the reaction mixture was concentrated. The material obtained was azeotroped with MeOH (twice) and concentrated under reduced pressure to provide 3-amino-1-methylcyclopentanol.

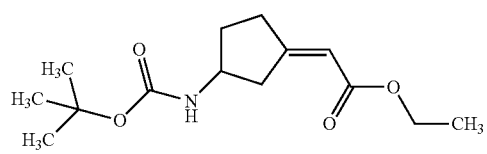 [SMILES: CCOC(=O)/C=C1/CCC(NC(=O)OC(C)(C)C)C1]

Synthesis of ethyl 2-(3-(tert-butoxycarbonylamino)cyclopentylidene)acetate: To a stirred suspension of NaH (72.3 mg, 1.2 equiv.) in THF (10 mL) at 0° C. was added triethyl phosphonoacetate (0.55 mL, 1.1 equiv.) in THF (5 mL) and allowed to stir for 30 min. tert-Butyl(3-oxocyclopentyl) carbamate (500 mg, 1 equiv.) in THF (5 mL) was added to the reaction mixture at 0° C. The reaction was allowed to slowly warm to room temperature and stir for 12 h. The reaction mixture was then concentrated and the residue was diluted with EtOAc and washed with brine solution and water. The organic layer was separated, dried over anhydrous sodium sulfate, filtered and concentrated. The crude material was purified by column chromatography through silica gel and EtOAC: pet ether as eluent to afford ethyl 2-(3-(tert-butoxycarbonylamino)cyclopentylidene)acetate. GCMS: 269 (M); Retention time: 9.051 min.

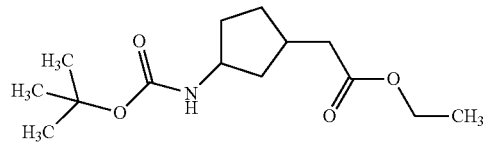

Synthesis of ethyl 2-(3-(tert-butoxycarbonylamino)cyclopentyl)acetate: A solution of ethyl 2-(3-(tert-butoxycarbonylamino)cyclopentylidene)acetate (500 mg, 1 equiv.) in MeOH (15 mL) was degassed with N₂ followed by addition of PdOH₂ (261 mg, 1 equiv.). The reaction mixture was allowed to stir at ambient temperature for 12 h under H₂ atm. The reaction mixture was filtered through CELITE®. The filtrate obtained was concentrated to afford ethyl 2-(3-(tert-butoxycarbonylamino)cyclopentyl)acetate. ¹H NMR: 400 MHz, CDCl₃: δ 4.12 (q, J=6.80 Hz, 2H), 3.66 (s, 1H), 2.25-2.41 (m, 4H), 1.85-1.99 (m, 3H), 1.72-1.78 (m, 1H), 1.61-1.65 (m, 1H), 1.44 (s, 9H), 1.22 (t, J=4.40 Hz, 3H).

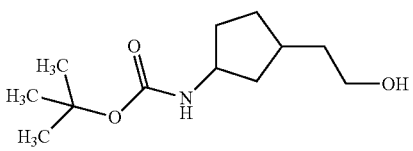 [SMILES: CC(C)(C)OC(=O)NC1CCC(CCO)C1]

Synthesis of tert-butyl 3-(2-hydroxyethyl)cyclopentylcarbamate: To an ice cooled solution of ethyl 2-(3-(tert-butoxycarbonylamino)cyclopentyl)acetate (400 mg, 1 equiv.) in THF was added LAH (112 mg, 2 equiv.) and the reaction mixture was stirred at 0° C. for 1 h. After the completion of 1 h, the reaction was quenched with saturated solution of sodium sulfate and the suspension was filtered. The filtrate was concentrated to provide tert-butyl 3-(2-hydroxyethyl)cyclopentylcarbamate. $^1$H NMR: 400 MHz, CDCl$_3$: δ 3.64-3.61.89-1.99 (m, 2H), 5 (m, 2H), 2.24-2.31 (m, 1H), 2.01-2.10 (m, 1H), 1.60-1.67 (m, 3H), 1.54-1.59 (m, 1H), 1.41 (s, 9H), 1.45-1.32 (m, 3H).

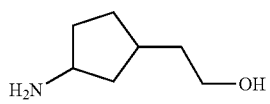

Synthesis of 2-(3-aminocyclopentyl)ethanol: tert-Butyl 3-(2-hydroxyethyl)cyclopentylcarbamate was treated with 4 M HCl in dioxane at 0° C. The reaction mixture was stirred for 1 h then concentrated to dryness to furnish 2-(3-aminocyclopentyl)ethanol.

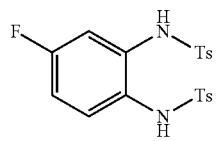

Synthesis of N,N'-(4-fluoro-1,2-phenylene)bis(4-methylbenzenesulfonamide): A solution of 4-fluorobenzene-1,2-diamine (4 g, 1 equiv.) in pyridine (40 mL) was cooled to 0° C. Tosyl chloride (15 g, 2.5 equiv.) was added slowly. The reaction mixture was then stirred at room temperature for 4 h and then quenched with 1.5 N HCl solution. The product was extracted in ethyl acetate (twice). The organic layers were collected, dried over anhydrous sodium sulfate, filtered and concentrated. The crude material was purified by flash column chromatography using silica gel and EtOAc:pet ether as eluent to afford N,N'-(4-fluoro-1,2-phenylene)bis(4-methylbenzenesulfonamide). $^1$H NMR 400 MHz, DMSO-d$_6$: δ 9.34-9.38 (m, 2H), 7.66-7.68 (m, 2H), 7.53-7.55 (m, 2H), 7.35-7.39 (m, 4H), 6.80-6.90 (m, 3H), 2.37 (s, 6H).

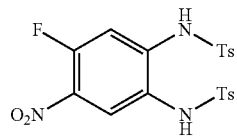 [SMILES: Cc1ccc(S(=O)(=O)Nc2cc(F)c([N+](=O)[O-])cc2NS(=O)(=O)c2ccc(C)cc2)cc1]

Synthesis of N,N'-(4-fluoro-5-nitro-1,2-phenylene)bis(4-methylbenzenesulfonamide): N,N'-(4-Fluoro-1,2-phenylene)bis(4-methylbenzenesulfonamide) (4 g, 1 equiv.) in acetic acid (40 mL) was cooled to 0° C. Fuming HNO$_3$ (0.96 mL, 2.5 equiv.) was added slowly. The reaction mixture was then allowed to stir at room temperature for 4 h. After completion of 4 h, the reaction mixture was poured into ice cool water. The product precipitated and was stirred for 5 min and filtered to afford N,N'-(4-fluoro-5-nitro-1,2-phenylene)bis(4-methylbenzenesulfonamide).

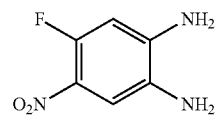

Synthesis of 4-fluoro-5-nitrobenzene-1,2-diamine: To a solution of N,N'-(4-fluoro-5-nitro-1,2-phenylene)bis(4-methylbenzenesulfonamide) (0.4 g, 0.83 mmol) in water (0.5 mL) was added H$_2$SO$_4$ (1 mL, 37.5 mmol). The reaction mixture was heated for 1 h at 80° C. The reaction mixture was cooled to rt then added water to dissolve the solids. Aqueous ammonia was added to neutralize the reaction and a red colored solution was formed. The mixture was extracted with ethyl acetate (3×) and the combined organic extracts were washed with water, dried and concentrated to afford 4-fluoro-5-nitrobenzene-1,2-diamine (0.12 g, 84% yield). LCMS m/z 170.0 (M−H).

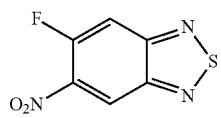

Synthesis of 5-fluoro-6-nitrobenzo[c][1,2,5]thiadiazole: A solution of 4-fluoro-5-nitrobenzene-1,2-diamine (2 g, 1 equiv.) in DCM (40 mL) was treated with triethyl amine (2.3 mL, 4 equiv.) and cooled to 0° C. Thionyl chloride (0.6 mL, 2 equiv.) was added to the reaction mixture and stirred at room temperature for 6 h. The reaction mixture was concentrated and the crude material was purified by flash column chromatography using silica gel and EtOAc:pet ether as eluent to provide 5-fluoro-6-nitrobenzo[c][1,2,5]thiadiazole.

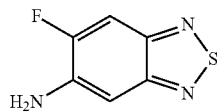

Synthesis of 6-fluorobenzo[c][1,2,5]thiadiazol-5-amine: To a solution of 5-fluoro-6-nitrobenzo[c][1,2,5]thiadiazole (0.6 g, 1 equiv.) in ethanol (10 mL): water (2 mL), ammonium chloride (2.2 g, 5 equiv.) and iron powder (2.3 g, 5 equiv.) were added. The reaction mixture was refluxed at 80° C. for 2 h. After completion of 2 h the reaction mixture was filtered through a bed of CELITE®. Filtrate was concentrated to get the crude product which was purified by flash column chromatography using silica gel and EtOAc:pet ether as eluent to afford 6-fluorobenzo[c][1,2,5]thiadiazol-5-amine. LC/MS: ZORBAX® SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.197 min; LCMS (ES-API), m/z 170.0 (M+H).

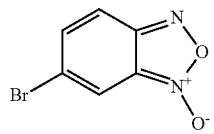

Synthesis of 5-bromobenzo[c][1,2,5]oxadiazole 1-oxide: To a stirred solution of 4-bromo-2-nitroaniline (50 g, 230 mmol) in ethanol (500 mL), was added (38.8 g, 691 mmol). The reaction became red brown in color and was heated at 60° C. for 2 h. After cooling to 0° C., a solution of sodium hypochlorite (501 mL, 8110 mmol) was added over period of 5-10 min and then stirred for 20 min. While maintaining cooling the solids were filtered and washed with cold water (500 mL). A light greenish yellow solid was obtained and dried on vacuum to afford 5-bromobenzo[c][1,2,5]oxadiazole 1-oxide (42 g, 83% yield). GCMS: 214 (M); Retention time: 7.143 min; $^1$H NMR 400 MHz, CDCl$_3$: δ 7.76 (br s, 1H), 7.36 (br s, 2H).

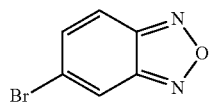

Synthesis of 5-bromobenzo[c][1,2,5]oxadiazole: To a stirred slurry of 5-bromobenzo[c][1,2,5]oxadiazole 1-oxide (42 g, 195 mmol) in Ethanol (420 mL) was added a solution of triethyl phosphite (35.2 mL, 201 mmol). After addition of triethylphosphite the reaction mass became dark brown in color. The reaction was heated to 60° C. for 1 hour. The mixture was cooled to 0° C. and added pet ether (200 mL) and stirred for 10 min. The reaction mass was concentrated to afford a brown liquid. The crude product was purified via column chromatography (1% EA/PE) to afford 5-bromobenzo[c][1,2,5]oxadiazole (26 g, 66% yield) as a light orange fluffy solid. GCMS: 198 (M); Retention time: 5.797 min; $^1$H NMR 400 MHz, CDCl$_3$: δ 8.09 (s, 1H), 7.76 (dd, J=0.8, 9.2 Hz, 1H), 7.48 (dd, J=1.6, 9.6 Hz, 1H).

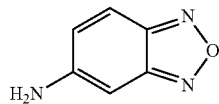

Synthesis of benzo[c][1,2,5]oxadiazol-5-amine: To a stirred solution of 5-bromobenzo[c][1,2,5]oxadiazole (25 g, 126 mmol) in NMP (28 mL), ammonia solution (300 mL) and copper powder (1.63 g, 26 mmol) was added. The reaction mixture was heated at 60° C. for 14 h. The reaction mass was filtered through CELITE® and washed thoroughly with ethyl acetate (500 mL). The filtrate was washed also with water (500 mL) and ammonia solution (250 mL). The ethyl acetate layer was washed with brine solution (200 mL). The organic layers were separated, dried over Na$_2$SO$_4$ and concentrated to afford a yellow solid which was purified via column chromatography (20% EA/PE) to afford benzo[c][1,2,5]oxadiazol-5-amine (13.5 g, 79% yield) as a greenish yellow fluffy solid. $^1$H NMR 400 MHz, DMSO-d$_6$: δ 7.75 (dd, J=0.4, 9.6 Hz, 1H), 7.14 (dd, J=2.0, 9.6 Hz, 1H), 6.42 (br s, 2H), 6.35 (s, 1H).

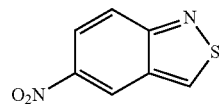

Synthesis of 5-nitrobenzo[c]isothiazole: A solution of 5-nitrobenzo[c]isothiazol-3-amine (4.0 g, 1 equiv.) in 1,4-dioxane (120 mL) was cooled to 0° C. To the reaction mixture, isoamyl nitrite (11.56 mL, 4.2 equiv.) was added. The reaction mixture was slowly allowed to attain room temperature and stirred overnight. The reaction mixture was concentrated to remove excess of solvent. The crude product was purified by flash column chromatography using silica and EtOAc:pet ether as eluent to obtain 5-nitrobenzo[c]isothiazole (3.5 g, 80% yield). GCMS: 180 (M); Retention time: 8.191 min.

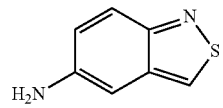 [SMILES: O=[N+]([O-])c1ccc2nscc2c1]

Synthesis of benzo[c]isothiazol-5-amine: A solution of 5-nitrobenzo[c]isothiazole (4.0 g, 1 equiv.) in ethanol (24 mL) and water (6 mL) at 0° C. was added conc. HCl (0.3 mL, 9.87 mmol) and iron powder (0.5 g, 0.4 equiv.). The reaction mixture was refluxed for 2 h. After completion of 2 h, the reaction mixture was filtered through CELITE® and washed the bed thoroughly with DCM. The filtrate was concentrated to obtain benzo[c]isothiazol-5-amine (3.1 g, 74% yield). LC/MS: Ascentis Express C18, 5×2.1 mm, 2.7 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.0 min; LCMS (ES-API), m/z 10.4 (M+H).

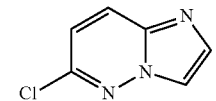

Synthesis of 6-chloroimidazo[1,2-b]pyridazine: To a solution of 6-chloropyridazin-3-amine (2 g, 15.4 mmol) in n-butanol (15 mL) was added 2-chloroacetaldehyde (1.2 g, 15.4 mmol). The reaction mixture was heated at reflux for 14 h. The reaction mixture was cooled in an ice bath which resulted in precipitation of product. The solid obtained was filtered washed with cold n-Butanol and diethyl ether. The solid material was dissolved in a minimum amount of water, and added 1N NaOH solution slowly. The product was extracted into ethyl acetate. The organic layer was washed with a 10% NaHCO$_3$ solution, dried over anhydrous sodium sulfate, filtered and concentrated to afford 6-chloroimidazo[1,2-b]pyridazine (2.1 g, 86% yield). LCMS m/z 154.5 (M+H); $^1$H NMR 400 MHz, DMSO-d$_6$: δ 8.35 (s, 1H), 8.23 (d, J=9.60 Hz, 1H), 7.86 (d, J=1.20 Hz, 1H), 7.37 (d, J=9.20 Hz, 1H).

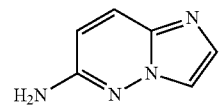

Synthesis of imidazo[1,2-b]pyridazin-6-amine: A mixture of 6-chloroimidazo[1,2-b]pyridazine (0.5 g, 3.26 mmol) and ammonia (8 mL, 3.26 mmol) was heated to 180° C. for 16 h. The reaction was concentrated and purified by Pre-HPLC to afford imidazo[1,2-b]pyridazin-6-amine (120 mg, 27% yield). LC/MS: ZORBAX® SB C18, 4.6×50 mm, 5 μm; Solvent A=10% MeOH: 90% H₂O: 0.1% TFA; Solvent B=90% MeOH: 10% H₂O: 0.1% TFA; gradient 0-100% B over 2 min (3 min run time); retention time: 0.136 min; LCMS (ES-API), m/z 135.2 (M+H); ¹H NMR 400 MHz, CD₃OD: δ 7.61 (m, 2H), 7.41 (s, 1H), 6.72 (m, 1H).

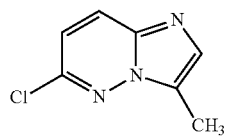

Synthesis of 6-chloro-3-methylimidazo[1,2-b]pyridazine: To a stirred solution of 6-chloropyridazin-3-amine (1 g, 7.72 mmol) in EtOH (20 mL) was added 2-chloropropanal (0.857 g, 9.26 mmol). The mixture was heated at reflux for 18 h then concentrated. The crude residue was dissolved in water and neutralized with solid sodium bicarbonate (pH=7). The precipitate formed was filtered and washed with water to get 6-chloro-3-methylimidazo[1,2-b]pyridazine (0.920 g, 69% yield). ¹H NMR 400 MHz, DMSO-d₆: δ 8.19 (d, J=9.6 Hz, 1H), 7.71 (d, J=0.4 Hz, 1H), 7.32 (d, J=9.60 Hz, 1H)

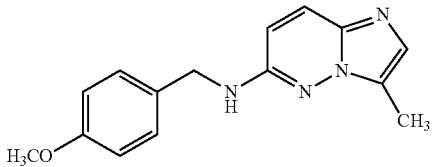 [SMILES: COc1ccc(CNc2ccc3ncc(C)n3n2)cc1]

Synthesis of N-(4-methoxybenzyl)-3-methylimidazo[1,2-b]pyridazin-6-amine: A solution of 6-chloro-3-methylimidazo[1,2-b]pyridazine (0.900 g, 5.37 mmol) in DMSO (3.00 mL) was added (4-methoxyphenyl)methanamine (3.68 g, 26.9 mmol) and the mixture was heated to 150° C. for 5 hours. The compound was precipitated from the reaction by the addition of water and the precipitate was isolated by filtration and successively washed with ether to afford N-(4-methoxybenzyl)-3-methylimidazo[1,2-b]pyridazin-6-amine (0.910 g, 63% yield).

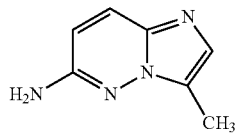

Synthesis of 3-methylimidazo[1,2-b]pyridazin-6-amine: A mixture of N-(4-methoxybenzyl)-3-methylimidazo[1,2-b]pyridazin-6-amine (0.8 g, 2.98 mmol) and TFA (5 mL) was heated at 65° C. for 2 h. The TFA was removed and the residue was dissolved in EtOAc and washed with a 2N aqueous NaOH solution. During neutralization, the reaction product precipitated from the EtOAc solution. The product was isolated by filtration and washed with ether to afford 3-methylimidazo[1,2-b]pyridazin-6-amine (0.27 g, 53% yield). LCMS m/z 149.2 (M+H).

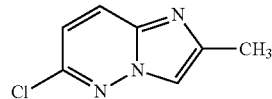

Synthesis of 6-chloro-2-methylimidazo[1,2-b]pyridazine: To a stirred solution of 6-chloropyridazin-3-amine (0.5 g, 3.86 mmol) in EtOH (5 mL) was added 1-chloropropan-2-one (0.429 g, 4.63 mmol) and the mixture was heated at reflux for 18 h. The mixture was cooled and the solvents removed to provide a crude residue which was dissolved in water and neutralized with solid sodium bicarbonate (pH=7). The precipitate formed was filtered and washed with water to afford 6-chloro-2-methylimidazo[1,2-b]pyridazine (0.516 g, 80% yield). ¹H NMR 400 MHz, DMSO-d₆: δ 8.12 (s, 1H), 8.08 (d, J=8.8 Hz, 1H), 7.29 (d, J=9.6 Hz, 1H), 2.40 (s, 3H).

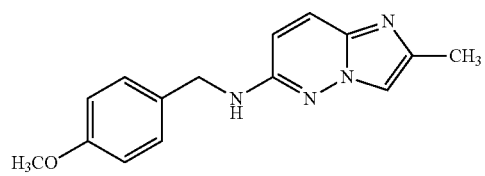 [SMILES: COc1ccc(CNc2ccc3nc(C)cn3n2)cc1]

Synthesis of N-(4-methoxybenzyl)-2-methylimidazo[1,2-b]pyridazin-6-amine: (4-Methoxyphenyl)methanamine (2.046 g, 14.9 mmol) was added to a solution of 6-chloro-2-methylimidazo[1,2-b]pyridazine (0.5 g, 2.98 mmol) in DMSO (2 mL) and the mixture was heated to 150° C. for 5 hours. The compound was precipitated from the reaction by the addition of water. The precipitate was isolated by filtration and successively washed with ether to afford N-(4-methoxybenzyl)-2-methylimidazo[1,2-b]pyridazin-6-amine (0.648 g, 65% yield) as a yellow solid. LCMS m/z 269.2 (M+).

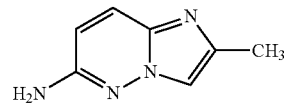

Synthesis of 2-methylimidazo[1,2-b]pyridazin-6-amine: N-(4-Methoxybenzyl)-2-methylimidazo[1,2-b]pyridazin-6-amine (0.6 g, 2.24 mmol) was mixed with TFA (3 mL) and heated at 65° C. for 2 h. The solvents were evaporated in vacuo. The residue was dissolved in EtOAc and washed with a 2N aqueous NaOH solution. During neutralization, the reaction product precipitated from the EtOAc solution. The product was isolated by filtration and washed with ether to afford 2-methylimidazo[1,2-b]pyridazin-6-amine (0.21 g, 60% yield). LCMS m/z 149.2 (M+H).

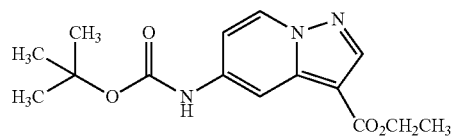

Synthesis of ethyl 5-(tert-butoxycarbonylamino)pyrazolo[1,5-a]pyridine-3-carboxylate: A solution of tert-butyl pyridin-4-ylcarbamate (10 g, 1 equiv.) and O-(2,4-dinitrophenyl)hydroxylamine (11.28 g, 1.1 equiv.) in THF (100 mL) and water (100 mL) were heated at 45° C. in a sealed tube in closed condition for 12 h. The reaction mixture was concentrated under reduced pressure and the crude product dissolved in DMF (200 mL). K₂CO₃ (14.23 g, 2 equiv.) and ethyl propiolate (6.06 g, 1.2 equiv.) were added to the reaction mixture and stirred at room temperature for 24 h. The reaction mixture was concentrated under reduced pressure to remove excess of DMF. The crude material was diluted with water and extracted in ethyl acetate (twice). The combined organic layers were dried over anhydrous sodium sulfate, filtered and concentrated. The crude product was purified by flash column chromatography using silica and EtOAc:pet ether as eluent to obtain ethyl 5-(tert-butoxycarbonylamino)pyrazolo[1,5-a]pyridine-3-carboxylate (7 g, 45% yield). LC/MS: Acquity BEH C18 2.1×50 mm, 1.8µ; Solvent A=0.1% TFA in water; Solvent B=0.1% TFA in ACN; gradient 0-100% B over 2 min; retention time: 0.96 min; LCMS (ES-API), m/z 306.17 (M+H). ¹H NMR 400 MHz, MeOD₄: δ 8.51 (d, J=6.8 Hz, 1H), 8.34 (s, 1H), 8.29 (s, 1H), 7.17 (dd, J=7.2, 2.4 Hz, 1H), 4.37 (q, J=7.2 Hz, 2H), 1.57 (s, 9H), 1.43 (t, J=7.2 Hz, 3H).

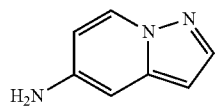

Synthesis of pyrazolo[1,5-a]pyridin-5-amine: Ethyl 5-((tert-butoxycarbonyl)amino)pyrazolo[1,5-a]pyridine-3-carboxylate (4 g, 1 equiv.) was dissolved in 40% H₂SO₄ (40 mL) and heated at reflux for 6 h. The reaction mixture was concentrated and the crude product was basified with saturated sodium hydroxide solution and extracted with ethyl acetate (twice). The organic layer was dried over anhydrous sodium sulfate, filtered and concentrated to afford pyrazolo[1,5-a]pyridin-5-amine (1.3 g, 75% yield). LC/MS: ZORBAX® SB C18, 4.6×50 mm, 5 µm; Solvent A=10% MeOH: 90% H₂O: 0.1% TFA; Solvent B=90% MeOH: 10% H₂O: 0.1% TFA; gradient 0-100% B over 2 min (3 min run time); retention time: 0.27 min; LCMS (ES-API), m/z 134.2 (M+H); ¹H NMR 400 MHz, DMSO-d₆: δ 7.76 (d, J=7.6 Hz, 1H), 7.65 (d, J=2.0 Hz, 1H), 6.41 (m, 1H), 6.31 (dd, J=2.4, 7.6 Hz, 1H), 5.99 (m, 1H), 5.55 (br s, 2H).

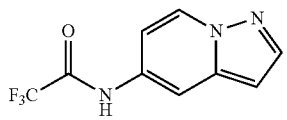 [SMILES: O=C(Nc1ccn2nccc2c1)C(F)(F)F]

Synthesis of 2,2,2-trifluoro-N-(pyrazolo[1,5-a]pyridin-5-yl)acetamide: TFAA (0.636 mL, 1.2 equiv.) was added to a solution of pyrazolo[1,5-a]pyridin-5-amine (0.5 g, 1 equiv.) and TEA (0.680 mL, 1.3 equiv.) in DCM (10 mL) at 0° C. After 1 h, the solvent was removed and the residue was triturated in water, stirred for 5 min and then filtered and dried to afford 2,2,2-trifluoro-N-(pyrazolo[1,5-a]pyridin-5-yl)acetamide as a brown solid (0.42 g, 49% yield). ¹H NMR (400 MHz, DMSO-d₆) δ 11.50 (s, 1H), 8.71 (d, J=7.6 Hz, 1H), 8.15 (d, J=2 Hz, 1H), 8.00 (d, J=2 Hz, 1H), 7.10 (dd, J=2.4, 7.6 Hz, 1H), 6.64 (dd, J=0.4, 2.2 Hz, 1H).

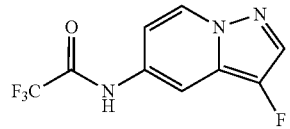 [SMILES: O=C(Nc1ccn2ncc(F)c2c1)C(F)(F)F]

Synthesis of 2,2,2-trifluoro-N-(3-fluoropyrazolo[1,5-a]pyridin-5-yl)acetamide: To a solution of 2,2,2-trifluoro-N-(pyrazolo[1,5-a]pyridin-5-yl)acetamide (0.2 g, 1 equiv.) in acetonitrile (5 mL), 1-Fluoro-4-hydroxy-1,4-diazoniabicyclo[2,2,2]octane-bis (tetrafluoroborate) (0.304 g, 1 equiv.) was added at room temperature and stirred for 16 h. The reaction mixture was concentrated and diluted in EtOAc (25 mL) and washed with saturated NaHCO₃ solution followed by brine. The organic layer was collected, dried over Na₂SO₄, filtered and concentrated. The crude product was purified by silica gel column chromatography with EtOAc: pet. ether (3:7) as eluent to afford 2,2,2-trifluoro-N-(3-fluoropyrazolo[1,5-a]pyridin-5-yl)acetamide as a off-white color solid (0.08 g, 37% yield). ¹H NMR (400 MHz, DMSO-d₆) δ 11.49-11.58 (m, 1H), 8.60-8.72 (m, 1H), 8.12-8.14 (m, 1H), 7.99-8.07 (m, 1H), 7.08-7.12 (m, 1H).

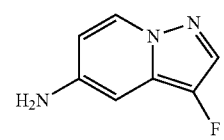

Synthesis of 3-fluoropyrazolo[1,5-a]pyridin-5-amine: A solution of 2,2,2-trifluoro-N-(3-fluoropyrazolo[1,5-a]pyridin-5-yl)acetamide (0.2 g, 0.81 mmol) in methanol (2 mL): water (2 mL), was added K₂CO₃ (0.224 g, 1.62 mmol) and the mixture was stirred at room temperature for 6 h. The mixture was concentrated and the crude product was dissolved in EtOAc (25 mL), washed with saturated sodium NaHCO₃ solution, brine and dried over sodium sulphate and concentrated to afford 3-fluoropyrazolo[1,5-a]pyridin-5-amine as a off-white solid (80 mg, 65% yield). ¹H NMR (400 MHz, DMSO-d₆) δ 8.16-8.28 (m, 1H), 7.65-7.76 (m, 1H), 6.29-6.42 (m, 2H), 5.56-5.75 (m, 2H).

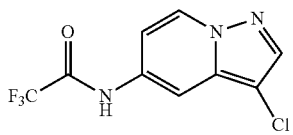 [SMILES: O=C(Nc1ccn2ncc(Cl)c2c1)C(F)(F)F]

Synthesis of N-(3-chloropyrazolo[1,5-a]pyridin-5-yl)-2,2,2-trifluoroacetamide: A solution of 2,2,2-trifluoro-N-(pyrazolo[1,5-a]pyridin-5-yl)acetamide (0.2 g, 0.87 mmol) in acetonitrile (5 mL) was added NCS (0.117 g, 0.87 mmol) and stirred at RT for 6 hrs. The reaction mixture was concentrated and the crude product was dissolved in EtOAc (25 mL), washed with saturated sodium NaHCO₃ solution, brine and dried over sodium sulphate and concentrated to afford N-(3-chloropyrazolo[1,5-a]pyridin-5-yl)-2,2,2-trifluoroacetamide (0.18 g, 78% yield) as a brown solid. LCMS 263.1 (M+).

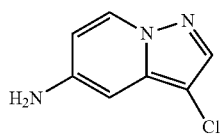 [SMILES: Nc1ccn2ncc(Cl)c2c1]

Synthesis of 3-chloropyrazolo[1,5-a]pyridin-5-amine: A solution of N-(3-chloropyrazolo[1,5-a]pyridin-5-yl)-2,2,2-trifluoroacetamide (0.2 g, 0.76 mmol) in methanol (4 mL) and water (4 mL) was added $K_2CO_3$ (0.210 g, 1.52 mmol) and the mixture was stirred at RT for 16 h. The reaction mixture was concentrated and the crude product was dissolved in EtOAc (25 mL), washed with saturated sodium $NaHCO_3$ solution, brine and dried over sodium sulphate and concentrated to afford 3-chloropyrazolo[1,5-a]pyridin-5-amine (0.1 g, 71% yield) as a brown solid. $^1$H NMR (400 MHz, DMSO-$d_6$) δ 5.92 (s, 2H), 6.31 (dd, J=0.40, 2.60 Hz, 1H), 6.41 (dd, J=2.00, 7.40 Hz, 1H), 7.78 (s, 1H), 8.29 (d, J=7.60 Hz, 1H).

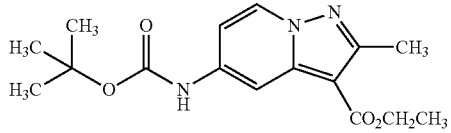

Ethyl 5-((tert-butoxycarbonyl)amino)-2-methylpyrazolo[1,5-a]pyridine-3-carboxylate was prepared in an identical fashion as ethyl 5-((tert-butoxycarbonyl)amino)pyrazolo[1,5-a]pyridine-3-carboxylate by substituting ethyl butanoate instead of ethyl propiolate as one of the starting materials. $^1$H NMR (400 MHz, DMSO-$d_6$) δ 9.97 (s, 1H), 8.59 (dd, J=0.4, 7.6 Hz, 1H), 8.28 (d, J=2.4 Hz, 1H), 7.09 (dd, J=2.4, 7.2 Hz, 1H), 4.26 (q, J=7.2 Hz, 2H), 1.52 (s, 9H), 1.34-1.39 (m, 3H).

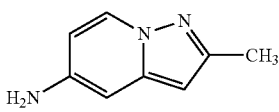

Synthesis of 2-methylpyrazolo[1,5-a]pyridin-5-amine: Ethyl 5-((tert-butoxycarbonyl)amino)-2-methylpyrazolo[1,5-a]pyridine-3-carboxylate (1 g, 3.13 mmol) was taken in 40% $H_2SO_4$ (40 ml, 750 mmol) and heated to reflux for 6 h. The reaction was concentrated and basified with saturated sodium hydroxide solution and extracted with ethyl acetate (3×25 mL). The organic layer was dried over sodium sulphate and evaporated to afford 2-methylpyrazolo[1,5-a]pyridin-5-amine (0.28 g, 61% yield) as a brown solid. $^1$H NMR (400 MHz, DMSO-$d_6$) δ 8.13 (d, J=7.2 Hz, 1H), 6.30 (d, J=1.6 Hz, 1H), 6.22 (dd, J=2.4, 7.60 Hz, 1H), 5.78 (s, 1H), 5.49 (s, 2H), 2.23 (s, 3H).

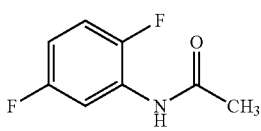

Synthesis of N-(2,5-difluorophenyl)acetamide: A solution of 2,5-difluoroaniline (3.5 g, 1 equiv.) in DCM (30 mL) at 0° C. was added pyridine (3.3 mL, 1.5 equiv.). The reaction mixture was stirred for 5 min and added acetyl chloride (2.9 mL, 1.5 equiv.) and stirred for 1 h. After completion of 1 h the reaction was quenched with 1.5 N HCl. The product was extracted into DCM (twice). The organic layers were collected, dried over anhydrous sodium sulfate, filtered and concentrated. The material obtained was washed with diethyl ether and dried to afford N-(2,5-difluorophenyl)acetamide. LC/MS: Acquity BEH C18 2.1×50 mm, 1.8µ; Solvent A=0.1% TFA in water; Solvent B=0.1% TFA in ACN; gradient 0-100% B over 2 min; retention time: 0.68 min; LCMS (ES-API), m/z 172.6 (M+H).

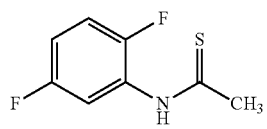

Synthesis of N-(2,5-difluorophenyl)ethanethioamide: A solution of N-(2,5-difluorophenyl)acetamide (2.6 g, 1 equiv.) in benzene (15 mL) was added $P_2S_5$ (6.7 g, 1 equiv.) and heated at 85° C. for 2 h. The reaction mixture was cooled to room temperature and diluted with ethyl acetate. The reaction mixture was quenched with 10% NaOH solution. The organic layer was collected, dried over anhydrous sodium sulfate, filtered and concentrated. The crude material obtained was purified by flash column chromatography using silica gel and EtOAc:pet ether as eluent to afford N-(2,5-difluorophenyl)ethanethioamide. GCMS: 187 (M); Retention time: 7.065 min.

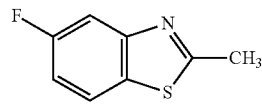

Synthesis of 5-fluoro-2-methylbenzo[d]thiazole: A stirred solution of N-(2,5-difluorophenyl)ethanethioamide (0.5 g, 1 equiv.) in xylene (10 mL) was added cesium carbonate (1.74 g, 2 equiv.) and heated at 150° C. for 24 h. The reaction mixture was cooled to room temperature and quenched with water. The product was extracted into ethyl acetate, dried over anhydrous sodium sulfate, filtered and concentrated. The crude material obtained was purified by flash column chromatography using silica gel and EtOAc:pet ether as eluent to afford 5-fluoro-2-methylbenzo[d]thiazole. GCMS: 167 (M); Retention time: 6.181 min.

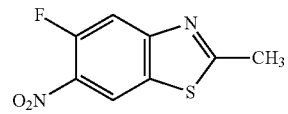

Synthesis of 5-fluoro-2-methyl-6-nitrobenzo[d]thiazole: 5-Fluoro-2-methylbenzo[d]thiazole (0.1 g, 1 equiv.) was taken in $H_2SO_4$ (5 mL) and cooled to 0° C. To the reaction mixture $KNO_3$ (0.12 g, 2 equiv.) was added and stirred for 4 h. The reaction was quenched with 10% NaOH solution and extracted in ethyl acetate. The organic layer was dried over anhydrous sodium sulfate, filtered and concentrated to afford 5-fluoro-2-methyl-6-nitrobenzo[d]thiazole. GCMS: 212 (M); Retention time: 8.4 min.

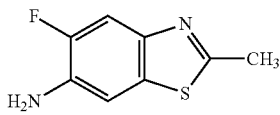

Synthesis of 5-fluoro-2-methylbenzo[d]thiazol-6-amine: A solution of 5-fluoro-2-methyl-6-nitrobenzo[d]thiazole (0.2 g, 1 equiv.) in 80% EtOH (10 mL), was added conc. HCl (0.5 mL) followed by iron powder (0.23 g, 4.5 equiv.). The reaction mixture was heated at 90° C. for 30 min. The reaction mixture was diluted with ethanol and cooled to room temperature. The reaction mixture was filtered through a bed of CELITE®. The filtrate was concentrated and residue obtained was partitioned between ethyl acetate and 10% $Na_2CO_3$. The product was extracted into ethyl acetate, dried over anhydrous sodium sulfate, filtered and concentrated. The crude material contained the desired product along with its other isomer (positional isomer). The crude material was purified by flash column chromatography using silica gel and EtOAc:pet ether as eluent to afford the desired compound. $^1$H NMR (400 MHz, DMSO-$d_6$): δ 7.54 (d, J=12.00 Hz, 1H), 7.22 (d, J=8.40 Hz, 1H), 5.33 (s, 2H), 2.68 (s, 3H).

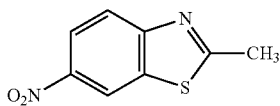

Synthesis of 2-methyl-6-nitrobenzo[d]thiazole: To 2-methylbenzo[d]thiazole (2 g, 1 equiv.) $H_2SO_4$ was added at 0° C. and stirred for 5 min. To the reaction mixture nitrating agent ($HNO_3$:$H_2SO_4$:2:1) was added and vigorously stirred for 15 min. Slowly then reaction was allowed to warm to ambient temperature and stirred for 1 h. The reaction mixture was quenched by pouring into ice cold water. The compound precipitated out, filtered and dried under vacuum to provide 2-methyl-6-nitrobenzo[d]thiazole. $^1$H NMR (400 MHz, CDCl$_3$): δ 8.78 (d, J=2.4 Hz, 1H), 8.34 (dd, J=2.0, 9.0 Hz, 1H), 8.04 (d, J=8.8 Hz, 1H), 2.92 (s, 3H).

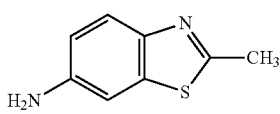

Synthesis of 2-methylbenzo[d]thiazol-6-amine: A solution of 2-methyl-6-nitrobenzo[d]thiazole (1 g, 5.15 mmol) in EtOH/water (8:1, 45 mL) was added iron (0.86 g, 15.5 mmol) and HCl (0.47 mL). The mixture was heated at reflux for 2 h, cooled and filtered through CELITE®. EtOH was removed in vacuo and the mixture was partitioned between water and EtOAc. The layers were separated and the organic layer was washed with 10% $NaHCO_3$. The organic layer was dried ($Na_2SO_4$), filtered and concentrated. The product was isolated via column chromatography (5% MeOH/CHCl$_3$) to afford 2-methylbenzo[d]thiazol-6-amine (0.8 g, 95% yield). LCMS 165.3 (M+H).

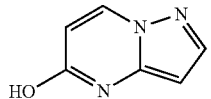

Synthesis of pyrazolo[1,5-a]pyrimidin-5-ol: 1H-Pyrazol-5-amine (80 g, 963 mmol) was added to a 1 L multineck RBF fitted with reflux condenser and $N_2$ outlet with mechanical stirring. DMF (1 L) and ethyl 3-ethoxyacrylate (153 g, 1059 mmol) was added followed by cesium carbonate (471 g, 1444 mmol) and the mixture heated at 110° C. for 18-24 h with stirring. The mixture was concentrated to remove DMF and then added water (200 mL). The mixture was extracted with EtOAc (700 ml×3), and CHCl$_3$ (500 mL×2). The combined organic layers were dried over $Na_2SO_4$, filtered and evaporated to give crude desired product, which was triturated with EtOAc (3 volumes) and filtered to obtain pyrazolo[1,5-a]pyrimidin-5-ol (60 g, 46% yield) as yellow solid. LCMS m/z 136.2 (M+H); $^1$H NMR (400 MHz, DMSO-$d_6$): δ 12.08 (s, 1H), 8.47 (dd, J=8.0, 0.8 Hz, 1H), 7.75 (d, J=2.0 Hz, 1H), 5.94 (d, J=8.0 Hz, 1H), 5.81 (dd, J=2.0, 0.8 Hz, 1H).

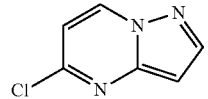

Synthesis of 5-chloropyrazolo[1,5-a]pyrimidine: A mixture of pyrazolo[1,5-a]pyrimidin-5-ol (60 g, 444 mmol) in acetonitrile (180 mL) in a 1 L single neck RBF fitted with reflux condenser under magnetic stirring with $N_2$ outlet was added POCl$_3$ (112 mL, 1202 mmol) and then heated at 80° C. for 3 h. The mixture was quenched into an ice cold solution of saturated NaHCO$_3$ slowly until pH=7-8 and then extracted in EtOAC (700 mL). The organic layer was separated and then washed with NaHCO$_3$ solution, followed by brine. The organic layer obtained was washed with 10% NaHCO$_3$ solution (150 mL) dried over Na$_2$SO$_4$, filtered and evaporated to give 5-chloropyrazolo[1,5-a]pyrimidine (65 g, 95% yield) as yellow solid. LCMS m/z 154.0 (M+H); $^1$H NMR (400 MHz, DMSO-$d_6$): δ 9.18 (dd, J=7.2, 0.8 Hz, 1H), 8.29 (d, J=2.4 Hz, 1H), 7.13 (d, J=7.2 Hz, 1H), 6.73 (dd, J=2.4, 0.8 Hz, 1H).

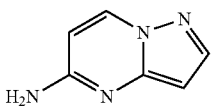

Synthesis of pyrazolo[1,5-a]pyrimidin-5-amine: 5-Chloropyrazolo[1,5-a]pyrimidine (65 g, 423 mmol) in a 1 L autoclave was added aqueous NH$_4$OH and then heated at 100° C. for 18-24 h. The cooled reaction mixture was filtered and then extracted in EtOAC (250 mL×4). The organic layer was dried over Na$_2$SO$_4$ and then filtered and concentrated to give pyrazolo[1,5-a]pyrimidin-5-amine (50 g, 88% yield) as yellow solid. LCMS m/z 135.2 (M+H); $^1$H NMR (400 MHz, DMSO-$d_6$): δ 8.46 (d, J=7.6 Hz, 1H), 7.76 (d, J=2.0 Hz, 1H), 6.75 (s, 2H), 6.20 (d, J=7.6 Hz, 1H), 5.87 (s, 1H).

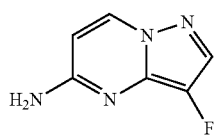 [SMILES: Nc1ccn2ncc(F)c2n1]

Synthesis of 3-fluoropyrazolo[1,5-a]pyrimidin-5-amine: To a stirred suspension of pyrazolo[1,5-a]pyrimidin-5-amine (0.3 g, 2.24 mmol) in THF (15 mL) was added 1-fluoro-4-hydroxy-1,4-diazoniabicyclo[2,2,2]octane-bis tetrafluoroborate (1.17 g, 3.35 mmol) and the reaction was allowed to stir for 16 h. The mixture was concentrated to obtain an off-white solid and the crude product which was purified by preparative TLC (100% EtOAc) to afford 3-fluoropyrazolo[1,5-a]pyrimidin-5-amine as a white solid (70 mg, 20% yield). LCMS m/z 153.0 (M+H)'; $^1$H NMR (400 MHz, DMSO-d$_6$) δ 8.39 (dd, J=1.60, 7.60 Hz, 1H), 7.89 (d, J=3.60 Hz, 1H), 6.99 (bs, 2H), 6.22 (d, J=7.60 Hz, 1H).

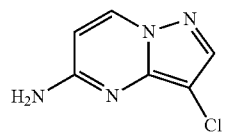 [SMILES: Nc1ccn2ncc(Cl)c2n1]

Synthesis of 3-chloropyrazolo[1,5-a]pyrimidin-5-amine: To a stirred solution of pyrazolo[1,5-a]pyrimidin-5-amine (200 mg, 1.5 mmol) in THF (10 mL) at −78° C. was added NCS (200 mg, 1.5 mmol) and the reaction was allowed to warm to rt and stir for 16 h. The reaction was concentrated, added water and the solid precipitate was filtered and dried to afford 3-chloropyrazolo[1,5-a]pyrimidin-5-amine (140 mg, 54% yield). LCMS m/z 169.0 (M+H)$^+$; $^1$H NMR (400 MHz, DMSO-d$_6$) δ 8.48 (d, J=7.20 Hz, 1H), 7.16 (bs, 2H), 7.89 (s, 1H), 6.27 (d, J=7.20 Hz, 1H).

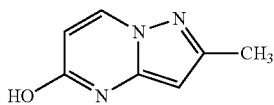

Synthesis of 2-methylpyrazolo[1,5-a]pyrimidin-5-ol: To a stirred solution of 3-methyl-1H-pyrazol-5-amine (5.0 g, 51.5 mmol) in DMF (50 mL) was added Cs$_2$CO$_3$ (33.5 g, 103 mmol) and (E)-ethyl 3-ethoxyacrylate (8.91 g, 61.8 mmol). The mixture wad heated at 110° C. for 16 h. The mixture was cooled to rt, added acetic acid (50 mL) and stirred for 30 min at rt. The crude solid was partitioned between water and EtOAc. The organic layer was washed with brine, dried over Na$_2$SO$_4$, and concentrated. The solids were treated with EtOAc to obtain 2-methylpyrazolo[1,5-a]pyrimidin-5-ol (2.5 g, 30% yield) as a pale yellow solid. LCMS m/z 148.2 (M−H); $^1$H NMR (400 MHz, DMSO-d$_6$) δ 11.92 (bs, 1H), 8.33 (d, J=8.00 Hz, 1H), 5.82 (d, J=7.60 Hz, 1H), 5.64 (s, 1H), 2.21 (s, 3H).

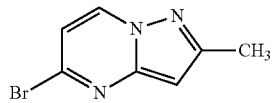

Synthesis of 5-bromo-2-methylpyrazolo[1,5-a]pyrimidine: 2-Methylpyrazolo[1,5-a]pyrimidin-5-ol (2.0 g, 13.4 mmol) was in DCE (40 mL) was added POBr$_3$ (11.53 g, 40.2 mmol) at rt and then heated to 100° C. for 5 h. The reaction mixture was cooled to rt, concentrated and quenched into ice water. The mixture was basified with Na$_2$CO$_3$, extracted with EtOAc, and the combined organic layers were washed with brine. The organic layer was dried over Na$_2$SO$_4$, filtered and concentrated to obtain crude product as yellow color solid. The material was purified via column chromatography (20% EtOAc:pet ether) to afford 5-bromo-2-methylpyrazolo[1,5-a]pyrimidine (1.6 g, 51% yield) as pale yellow solid. LCMS m/z 212.2 (M+H)$^+$; $^1$H NMR (400 MHz, CDCl$_3$) δ 8.45 (dd, J=0.40, 7.00 Hz, 1H), 6.70 (d, J=7.20 Hz, 1H), 6.40 (s, 1H), 2.50 (s, 3H).

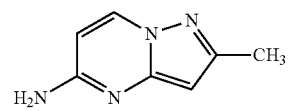

Synthesis of 2-methylpyrazolo[1,5-a]pyrimidin-5-amine: 5-Chloro-2-methylpyrazolo[1,5-a]pyrimidine (1.6 g, 7.55 mmol) was heated in methanolic ammonia (32 ml, 224 mmol) and at 100° C. for 16 h. The reaction was concentrated and the product purified via column chromatography (5% MeOH:CHCl$_3$) to afford 2-methylpyrazolo[1,5-a]pyrimidin-5-amine (1.0 g, 83% yield). LCMS m/z 149.2 (M+H)$^+$; $^1$H NMR (400 MHz, DMSO-d$_6$) δ 8.33 (d, J=7.60 Hz, 1H), 6.65 (bs, 2H), 6.10 (d, J=7.20 Hz, 1H), 5.68 (s, 1H), 2.23 (s, 3H).

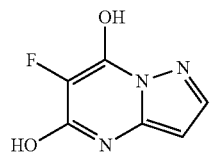 [SMILES: Oc1nc2ccnn2c(O)c1F]

Step 1: Synthesis of 6-fluoropyrazolo[1,5-a]pyrimidine-5,7-diol: To a stirred solution of 1H-pyrazol-5-amine (1 g, 12 mmol) in EtOH (10 mL) was added diethyl 2-fluoromalonate (3.22 g, 18 mmol) and sodium ethoxide (7.8 g, 24 mmol, 9 mL of a 21% solution). The mixture was heated at reflux for 18 h. The mixture was cooled to rt and concentrated. Water was added and the pH adjusted to 3. The resulting precipitate was filtered and dried to afford 6-fluoropyrazolo[1,5-a]pyrimidine-5,7-diol (0.8 g, 39% yield) as a white solid. LCMS m/z 168.2 (M−).

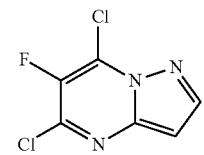 [SMILES: Fc1c(Cl)nc2ccnn2c1Cl]

Step 2 [see previous]: 6-Fluoropyrazolo[1,5-a]pyrimidine-5,7-diol (1 g, 5.91 mmol) was added POCl$_3$ (2.76 ml, 29.6 mmol) and heated at reflux for 16 hours. The reaction mixture was concentrated and the crude was dissolved in NaHCO$_3$ solution and extracted with ethyl acetate. The organic layer was separated, dried over Na$_2$SO$_4$, and concentrated. The crude was purified by column chromatography (20% EtOAc:hexane) to afford 5,7-dichloro-6-fluoropyrazolo[1,5-a]pyrimidine (0.35 g, 36% yield) as a white solid. LCMS m/z 206.0 (M+); ¹H NMR (400 MHz, CDCl₃) δ 8.23 (d, J=2.4 Hz, 1H), 6.79 (d, J=2.4 Hz, 1H).

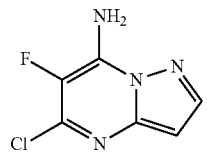 [SMILES: Nc1c(F)c(Cl)nc2ccnn12]

Step 3: 5,7-Dichloro-6-fluoropyrazolo[1,5-a]pyrimidine (0.8 g, 3.88 mmol) in a sealed tube was added NH₄OH (5 mL, 128 mmol) and stirred for 12 h at 80° C. The mixture was cooled to rt, concentrated and the crude product, 5-chloro-6-fluoropyrazolo[1,5-a]pyrimidin-7-amine (0.7 g, 97% yield) was used without further purification. LCMS m/z 187.1 (M+H); ¹H NMR (400 MHz, DMSO-d₆) δ 8.17 (d, J=2.4 Hz, 1H), 7.14 (br s, 2H), 6.44 (d, J=2.4 Hz, 1H).

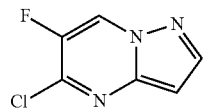

Step 4: To a solution of 5-chloro-6-fluoropyrazolo[1,5-a]pyrimidin-7-amine (0.7 g, 3.75 mmol) in dioxane (10 mL), was added isoamyl nitrite (1.01 mL, 7.50 mmol) and refluxed at 110° C. for 2 hours. The reaction mixture was concentrated and the crude material was washed with water. The organic layer was separated, dried over Na₂SO₄ and concentrated. The product was isolated by column chromatography (EtOAc:Pet ether, 22%) to afford 5-chloro-6-fluoropyrazolo[1,5-a]pyrimidine (0.6 g, 93%) as an off-white solid.

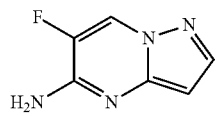

Step 5: A solution of 5-chloro-6-fluoropyrazolo[1,5-a]pyrimidine (0.6 g, 3.50 mmol) in MeOH (10 mL) in a sealed tube was purged with ammonia gas for 5 minutes at −20° C. The vessel was sealed and heated at 75° C. for 3 h. The mixture was concentrated and the crude product 6-fluoropyrazolo[1,5-a]pyrimidin-5-amine (0.5 g, 94% yield) was used directly in subsequent transformations. LCMS m/z 152.5 (M+). (M+H); ¹H NMR (400 MHz, DMSO-d₆) δ 8.98 (dd, J=0.8, 8.4 Hz, 1H), 7.81 (d, J=2.8 Hz, 1H), 7.20 (br s, 2H), 5.97 (dd, J=1.2, 3.2 Hz, 1H).

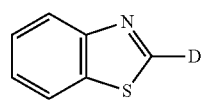

Synthesis of 2-deuterobenzothiazole: A stirred solution of benzo[d]thiazole (1.5 g, 11.10 mmol) in THF (20 mL) was cooled to −78° C. and n-BuLi (1.78 g, 27.7 mmol) was added dropwise. Just before the addition had been completed, the anion solution gave rise to clear and orange colored solution. At this point reaction mixture was added D₂O and stirred for additional half an hour. The reaction mixture was quenched by NH₄Cl solution and extracted with DCM (50 mL×3). The combined organic layers were dried over Na₂SO₄ and evaporated to get the crude compound which was purified via column chromatography using EtOAc and hexanes (2:3) to afford 2-deuterobenzothiazole (1.14 g, 75% yield). ¹H NMR (400 MHz, DMSO-d₆) δ 8.09-8.19 (m, 2H), 7.46-7.58 (m, 2H).

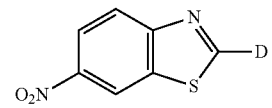

Synthesis of 2-deutero-6-nitrobenzothiazole: To a mixture of HNO₃ (0.82 mL, 18.36 mmol) and H₂SO₄ (0.98 mL, 18.36 mmol) was added 2-deuterobenzothiazole (0.50 g, 3.67 mmol) over a period of 1 h at −25° C. Resulting solution was stirred for 12 h and was poured into ice water to produce a yellow precipitate which was filtered and used without further purification. ¹H NMR (400 MHz, DMSO-d₆) δ 9.26 (d, J=2.40 Hz, 1H), 8.36-8.39 (m, 1H), 8.28-8.31 (m, 1H).

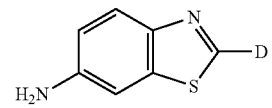 [SMILES: [2H]c1nc2ccc([N+](=O)[O-])cc2s1]

Synthesis of 2-deutero-6-aminobenzothiazole: To a mixture of 2-deutero-6-nitrobenzothiazole (0.300 g, 1.656 mmol) and concentrated HCl (0.075 mL, 2.484 mmol) in ethanol (20.00 mL) was added iron powder (0.370 g, 6.62 mmol). The reaction was stirred for 1 h at reflux and then cooled to room temperature. The precipitate of iron oxides and hydroxy salts were removed by filtration. The solvent was removed and the resulting solid was extracted into a heterogeneous mixture of EtOAc (50 mL×2) and 10% aqueous solution of Na₂CO₃ (50 mL). The EtOAc extract was dried and solvent was removed under vacuum. The crude material was purified by combiflash using EtOAc and hexane (2:3) system to afford 2-deutero-6-aminobenzothiazole (110 mg, 97% yield). LCMS m/z 152.2 (M+H).

Synthesis of 6-bromo-4-fluorobenzo[d]thiazol-2-amine: To a stirred solution of 4-bromo-2-fluoroaniline (2 g, 10.53 mmol) in acetic acid (20 mL) at rt was added potassium thiocyanate (4.09 g, 42.1 mmol) then Br₂ (1.085 mL, 21.05 mmol) in 5 mL acetic acid dropwise. The mixture was stirred for 2 h then concentrated to dryness. NaHCO₃ solution was added and the product was extracted into EtOAc. The organic layer was dried over Na₂SO₄, filtered, and concentrated to afford 6-bromo-4-fluorobenzo[d]thiazol-2-amine

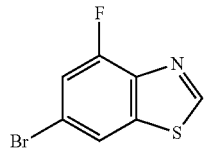

Synthesis of 6-bromo-4-fluorobenzo[d]thiazole: To a stirred solution of 6-bromo-4-fluorobenzo[d]thiazol-2-amine (2 g, 8.09 mmol) in DMF (20 mL) at rt was added isoamyl nitrite (3.27 mL, 24.28 mmol). The mixture was heated at 80° C. for 1 h. The reaction was monitored by LC/MS. After the complete consumption of starting material the reaction mixture was concentrated under reduced pressure to give the crude product. The crude material was purified by combiflash using silica gel and EtOAc:pet. ether (2:8) system to afford 6-bromo-4-fluorobenzo[d]thiazole (0.8 g, 42% yield). $^1$H NMR (400 MHz, CDCl$_3$) δ 8.97 (d, J=0.4 Hz, 1H), 7.90 (dd, J=1.6, 0.8 Hz, 1H), 7.40 (dd, J=2.0, 9.6 Hz, 1H).

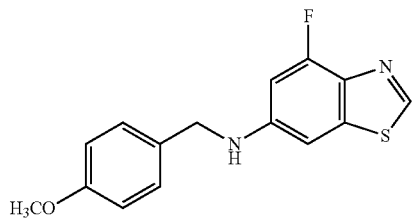 [SMILES: COc1ccc(CNc2cc(F)c3ncsc3c2)cc1]

Synthesis of 4-fluoro-N-(4-methoxybenzyl)benzo[d]thiazol-6-amine: A stirred solution of 6-bromo-4-fluorobenzo[d]thiazole (200 mg, 0.862 mmol), 4-methoxybenzylamine (0.169 mL, 1.29 mmol), Xantphos (249 mg, 0.431 mmol) and Cs$_2$CO$_3$ (562 mg, 1.724 mmol) in 1,4-dioxane (16 mL) was degassed with N$_2$ for 5 mins then added Pd$_2$(dba)$_3$ (197 mg, 0.215 mmol). The mixture was further degassed with N$_2$ for 5 mins, sealed and heated at 110° C. for 12 hours. The mixture was cooled to rt, filtered, and concentrated. The crude compound was purified by column chromatography (10% EA:pet ether) to afford 4-fluoro-N-(4-methoxybenzyl)benzo[d]thiazol-6-amine (200 mg, 80% yield). LCMS m/z 289.1 (M+H).

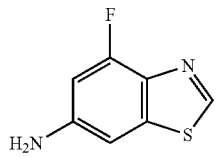

Synthesis of 4-fluorobenzo[d]thiazol-6-amine: A mixture of 4-fluoro-N-(4-methoxybenzyl)benzo[d]thiazol-6-amine (200 mg, 0.694 mmol) and TFA (8 mL) was stirred at 25° C. for 1 hour. The mixture was concentrated and partitioned between EtOAc and water. The separated organic layer was dried over Na$_2$SO$_4$, filtered, and concentrated to get the crude compound was purified by column chromatography (15% EA:pet ether) to afford 4-fluorobenzo[d]thiazol-6-amine (100 mg, 74% yield). LCMS m/z 168.9 (M+).

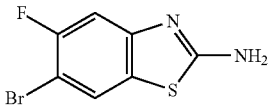 [SMILES: Nc1nc2cc(F)c(Br)cc2s1]

Synthesis of 6-bromo-5-fluorobenzo[d]thiazol-2-amine: To a stirred solution of 4-bromo-3-fluoroaniline (2 g, 10.53 mmol) in acetic acid (20 mL) was added potassium thiocyanate (4.09 g, 42.1 mmol) at rt followed by Br$_2$ (0.542 mL, 10.53 mmol) in 5 ml acetic acid dropwise. The reaction was stirred for 2 h then concentrated to dryness. NaHCO$_3$ solution was added and the product was extracted with EtOAc. The organic layer was dried over Na$_2$SO$_4$, filtered, and concentrated to afford 6-bromo-5-fluorobenzo[d]thiazol-2-amine (2 g, 77% yield) which was used without further purification.

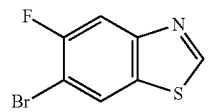

Synthesis of 6-bromo-5-fluorobenzo[d]thiazole: To a stirred solution of 6-bromo-5-fluorobenzo[d]thiazol-2-amine (2 g, 8.09 mmol) in 1,4-dioxane (100 mL) was added isoamyl nitrite (3.27 mL, 24.28 mmol) at rt. The mixture was then heated at 110° C. for 3 h. The reaction was monitored by LC/MS. After the complete consumption of starting material the reaction mixture was concentrated under reduced pressure to give the crude product. The crude material was purified by combiflash using silica gel and EtOAc:pet. ether (2:8) system. To afford 6-bromo-5-fluorobenzo[d]thiazole (1 g, 53% yield). $^1$H NMR (400 MHz, CDCl$_3$) δ 9.04 (s, 1H), 8.15 (d, J=6.40 Hz, 1H), 7.88 (d, J=8.80 Hz, 1H).

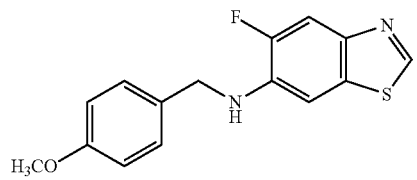 [SMILES: COc1ccc(CNc2cc3scnc3cc2F)cc1]

Synthesis of 5-fluoro-N-(4-methoxybenzyl)benzo[d]thiazol-6-amine: A stirred solution of 6-bromo-5-fluorobenzo[d]thiazole (1 g, 4.31 mmol), 4-methoxybenzylamine (0.676 mL, 5.17 mmol), Xantphos (1.247 g, 2.154 mmol) and Cs$_2$CO$_3$ (2.81 g, 8.6 mmol) in 1,4-dioxane (100 mL) was degassed with N$_2$ for 5 mins then added Pd$_2$(dba)$_3$ (0.99 g, 1.08 mmol). The mixture was further degassed with N$_2$ for 5 mins then sealed and heated at 110° C. for 12 hours. After cooling to rt, the mixture was filtered and concentrated. The crude compound was purified by column chromatography (10% EA:pet ether) to afford 5-fluoro-N-(4-methoxybenzyl)benzo[d]thiazol-6-amine (0.8 g, 64% yield). LCMS m/z 289.1 (M+H).

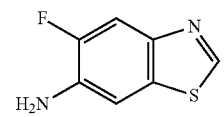

Synthesis of 5-fluorobenzo[d]thiazol-6-amine: 5-Fluoro-N-(4-methoxybenzyl)benzo[d]thiazol-6-amine (0.8 g, 2.77 mmol) in TFA (10 mL) was stirred for 1 h at rt. The mixture was concentrated to dryness, and extracted between EtOAc and water. The organic layer was dried over $Na_2SO_4$, filtered, and concentrated. The crude compound was purified by column chromatography (15% EA:pet ether) to afford 5-fluorobenzo[d]thiazol-6-amine (0.25 g, 52% yield). LCMS m/z 169.5 (M+H).

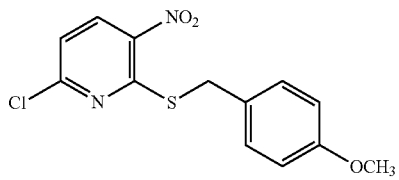

Synthesis of 6-chloro-2-((4-methoxybenzyl)thio)-3-nitropyridine: 2,6-Dichloro-3-nitropyridine (0.1 g, 1 equiv.) and 4-methoxybenzenethiol (0.080 g, 1.1 equiv.) were taken in THF (2 mL) and cooled to 0° C. Sodium hydride (0.025 g, 1.2 equiv.) was added in portions to the reaction mixture and stirred for 3 h at 0° C. The reaction mixture was concentrated to remove excess THF. Diluted the reaction mixture with EtOAc and washed with water. The organic layer was collected, dried over $Na_2SO_4$, filtered and concentrated to get 6-chloro-2-((4-methoxybenzyl)thio)-3-nitropyridine as yellow solid (0.12 g, 74.5% yield). $^1$H NMR (400 MHz, $CDCl_3$) δ 8.41 (d, J=8.4 Hz, 1H), 7.34-7.47 (m, 2H), 7.16 (d, J=14.0 Hz, 1H), 6.84-6.87 (m, 3H), 4.38 (s, 2H), 3.80 (s, 3H).

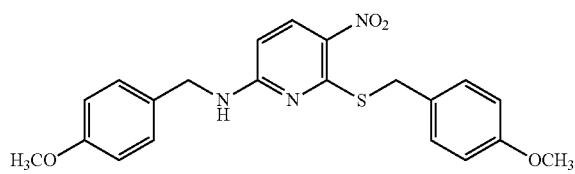 [SMILES: COc1ccc(CNc2ccc([N+](=O)[O-])c(SCc3ccc(OC)cc3)n2)cc1]

Synthesis of N-(4-methoxybenzyl)-6-((4-methoxybenzyl)thio)-5-nitropyridin-2-amine: 6-chloro-2-((4-methoxybenzyl)thio)-3-nitropyridine (0.5 g, 1 equiv.) and (4-methoxyphenyl)methanamine (2.207 g, 10 equiv.) were taken in a pressure tube and heated to 120° C. in a closed condition for 30 min. After 30 min the reaction mixture was cooled to ambient temperature and added water and filtered. The yellow solid obtained was washed with water and pet ether, dried under vacuum. The crude product was purified by combiflash using silica gel and ethyl acetate: pet ether (3:7) system to afford N-(4-methoxybenzyl)-6-((4-methoxybenzyl)thio)-5-nitropyridin-2-amine as yellow solid (0.5 g, 76% yield). LC/MS: Acquity BEH C18 2.1×50 mm, 1.8µ; Solvent A=0.1% TFA in water; Solvent B=0.1% TFA in ACN; gradient 0-100% B over 2 min; retention time: 1.17 min; LCMS (ES-API), m/z 412.2 (M+H).

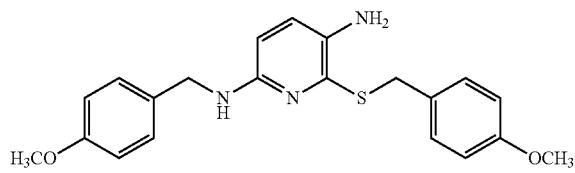

Synthesis of N2-(4-methoxybenzyl)-6-((4-methoxybenzyl)thio)pyridine-2,5-diamine: To a solution of N-(4-methoxybenzyl)-6-((4-methoxybenzyl)thio)-5-nitropyridin-2-amine (0.5 g, 1.215 mmol) in MeOH (5 mL), ammonium chloride (0.650 g, 10 equiv.) and zinc (0.397 g, 5 equiv.) were added sequentially and stirred at ambient temperature for 1 h. The reaction mixture was filtered through a bed of CELITE® and washed with methanol. The filtrate obtained was concentrated, diluted with EtOAc and washed with water. The aqueous layer was extracted with ethyl acetate (twice). Collected the organic layers together, dried over $Na_2SO_4$, filtered and concentrated to get crude material. The crude product was purified by combiflash using silica gel and ethyl acetate: pet ether (3:7) system to afford N2-(4-methoxybenzyl)-6-((4-methoxybenzyl)thio)pyridine-2,5-diamine (0.25 g, 54% yield). LC/MS: Acquity BEH C18 2.1×50 mm, 1.8µ; Solvent A=0.1% TFA in water; Solvent B=0.1% TFA in ACN; gradient 0-100% B over 2 min; retention time: 0.88 min; LCMS (ES-API), m/z 382.2 (M+H).

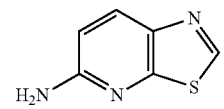

Synthesis of thiazolo[5,4-b]pyridin-5-amine: A solution of N2-(4-methoxybenzyl)-6-((4-methoxybenzyl)thio)pyridine-2,5-diamine (0.3 g, 0.786 mmol) in formic acid (2 mL) was heated to 90° C. for 1 h. Then added TFA (2 mL) and heated again for 1 h. TFA was removed under reduced pressure and purified by combiflash using silica gel and MeOH: $CHCl_3$ (3%) system to afford thiazolo[5,4-b]pyridin-5-amine as dark solid (0.1 g, 84% yield). LC/MS: Acquity BEH C18 2.1×50 mm, 1.8µ; Solvent A=0.1% TFA in water; Solvent B=0.1% TFA in ACN; gradient 0-100% B over 2 min; retention time: 0.52 min; LCMS (ES-API), m/z 152.14 (M+H).

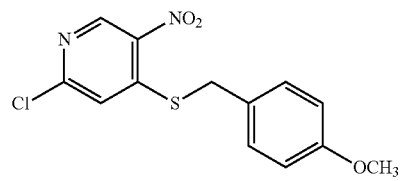

Synthesis of 2-chloro-4-((4-methoxybenzyl)thio)-5-nitropyridine: A suspension of sodium hydride (3.11 g, 78 mmol) in THF (20 mL) under nitrogen was cooled to −40° C. A solution of 2,4-dichloro-5-nitropyridine (15 g, 78 mmol) and (4-methoxyphenyl)methanethiol (12 g, 78 mmol) in THF (50 mL) was added dropwise to the NaH suspension. It was allowed to stir at −40° C. for 10 minutes then at rt. After completion of the reaction, the mixture was quenched into ice and extracted with ethyl acetate (3×). The combined organic layer was washed with brine, dried over sodium sulphate, and concentrated to residue. The residue was purified by flash column chromatography (8-10% EtOAc/pet ether) to afford 2-chloro-4-((4-methoxybenzyl)thio)-5-nitropyridine (15 g, 61% yield). LCMS m/z 311.2 (M+H); $^1$H NMR (400 MHz, $CDCl_3$) δ 9.14 (s, 1H), 7.26-7.38 (m, 3H), 6.90-6.93 (m, 2H), 4.18 (s, 2H), 3.82 (s, 3H).

Synthesis of N-(4-methoxybenzyl)-4-(4-methoxybenzyl)thio)-5-nitropyridin-2-amine: A mixture of 2-chloro-4-((4-methoxybenzyl)thio)-5-nitropyridine (5 g, 16.1 mmol) and (4-methoxyphenyl) methanamine (11 g, 80 mmol) was heated at 100° C. for 30 minutes. The completion of the reaction was confirmed by LCMS. After completion of the reaction, water was added to the mixture and allowed to stir until getting a free solid. The solid was filtered to afford N-(4-methoxybenzyl)-4-((4-methoxybenzyl)thio)-5-nitropyridin-2-amine (5 g, 76% yield) as yellow solid. LCMS m/z 412.6 (M+H); $^1$H NMR (400 MHz, DMSO-$d_6$) δ 8.94 (d, J=5.20 Hz, 1H), 8.37 (bs, 1H), 7.24-7.37 (m, 4H), 6.82-6.92 (m, 4H), 4.55 (bs, 2H), 4.11 (s, 2H), 3.71-3.75 (m, 6H).

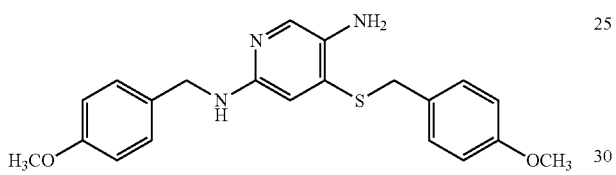

Synthesis of N2-(4-methoxybenzyl)-4-(4-methoxybenzyl)thio)pyridine-2,5-diamine: N-(4-Methoxybenzyl)-4-((4-methoxybenzyl)thio)-5-nitropyridin-2-amine (15 g, 36.5 mmol) in EtOH (150 mL) was added Pd/C (6 g, 56.4 mmol) and was allowed to stir RT under hydrogen for overnight. After completion of the reaction, the reaction was filtered through CELITE® and washed with ethanol (500 mL). It was concentrated under high vacuum to afford N2-(4-methoxybenzyl)-4-(4-methoxybenzyl)thio)pyridine-2,5-diamine (12 g, 86% yield) as brown solid. It was taken to next step without purification.

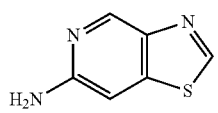

Synthesis of thiazolo[4,5-c]pyridin-6-amine: N2-(4-Methoxybenzyl)-4-((4-methoxybenzyl)thio)pyridine-2,5-diamine (4 g, 9.33 mmol) and formic acid (6 mL, 9.33 mmol) was heated at 90° C. for 1 h under an atmosphere on $N_2$. The completion of the formylation was confirmed by LCMS. After removal of the formic acid, TFA (25 mL) and Silver tetrafluoroborate (800 mg, 4.11 mmol) were added and heated to 80° C. for 5 hours. After completion of the reaction as judged by LCMS, the volatiles were removed and the residue was diluted with water (20 mL). The aqueous layer was washed with MTBE (3×20 mL). The pH of the aqueous layer was adjusted to 8 with saturated solution of sodium bicarbonate and the basic solution was extracted by ethyl acetate (3×20 mL). The combined organic layer was washed with brine and dried over sodium sulphate. It was concentrated and dried under high vacuum to obtain thiazolo[4,5-c]pyridin-6-amine (1 g, 70% yield) as pale brown solid.

$^1$H NMR (400 MHz, DMSO-$d_6$) δ 8.93 (s, 1H), 8.70 (d, J=0.80 Hz, 1H), 7.00 (d, J=0.80 Hz, 1H), 6.08 (s, 1H).

Additional Intermediate Preparations

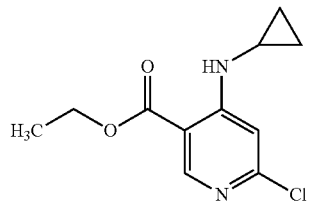 [SMILES: CCOC(=O)c1cnc(Cl)cc1NC1CC1]

To a solution of ethyl 4,6-dichloronicotinate (50 g, 227 mmol) in DMA (500 mL) was added DIPEA (39.7 mL, 227 mmol) and cyclopropyl amine (17.6 mL, 250 mmol). The mixture was then heated at 90° C. for 5 h. The reaction mixture was quenched into crushed ice with stirring. The resulting slurry was stirred and filtered to afford the crude product (42 g, 91% yield) which was used without further purification. LCMS m/z 241.1 (M+H)$^+$. $^1$H NMR (400 MHz, DMSO-$d_6$) δ 8.54 (s, 1H), 8.09 (s, 1H), 7.03 (s, 1H), 4.29 (q, J=7.2 Hz, 2H), 2.61 (m, 1H), 1.31 (t, J=7.2 Hz, 3H), 0.86 (m, 2H), 0.58 (m, 2H).

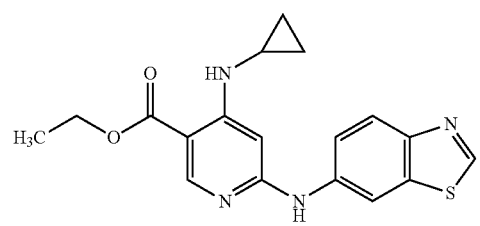 [SMILES: CCOC(=O)c1cnc(Nc2ccc3ncsc3c2)cc1NC1CC1]

Ethyl 6-chloro-4-(cyclopropylamino)nicotinate (10 g, 41.5 mmol) and benzo[d]thiazol-6-amine (7.49 g, 49.9 mmol) were heated at 150° C. in a sealed tube for 3 hrs. This process was repeated and the crude products of both reactions were combined and taken directly to the next step.

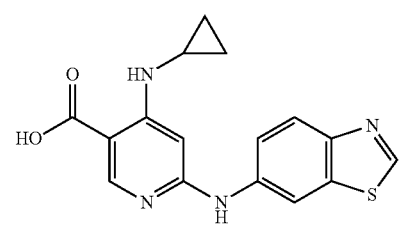 [SMILES: O=C(O)c1cnc(Nc2ccc3ncsc3c2)cc1NC1CC1]

Ethyl 6-(benzo[d]thiazol-6-ylamino)-4-(cyclopropylamino)nicotinate (19.2 g, 54.2 mmol) was dissolved in a mixture of EtOH (50 mL), water (50 mL) and THF (40 ml). To this stirred solution was added LiOH (3.9 g) and the mixture was stirred at RT for 18 h. The reaction mixture was concentrated under vacuum to remove the volatile solvents. The aqueous phase was extracted with 2×200 mL of EtOAc and the separated aqueous phase was neutralized with 1.5N HCl. The precipitated product was filtered and dried to afford 6-(benzo[d]thiazol-6-ylamino)-4-(cyclopropylamino) nicotinic acid (17 g, 96% yield) which was used without further purification. LCMS m/z 327.0 (M+H)$^+$.

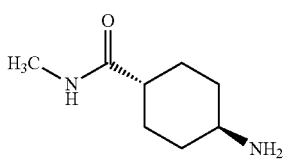

Step 1: To a stirred solution of (1r,4r)-4-((tert-butoxycarbonyl)amino)cyclohexanecarboxylic acid (250 mg, 1.03 mmol), PyBOP (535 mg, 1.03 mmol) and Hunig's Base (0.538 mL, 3.08 mmol) in DMF (5 mL) at 25° C. was added methanamine, HCl (104 mg, 1.541 mmol). After 2 hours, the reaction mixture was diluted with ethyl acetate and rinsed with 10% LiCl (3×). The organic layer was dried over $Na_2SO_4$ and concentrated to provide tert-butyl ((1r,4r)-4-(methylcarbamoyl)cyclohexyl)carbamate (250 mg, 85% yield) of white solids as product. LCMS (TFA) 201.1 (M+H-t-butyl)$^+$.

Step 2: To a stirred solution of tert-butyl ((1r,4r)-4-(methylcarbamoyl)cyclohexyl)carbamate (250 mg, 0.975 mmol) in dioxane (5 mL) at 25° C. was added 4N HCl in dioxane (2.438 mL, 9.75 mmol). The reaction was stirred for 3 hours then was concentrated from methylene chloride (5×) to provide (1r,4r)-4-amino-N-methylcyclohexanecarboxamide, HCl (150 mg, 71.8% yield) as a tan solid.

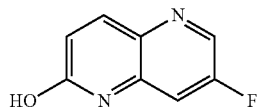 [SMILES: Oc1ccc2ncc(F)cc2n1]

To a stirred solution of tri-tert-butylphosphonium tetrafluoroborate (99 mg, 0.341 mmol) and palladium acetate (38.3 mg, 0.171 mmol) in cumene (10 g, 83 mmol) was added N-cyclohexyl-N-methylcyclohexanamine (2666 mg, 13.65 mmol), 2-chloro-5-fluoropyridin-3-amine (500 mg, 3.41 mmol) and butyl acrylate (525 mg, 4.09 mmol). The mixture was degassed by evacuation and back filling with $N_2$, and heated at 150° C. for 4 h.

The reaction mixture was cooled to room temperature and filtered through a sintered funnel. The solid obtained was identified as product with phosphine impurities which was suspended in MTBE and treated with 4N NaOH solution. The organic layer was separated and the aqueous layer was neutralized using 3N HCl. The solid obtained was filtered and dried in vacuo to give 7-fluoro-1,5-naphthyridin-2-ol (300 mg, 1.828 mmol, 53.6% yield) as off-white solid.

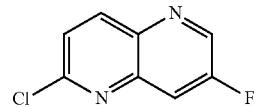 [SMILES: Fc1cnc2ccc(Cl)nc2c1]

To a stirred solution of 7-fluoro-1,5-naphthyridin-2-ol (240 mg, 1.462 mmol) in acetonitrile (5 mL) was added $POCl_3$ (0.545 mL, 5.85 mmol) and heated at 100° C. for 4 h. LCMS showed product formation [m/z: 183.0 (M+H) RT: 0.76]. The reaction mixture was concentrated in vacuo to give crude compound, which was cooled to 0° C., diluted with ethylacetate, quenched with 10% $NaHCO_3$ solution. The organic layer was separated and the aqueous layer was extracted with ethyl acetate (1×). The combined organic layer was washed with NaCl solution, dried over $Na_2SO_4$ and concentrated in vacuo to give 2-chloro-7-fluoro-1,5-naphthyridine (200 mg, 1.095 mmol, 74.9% yield) as off-white solid.

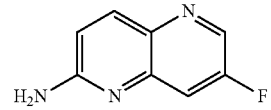

To a solution of 2-chloro-7-fluoro-1,5-naphthyridine (120 mg, 0.657 mmol) in dioxane (3 mL) was added $NH_4OH$ (5 mL, 64.7 mmol) and heated at 80° C. in autoclave for 24 h. The reaction mixture was concentrated in vacuo to give crude product, which was suspended in water, saturated with solid NaCl, extracted with ethyl acetate (4×). The combined organic layer was concentrated in vacuo to give the 7-fluoro-1,5-naphthyridin-2-amine (80 mg, 0.490 mmol, 74.6% yield) as off-white solid. LCMS showed product formation [m/z: 164.3; RT 0.46].

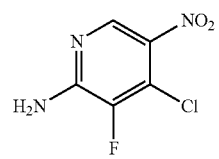

Sulfuric acid (5 mL) under nitrogen was cooled to 0° C. Next, 4-chloro-3-fluoropyridin-2-amine (5 g, 34.1 mmol) was added and allowed to stir for 15 minutes at 0° C. Potassium nitroperoxous acid (3.45 g, 34.1 mmol) was added and allowed to stir for 2 h at 0° C. After completion of the reaction, the reaction mass was heated to 50° C. for 30 minutes. The reaction was quenched into ice and basified it to pH 7 using ammonium hydroxide. The formed pale yellow solid 4-chloro-3-fluoro-5-nitropyridin-2-amine (2.5 g, 36% yield) was filtered.

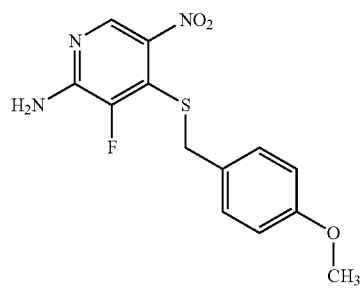

Sodium hydride (1.253 g, 31.3 mmol) and 4-chloro-3-fluoro-5-nitropyridin-2-amine (3 g, 15.66 mmol) under nitrogen at 0° C. was added THF (30 mL). Next, 4-methoxy-alpha-toluenethiol (2.62 mL, 18.79 mmol) in THF (30 mL) solution was added dropwise to the sodium hydride solution. It was allowed to stir at 0° C. for 1 hour. After completion of the reaction, the reaction mixture was slowly quenched into ice and diluted with water. The solid formed was filtered and dried overnight. The free following solid was slurried in MTBE and filtered to afford 3-fluoro-4-((4-methoxybenzyl)thio)-5-nitropyridin-2-amine (2.52 g, 39% yield) as green solid.

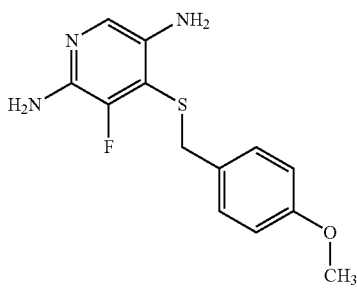 [SMILES: COc1ccc(CSc2c(N)cnc(N)c2F)cc1]

A solution of 3-fluoro-4-((4-methoxybenzyl)thio)-5-nitropyridin-2-amine (4 g, 12.93 mmol) in MeOH (70 mL) was added zinc (8.45 g, 129 mmol) and NH$_4$Cl (6.92 g, 129 mmol). The mixture was stirred for 3 h and then filtered through CELITE® with MeOH. The filtrate was concentrated and the residue was diluted with DCM and filtered to remove any inorganic solids. The DCM layer was concentrated to get 3-fluoro-4-((4-methoxybenzyl)thio)pyridine-2,5-diamine (2.6 g, 72.0% yield) as brown solid which was used without further purification.

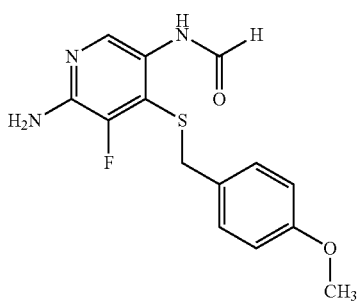 [SMILES: COc1ccc(CSc2c(NC=O)cnc(N)c2F)cc1]

A mixture of 3-fluoro-4-((4-methoxybenzyl)thio)pyridine-2,5-diamine (2.6 g, 6.52 mmol) and formic acid (35 mL, 6.52 mmol) under nitrogen was heated at 90° C. for 1 hour. After completion of the reaction, the reaction mixture was concentrated and taken to next step without purification.

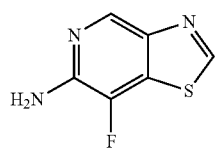

A solution of N-(6-amino-5-fluoro-4-((4-methoxybenzyl) thio)pyridin-3-yl)formamide (2.6 g, 8.46 mmol) in TFA (25 mL) was added silver tetrafluoroborate (0.659 g, 3.38 mmol) and then heated at 80° C. for 3 hours. The completion of the reaction was confirmed by LCMS. After completion of the reaction, the reaction mass was completely distilled off and diluted with water (20 mL). The aqueous layer was washed with MTBE (3×20 mL). The pH of the aqueous layer was adjusted to 8 with saturated solution of sodium bicarbonate. The basic solution was extracted by ethyl acetate in three times (3×20 mL). The combined organic layer was washed with brine and dried over sodium sulphate. The filtrate was concentrated and dried under high vacuum to obtain 7-fluorothiazolo[4,5-c]pyridin-6-amine (650 mg, 45% yield) as pale brown solid.

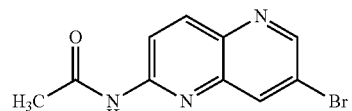

To a stirred solution of N-(1,5-naphthyridin-2-yl)acetamide (2 g, 10.68 mmol) in CCl$_4$ (30 mL) was added pyridine (2.59 mL, 32.1 mmol) and Br$_2$ (0.605 mL, 11.75 mmol) at 0° C. The mixture was then heated at 90° C. for 3 hours. The reaction was cooled to rt and concentrated to dryness. The residue was partitioned between EtOAc and NaHCO$_3$ solution and the separated organic layer was dried over Na$_2$SO$_4$, filtered, and concentrated. Purification via column chromatography afforded N-(7-bromo-1,5-naphthyridin-2-yl)acetamide (1.0 g, 37% yield).

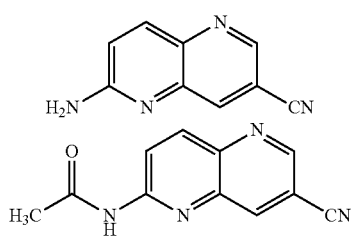

To a stirred solution of N-(7-bromo-1,5-naphthyridin-2-yl)acetamide (800 mg, 3.01 mmol) in DMF (10 mL) was added zinc (59.0 mg, 0.902 mmol) and zinc cyanide (706 mg, 6.01 mmol). The mixture was degassed with N$_2$ for 5 mins then PdCl$_2$(dppf)-CH$_2$Cl$_2$ adduct (246 mg, 0.301 mmol) was added. The mixture was degassed with N$_2$ for 5 mins and then heated at 110° C. for 14 hours. The reaction was cooled to rt, diluted with cold water and extracted with EtOAc (2×20 mL). The organic layer was dried over Na$_2$SO$_4$, filtered and concentrated. The product was isolated via column chromatography to afford 6-amino-1,5-naphthyridine-3-carbonitrile (250 mg, 49% yield) in addition to N-(7-cyano-1,5-naphthyridin-2-yl)acetamide (200 mg, 31% yield).

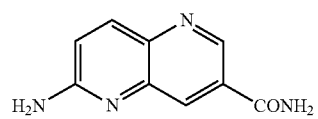

To a stirred solution of N-(7-cyano-1,5-naphthyridin-2-yl)acetamide (200 mg, 0.942 mmol) in MeOH (10 mL) was added K$_2$CO$_3$ (391 mg, 2.83 mmol). The mixture was stirred for 2 h at rt then concentrated and partitioned between EtOAc and water. The layers were separated and the organic layer was dried over Na$_2$SO$_4$, filtered, and concentrated to afford the crude product which was purified via column chromatography to afford 6-amino-1,5-naphthyridine-3-carboxamide (100 mg, 56% yield). LCMS 188.2 (M+)$^+$.

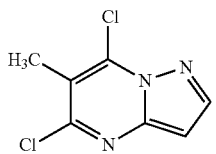

6-Methylpyrazolo[1,5-a]pyrimidine-5,7-diol (4.7 g, 28.5 mmol) was dissolved in POCl₃ (40 mL) and heated at 100° C. for 16 h. After cooling to rt, the excess POCl₃ was removed in vacuo and the crude residue was treated with aq. NaHCO₃ then extracted with EtOAc. The organic extracts were washed with water and brine, dried over anhydrous Na₂SO₄, filtered and concentrated. The product was purified via column chromatography to afford the product (1 g, 17% yield). LCMS 202.0 (M+2)⁺.

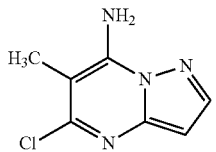

5,7-Dichloro-6-methylpyrazolo[1,5-a]pyrimidine (1 g, 4.95 mmol) was taken in a seal tube and dissolved in NH₄OH (10 mL). The reaction mixture was heated for 2 h at 80° C. and then cooled to room temperature. The solvents were removed and the product used without further purification. LCMS 183.3 (M+H)⁺.

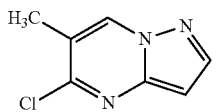

To a stirred solution of 5-chloro-6-methylpyrazolo[1,5-a]pyrimidin-7-amine (0.8 g, 4.38 mmol) in 1,4-dioxane (15 mL) was added isoamyl nitrate (1.180 mL, 8.76 mmol) at 0° C. dropwise. The reaction was then heated at 100° C. for 1 h. The solvent was removed and the product isolated via column chromatography to afford 5-chloro-6-methylpyrazolo[1,5-a]pyrimidine (410 mg, 55% yield). LCMS 168.0 (M+H)'.

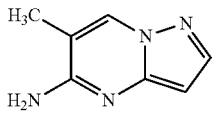

A stirred solution of 5-chloro-6-methylpyrazolo[1,5-a]pyrimidine (0.410 g, 2.446 mmol) in NH₄OH (10 mL) was sealed in a tube and heated for 3 h at 80° C. The mixture was cooled and concentrated to afford the crude product (310 mg, 77% yield) which was used without further purification. LCMS 149.4 (M+H)⁺.

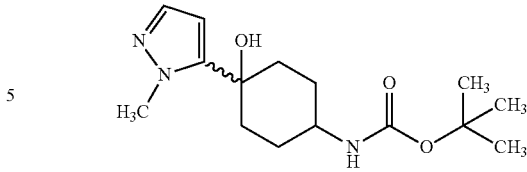

A solution of 1-methyl-1H-pyrazole (1.012 mL, 12.18 mmol) in THF (50 mL) was cooled to −78° C. and n-BuLi (4.87 mL, 12.18 mmol) was added. The mixture was allowed to stir at RT for 1 hr. Afterwards a solution of tert-butyl(4-oxocyclohexyl)carbamate (1.299 g, 6.09 mmol) in THF (10 mL) was added and the mixture stirred at RT overnight. The reaction was worked up by quenching with water, evaporating the THF, adding EtOAc, and washing the product with water (2x). The organic layer was dried (sodium sulfate) and the solvent removed in vacuo to yield 1.061 g of a viscous yellow oil which was purified via column chromatography to afford a mixture of cis and trans isomers (0.85 g, 46% yield). ¹H NMR (400 MHz, CDCl₃-d) δ 7.40-7.33 (m, 1H), 6.24-6.00 (m, 1H), 5.31 (s, 1H), 4.48 (br. s., 1H), 4.12-4.00 (m, 3H), 2.23-1.80 (m, 6H), 1.73-1.59 (m, 2H), 1.50-1.43 (m, 9H). Note that there were two sets of vinyl peaks in a ration of 3:1 designating the ratio of trans/cis products.

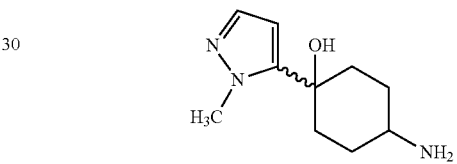

tert-Butyl (4-hydroxy-4-(1-methyl-1H-pyrazol-5-yl)cyclohexyl)carbamate (0.85 g, 2.88 mmol) was dissolved in DCM (20 mL) and to this solution was added HCl (4N in dioxane) (7.19 mL, 28.8 mmol). The contents were stirred at RT. The reaction appeared to be precipitating and thus a little MeOH was added to help make the product more soluble. The reaction was evaporated and the residue evaporated from methylene chloride 3x to remove traces of HCl. The solid thus obtained was dried under house vacuum to afford 0.75 g of a light yellow solid which was used without further purification: ¹H NMR (400 MHz, DMSO-d₆) δ 8.31-8.14 (m, 3H), 7.39 (d, J=2.0 Hz, 1H), 6.14 (d, J=2.0 Hz, 1H), 3.98 (s, 3H), 3.08-2.95 (m, 1H), 2.08-1.96 (m, 2H), 1.82 (br. s., 5H).

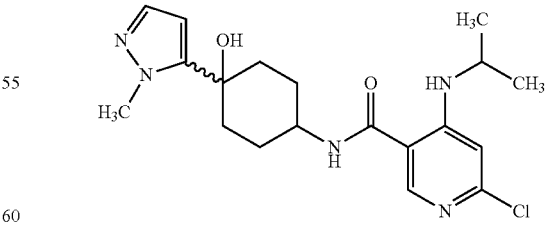

A 4-amino-1-(1-methyl-1H-pyrazol-5-yl)cyclohexanol, HCl (200 mg, 0.863 mmol), 6-chloro-4-(isopropylamino) nicotinic acid (185 mg, 0.863 mmol), Hunig's Base (0.754 mL, 4.32 mmol), and PyBOP (898 mg, 1.726 mmol) were mixed and stirred in DMF (3 mL) at RT. The reaction was quenched with 1N NaOH, and EtOAc was added. The layers were separated and the organic layer rinsed with 1N NaOH (2×), brine (1×), dried (sodium sulfate) and the solvent removed in vacuo to yield 1.25 g of a brown oily solid. The residue was purified via column chromatography to afford 245 mg (69% yield) of a mixture of 4-5:1 ratio of trans to cis isomers. $^1$H NMR (400 MHz, DMSO-$d_6$) δ 8.46 (d, J=7.7 Hz, 1H), 8.42-8.25 (m, 2H), 7.33-7.19 (m, 1H), 6.74-6.61 (m, 1H), 6.25-6.02 (m, 1H), 5.22-5.08 (m, 1H), 4.01-3.91 (m, 3H), 3.88-3.69 (m, 2H), 2.11-1.60 (m, 7H), 1.20 (d, J=6.6 Hz, 1H), 1.16 (d, J=6.4 Hz, 5H), 1.09-1.09 (m, 1H).

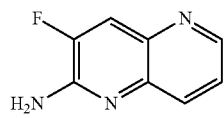

A mixture of 3-fluoropyridine-2,5-diamine (1 g, 7.87 mmol), 3-nitrobenzenesulfonic acid sodium salt (3.54 g, 15.73 mmol), glycerol (2.87 mL, 39.3 mmol), $H_2SO_4$ (4 mL, 75 mmol) in water (6 mL) was heated at 150° C. for 16 h. The reaction mixture was cooled to rt and poured in crushed ice. The pH was adjusted to ~9 and extracted with EtOAc. The organic layer was separated and concentrated and the product was purified via column chromatography to afford 3-fluoro-1,5-naphthyridin-2-amine. LCMS 164.0 (M+H)$^+$.

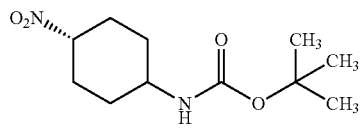

Step 1. To a refluxing solution of mCPBA (0.460 g, 1.867 mmol) in DCE was added tert-butyl ((trans)-4-aminocyclohexyl)carbamate (0.1 g, 0.467 mmol) in DCE. The mixture was refluxed for 3 hours. The reaction was worked up by adding EtOAc, washing with 1N NaOH (3×), and brine (1×). The organic layer was dried (sodium sulfate) and the solvent removed in vacuo to yield 0.0654 g of tert-butyl ((trans)-4-nitrocyclohexyl) carbamate as a yellow viscous oil. $^1$H NMR (400 MHz, CDCl$_3$) δ 3.51 (br. s., 1H), 2.42-2.31 (m, 2H), 2.24-2.15 (m, 2H), 2.04-1.91 (m, 2H), 1.47 (s, 9H), 1.33-1.19 (m, 4H).

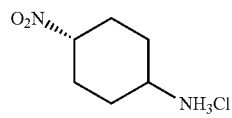

tert-Butyl ((trans)-4-nitrocyclohexyl)carbamate (0.0654 g, 0.268 mmol) was dissolved in DCM (1 mL) and to this solution was added HCl (0.669 mL, 2.68 mmol). The contents were stirred overnight at RT. TLC in 100% EtOAc shows only baseline product. The solvent was removed in vacuo and the residue re-evaporated from methylene chloride (3×) to remove traces of HCl. There was obtained 0.059 mg of trans-4-nitrocyclohexanamine, HCl as an off-white solid.

The Examples shown in Table 10 can be prepared using variations of the procedures already described in the preceding text.

TABLE 10

| Ex. No. | Structure | | HPLC RT (min) | HPLC cond. | LCMS (M + H) |
| --- | --- | --- | --- | --- | --- |
| 386 | 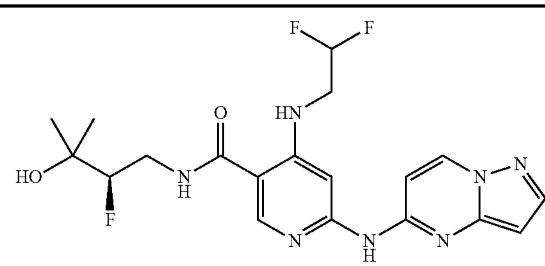 | | 5.18 | E | 438.4 |
| 387 | 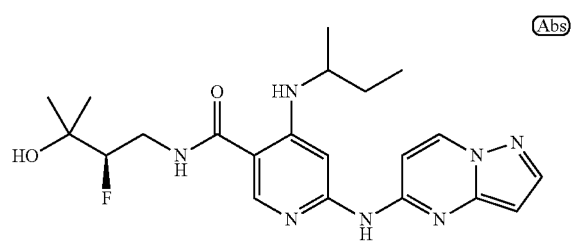 [SMILES: CCC(C)Nc1cc(Nc2ccn3nccc3n2)ncc1C(=O)NC[C@@H](F)C(C)(C)O] | (Abs) | 5.66 | E | 430.2 |
| 388 | 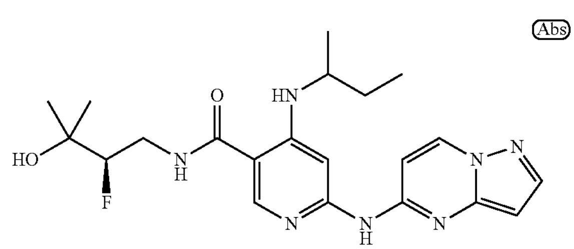 [SMILES: CCC(C)Nc1cc(Nc2ccn3nccc3n2)ncc1C(=O)NC[C@@H](F)C(C)(C)O] | (Abs) | 6.59 | A | 430.2 |

TABLE 10-continued

| Ex. No. | Structure | HPLC RT (min) | HPLC cond. | LCMS (M + H) |
|---|---|---|---|---|
| 389 | 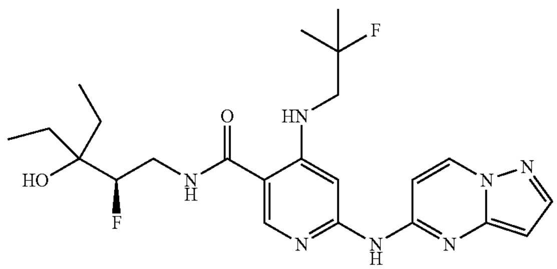 [SMILES: CCC(O)(CC)[C@H](F)CNC(=O)c1cnc(Nc2ccn3nccc3n2)cc1NCC(C)(C)F] | 6.61 | A | 476.2 |
| 390 | 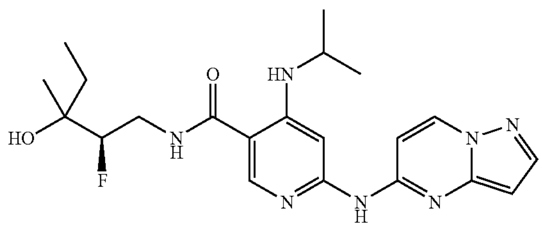 [SMILES: CCC(C)(O)[C@H](F)CNC(=O)c1cnc(Nc2ccn3nccc3n2)cc1NC(C)C] | 6.12 | E | 445.8 |
| 391 | (Abs) | 7.04 | A | 495.7 |
| 392 | (Abs) | 7.05 | A | 495.7 |
| 393 | (Abs) | 1.06 | O | 431.6 |

TABLE 10-continued

| Ex. No. | Structure | HPLC RT (min) | HPLC cond. | LCMS (M + H) |
| --- | --- | --- | --- | --- |
| 394 | 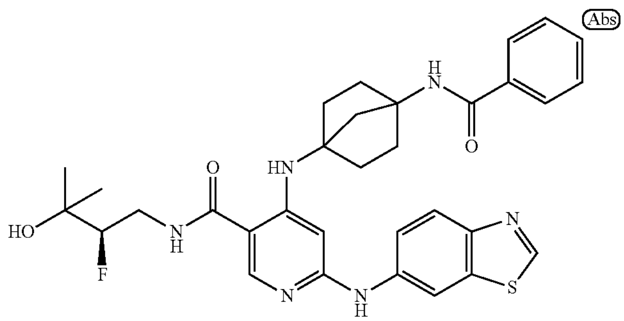 [SMILES: CC(C)(O)[C@H](F)CNC(=O)c1cnc(Nc2ccc3ncsc3c2)cc1NC12CCC(NC(=O)c3ccccc3)(CC1)C2] | 1.56 | G | 603.2 |
| 395 | 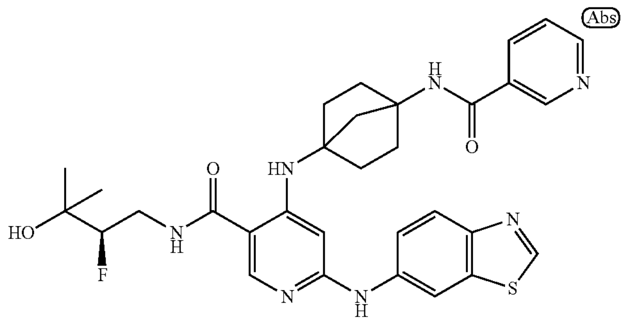 [SMILES: CC(C)(O)[C@H](F)CNC(=O)c1cnc(Nc2ccc3ncsc3c2)cc1NC12CCC(NC(=O)c3cccnc3)(CC1)C2] | 1.29 | G | 604.2 |
| 396 | 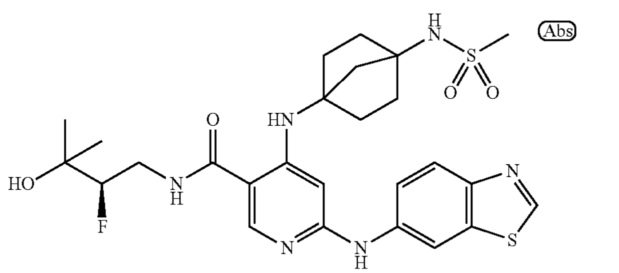 [SMILES: CC(C)(O)[C@H](F)CNC(=O)c1cnc(Nc2ccc3ncsc3c2)cc1NC12CCC(NS(C)(=O)=O)(CC1)C2] | 1.25 | G | 577.2 |
| 397 | 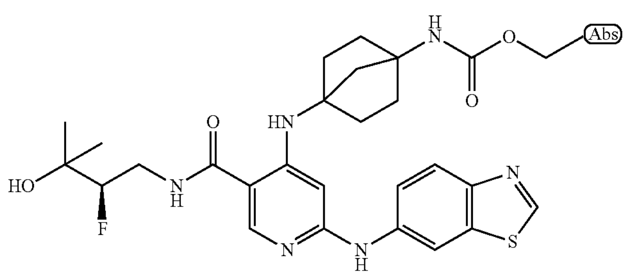 [SMILES: CCOC(=O)NC12CCC(Nc3cc(Nc4ccc5ncsc5c4)ncc3C(=O)NC[C@@H](F)C(C)(C)O)(CC1)C2] | 1.48 | G | 571.2 |
| 398 | 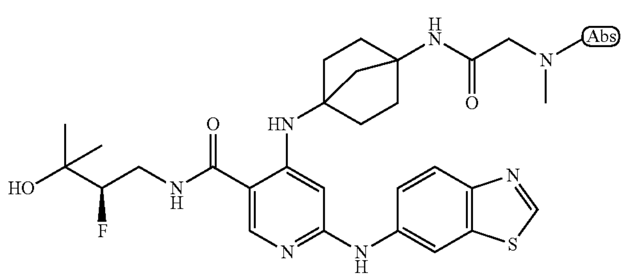 [SMILES: CN(C)CC(=O)NC12CCC(Nc3cc(Nc4ccc5ncsc5c4)ncc3C(=O)NC[C@@H](F)C(C)(C)O)(CC1)C2] | 1.16 | G | 584.3 |

TABLE 10-continued

| Ex. No. | Structure | HPLC RT (min) | HPLC cond. | LCMS (M + H) |
|---|---|---|---|---|
| 399 | 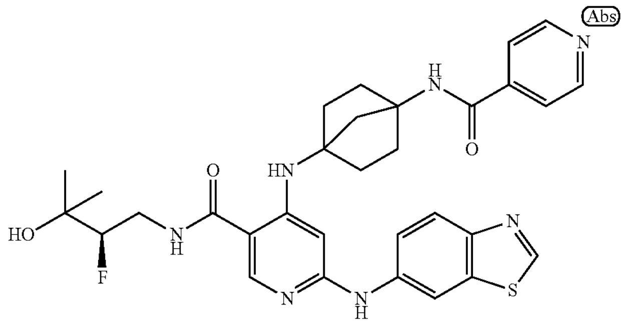 [SMILES: CC(C)(O)[C@H](F)CNC(=O)c1cnc(Nc2ccc3ncsc3c2)cc1NC12CCC(NC(=O)c3ccncc3)(CC1)C2] | 1.30 | G | 604.2 |
| 400 | 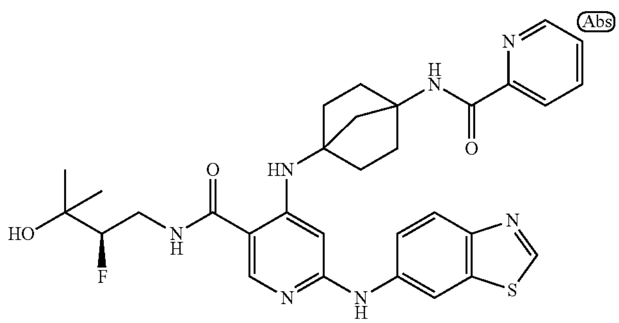 [SMILES: CC(C)(O)[C@H](F)CNC(=O)c1cnc(Nc2ccc3ncsc3c2)cc1NC12CCC(NC(=O)c3ccccn3)(CC1)C2] | 1.38 | G | 604.2 |
| 401 | 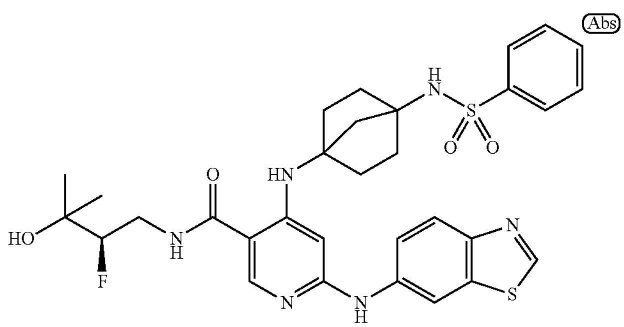 [SMILES: CC(C)(O)[C@H](F)CNC(=O)c1cnc(Nc2ccc3ncsc3c2)cc1NC12CCC(NS(=O)(=O)c3ccccc3)(CC1)C2] | 1.93 | G | 637.2 (M − H) |
| 402 | 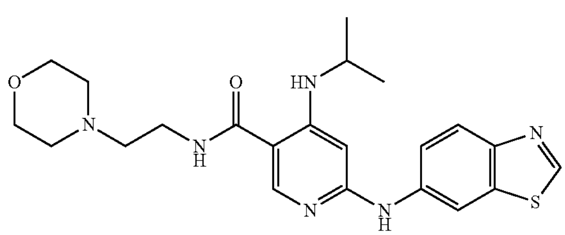 [SMILES: CC(C)Nc1cc(Nc2ccc3ncsc3c2)ncc1C(=O)NCCN1CCOCC1] | 8.48 | K | 441.2 |
| 403 | 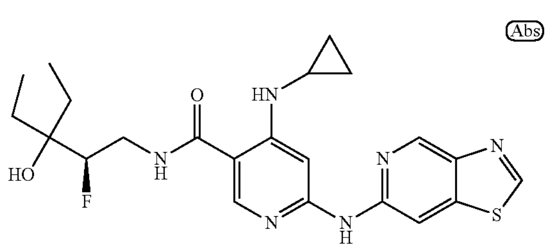 [SMILES: CCC(O)(CC)[C@H](F)CNC(=O)c1cnc(Nc2cc3scnc3cn2)cc1NC1CC1] | 7.41 | A | 459.2 |

TABLE 10-continued

| Ex. No. | Structure | | HPLC RT (min) | HPLC cond. | LCMS (M + H) |
|---|---|---|---|---|---|
| 404 | 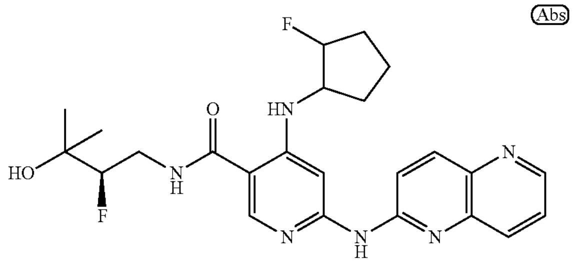 [SMILES: CC(C)(O)[C@H](F)CNC(=O)c1cnc(Nc2ccc3ncccc3n2)cc1NC1CCCC1F] | (Abs) | 5.80 | E | 471.2 |
| 405 | 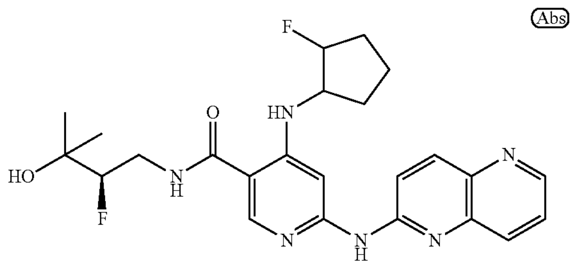 [SMILES: CC(C)(O)[C@H](F)CNC(=O)c1cnc(Nc2ccc3ncccc3n2)cc1NC1CCCC1F] | (Abs) | 5.79 | E | 471.2 |
| 406 | 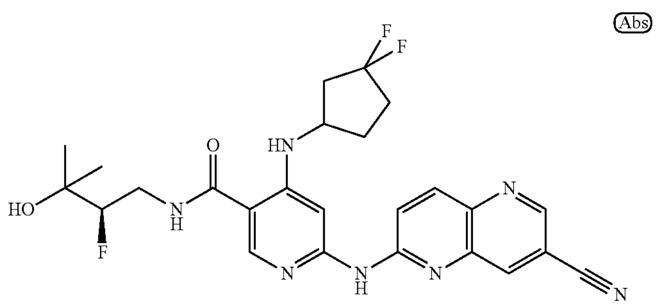 [SMILES: CC(C)(O)[C@H](F)CNC(=O)c1cnc(Nc2ccc3ncc(C#N)cc3n2)cc1NC1CCC(F)(F)C1] | (Abs) | 6.17 | E | 513.8 |
| 407 | 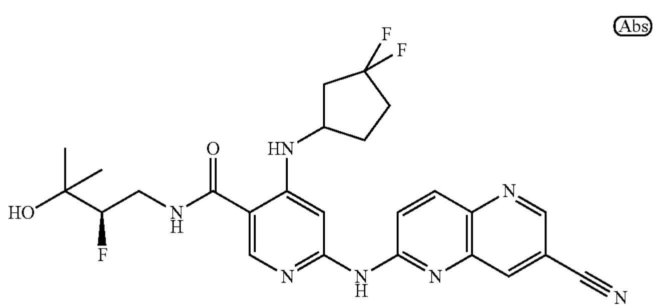 [SMILES: CC(C)(O)[C@H](F)CNC(=O)c1cnc(Nc2ccc3ncc(C#N)cc3n2)cc1NC1CCC(F)(F)C1] | (Abs) | 6.23 | E | 513.8 |
| 408 | 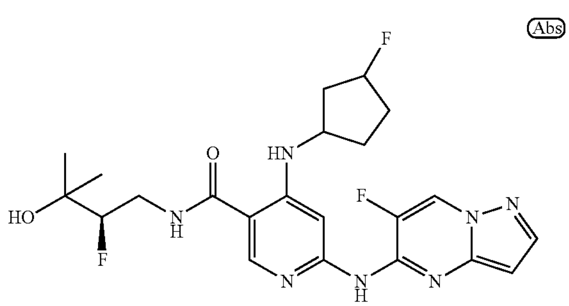 [SMILES: CC(C)(O)[C@H](F)CNC(=O)c1cnc(Nc2nc3ccnn3cc2F)cc1NC1CCC(F)C1] | (Abs) | 5.64 | E | 478.2 |

TABLE 10-continued

| Ex. No. | Structure | HPLC RT (min) | HPLC cond. | LCMS (M + H) |
|---|---|---|---|---|
| 409 | (Abs) | 5.88 | E | 478.2 |
| 410 | (Abs) | 5.89 | E | 478.6 |
| 411 | (Abs) | 6.10 | E | 496.2 |
| 412 | (Abs) | 6.09 | E | 496.2 |
| 413 | (Abs) | 6.41 | E | 496.2 |

TABLE 10-continued

| Ex. No. | Structure | HPLC RT (min) | HPLC cond. | LCMS (M + H) |
|---|---|---|---|---|
| 414 | 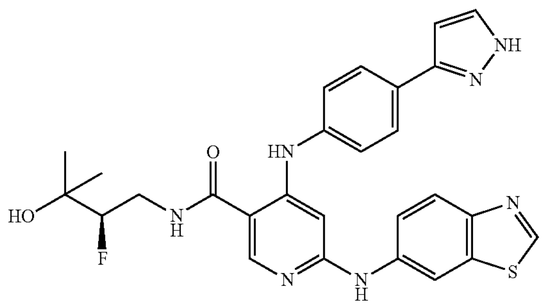 [SMILES: CC(C)(O)[C@H](F)CNC(=O)c1cnc(Nc2ccc3ncsc3c2)cc1Nc1ccc(-c2cc[nH]n2)cc1] | 1.45 | G | 533.2 |
| 415 | 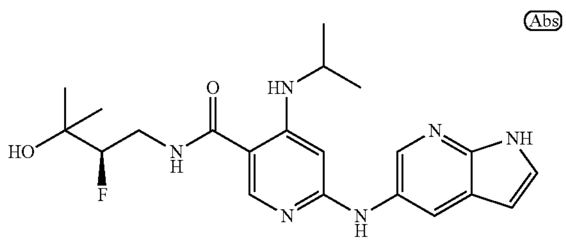 [SMILES: CC(C)Nc1cc(Nc2cnc3[nH]ccc3c2)ncc1C(=O)NC[C@@H](F)C(C)(C)O] | 1.12 | O | 415.1 |
| 416 | 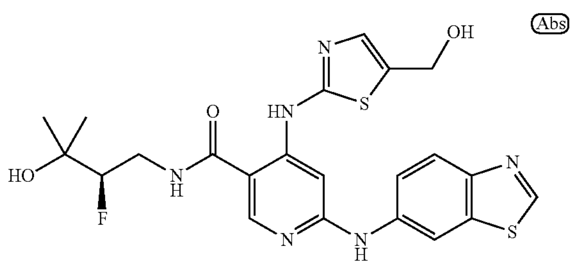 [SMILES: CC(C)(O)[C@H](F)CNC(=O)c1cnc(Nc2ccc3ncsc3c2)cc1Nc1ncc(CO)s1] | 9.58 | K | 501.0 (M − H) |
| 417 | 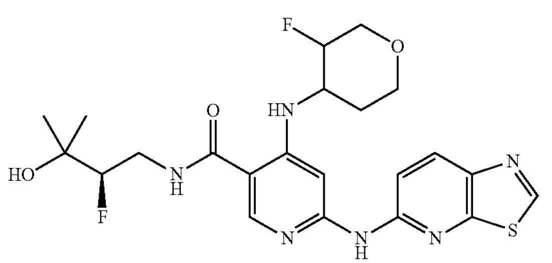 [SMILES: CC(C)(O)[C@H](F)CNC(=O)c1cnc(Nc2ccc3ncsc3n2)cc1NC1CCOCC1F] | 5.30 | A | 493.2 |
| 418 | 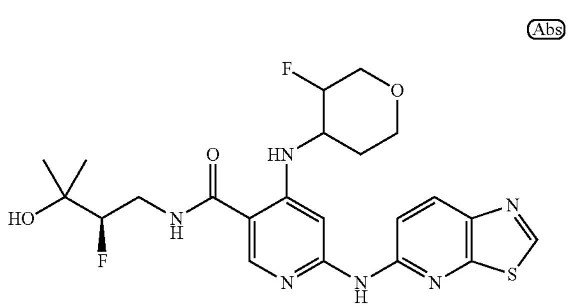 [SMILES: CC(C)(O)[C@H](F)CNC(=O)c1cnc(Nc2ccc3ncsc3n2)cc1NC1CCOCC1F] | 5.94 | A | 492.6 |

TABLE 10-continued

| Ex. No. | Structure | HPLC RT (min) | HPLC cond. | LCMS (M + H) |
|---|---|---|---|---|
| 419 | (Abs) | 2.00 | g | 512.2 |
| 420 | (Abs) | 6.14 | E | 481.2 |
| 421 | (Abs) | 5.25 | E | 515.2 |
| 422 | (Abs) | 5.04 | E | 476.0 |
| 423 | (Abs) | 8.55 | K | 450.2 |

TABLE 10-continued

| Ex. No. | Structure | HPLC RT (min) | HPLC cond. | LCMS (M + H) |
|---|---|---|---|---|
| 424 | 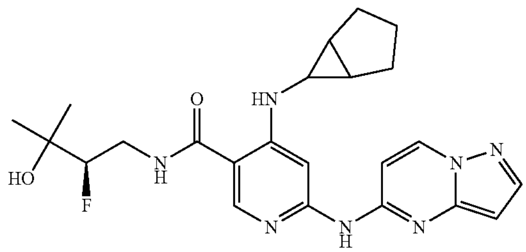 [SMILES: CC(C)(O)[C@H](F)CNC(=O)c1cnc(Nc2ccn3nccc3n2)cc1NC1C2CCCC21] | 6.64 | A | 484.2 (M − H) |
| 425 | 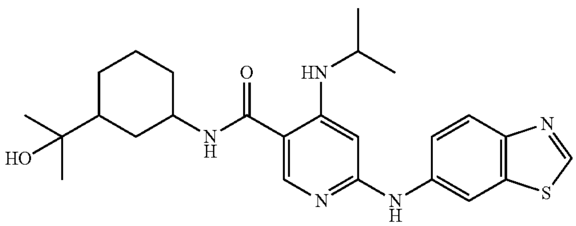 [SMILES: CC(C)Nc1cc(Nc2ccc3ncsc3c2)ncc1C(=O)NC1CCCC(C(C)(C)O)C1] | 6.49 | E | 468.9 |
| 426 | (Abs) | 0.97 | O | 473.2 (M + Na) |
| 427 | 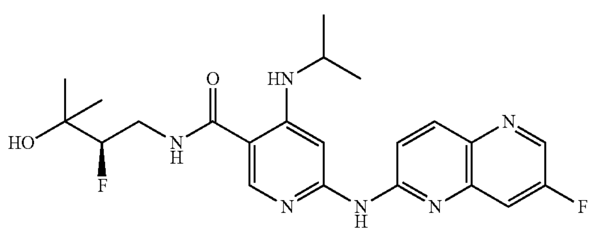 [SMILES: CC(C)Nc1cc(Nc2ccc3ncc(F)cc3n2)ncc1C(=O)NC[C@@H](F)C(C)(C)O] | 5.96 | B | 445.2 |
| 428 | 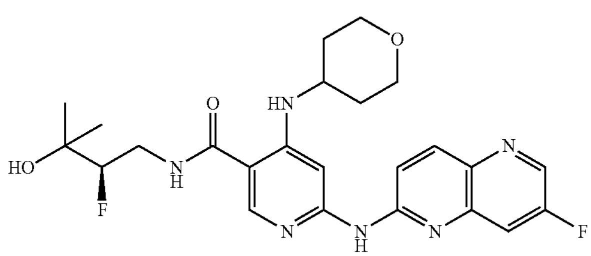 [SMILES: CC(C)(O)[C@H](F)CNC(=O)c1cnc(Nc2ccc3ncc(F)cc3n2)cc1NC1CCOCC1] | 5.53 | B | 487.2 |
| 429 | 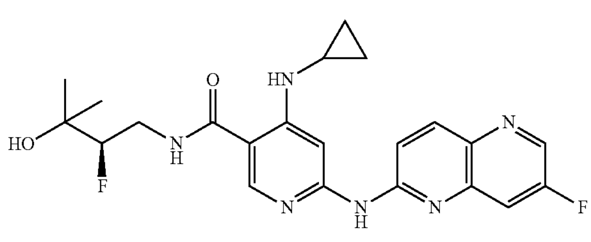 [SMILES: CC(C)(O)[C@H](F)CNC(=O)c1cnc(Nc2ccc3ncc(F)cc3n2)cc1NC1CC1] | 6.92 | A | 443.5 |

TABLE 10-continued
| Ex. No. | Structure | HPLC RT (min) | HPLC cond. | LCMS (M + H) |
|---|---|---|---|---|
| 430 |  (Abs) | 11.69 | A, 18 min grad | 469.2 |
| 431 |  (Abs) | 9.62 | K | 468.6 |
| 432 |  (Abs) | 9.64 | K | 468.6 |
| 433 |  (Abs) | 9.27 | C | 513.7 |
| 434 |  (Abs) | 1.29 | G | 413 |

TABLE 10-continued

| Ex. No. | Structure | HPLC RT (min) | HPLC cond. | LCMS (M + H) |
|---|---|---|---|---|
| 435 | 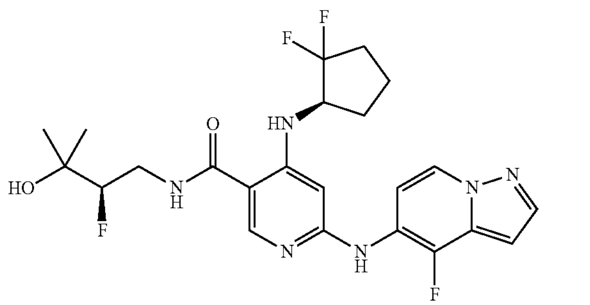 [SMILES: CC(C)(O)[C@H](F)CNC(=O)c1cnc(Nc2ccn3nccc3c2F)cc1N[C@@H]1CCCC1(F)F] | 6.41 | B | 495.2 |
| 436 | (Abs) | 5.06 | B | 494.2 |
| 437 | 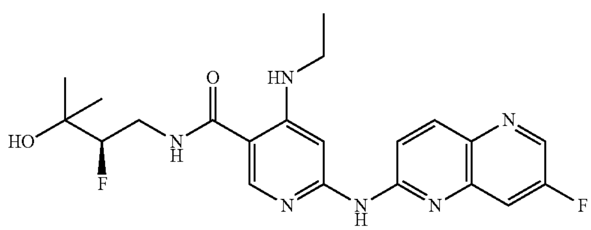 [SMILES: CCNc1cc(Nc2ccc3ncc(F)cc3n2)ncc1C(=O)NC[C@@H](F)C(C)(C)O] | 5.77 | E | 429.2 (M − H) |
| 438 | (Abs) | 10.11 | K | 486.7 |
| 439 | (Abs) | 10.08 | K | 486.7 |

TABLE 10-continued
| Ex. No. | Structure | | HPLC RT (min) | HPLC cond. | LCMS (M + H) |
|---|---|---|---|---|---|
| 440 | 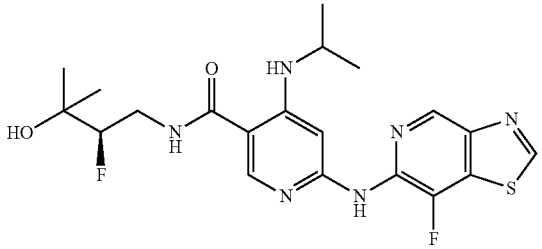 [SMILES: CC(C)Nc1cc(Nc2ncc3ncsc3c2F)ncc1C(=O)NC[C@@H](F)C(C)(C)O] | | 6.69 | A | 450.6 |
| 441 | 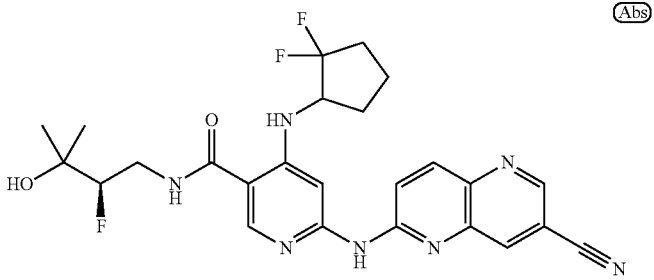 [SMILES: CC(C)(O)[C@H](F)CNC(=O)c1cnc(Nc2ccc3ncc(C#N)cc3n2)cc1NC1CCCC1(F)F] | (Abs) | 9.27 | C | 513.7 |
| 442 | 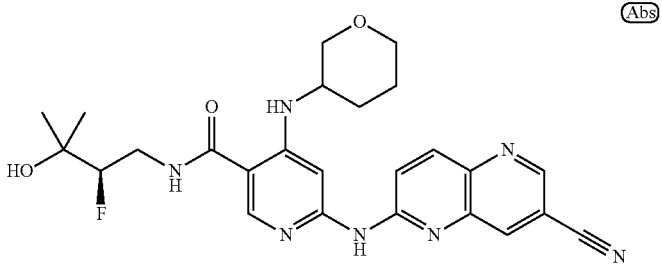 [SMILES: CC(C)(O)[C@H](F)CNC(=O)c1cnc(Nc2ccc3ncc(C#N)cc3n2)cc1NC1CCCOC1] | (Abs) | 8.51 | C | 493.7 |
| 443 | 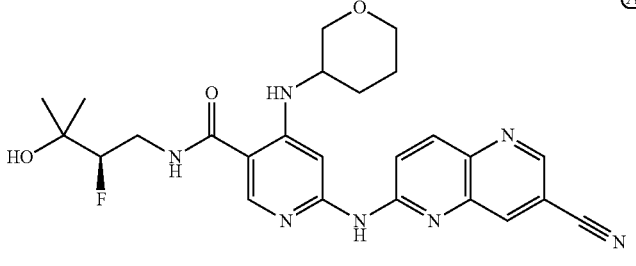 | (Abs) | 8.52 | C | 493.7 |
| 444 | 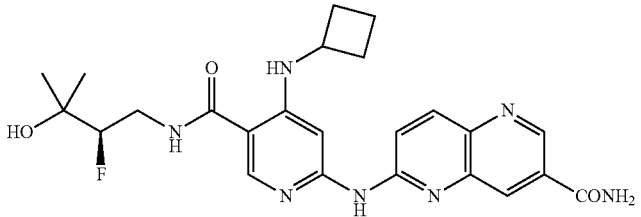 [SMILES: CC(C)(O)[C@H](F)CNC(=O)c1cnc(Nc2ccc3ncc(C(N)=O)cc3n2)cc1NC1CCC1] | | 5.05 | B | 481.7 |

TABLE 10-continued

| Ex. No. | Structure | HPLC RT (min) | HPLC cond. | LCMS (M + H) |
|---|---|---|---|---|
| 445 | 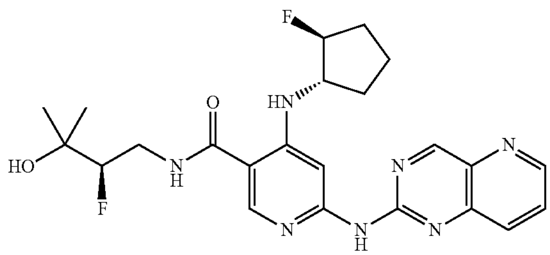 [SMILES: CC(C)(O)[C@H](F)CNC(=O)c1cnc(Nc2ncc3ncccc3n2)cc1N[C@H]1CCC[C@@H]1F] | 1.26 | G | 472.3 |
| 446 | 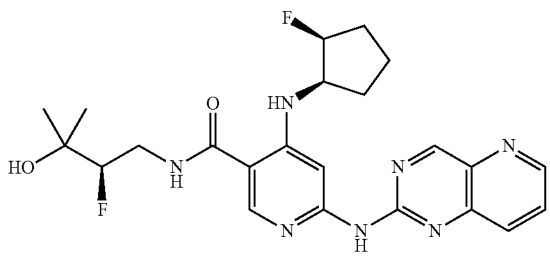 [SMILES: CC(C)(O)[C@H](F)CNC(=O)c1cnc(Nc2ncc3ncccc3n2)cc1N[C@@H]1CCC[C@@H]1F] | 1.2 | G | 472.2 |
| 447 | 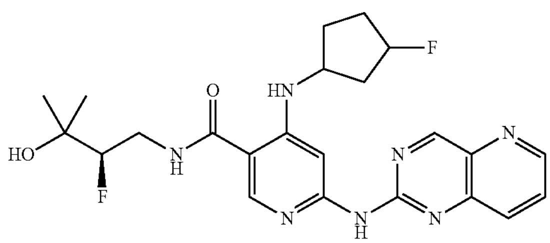 [SMILES: CC(C)(O)[C@H](F)CNC(=O)c1cnc(Nc2ncc3ncccc3n2)cc1NC1CCC(F)C1] | 1.12 | L | 472.1 |
| 448 | 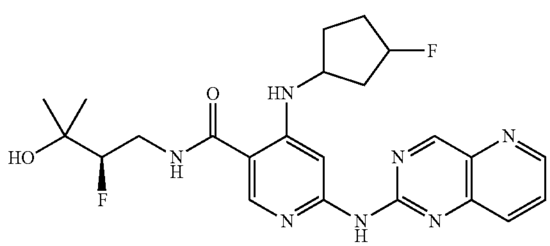 [SMILES: CC(C)(O)[C@H](F)CNC(=O)c1cnc(Nc2ncc3ncccc3n2)cc1NC1CCC(F)C1] | 1.14 | L | 472.2 |
| 449 | 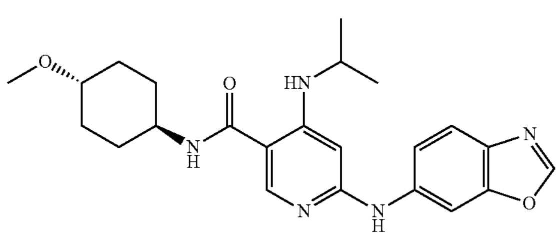 [SMILES: CO[C@H]1CC[C@H](NC(=O)c2cnc(Nc3ccc4ncoc4c3)cc2NC(C)C)CC1] | 7.29 | A | 440.1 |
| 450 | 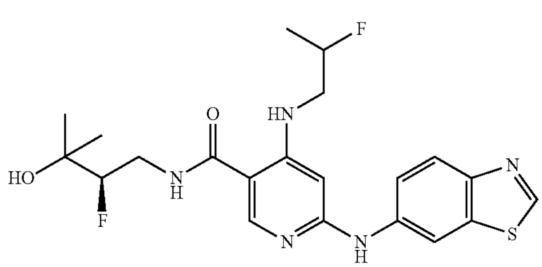 [SMILES: CC(F)CNc1cc(Nc2ccc3ncsc3c2)ncc1C(=O)NC[C@@H](F)C(C)(C)O] | 11.04 | K | 450.2 |

TABLE 10-continued
| Ex. No. | Structure | HPLC RT (min) | HPLC cond. | LCMS (M + H) |
|---|---|---|---|---|
| 451 | 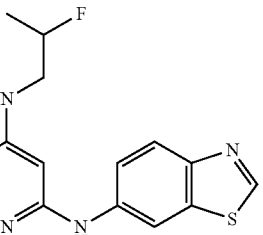 | 5.62 | E | 450.2 |
| 452 | 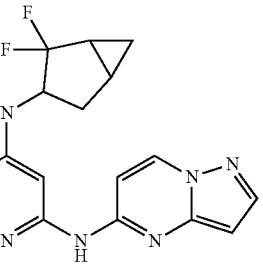 | 6.87 | A | 490.2 |
| 453 | 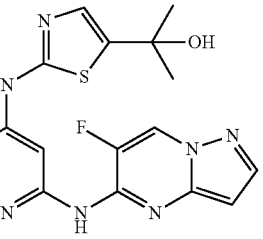 | 5.37 | B | 533 |
| 454 | 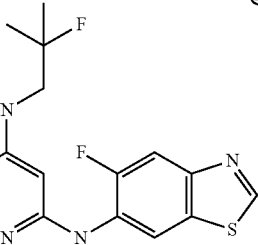 | 6.08 | E | 482.2 |
| 455 | 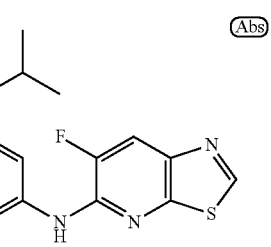 | 5.66 | E | 451.2 |
| 456 | 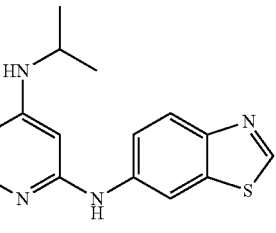 | 7.13 | A | 468.3 |

TABLE 10-continued

| Ex. No. | Structure | HPLC RT (min) | HPLC cond. | LCMS (M + H) |
|---|---|---|---|---|
| 457 | 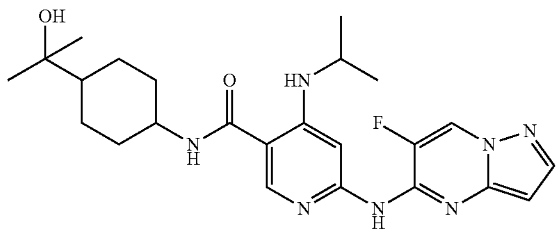 [SMILES: CC(C)Nc1cc(Nc2nc3ccnn3cc2F)ncc1C(=O)NC1CCC(C(C)(C)O)CC1] | 6.75 | A | 470.3 |
| 458 | 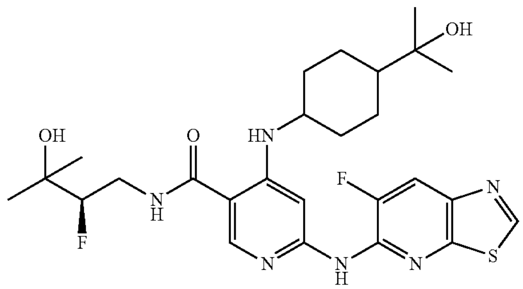 [SMILES: CC(C)(O)C1CCC(Nc2cc(Nc3nc4scnc4cc3F)ncc2C(=O)NC[C@@H](F)C(C)(C)O)CC1] | 5.74 | E | 530.3 |
| 459 | (Abs) | 10.17 | A, 12 min grad. | 467.2 |
| 460 | (Abs) | 9.94 | A | 467.2 |
| 461 | (Abs) | 6.31 | B | 495.2 |

TABLE 10-continued

| Ex. No. | Structure | | HPLC RT (min) | HPLC cond. | LCMS (M + H) |
|---|---|---|---|---|---|
| 462 | 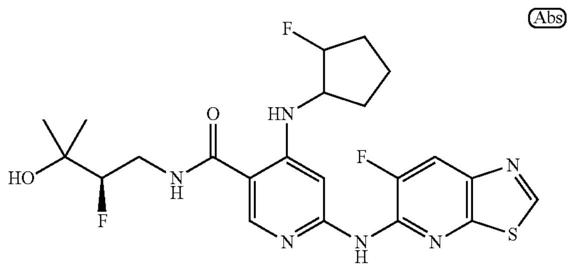 [SMILES: CC(C)(O)[C@H](F)CNC(=O)c1cnc(Nc2nc3scnc3cc2F)cc1NC1CCCC1F] | (Abs) | 6.29 | B | 495.2 |
| 463 | 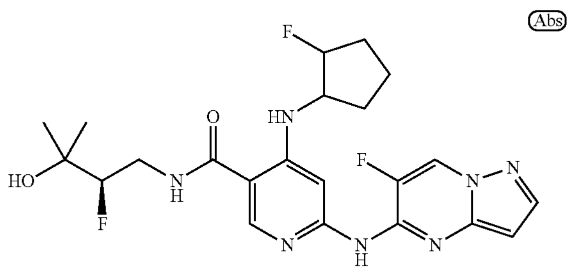 [SMILES: CC(C)(O)[C@H](F)CNC(=O)c1cnc(Nc2nc3ccnn3cc2F)cc1NC1CCCC1F] | (Abs) | 12.92 | A, 18 min grad. | 478.2 |
| 464 | 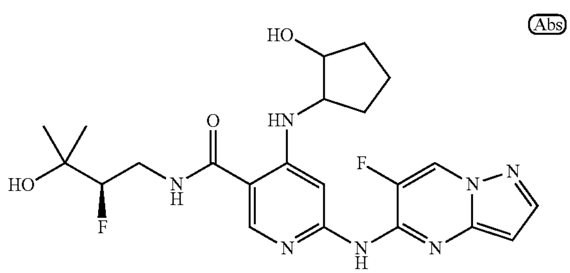 [SMILES: CC(C)(O)[C@H](F)CNC(=O)c1cnc(Nc2nc3ccnn3cc2F)cc1NC1CCCC1O] | (Abs) | 10.60 | A, 18 min grad. | 476.2 |
| 465 | 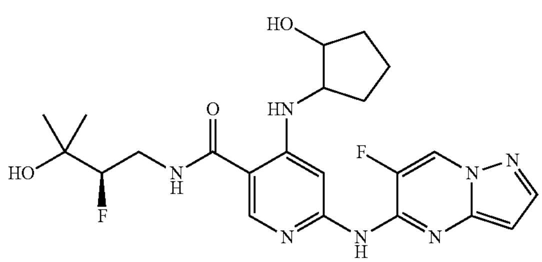 [SMILES: CC(C)(O)[C@H](F)CNC(=O)c1cnc(Nc2nc3ccnn3cc2F)cc1NC1CCCC1O] | | 5.58 | A | 476.2 |
| 466 | 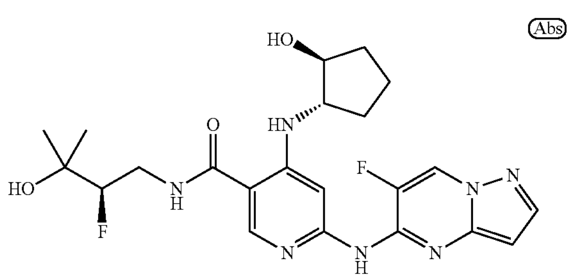 [SMILES: CC(C)(O)[C@H](F)CNC(=O)c1cnc(Nc2nc3ccnn3cc2F)cc1N[C@H]1CCC[C@@H]1O] | (Abs) | 5.54 | A | 476.2 |

TABLE 10-continued
| Ex. No. | Structure | | HPLC RT (min) | HPLC cond. | LCMS (M + H) |
|---|---|---|---|---|---|
| 467 | 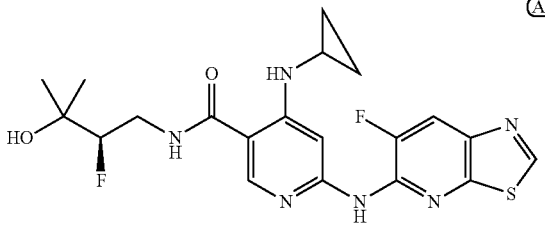 | (Abs) | 5.68 | E | 449.2 |
| 468 | 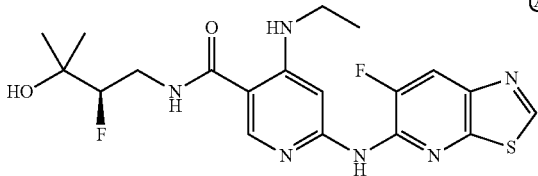 | (Abs) | 5.51 | E | 437.2 |
| 469 | 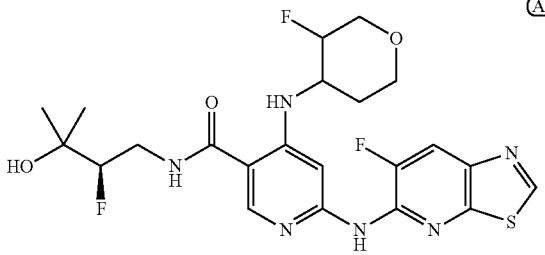 | (Abs) | 10.62 | K. | 511.5 |
| 470 | 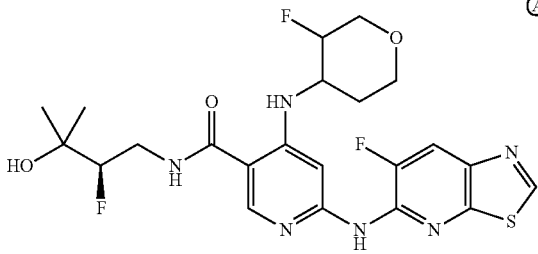 | (Abs) | 10.63 | K | 511.5 |
| 471 | 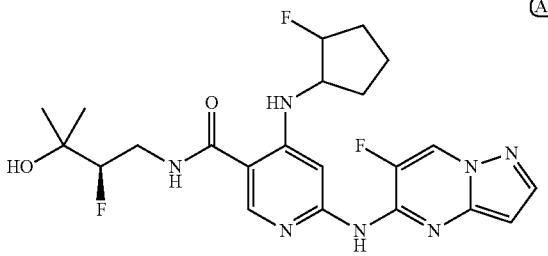 | (Abs) | 7.46 | A | 476.0 (M − H) |
| 472 | 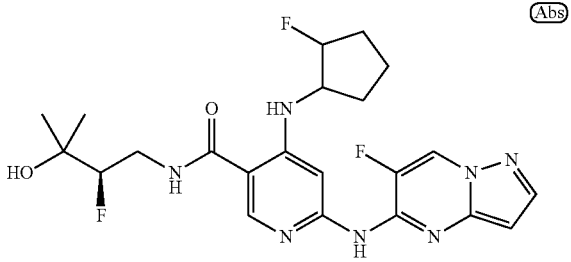 [SMILES: CC(C)(O)[C@H](F)CNC(=O)c1cnc(Nc2nc3ccnn3cc2F)cc1NC1CCCC1F] | (Abs) | 7.45 | A | 476.0 (M − H) |

TABLE 10-continued
| Ex. No. | Structure | | HPLC RT (min) | HPLC cond. | LCMS (M + H) |
|---|---|---|---|---|---|
| 473 | 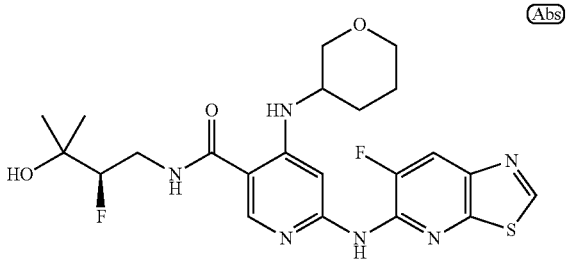 | (Abs) | 6.25 | A | 493.5 |
| 474 | 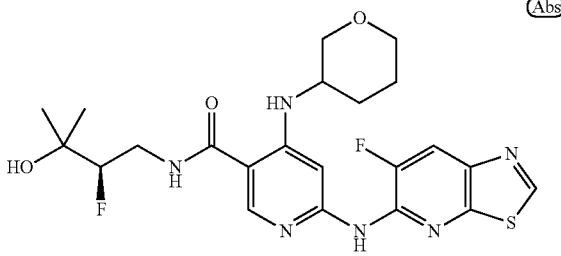 | (Abs) | 6.25 | A | 493.5 |
| 475 | 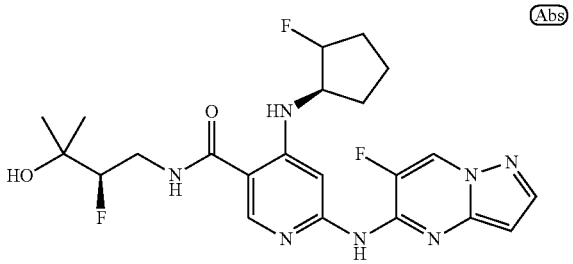 [SMILES: CC(C)(O)[C@H](F)CNC(=O)c1cnc(Nc2nc3ccnn3cc2F)cc1N[C@@H]1CCCC1F] | (Abs) | 6.08 | B | 496.2 |
| 476 | 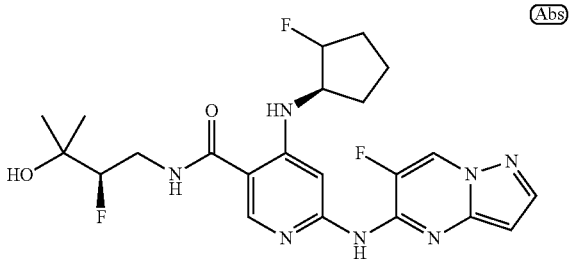 [SMILES: CC(C)(O)[C@H](F)CNC(=O)c1cnc(Nc2nc3ccnn3cc2F)cc1N[C@@H]1CCCC1F] | (Abs) | 6.08 | B | 496.2 |
| 477 | 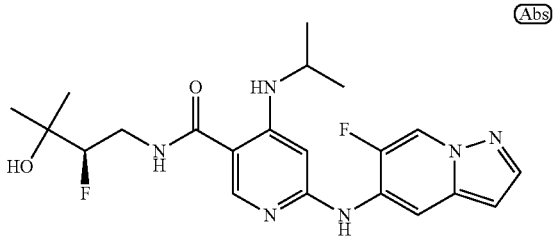 [SMILES: CC(C)Nc1cc(Nc2cc3ccnn3cc2F)ncc1C(=O)NC[C@@H](F)C(C)(C)O] | (Abs) | 6.42 | A | 433.2 |

TABLE 10-continued

| Ex. No. | Structure | HPLC RT (min) | HPLC cond. | LCMS (M + H) |
|---|---|---|---|---|
| 478 | 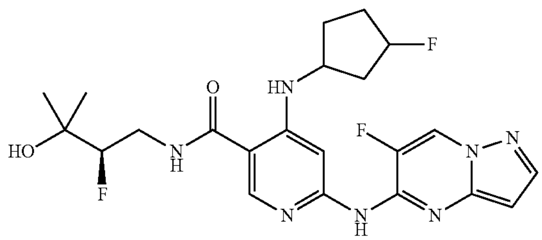 [SMILES: CC(C)(O)[C@H](F)CNC(=O)c1cnc(Nc2nc3ccnn3cc2F)cc1NC1CCC(F)C1] | 6.19 | A | 478.2 |
| 479 | 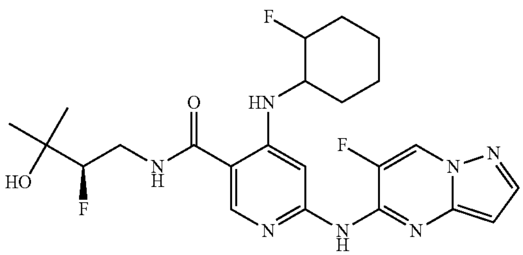 [SMILES: CC(C)(O)[C@H](F)CNC(=O)c1cnc(Nc2nc3ccnn3cc2F)cc1NC1CCCCC1F] | 7.12 | A | 492.2 |
| 480 | 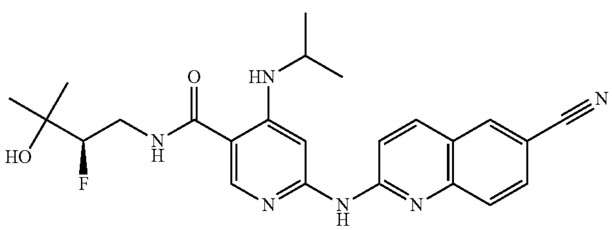 [SMILES: CC(C)Nc1cc(Nc2ccc3cc(C#N)ccc3n2)ncc1C(=O)NC[C@@H](F)C(C)(C)O] | 7.59 | A | 451.6 |
| 481 | 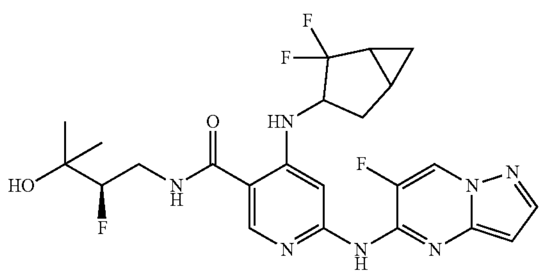 [SMILES: CC(C)(O)[C@H](F)CNC(=O)c1cnc(Nc2nc3ccnn3cc2F)cc1NC1CC2CC2C1(F)F] | 6.23 | B | 508.2 |
| 482 | 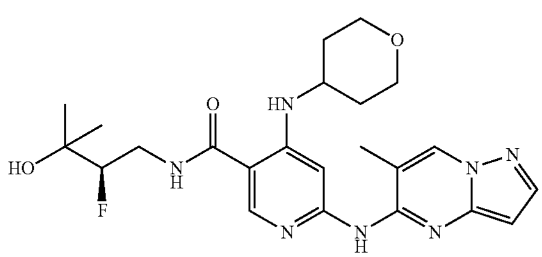 [SMILES: Cc1cn2nccc2nc1Nc1cc(NC2CCOCC2)c(C(=O)NC[C@@H](F)C(C)(C)O)cn1] | 10.6 | B | 472.6 |
| 483 | 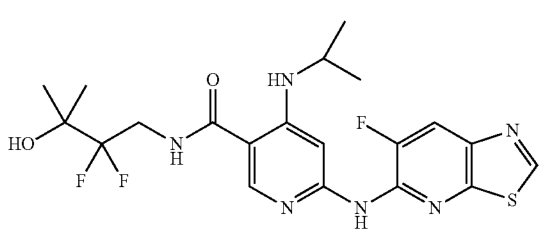 [SMILES: CC(C)Nc1cc(Nc2nc3scnc3cc2F)ncc1C(=O)NCC(F)(F)C(C)(C)O] | 6.24 | E | 467.2 (M − H) |

TABLE 10-continued
| Ex. No. | Structure | HPLC RT (min) | HPLC cond. | LCMS (M + H) |
|---|---|---|---|---|
| 484 | 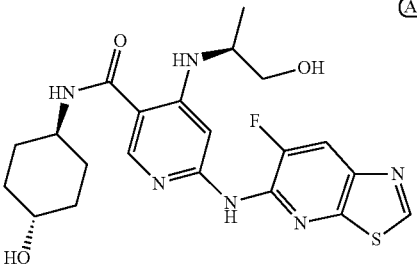 (Abs) | 9.47 | A, 18 min grad. | 461.2 |
| 485 | 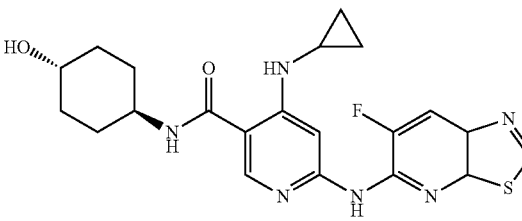 (Abs) | 10.49 | B, 23 min grad. | 443.0 |
| 486 | 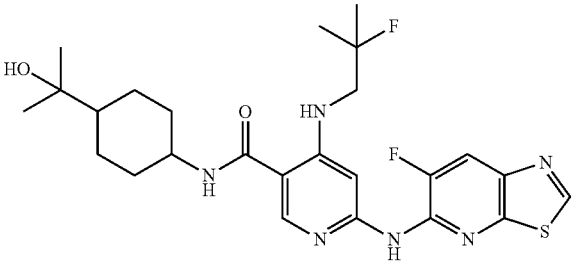 [SMILES: CC(C)(F)CNc1cc(Nc2nc3scnc3cc2F)ncc1C(=O)NC1CCC(C(C)(C)O)CC1] | 6.17 | E | 502.7 |
| 487 | 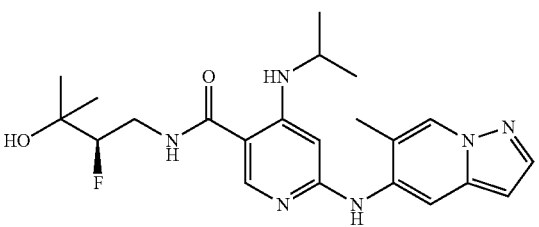 [SMILES: Cc1cn2nccc2cc1Nc1cc(NC(C)C)c(C(=O)NC[C@@H](F)C(C)(C)O)cn1] | 5.98 | B | 429.0 |
| 488 | 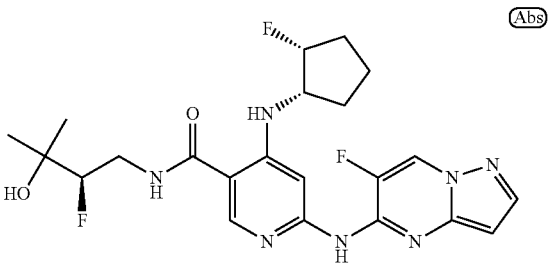 [SMILES: CC(C)(O)[C@H](F)CNC(=O)c1cnc(Nc2nc3ccnn3cc2F)cc1N[C@H]1CCC[C@H]1F] (Abs) | 6.81 | A | 478 |

TABLE 10-continued

| Ex. No. | Structure | HPLC RT (min) | HPLC cond. | LCMS (M + H) |
|---|---|---|---|---|
| 489 | 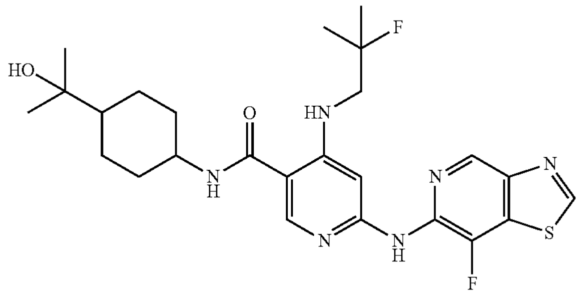 [SMILES: CC(C)(F)CNc1cc(Nc2ncc3ncsc3c2F)ncc1C(=O)NC1CCC(C(C)(C)O)CC1] | 7.66 | A | 519.3 |
| 490 | 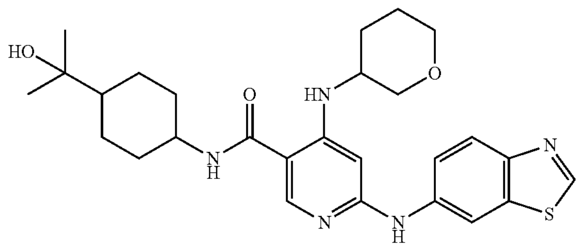 [SMILES: CC(C)(O)C1CCC(NC(=O)c2cnc(Nc3ccc4ncsc4c3)cc2NC2CCCOC2)CC1] | 6.93 | A | 510.9 |
| 491 | 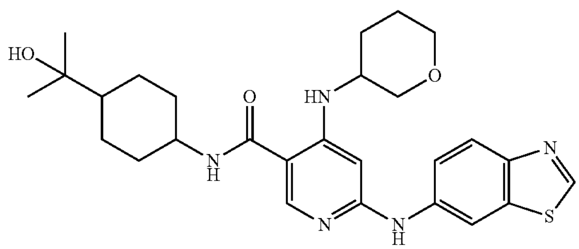 [SMILES: CC(C)(O)C1CCC(NC(=O)c2cnc(Nc3ccc4ncsc4c3)cc2NC2CCCOC2)CC1] | 6.94 | A | 510.8 |
| 492 | 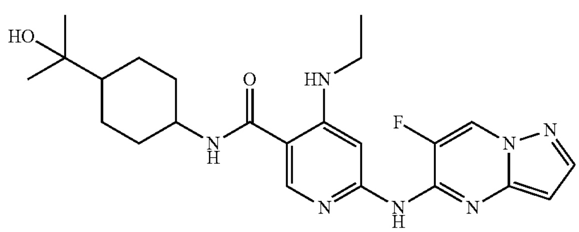 [SMILES: CCNc1cc(Nc2nc3ccnn3cc2F)ncc1C(=O)NC1CCC(C(C)(C)O)CC1] | 6.45 | A | 456.6 |
| 493 | 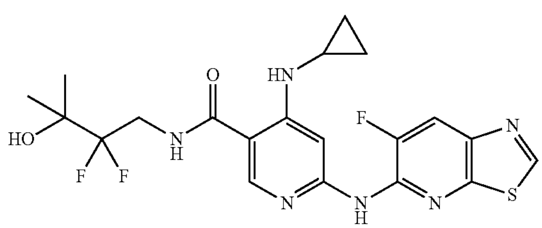 [SMILES: CC(C)(O)C(F)(F)CNC(=O)c1cnc(Nc2nc3scnc3cc2F)cc1NC1CC1] | 6.72 | A | 467.4 |
| 494 | 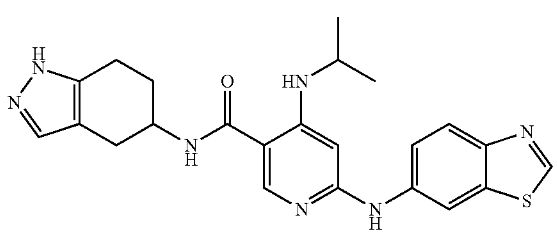 [SMILES: CC(C)Nc1cc(Nc2ccc3ncsc3c2)ncc1C(=O)NC1CCc2[nH]ncc2C1] | 1.35 | G | (M+) |

TABLE 10-continued

| Ex. No. | Structure | HPLC RT (min) | HPLC cond. | LCMS (M + H) |
|---|---|---|---|---|
| 495 | 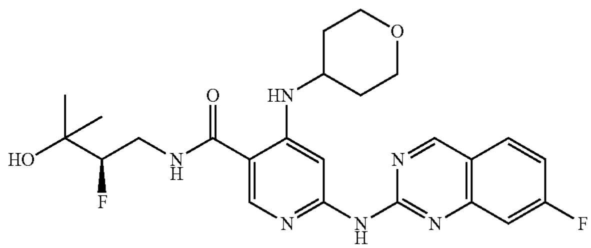 [SMILES: CC(C)(O)[C@H](F)CNC(=O)c1cnc(Nc2ncc3ccc(F)cc3n2)cc1NC1CCOCC1] | 1.43 | G | 487.2 |
| 496 | 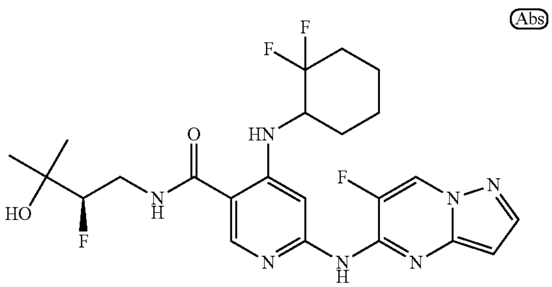 [SMILES: CC(C)(O)[C@H](F)CNC(=O)c1cnc(Nc2nc3ccnn3cc2F)cc1NC1CCCCC1(F)F] | 7.26 | A | 510.6 |
| 497 | 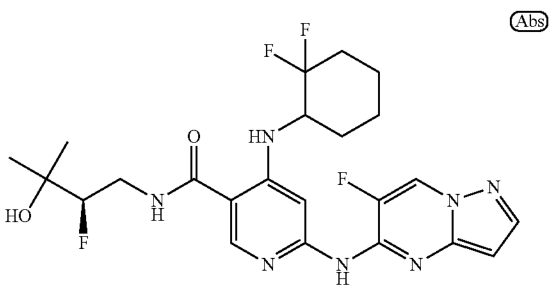 [SMILES: CC(C)(O)[C@H](F)CNC(=O)c1cnc(Nc2nc3ccnn3cc2F)cc1NC1CCCCC1(F)F] | 7.26 | A | 510.6 |
| 498 | 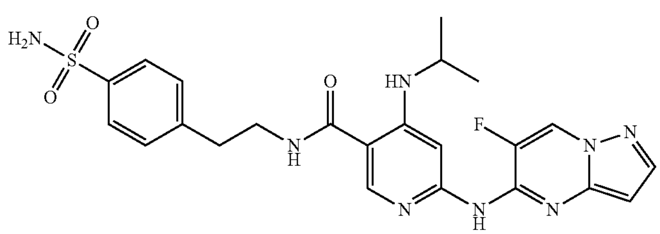 [SMILES: CC(C)Nc1cc(Nc2nc3ccnn3cc2F)ncc1C(=O)NCCc1ccc(S(N)(=O)=O)cc1] | 6.77 | A | 512 |
| 499 | 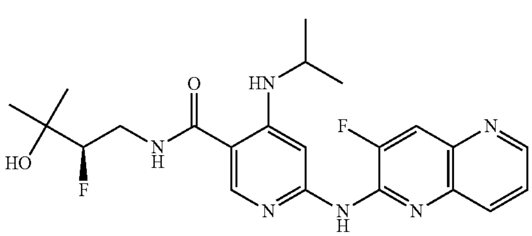 [SMILES: CC(C)Nc1cc(Nc2nc3cccnc3cc2F)ncc1C(=O)NC[C@@H](F)C(C)(C)O] | 11.94 | A | 444 |
| 500 | 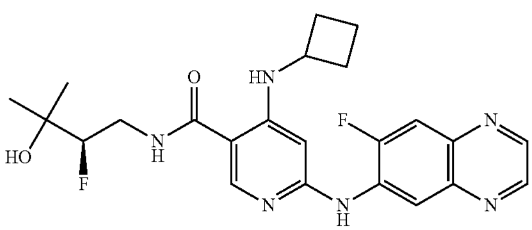 [SMILES: CC(C)(O)[C@H](F)CNC(=O)c1cnc(Nc2cc3nccnc3cc2F)cc1NC1CCC1] | 6.67 | A | 456.9 |

TABLE 10-continued

| Ex. No. | Structure | HPLC RT (min) | HPLC cond. | LCMS (M + H) |
|---|---|---|---|---|
| 501 | 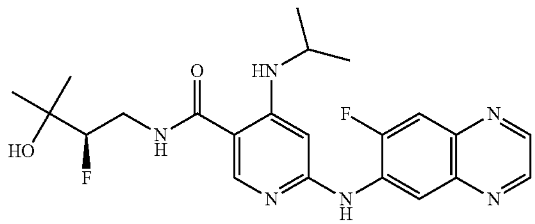 [SMILES: CC(C)Nc1cc(Nc2cc3nccnc3cc2F)ncc1C(=O)NC[C@@H](F)C(C)(C)O] | 1.45 | F | 445.0 |
| 502 | 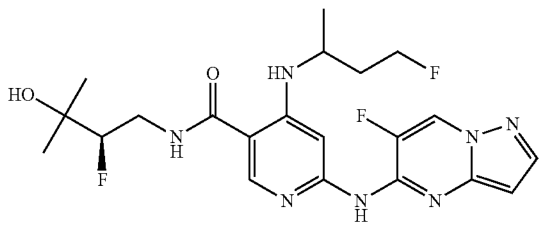 [SMILES: CC(CCF)Nc1cc(Nc2nc3ccnn3cc2F)ncc1C(=O)NC[C@@H](F)C(C)(C)O] | 5.60 | B | 466.4 |
| 503 | 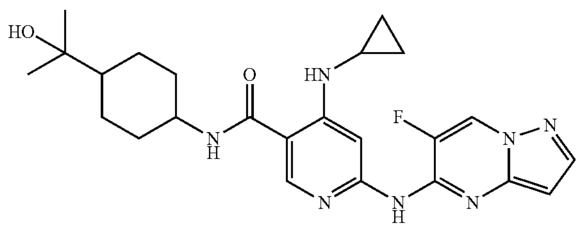 [SMILES: CC(C)(O)C1CCC(NC(=O)c2cnc(Nc3nc4ccnn4cc3F)cc2NC2CC2)CC1] | 7.00 | A | 483.2 (M − H) |
| 504 | 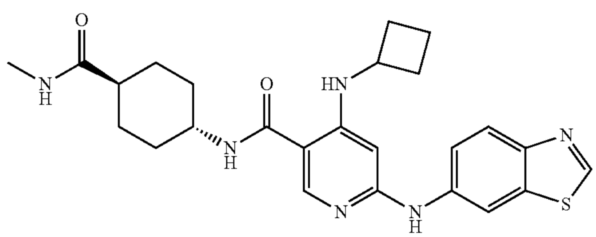 [SMILES: CNC(=O)[C@H]1CC[C@H](NC(=O)c2cnc(Nc3ccc4ncsc4c3)cc2NC2CCC2)CC1] | 1.39 | G | 479.2 |
| 505 | 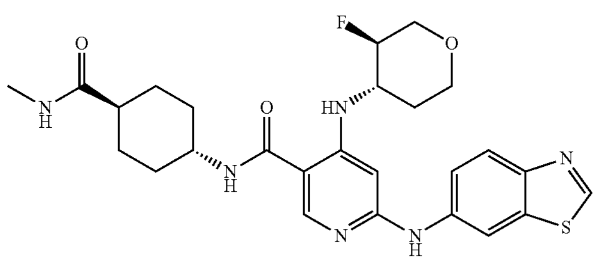 [SMILES: CNC(=O)[C@H]1CC[C@H](NC(=O)c2cnc(Nc3ccc4ncsc4c3)cc2N[C@H]2CCOC[C@@H]2F)CC1] | 1.31 | G | 547.3 (M + Na) |
| 506 | 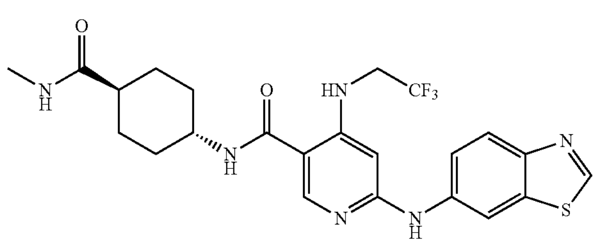 [SMILES: CNC(=O)[C@H]1CC[C@H](NC(=O)c2cnc(Nc3ccc4ncsc4c3)cc2NCC(F)(F)F)CC1] | 1.34 | G | 507.1 |

TABLE 10-continued

| Ex. No. | Structure | HPLC RT (min) | HPLC cond. | LCMS (M + H) |
|---|---|---|---|---|
| 507 | 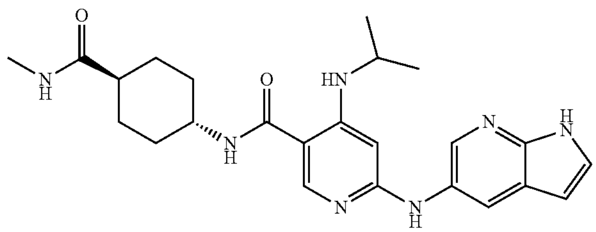 [SMILES: CNC(=O)[C@H]1CC[C@H](NC(=O)c2cnc(Nc3cnc4[nH]ccc4c3)cc2NC(C)C)CC1] | 1.02 | O | 450.2 |
| 508 | 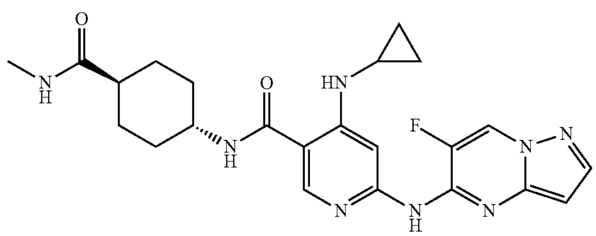 [SMILES: CNC(=O)[C@H]1CC[C@H](NC(=O)c2cnc(Nc3nc4ccnn4cc3F)cc2NC2CC2)CC1] | 1.32 | G | 467.1 |
| 509 | 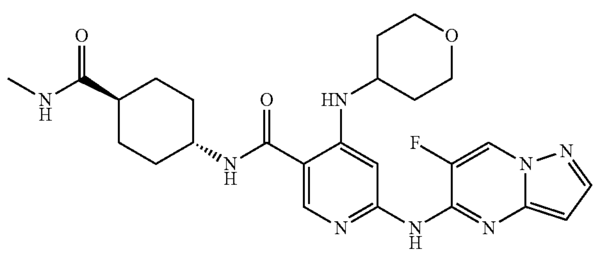 [SMILES: CNC(=O)[C@H]1CC[C@H](NC(=O)c2cnc(Nc3nc4ccnn4cc3F)cc2NC2CCOCC2)CC1] | 1.22 | G | 511.5 |
| 510 | 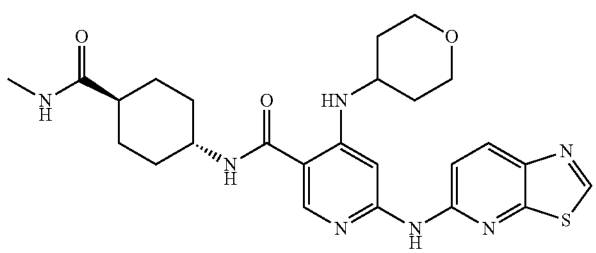 [SMILES: CNC(=O)[C@H]1CC[C@H](NC(=O)c2cnc(Nc3ccc4ncsc4n3)cc2NC2CCOCC2)CC1] | 1.11 | G | 510.3 |
| 511 | 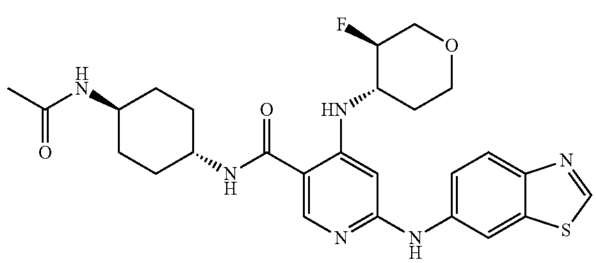 [SMILES: CC(=O)N[C@H]1CC[C@H](NC(=O)c2cnc(Nc3ccc4ncsc4c3)cc2N[C@H]2CCOC[C@@H]2F)CC1] | 1.23 | G | 527.2 |
| 512 | 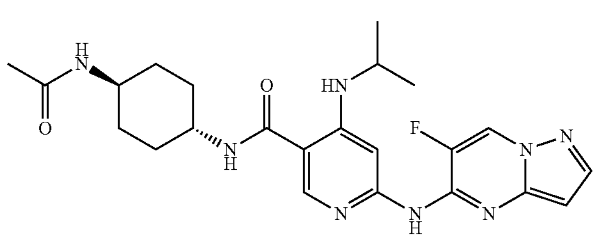 [SMILES: CC(=O)N[C@H]1CC[C@H](NC(=O)c2cnc(Nc3nc4ccnn4cc3F)cc2NC(C)C)CC1] | 5.63 | A | 469.2 |

TABLE 10-continued
| Ex. No. | Structure | HPLC RT (min) | HPLC cond. | LCMS (M + H) |
|---|---|---|---|---|
| 513 | 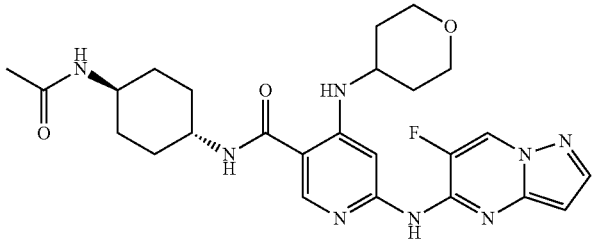 [SMILES: CC(=O)N[C@H]1CC[C@H](NC(=O)c2cnc(Nc3nc4ccnn4cc3F)cc2NC2CCOCC2)CC1] | 1.0 | O | 511.1 |
| 514 | 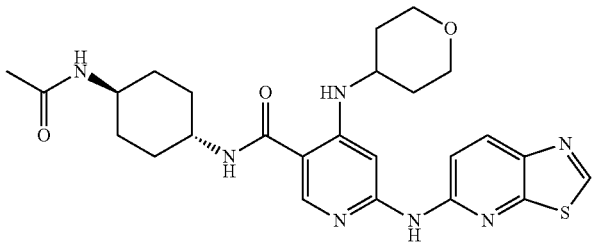 [SMILES: CC(=O)N[C@H]1CC[C@H](NC(=O)c2cnc(Nc3ccc4ncsc4n3)cc2NC2CCOCC2)CC1] | 1.01 | O | 510.1 |
| 515 | 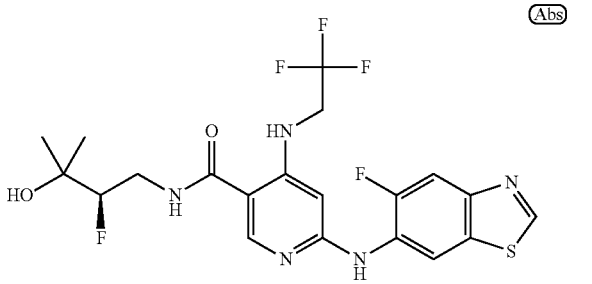 [SMILES: CC(C)(O)[C@H](F)CNC(=O)c1cnc(Nc2cc3scnc3cc2F)cc1NCC(F)(F)F] (Abs) | 6.71 | A | 490.0 |
| 516 | 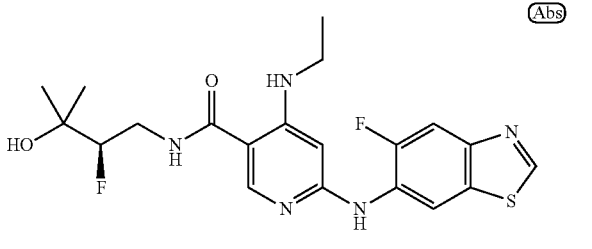 [SMILES: CCNc1cc(Nc2cc3scnc3cc2F)ncc1C(=O)NC[C@@H](F)C(C)(C)O] (Abs) | 6.25 | A | 436.2 |
| 517 | 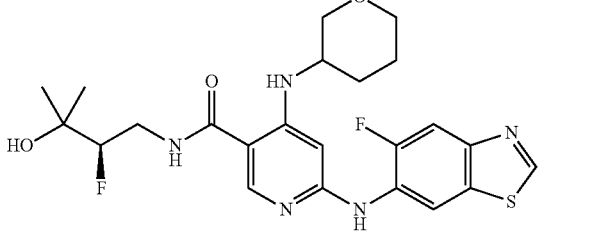 (Abs) | 6.04 | A | 492.2 |

TABLE 10-continued
| Ex. No. | Structure | | HPLC RT (min) | HPLC cond. | LCMS (M + H) |
|---|---|---|---|---|---|
| 518 | 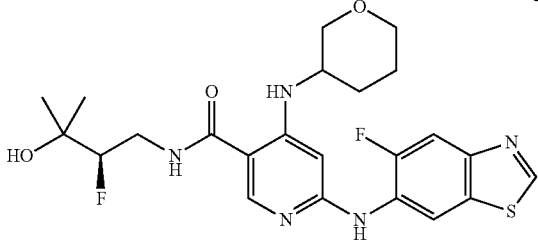 | (Abs) | 6.13 | A | 492.2 |
| 519 | 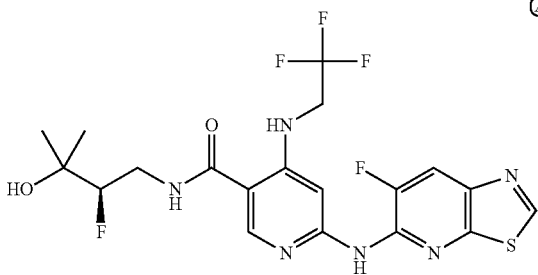 | (Abs) | 6.57 | A | 491.0 |
| 520 | 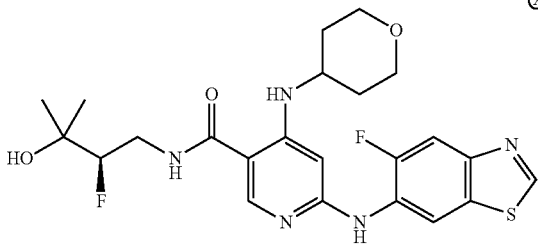 | (Abs) | 5.42 | B | 492.4 |
| 521 | 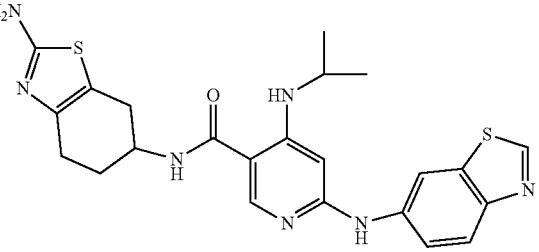 | | 1.45 | G | 480.5 |
| 522 | 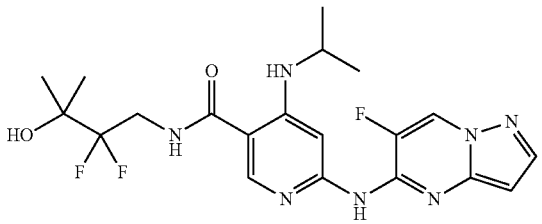 [SMILES: CC(C)Nc1cc(Nc2nc3ccnn3cc2F)ncc1C(=O)NCC(F)(F)C(C)(C)O] | | 6.59 | A | 452.2 |

Example 523

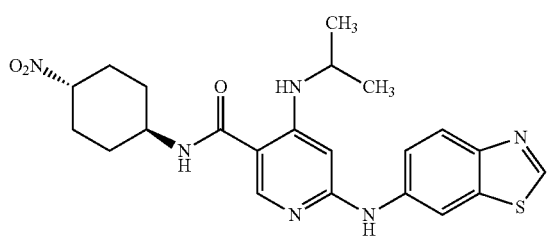 [SMILES: CC(C)Nc1cc(Nc2ccc3ncsc3c2)ncc1C(=O)N[C@H]1CC[C@H]([N+](=O)[O-])CC1]

6-(Benzo[d]thiazol-6-ylamino)-4-(isopropylamino)nicotinic acid (0.055 g, 0.166 mmol), trans-4-nitrocyclohexanamine, HCl (0.030 g, 0.166 mmol), and Hunig's Base (0.290 mL, 1.661 mmol) were dissolved in DMF (2 mL) and to this mixture was added PyBOP (0.190 g, 0.365 mmol). The mixture was stirred at RT and monitored by LCMS. The reaction mixture was filtered and purified by preparative LC/MS. Fractions containing the desired product were combined and dried via centrifugal evaporation to yield 8.3 mg (11%) of 6-(benzo[d]thiazol-6-ylamino)-4-(isopropylamino)-N-((trans)-4-nitrocyclohexyl)nicotinamide. $^1$H NMR (500 MHz, DMSO-$d_6$) δ 9.85-9.18 (m, 1H), 8.65-8.22 (m, 3H), 8.09-7.91 (m, 1H), 7.52 (d, J=8.8 Hz, 1H), 6.02 (s, 1H), 4.83-4.54 (m, 1H), 3.98-3.55 (m, 1H), 2.30 (d, J=11.4 Hz, 2H), 2.00-1.69 (m, 4H), 1.64-1.38 (m, 2H), 1.20 (d, J=6.1 Hz, 6H). HPLC rt, 1.87 min, conditions G, respectively. LCMS 455.1 (M+H)$^+$.

Example 524

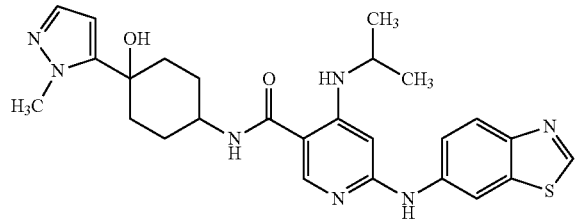 [SMILES: CC(C)Nc1cc(Nc2ccc3ncsc3c2)ncc1C(=O)NC1CCC(O)(c2ccnn2C)CC1]

4-Amino-1-(1-methyl-1H-pyrazol-5-yl)cyclohexanol, HCl (79 mg, 0.339 mmol) was added to a mixture of 6-(benzo[d]thiazol-6-ylamino)-4-(isopropylamino)nicotinic acid (111 mg, 0.34 mmol) and Hunig's Base (0.592 mL, 3.39 mmol) in DMF (3 mL) and to this mixture was added PyBOP (388 mg, 0.746 mmol). The reaction mixture was stirred at rt and monitored by LCMS. The following day, the reaction was worked up by adding EtOAc, washing with 1N NaOH (3×), brine (1×), drying (sodium sulfate) and removing the solvent in vacuo to yield a brown oil. The crude mixture was purified by preparative LC/MS with isolate 02 being isolated first followed by repurifying collected impure isolate 1. Fractions containing the desired products were combined and dried via centrifugal evaporation to yield the regioisomeric isomers-6-(benzo[d]thiazol-6-ylamino)-N-(4-hydroxy-4-(1-methyl-1H-pyrazol-5-yl)cyclohexyl)-4-(isopropylamino)nicotinamide. Weights of isolates 1 and 2 were 39.0 (23%) and 5.6 mg (3%), respectively. $^1$H NMR isolate 1 (500 MHz, DMSO-$d_6$) δ 9.23 (s, 1H), 8.70 (s, 1H), 8.42 (s, 1H), 8.26 (d, J=7.4 Hz, 1H), 8.09 (d, J=7.7 Hz, 1H), 7.95 (d, J=3.0 Hz, 1H), 7.56 (d, J=8.8 Hz, 1H), 7.25 (s, 1H), 6.10 (s, 1H), 6.00 (s, 1H), 3.97 (s, 3H), 3.77 (br. s., 1H), 3.64-3.51 (m, 1H), 3.17 (d, J=4.7 Hz, 1H), 2.03 (d, J=11.1 Hz, 2H), 1.90 (s, 1H), 1.89-1.79 (m, 2H), 1.75-1.59 (m, 4H), 1.20 (d, J=6.4 Hz, 6H). HPLC rt isolate 1, 1.60 min, conditions G. LCMS 506.2 (M+H)$^+$.

Example 525

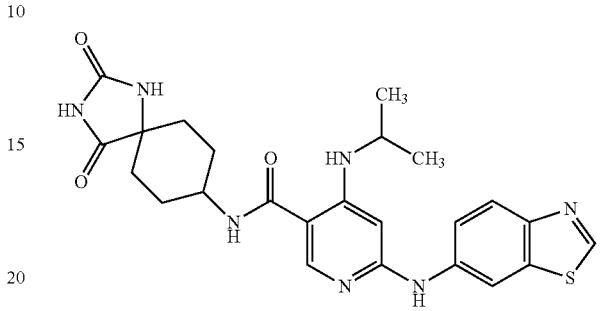

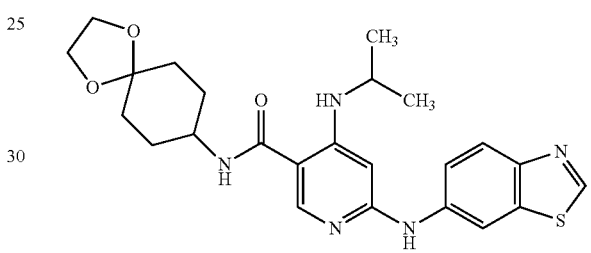

Step 1. 6-(Benzo[d]thiazol-6-ylamino)-4-(isopropylamino)nicotinic acid (0.066 g, 0.2 mmol), 1,4-dioxaspiro[4.5]decan-8-amine (0.031 g, 0.200 mmol), and Hunig's Base (0.175 ml, 1.000 mmol) were dissolved in DMF. To this solution was then added PyBOP (0.104 g, 0.200 mmol) and the contents were stirred at rt. The reaction was monitored by LCMS. After 2 h, the reaction was quenched with water, and ethyl acetate was added. The layers were separated and the organic layer was washed with 1.000 N NaOH (3×), brine (1×), the organic layer was dried (sodium sulfate), and the solvent removed in vacuo to yield 0.158 g of 6-(benzo[d]thiazol-6-ylamino)-4-(isopropylamino)-N-(1,4-dioxaspiro[4.5]decan-8-yl)nicotinamide as a brown oil. LCMS 468.3 (M+H)$^+$.

Step 2. 6-(Benzo[d]thiazol-6-ylamino)-4-(isopropylamino)-N-(1,4-dioxaspiro[4.5]decan-8-yl)nicotinamide (0.094 g, 0.2 mmol) was dissolved in acetonitrile (2 mL). To this solution was added 1N HCl (2.000 mL, 2.000 mmol). The contents were stirred at RT. After one hour, LCMS detects product. The next day, the reaction was worked up by adding 2 mL 1.0 N NaOH followed by EtOAc. The layers were separated, and the aqueous layer extracted with EtOAc (2×). The organic layers were combined, dried (sodium sulfate) and the solvent removed in vacuo to yield a brown oil. The product was purified by flash chromatography in 1:1 hexanes/EtOAc to 100% EtOAc. The product fractions were collected and the solvent removed in vacuo to yield 0.0784 g of 6-(benzo[d]thiazol-6-ylamino)-4-(isopropylamino)-N-(4-oxocyclohexyl)nicotinamide as a brown gum. LCMS 424.3 (M+H)$^+$.

Step 3: 6-(Benzo[d]thiazol-6-ylamino)-4-(isopropylamino)-N-(4-oxocyclohexyl)nicotinamide (0.0784 g, 0.185 mmol), was slurried in EtOH (1 mL). Carbonic acid, ammonium salt (0.231 g, 2.406 mmol) (ammonium carbonate) and potassium cyanide (0.030 g, 0.463 mmol) were dissolved in water (1 mL). The two mixtures were combined and stirred in a 20 dram Teflon-capped vial equipped with a magnetic stir bar at 80° C. for 2.5 hours. The reaction was monitored by LCMS: 494.3 (M+H)⁺. Water and EtOAc were added to the mixture and the insoluble material was filtered. The layers were separated and the organic layer was washed with water (2×), dried (sodium sulfate), and the solvent removed in vacuo to yield a pink solid. The crude mixture was purified by preparative LC/MS (Fractions containing the desired products were combined and dried via centrifugal evaporation to yield the regioisomeric isolates E- or Z-6-(benzo[d]thiazol-6-ylamino)-N-(2,4-dioxo-1,3-diazaspiro[4.5]decan-8-yl)-4-(isopropylamino)nicotinamide. Weights of isolates 1 and 2 were 11.0 (11%) and 3.4 mg (4%), respectively. $^1$H NMR isolate 2 (500 MHz, 1:1 chloroform-d:methanol-d$_4$) δ 9.19 (s, 1H), 8.22-8.11 (m, 2H), 7.98 (d, J=2.0 Hz, 1H), 7.50 (dd, J=8.4, 2.0 Hz, 1H), 5.97 (s, 1H), 4.03-3.89 (m, 1H), 3.66-3.55 (m, 1H), 2.15-1.91 (m, 4H), 1.82-1.73 (m, 2H), 1.60-1.47 (m, 2H), 1.26 (d, J=6.4 Hz, 6H). HPLC rt isolate 2: 1.17 min, conditions 0. LCMS isolate 2, 494.2 (M+H)⁺.

Example 526

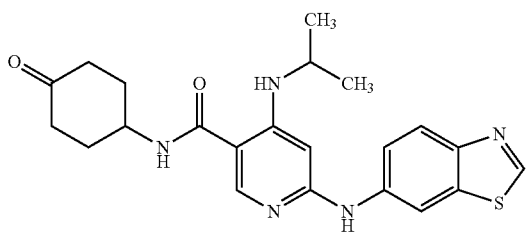 [SMILES: CC(C)Nc1cc(Nc2ccc3ncsc3c2)ncc1C(=O)NC1CCC(=O)CC1]

6-(Benzo[d]thiazol-6-ylamino)-4-(isopropylamino)nicotinic acid (0.318 g, 0.969 mmol), 4-aminocyclohexanone, HCl (0.1450 g, 0.969 mmol), and Hunig's Base (1.693 mL, 9.69 mmol) were dissolved in DMF (9 mL) and to this mixture was added PyBOP (0.555 g, 1.066 mmol). The mixture was stirred at rt. The following day, product was detected by LCMS and the reaction was worked up by adding EtOAc, washing the organic mixture with 1N NaOH (3×), and brine (1×). The organic layer was dried (sodium sulfate) and the solvent removed in vacuo to yield 0.557 g of a yellow solid. The crude product was flash chromatographed over silica gel in 100% EtOAc to yield 0.272 g (64%) of 6-(benzo[d]thiazol-6-ylamino)-4-(isopropylamino)-N-(4-oxocyclohexyl)nicotinamide as an off-white glass. $^1$H NMR (400 MHz, DMSO-d$_6$) δ 9.23 (s, 1H), 9.14 (s, 1H), 8.70 (d, J=2.2 Hz, 1H), 8.42 (s, 1H), 8.20 (d, J=7.0 Hz, 1H), 8.12 (d, J=7.5 Hz, 1H), 7.94 (d, J=8.8 Hz, 1H), 7.57 (dd, J=9.0, 2.2 Hz, 1H), 6.02 (s, 1H), 4.33-4.17 (m, 1H), 3.71-3.51 (m, 1H), 2.49-2.42 (m, 2H), 2.38-2.28 (m, 2H), 2.08 (dd, J=12.8, 4.2 Hz, 2H), 1.86-1.71 (m, 2H), 1.22 (d, J=6.2 Hz, 6H). LCMS 424.2 (M+H)⁺. R$_f$ (100% EtOAc)= 0.2.

Example 527

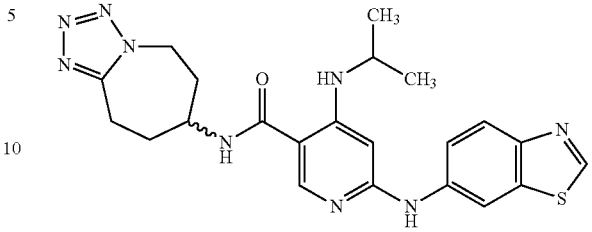

6-(Benzo[d]thiazol-6-ylamino)-4-(isopropylamino)-N-(4-oxocyclohexyl)nicotinamide (0.020 g, 0.047 mmol) was dissolved in acetonitrile (1 mL) and to this was sodium azide (9.21 mg, 0.142 mmol) and lastly silicon tetrachloride (5.42 µl, 0.047 mmol). The contents were stirred at rt overnight behind a blast shield. The following day, LCMS detects product together with starting material and several other peaks. Stirring for yet another day yielded essentially one product peak by LCMS. The reaction was taken up in EtOAc and washed with water (1×). The organic layer was evaporated, the crude product was purified by preparative LC/MS and fractions containing the desired product were combined and dried via centrifugal evaporation to yield 1.5 mg (7%) of 6-(benzo[d]thiazol-6-ylamino)-4-(isopropylamino)-N-(6,7,8,9-tetrahydro-5H-tetrazolo[1,5-a]azepin-7-yl)nicotinamide. $^1$H NMR (500 MHz, DMSO-d) δ 9.25 (s, 1H), 9.13 (s, 1H), 8.68 (d, J=2.2 Hz, 1H), 8.42 (s, 1H), 8.24 (d, J=7.8 Hz, 1H), 8.17 (d, J=6.9 Hz, 1H), 8.02-7.85 (m, 2H), 7.56 (dd, J=8.9, 2.2 Hz, 1H), 6.02 (s, 1H), 4.91-4.79 (m, 1H), 4.51-4.39 (m, 1H), 4.32-4.23 (m, 1H), 3.58 (d, J=6.4 Hz, 1H), 3.04-2.95 (m, 1H), 2.18 (d, J=9.7 Hz, 1H), 2.08 (dt, J=6.9, 3.4 Hz, 1H), 1.81-1.67 (m, 2H), 1.57 (dd, J=12.1, 1.8 Hz, 1H), 1.22 (d, J=6.1 Hz, 6H). LCMS 464.2 (M+H)⁺. HPLC rt 1.06 min, conditions 0. LCMS 463.8 (M+H)⁺.

What is claimed is:
1. A compound of Formula (II)

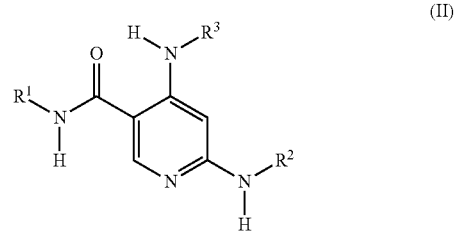

(II)

or a stereoisomer or pharmaceutically-acceptable salt thereof, wherein:

$R^1$ is:
(a) $C_{2-3}$ hydroxyalkyl substituted with zero to 4 $R^{1a}$ wherein $R^{1a}$ is independently selected from F, Cl, —OH, —CHF$_2$, —CN, —CF$_3$, —OCH$_3$, and cyclopropyl;
(b) $C_{4-8}$ alkyl substituted with zero to 7 $R^{1a}$ wherein $R^{1a}$ is independently selected from F, Cl, —OH, —CHF$_2$, —CF$_3$, —CN—OCH$_3$, and cyclopropyl;
(c) —(CH$_2$)$_{2-4}$NHC(O)(C$_{1-6}$ alkyl), —(CH$_2$)$_2$CH(CH$_3$)NHC(O)(C$_{1-6}$ alkyl), —(CH$_2$)$_2$CH(CH$_3$)NHC(O)O(C$_{1-6}$ alkyl), —(CH$_2$)$_2$CH(CH$_3$)NHC(O)(CH$_2$)$_{0-1}$NH(C$_{1-6}$ alkyl), —(CH$_2$)$_2$CH(CH$_3$)NHC(O)(CH$_2$)$_{0-1}$N (C$_{1-4}$ alkyl)$_2$, —(CH$_2$)$_2$CH(CH$_3$)NHC(O)(CH$_2$)$_{0-1}$ (C$_{3-6}$ cycloalkyl), —(CH$_2$)$_2$CH(CH$_3$)NHC(O)(CH$_2$)$_{0-1}$ (C$_{3-6}$ fluorocycloalkyl), —(CH$_2$)$_2$CH(CH$_3$)NHC(O) (C$_{1-6}$ hydroxyalkyl), —(CH$_2$)$_2$CH(CH$_3$)NHC(O)N (C$_{1-3}$ alkyl)(phenyl), or —(CH$_2$)$_2$CH(CH$_3$)NHC(O) (CH$_2$)$_{0-1}$R wherein R is phenyl, morpholinyl, pyrrolidinyl, triazolyl, or tetrahydropyranyl;

(d) cyclohexyl substituted with zero to 2 substituents selected from —OH, —OCH$_3$, =O, —NH$_2$, C$_{1-6}$ alkyl, C$_{1-6}$ hydroxyalkyl, —NHS(O)$_2$CH$_3$, —NO$_2$, —C(O)NH$_2$, —C(O)NH(C$_{1-3}$ alkyl), —C(O)NH(C$_{1-6}$ hydroxyalkyl), —C(O)NH(C$_{3-6}$ cycloalkyl), —C(O)NH(C$_{3-6}$ cyano cycloalkyl), —NHC(O)(C$_{1-3}$ alkyl), —NHC(O)(pyridinyl), —NHC(O)(morpholinyl), —NHC(O)(hydroxy bicyclo[2.2.1]heptanyl), —NHC(O)NH(C$_{1-4}$ alkyl), and methyl pyrazolyl; or (e) —(CH$_2$)$_2$(phenyl) wherein said phenyl is substituted with —C(O)NH$_2$, —C(O)NH(C$_{1-3}$ alkyl), or —S(O)$_2$NH$_2$; or (f)

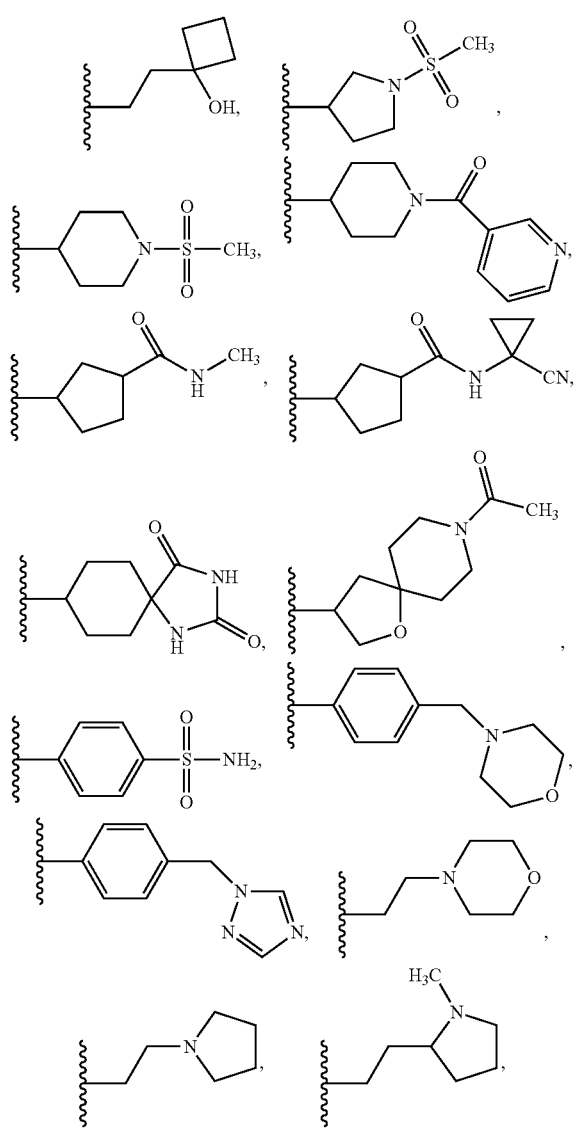

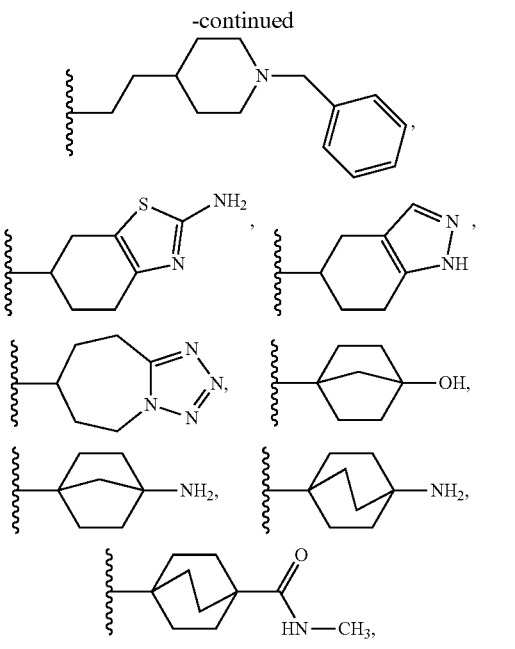

R$^2$ is benzooxazolyl, pyrazolopyridinyl, pyrrolopyridinyl, benzothiazolyl, thiazolopyridinyl, pyrazolopyrimidinyl, benzooxadiazolyl, benzothiadiazolyl, quinolinyl, isoquinolinyl, cinnolinyl, quinazolinyl, quinoxalinyl, 1,5-naphthyrindinyl, pyridopyrazinyl, or pyridopyrimidinyl, each substituted with zero to 2 substituents independently selected from F, Cl, —CH$_3$, —CN, —NH$_2$, —OCH$_3$, =O, and —C(O)NH$_2$;

R$^3$ is:

(a) C$_{2-6}$ alkyl or C$_{2-6}$ fluoroalkyl;

(b) C$_{1-3}$ alkyl substituted with 1 to 2 cyclopropyl;

(c) C$_{1-3}$ alkyl substituted with phenyl, tetrahydrofuranyl, or morpholinyl;

(d) C$_{2-6}$ hydroxyalkyl substituted with zero to 3 substituents selected from F, phenyl, fluorophenyl, difluorophenyl, and dichlorophenyl;

(e) —(CH$_2$)$_{0-2}$(C$_{3-7}$ cycloalkyl) substituted with zero to 2 substituents selected from F, —OH, C$_{1-3}$ hydroxyalkyl, —CH$_3$, —CF$_2$H, —NH$_2$, and —C(O)OCH$_2$CH$_3$;

(f) tetrahydropyranyl or tetrahydrothiopyranyl substituted with zero to 1 substituent selected from F and —CH$_3$;

(g) —(CH$_2$)$_{0-2}$phenyl wherein said phenyl is substituted with zero to 2 substituents selected from F, Cl, C$_{1-3}$ alkyl, C$_{1-3}$ hydroxyalkyl, —OH, —O(C$_{1-3}$ alkyl), —OCF$_3$, —C(O)NH$_2$, —C(O)NH(C$_{1-3}$ alkyl), —C(O)NH(C$_{1-3}$ fluoroalkyl), —C(O)NH(C$_{1-3}$ hydroxyalkyl), —C(O)NH(C$_{3-5}$ cycloalkyl), —C(O)N(C$_{1-3}$ alkyl)$_2$, —S(O)$_2$CH$_3$, and pyrazolyl;

(h) thiazolyl substituted with zero to 2 substituents selected from C$_{1-3}$ hydroxyalkyl; or (i)

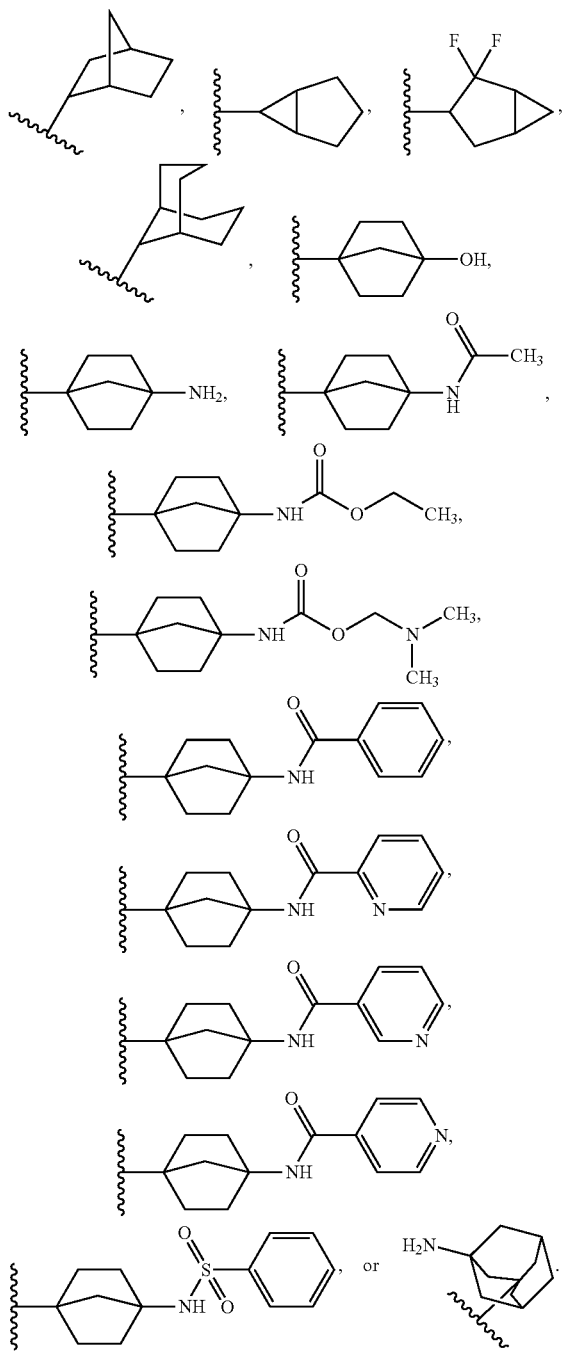

2. The compound according to claim 1 or a stereoisomer or pharmaceutically-acceptable salt thereof, wherein:
$R^1$ is:
(a) hydroxypropyl substituted with zero to 3 $R^{1a}$ wherein $R^{1a}$ is independently selected from F, —$CF_3$, and cyclopropyl;
(b) $C_{4-8}$ alkyl substituted with zero to 5 $R^{1a}$ wherein $R^{1a}$ is independently selected from F, Cl, —OH, —$CHF_2$, —$CF_3$, —CN—$OCH_3$, and cyclopropyl;
(c) —$(CH_2)_{2-4}$NHC(O)($C_{1-3}$ alkyl), —$(CH_2)_2$CH($CH_3$)NHC(O)($C_{1-3}$ alkyl), —$(CH_2)_2$CH($CH_3$)NHC(O)O ($C_{1-3}$ alkyl), —$(CH_2)_2$CH($CH_3$)NHC(O)$(CH_2)_{0-1}$NH ($C_{1-3}$ alkyl), —$(CH_2)_2$CH($CH_3$)NHC(O)$(CH_2)_{0-1}$N ($C_{1-3}$ alkyl)$_2$, —$(CH_2)_2$CH($CH_3$)NHC(O)$(CH_2)_{0-1}$ ($C_{3-6}$ cycloalkyl), —$(CH_2)_2$CH($CH_3$)NHC(O)$(CH_2)_{0-1}$ ($C_{3-6}$ fluorocycloalkyl), —$(CH_2)_2$CH($CH_3$)NHC(O) ($C_{1-6}$ hydroxyalkyl), —$(CH_2)_2$CH($CH_3$)NHC(O)N ($CH_3$)(phenyl), or —$(CH_2)_2$CH($CH_3$)NHC(O)$(CH_2)_{0-1}$ R wherein R is phenyl, morpholinyl, pyrrolidinyl, triazolyl, or tetrahydropyranyl;
(d) cyclohexyl substituted with zero or 2 substituents selected from —OH, —$OCH_3$, =O, —$NH_2$, $C_{1-3}$ alkyl, $C_{1-3}$ hydroxyalkyl, —NHS(O)$_2$$CH_3$, —$NO_2$, —C(O) $NH_2$, —C(O)NH($C_{1-2}$ alkyl), —C(O)NH($C_{1-4}$ hydroxyalkyl), —C(O)NH($C_{3-6}$ cycloalkyl), —C(O) NH($C_{3-4}$ cyano cycloalkyl), —NHC(O)($C_{1-3}$ alkyl), —NHC(O)(pyridinyl), —NHC(O)(morpholinyl), —NHC(O)(hydroxy bicyclo[2.2.1]heptanyl), —NHC(O)NH($C_{1-4}$ alkyl), and methyl pyrazolyl;
(e) —$(CH_2)_2$(phenyl) wherein said phenyl is substituted with —C(O)$NH_2$, —C(O)NH($C_{1-3}$ alkyl), or —S(O)$_2$ $NH_2$; or —$CH_2$(phenyl); or
(f)

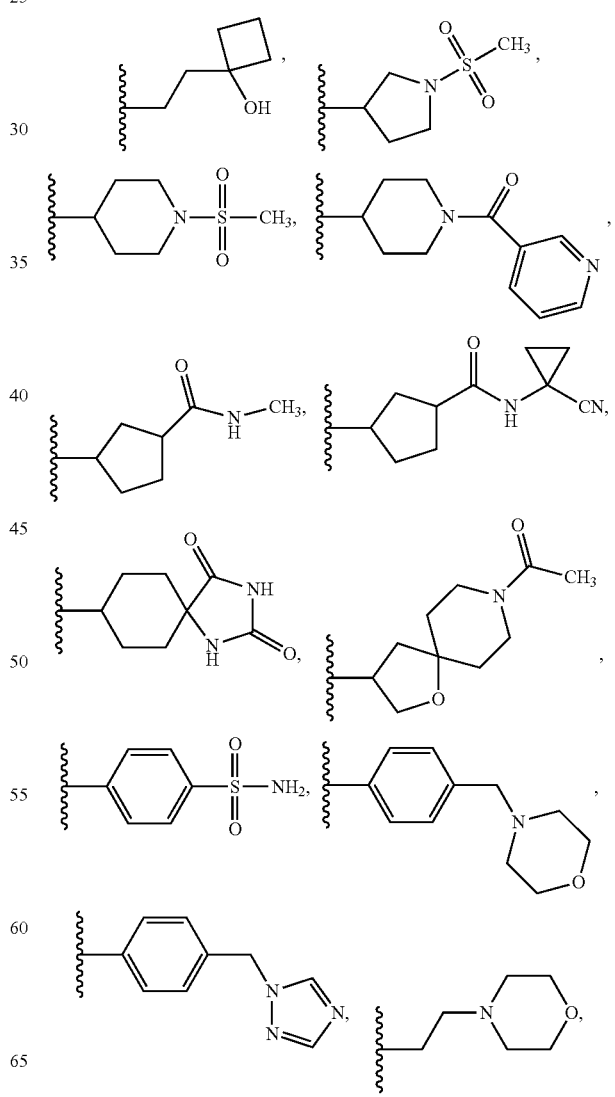

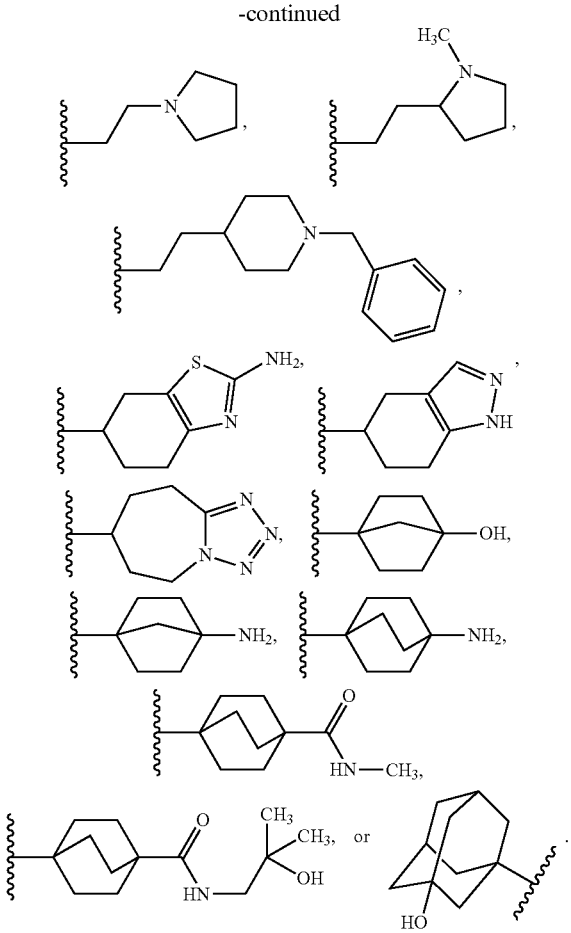
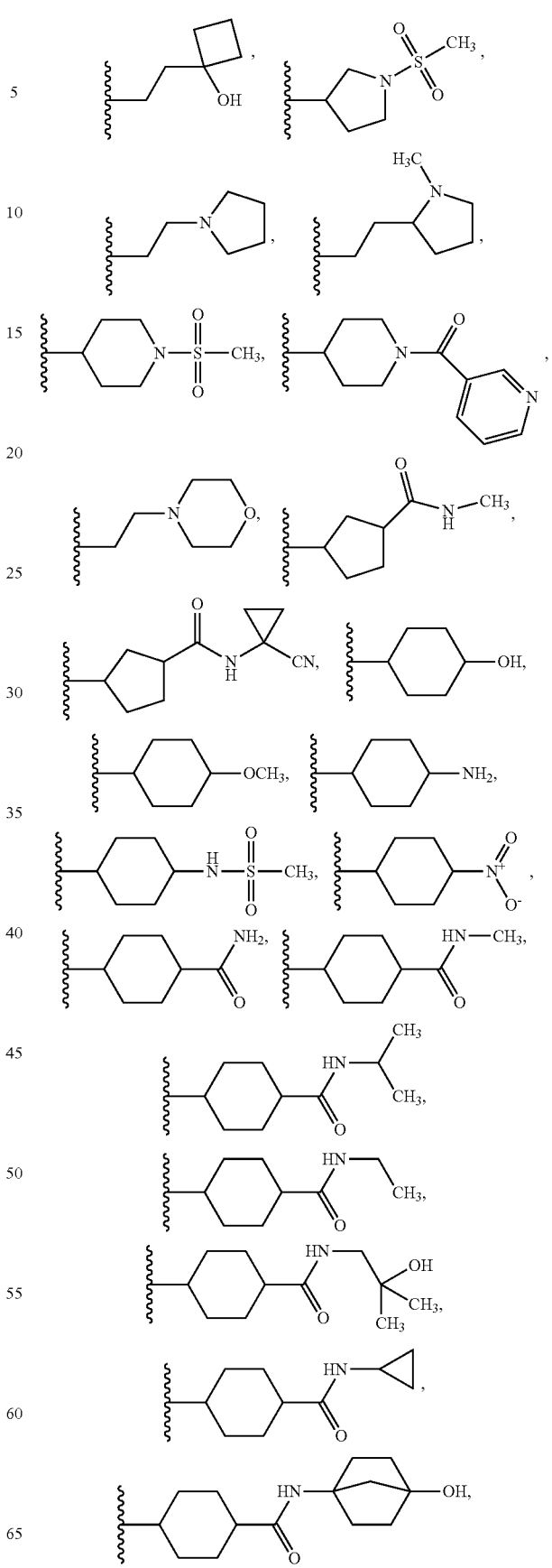

3. The compound according to claim 1 or a stereoisomer or pharmaceutically-acceptable salt thereof, wherein:

$R^1$ is: —CH$_2$CH$_2$CH(CH$_3$)$_2$, —(CH$_2$)$_2$C(CH$_3$)$_2$OH, —CH$_2$CHFCH$_2$OH, —CH$_2$CHFCH(CH(CH$_3$)$_2$)OH, —CH$_2$CHFCH(cyclopropyl)OH, —CH$_2$CHFCH(CH$_3$)OH, —CH$_2$CHFCH(cyclopropyl)(CF$_3$)OH, —CH$_2$CHFC(CH$_3$)$_2$OH, —CH$_2$CHFC(CH$_3$)(CH$_2$CH$_3$)OH, —CH$_2$CHFC(CH$_2$CH$_3$)$_2$OH, —CH$_2$CHFC(CH$_3$)(CF$_3$)OH, —CH$_2$CF$_2$C(CH$_3$)$_2$OH, —(CH$_2$)$_2$NHC(O)CH$_3$, —(CH$_2$)$_3$NHC(O)CH$_3$, —(CH$_2$)$_4$NHC(O)CH$_3$, —(CH$_2$)$_2$CH(CH$_3$)NHC(O)CH$_3$, —(CH$_2$)$_2$CH(CH$_3$)NHC(O)OCH(CH$_3$)$_2$, —(CH$_2$)$_2$CH(CH$_3$)NHC(O)OC(CH$_3$)$_3$, —(CH$_2$)$_2$CH(CH$_3$)NHC(O)CH$_2$N(CH$_3$)$_2$, —(CH$_2$)$_2$CH(CH$_3$)NHC(O)NHCH(CH$_3$)$_2$, —(CH$_2$)$_2$CH(CH$_3$)NHC(O)(cyclopropyl), —(CH$_2$)$_2$CH(CH$_3$)NHC(O)(3-fluorocyclopentyl), —(CH$_2$)$_2$CH(CH$_3$)NHC(O)(3,3-difluorocyclopentyl), —(CH$_2$)$_2$CH(CH$_3$)NHC(O)(morpholinyl), —(CH$_2$)$_2$CH(CH$_3$)NHC(O)(phenyl), —(CH$_2$)$_2$CH(CH$_3$)NHC(O)(pyrrolidinyl), —(CH$_2$)$_2$CH(CH$_3$)NHC(O)CH$_2$(tetrahydropyranyl), —(CH$_2$)$_2$CH(CH$_3$)NHC(O)CH$_2$(2,2-difluorocyclohexyl), —(CH$_2$)$_2$CH(CH$_3$)NHC(O)CH$_2$(triazolyl), —(CH$_2$)$_2$CH(CH$_3$)NHC(O)(CH$_2$)$_3$C(CH$_3$)$_2$OH, —(CH$_2$)$_2$CH(CH$_3$)NHC(O)(CH$_2$)$_4$C(CH$_3$)$_2$OH, —(CH$_2$)$_2$CH(CH$_3$)NHC(O)N(CH$_3$)(phenyl),

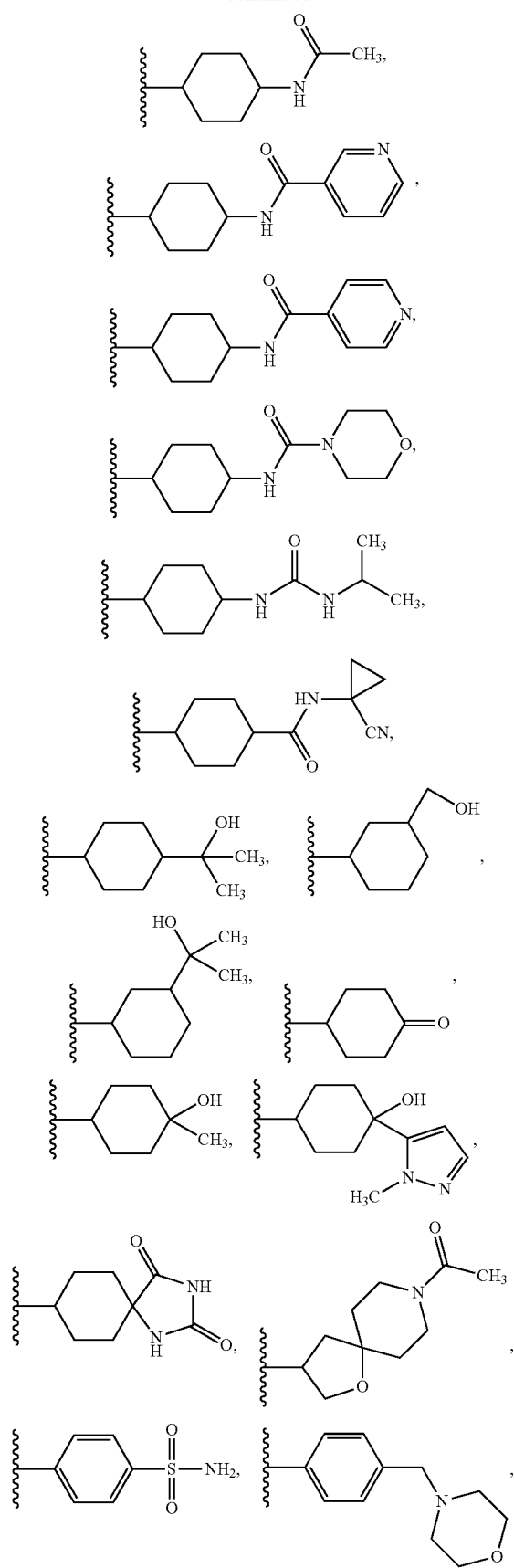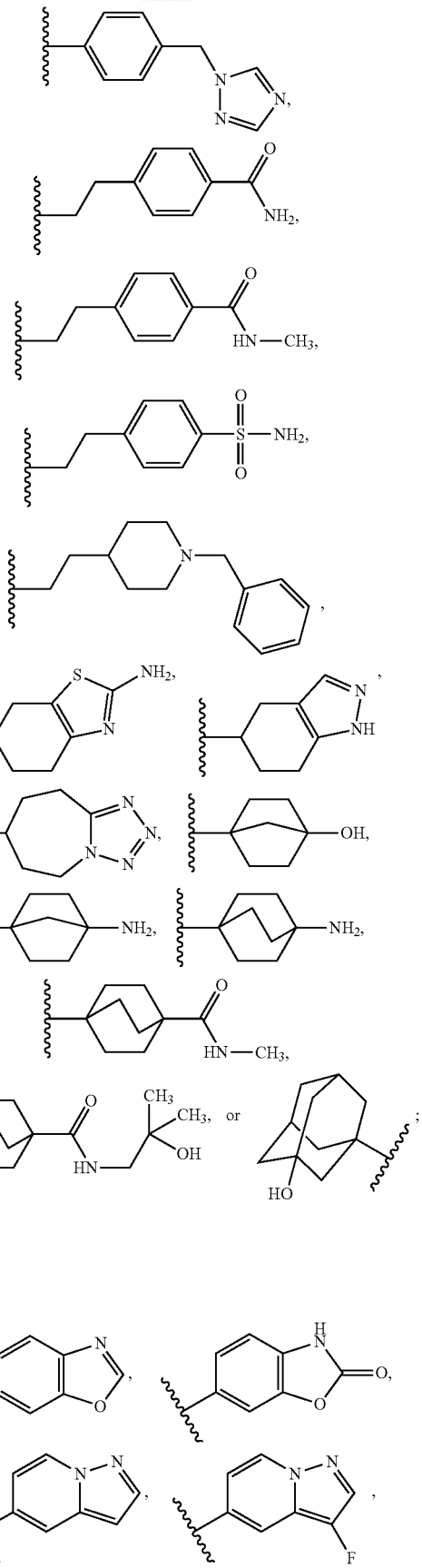

333
-continued
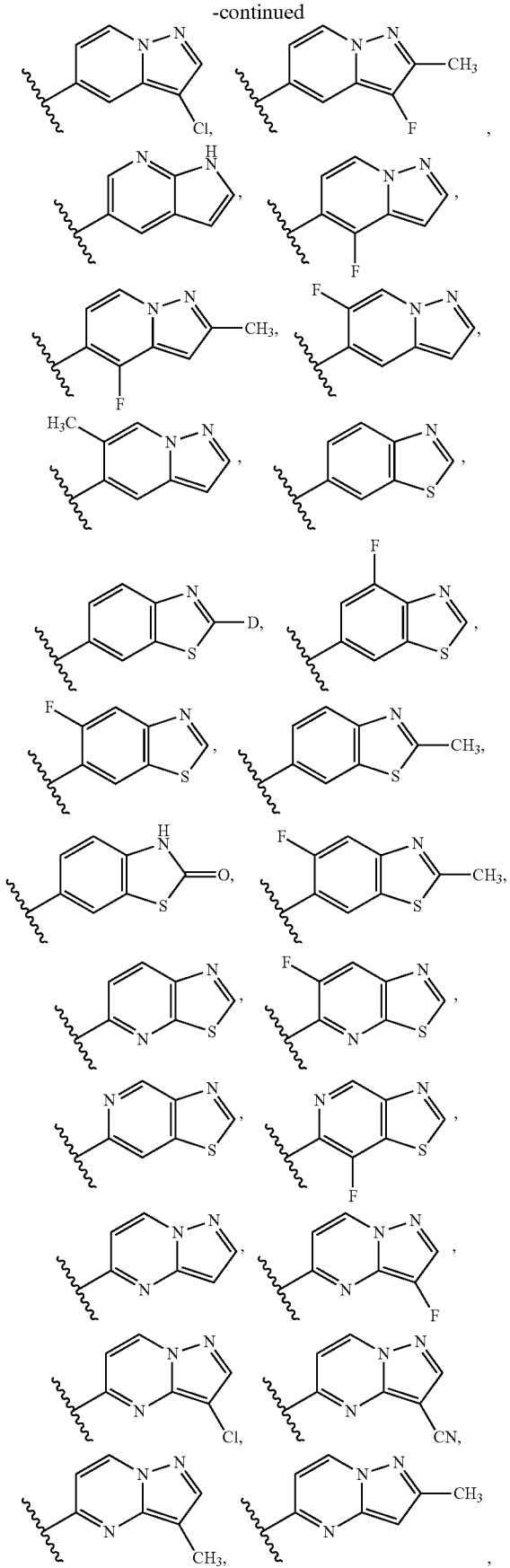
334
-continued
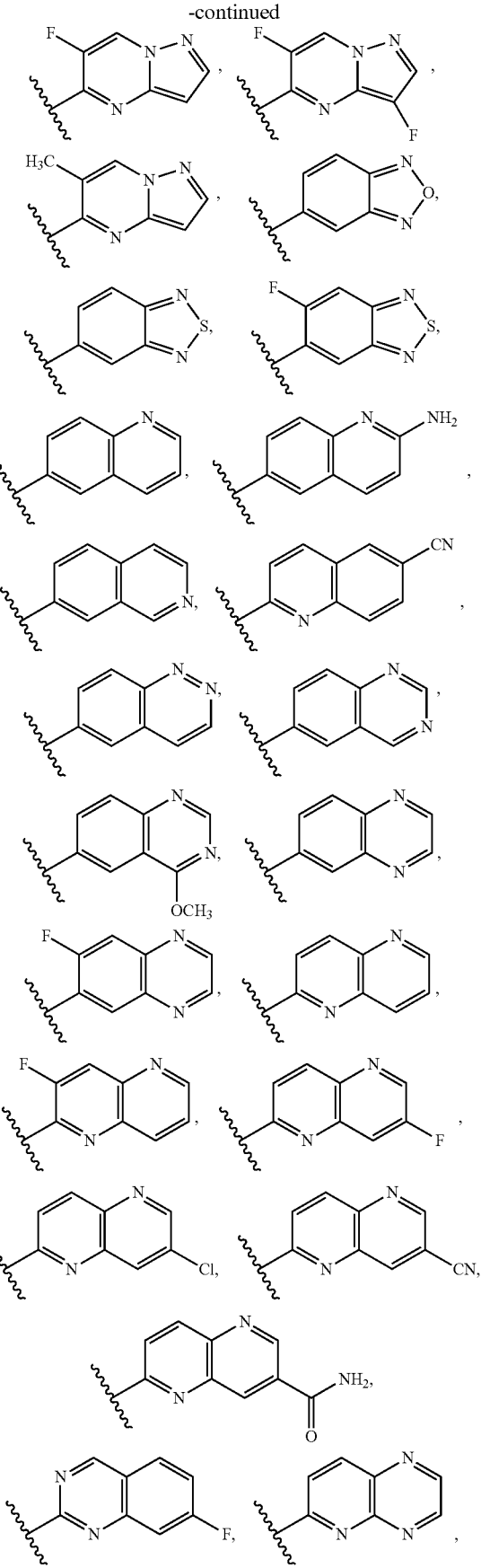

-continued

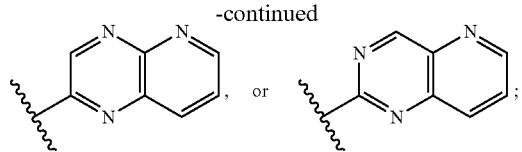

and

R³ is: C₂₋₅ alkyl, —CH₂CHF₂, —CH₂CF₃, —CH₂CHFCH₃, —CH₂CF₂CH₃, —CH(CH₃)CF₃, CH₂CF(CH₃)₂, —CH(CH₃)CH₂CH₂F, —CH(CH₃)(cyclopropyl), —CH(cyclopropyl)₂, —CH₂(cyclopropyl), —CH₂(tetrahydrofuranyl), —CH₂CH₂OH, —CH(CH₃)CH₂OH, —(CH₂)₂(cyclopropyl), C₃₋₇ cycloalkyl, tetrahydropyranyl, tetrahydrothiopyranyl, —CH(CH₃)CH₂OH, —CH(phenyl)CH₂OH, —CH₂CF₂C(CH₃)₂OH, —CH(phenyl)CH(OH)CH₂OH, —CH(3-fluorophenyl)CH(OH)CH₂OH, —CH(3,5-difluorophenyl)CH(OH)CH₂OH, —CH(2,5-difluorophenyl)CH(OH)CH₂OH, —CH(3,5-dichlorophenyl)CH(OH)CH₂OH, —(CH₂)₂(morpholinyl), —(CH₂)₂(phenyl),

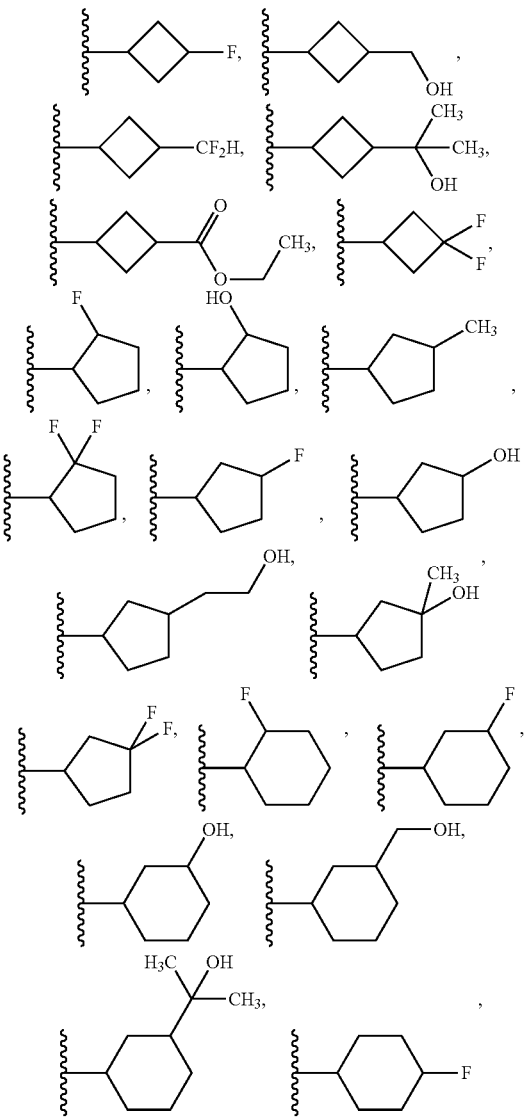

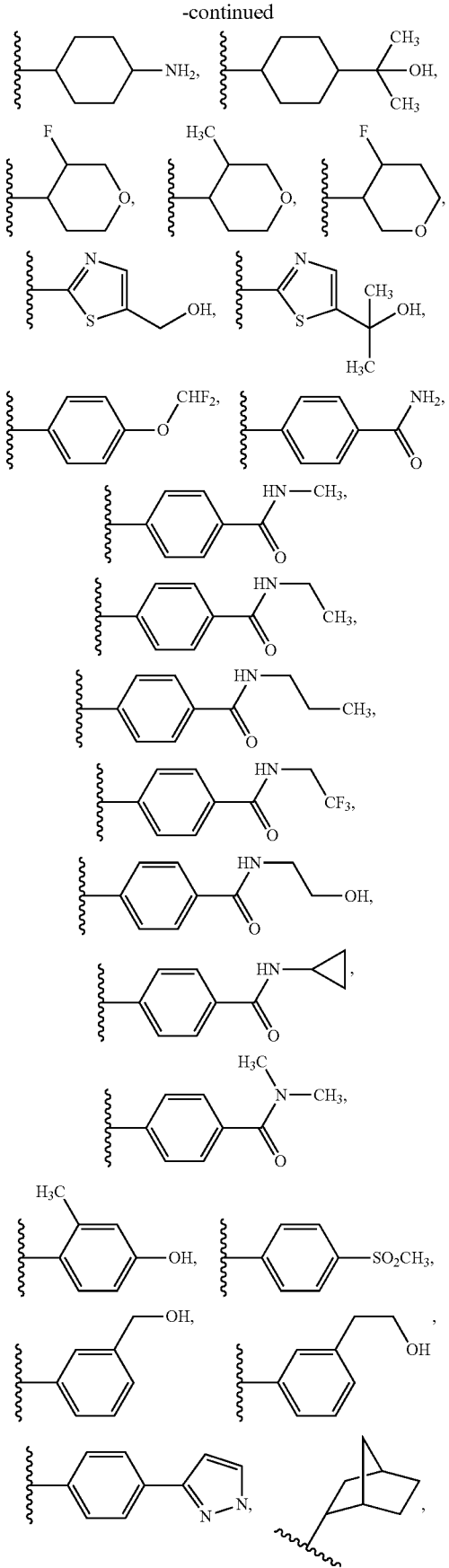

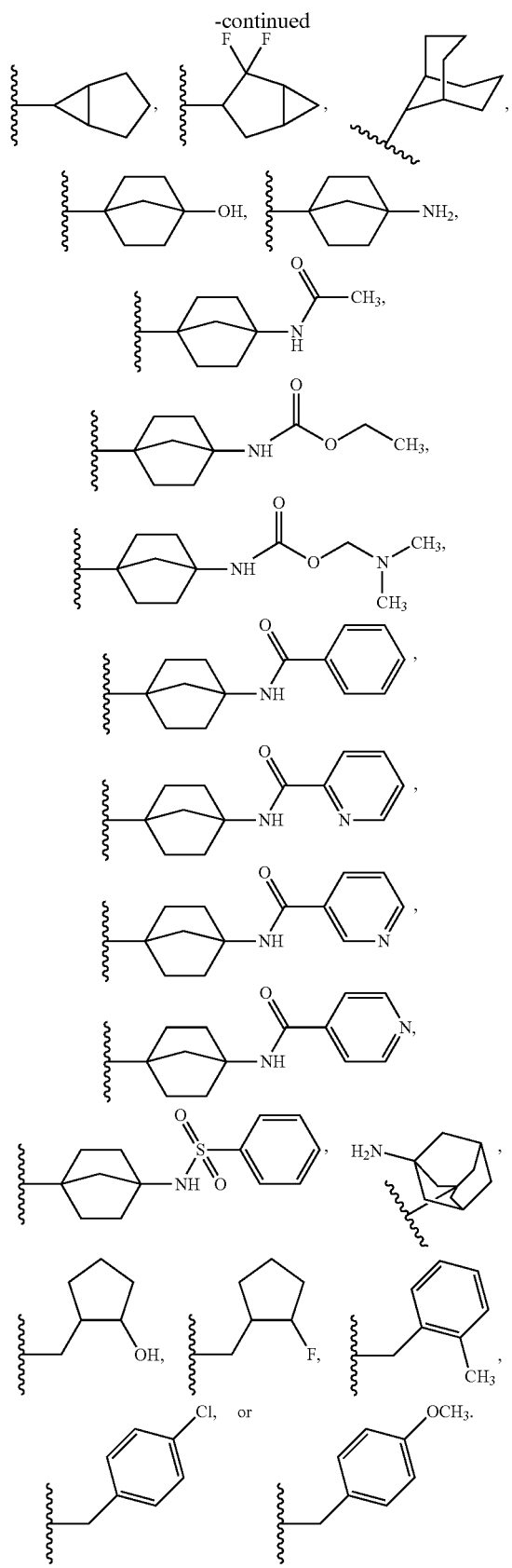

4. The compound according to claim 1 or a stereoisomer or pharmaceutically-acceptable salt thereof, wherein $R^1$ is —CH$_2$CH$_2$CH(CH$_3$)$_2$, —(CH$_2$)$_2$C(CH$_3$)$_2$OH, —CH$_2$CHFCH$_2$OH, —CH$_2$CHFCH(CH(CH$_3$)$_2$)OH, —CH$_2$CHFCH(cyclopropyl)OH, —CH$_2$CHFCH(CH$_3$)OH, —CH$_2$CHFCH(cyclopropyl)(CF$_3$)OH, —CH$_2$CHFC(CH$_3$)$_2$OH, —CH$_2$CHFC(CH$_3$)(CH$_2$CH$_3$)OH, —CH$_2$CHFC(CH$_2$CH$_3$)$_2$OH, —CH$_2$CHFC(CH$_3$)(CF$_3$)OH, —CH$_2$CF$_2$C(CH$_3$)$_2$OH, —(CH$_2$)$_2$NHC(O)CH$_3$, —(CH$_2$)$_3$NHC(O)CH$_3$, —(CH$_2$)$_4$NHC(O)CH$_3$, —(CH$_2$)$_2$CH(CH$_3$)NHC(O)CH$_3$, —(CH$_2$)$_2$CH(CH$_3$)NHC(O)OCH(CH$_3$)$_2$, —(CH$_2$)$_2$CH(CH$_3$)NHC(O)OC(CH$_3$)$_3$, —(CH$_2$)$_2$CH(CH$_3$)NHC(O)CH$_2$N(CH$_3$)$_2$, —(CH$_2$)$_2$CH(CH$_3$)NHC(O)NHCH(CH$_3$)$_2$, —(CH$_2$)$_2$CH(CH$_3$)NHC(O)(cyclopropyl), —(CH$_2$)$_2$CH(CH$_3$)NHC(O)(3-fluorocyclopentyl), —(CH$_2$)$_2$CH(CH$_3$)NHC(O)(3,3-difluorocyclopentyl), —(CH$_2$)$_2$CH(CH$_3$)NHC(O)(morpholinyl), —(CH$_2$)$_2$CH(CH$_3$)NHC(O)(phenyl), —(CH$_2$)$_2$CH(CH$_3$)NHC(O)(pyrrolidinyl), —(CH$_2$)$_2$CH(CH$_3$)NHC(O)CH$_2$(tetrahydropyranyl), —(CH$_2$)$_2$CH(CH$_3$)NHC(O)CH$_2$(2,2-difluorocyclohexyl), —(CH$_2$)$_2$CH(CH$_3$)NHC(O)CH$_2$(triazolyl), —(CH$_2$)$_2$CH(CH$_3$)NHC(O)(CH$_2$)$_3$C(CH$_3$)$_2$OH, —(CH$_2$)$_2$CH(CH$_3$)NHC(O)(CH$_2$)$_4$C(CH$_3$)$_2$OH, or —(CH$_2$)$_2$CH(CH$_3$)NHC(O)N(CH$_3$)(phenyl).

5. The compound according to claim 1 or a stereoisomer or pharmaceutically-acceptable salt thereof, wherein $R^1$ is:

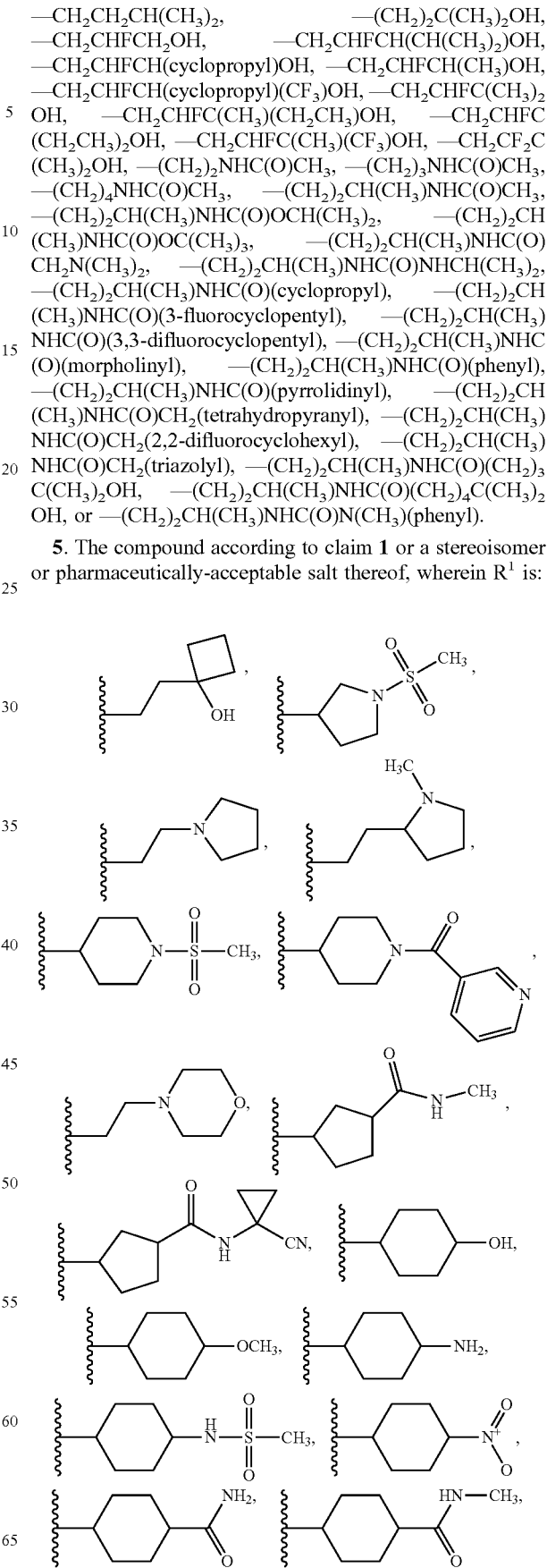

-continued
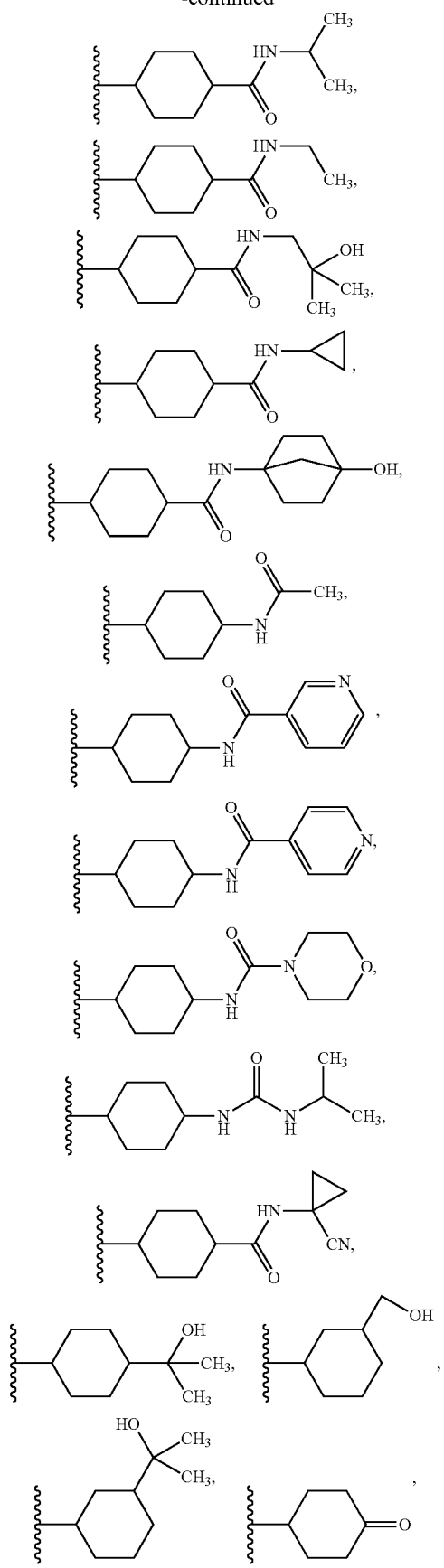
-continued
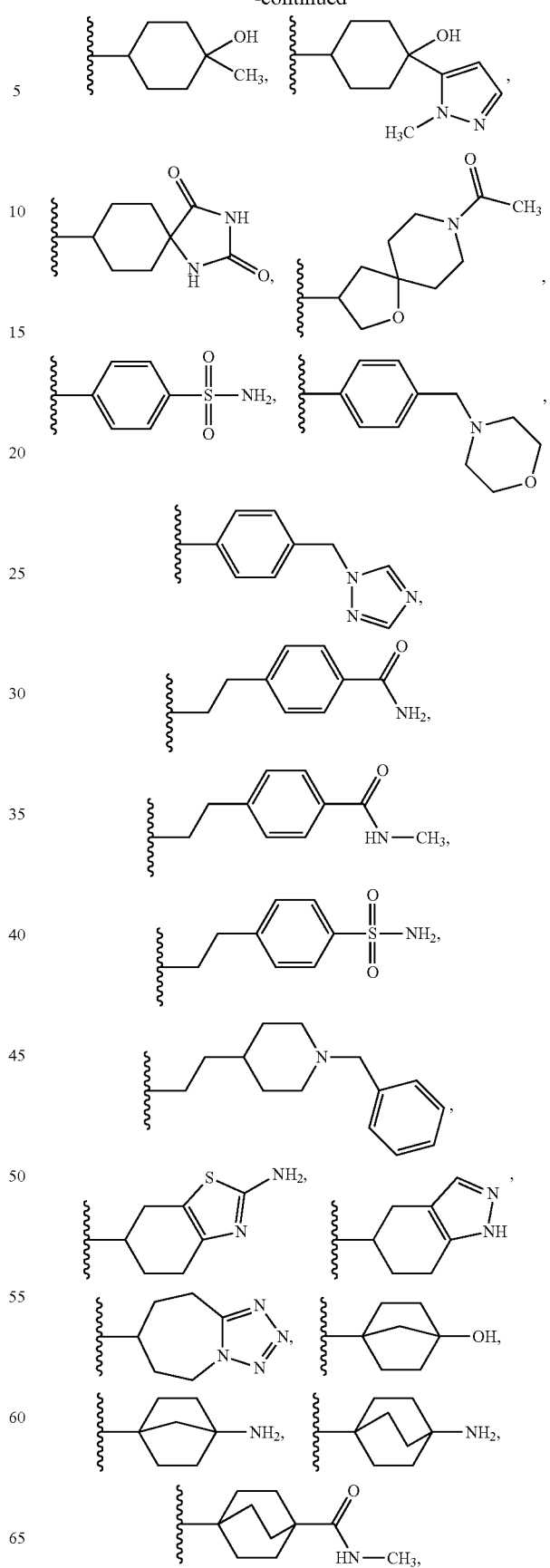

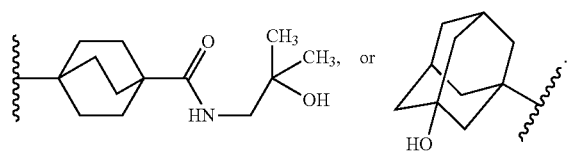

6. The compound according to claim 1 or a stereoisomer or pharmaceutically-acceptable salt thereof, wherein $R^2$ is:

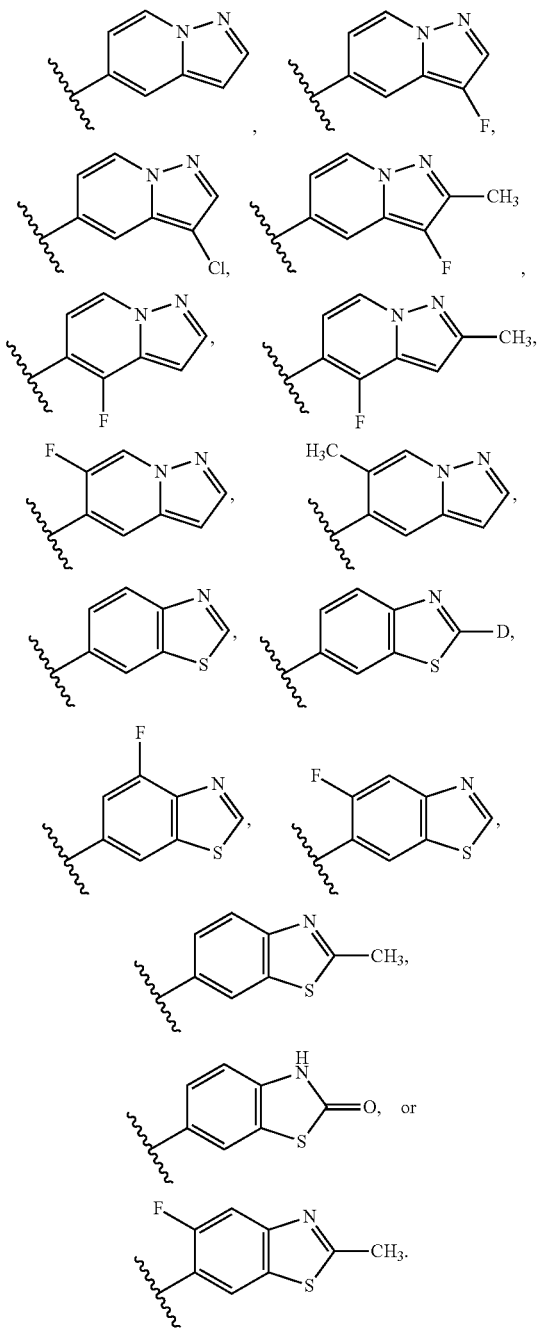

7. The compound according to claim 1 or a stereoisomer or pharmaceutically-acceptable salt thereof, wherein $R^2$ is:

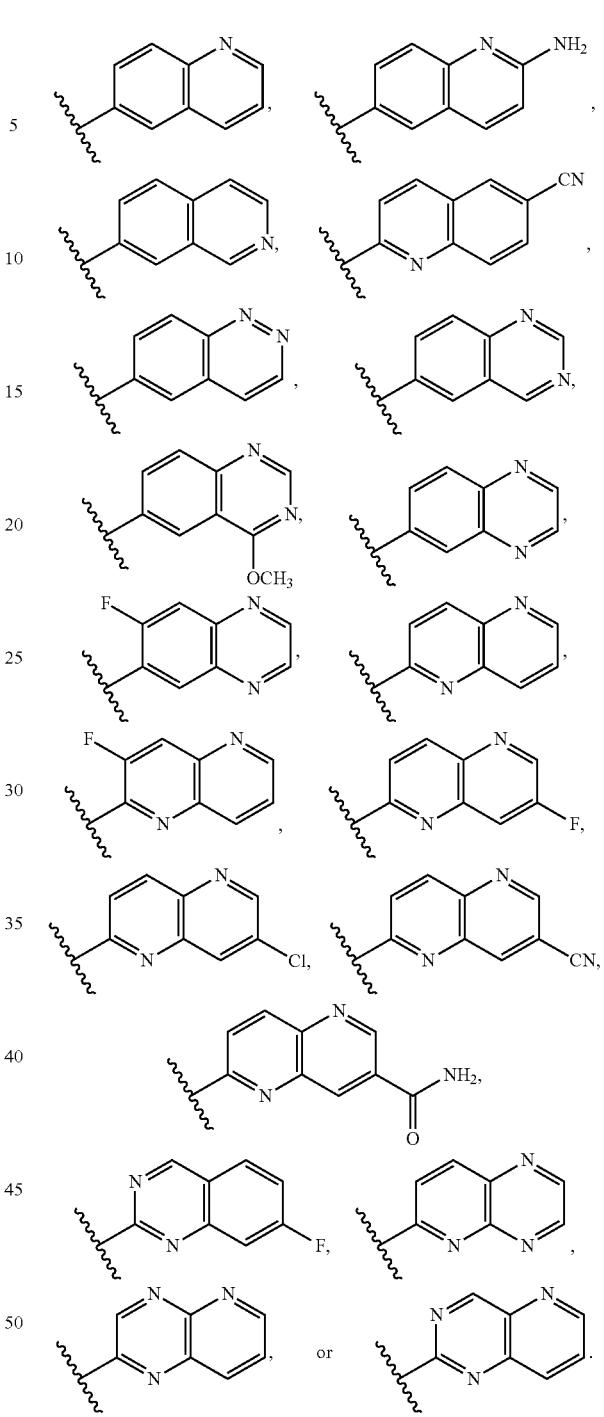

8. The compound according to claim 1 or a stereoisomer or pharmaceutically-acceptable salt thereof, wherein $R^3$ is:
 (a) $C_{2-6}$ alkyl or $C_{2-6}$ fluoroalkyl;
 (b) $C_{1-3}$ alkyl substituted with 1 to 2 cyclopropyl;
 (c) $C_{1-3}$ alkyl substituted with phenyl, tetrahydrofuranyl, or morpholinyl;
 (d) $C_{2-6}$ hydroxyalkyl substituted with zero to 3 substituents selected from F, phenyl, fluorophenyl, difluorophenyl, and dichlorophenyl; or
 (e) —$(CH_2)_{0-2}$($C_{3-6}$ cycloalkyl) substituted with zero to 2 substituents selected from F, —OH, $C_{1-3}$ hydroxyalkyl, —$CH_3$, —$CF_2H$, —$NH_2$, and —$C(O)OCH_2CH_3$.

9. A pharmaceutical composition comprising one or more compounds according to claim 1 and a pharmaceutically acceptable carrier or diluent.

* * * * *

UNITED STATES PATENT AND TRADEMARK OFFICE
CERTIFICATE OF CORRECTION

PATENT NO.       : 9,546,153 B2
APPLICATION NO.  : 14/441698
DATED            : January 17, 2017
INVENTOR(S)      : Rajeev S. Bhide et al.

Page 1 of 1

It is certified that error appears in the above-identified patent and that said Letters Patent is hereby corrected as shown below:

In the Claims

Claim 1, Column 326, Line 34, delete "benzooxazolyl," and insert -- benzoxazolyl, --;

Claim 1, Column 326, Line 36, delete "benzooxadiazolyl," and insert -- benzoxadiazolyl, --; and Claim 1, Column 326, Line 38, delete "5-naphthyrindinyl," and insert -- 5-naphthyridinyl, --, therefor.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*